US012590955B2

(12) United States Patent  (10) Patent No.: US 12,590,955 B2
Grisham et al.  (45) Date of Patent: Mar. 31, 2026

(54) METHODS AND SYSTEMS FOR PROCESSING PARTICLES

(71) Applicants:ZEON CORPORATION, Tokyo (JP); THE TRUSTEES OF PRINCETON UNIVERSITY, Princeton, NJ (US); UNIVERSITY OF MARYLAND, BALTIMORE, Baltimore, MD (US)

(72) Inventors: Michael Grisham, Richmond, VA (US); Curt I. Civin, Baltimore, MD (US); James C. Sturm, Princeton, NJ (US); Robert H. Austin, Princeton, NJ (US); Joseph D'Silva, Princeton, NJ (US); Yu Chen, Princeton, NJ (US)

(73) Assignees: ZEON CORPORATION, Tokyo (JP); THE TRUSTEES OF PRINCETON UNIVERSITY, Princeton, NJ (US); UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

(21) Appl. No.: 15/329,753

(22) PCT Filed: Aug. 3, 2015

(86) PCT No.: PCT/US2015/043500
§ 371 (c)(1),
(2) Date: Jan. 27, 2017

(87) PCT Pub. No.: WO2016/019393
PCT Pub. Date: Feb. 4, 2016

(65) Prior Publication Data
US 2017/0209864 A1 Jul. 27, 2017

Related U.S. Application Data

(60) Provisional application No. 62/032,520, filed on Aug. 1, 2014.

(51) Int. Cl.
| | | |
|---|---|---|
| *G01N 33/50* | (2006.01) | |
| *B01L 3/00* | (2006.01) | |
| *G01N 33/483* | (2006.01) | |

(52) U.S. Cl.
CPC .... *G01N 33/5094* (2013.01); *B01L 3/502746* (2013.01); *B01L 3/502753* (2013.01); (Continued)

(58) Field of Classification Search
CPC ......... B01L 2400/086; B01L 3/502746; B01L 3/502753; B01L 2300/0816; (Continued)

(56) References Cited

U.S. PATENT DOCUMENTS

| | | |
|---|---|---|
| 4,675,286 A | 6/1987 | Calenoff |
| 4,756,427 A | 7/1988 | Goehde et al. |
| | (Continued) | |

FOREIGN PATENT DOCUMENTS

| | | |
|---|---|---|
| CA | 1 248 873 | 1/1989 |
| EP | 1462800 A1 | 9/2004 |
| | (Continued) | |

OTHER PUBLICATIONS

Rhee, Advanced Components of Microfluidic Systems for Bioanalytical Applications, 2009 (Year: 2009).*

(Continued)

*Primary Examiner* — Dirk R Bass
(74) *Attorney, Agent, or Firm* — KENJA IP LAW PC

(57) ABSTRACT

Described herein are improved microfluidic devices and methods for processing cells that can improve cell quality, streamline workflows, and lower costs. Applications include research and clinical diagnostics in cancer, infectious disease, and inflammatory disease, among other disease areas.

13 Claims, 71 Drawing Sheets

(52) U.S. Cl.
CPC .. *G01N 33/4833* (2013.01); *B01L 2300/0883*
(2013.01); *B01L 2400/086* (2013.01)

(58) Field of Classification Search
CPC ....... B01L 3/502761; B01L 2400/0487; B01L
2200/0652; B01L 2200/0668; B01L
2200/12; B01L 2300/0681; B01L
2300/0864; B01L 2200/0647; B01L
2300/0867; B01L 2300/0883; B01L
2300/12; B01L 2400/0406; B01L
3/502707; B01L 1/52; B01L 2300/0877;
B01L 2400/0409; B01L 2400/0415; B01L
3/502784; B01L 9/54; B01L 2200/027;
B01L 2200/0636; B01L 2200/0663; B01L
2200/0673; B01L 2200/16; B01L
2300/042; B01L 2300/0645; B01L
2300/0654; B01L 2300/0803; B01L
2300/0829; B01L 2300/087; B01L
2300/088; B01L 2300/0896; B01L
2300/161; B01L 2300/165; B01L
2400/0424; B01L 2400/043; B01L
2400/0472; B01L 2400/049; B01L
2400/0688; B01L 3/5021; B01L 3/5023;
B01L 3/50255; B01L 3/5027; B01L
3/502715; B01L 3/502776; B01L
3/502792; B01L 2200/0689; B01L
3/502723; B01L 5/50273; C04B 41/009;
C04B 38/007; C04B 41/52; C04B 35/10;
C04B 14/047; C04B 38/00; C04B
41/4582; C04B 41/5024; C04B
2111/00612; C04B 2111/00801; C04B
2235/6021; C04B 2235/94; C04B 35/111;
C04B 35/6261; C04B 35/62625; C04B
41/89; B33Y 80/00; B33Y 70/00; B82Y
30/00; B82Y 10/00; B82Y 15/00; B82Y
5/00; C12M 47/04; C12M 35/00; C12M
47/02; C12M 47/06; G01N 1/40; G01N
2015/1006; G01N 2015/1081; G01N
33/5091; G01N 1/34; G01N 1/405; G01N
1/4077; G01N 2333/70582; G01N
2333/70589; G01N 2333/70596; G01N
33/54366; G01N 33/54386; G01N
33/56966; G01N 33/574; G01N
2001/4088; G01N 2015/1087; G01N
2015/1486; G01N 2015/149; G01N
2030/528; G01N 2035/00237; G01N
2035/1034; G01N 21/6486; G01N
27/44791; G01N 2800/2871; G01N
2800/347; G01N 2800/364; G01N
2800/52; G01N 30/0005; G01N 30/6069;
G01N 30/6095; G01N 30/90; G01N
33/4833; G01N 33/48721; G01N
33/5044; G01N 33/5094; G01N
33/54333; G01N 33/558; G01N
33/57407; G01N 33/57492; G01N
33/6893; G01N 35/0098; G01N 35/1002;
G01N 2015/1454; G01N 15/0227; G01N
15/1434; G01N 15/01; G01N 15/0211;
G01N 15/0255; G01N 15/08; G01N
15/088; G01N 15/1429; G01N 15/1433;
G01N 15/1459; G01N 15/1468; G01N
15/147; G01N 15/1484; G01N 2015/003;
G01N 2015/0038; G01N 2015/0053;
G01N 2015/0222; G01N 2015/0233;
G01N 2015/0288; G01N 2015/0846;
G01N 2015/1445; G01N 2015/1493;
G01N 2015/1497; G01N 33/483; Y10T
436/25; Y10T 29/49982; Y10T
428/24744; Y10T 436/11; Y10T
137/0318; Y10T 137/8593; Y10T 29/49;
Y10T 29/49826; Y10T 436/10; Y10T
436/117497; Y10T 436/118339; Y10T
436/143333; Y10T 436/25375; Y10T
436/2575; B01D 21/0087; B01D 2313/08;
B01D 2321/2016; B01D 2325/06; B01D
53/228; B01D 67/0051; B01D 69/046;
B01D 69/082; B01D 69/10; B01D 69/12;
B01D 71/028; B01D 21/0009; B01D
21/0042; B01D 21/2444; B01D 21/265;
B01D 2323/12; B01D 2325/02; B01D
2325/04; B01D 67/0072; B01D 71/025;
B03C 2201/26; B03C 1/288; B03C 1/30;
B03C 1/32; B03C 2201/18; B03C 5/005;
B03C 5/026; G03H 1/0005; G03H
2001/005; G03H 1/0443; G03H
2001/0033; G03H 2210/55; A61K
2039/5152; A61K 2039/5156; A61K
35/12; A61K 39/0011; A61K 39/001139;
A61P 35/00; B81B 2201/058; B81B
2203/0361; B81B 7/0061; B81C 1/00111;
B81C 1/00309; C12N 2502/99; C12N
2529/00; C12N 5/0693; G02B 21/0056;
G02B 21/0068; G02B 21/008; G06T
2207/10016; G06T 2207/10056; G06T
7/62; G16B 25/00
See application file for complete search history.

(56) References Cited

U.S. PATENT DOCUMENTS

| | | | |
|---|---|---|---|
| 5,030,002 A | 7/1991 | North, Jr. | |
| 5,240,856 A | 8/1993 | Goffe et al. | |
| 5,427,663 A | 6/1995 | Austin et al. | |
| 5,541,164 A | 7/1996 | Carson et al. | |
| 5,676,849 A | 10/1997 | Sammons et al. | |
| 5,707,799 A | 1/1998 | Hansmann et al. | |
| 5,837,115 A | 11/1998 | Austin et al. | |
| 5,872,128 A | 2/1999 | Patel et al. | |
| 5,948,278 A | 9/1999 | Sammons et al. | |
| 5,968,820 A | 10/1999 | Zborowski et al. | |
| 5,981,180 A | 11/1999 | Chandler et al. | |
| 6,241,894 B1 | 6/2001 | Briggs et al. | |
| 6,268,222 B1 | 7/2001 | Chandler et al. | |
| 6,514,295 B1 | 2/2003 | Chandler et al. | |
| 6,524,793 B1 | 2/2003 | Chandler et al. | |
| 6,528,165 B2 | 3/2003 | Chandler et al. | |
| 6,632,652 B1 | 10/2003 | Austin et al. | |
| 6,685,841 B2 | 2/2004 | Lopez et al. | |
| 6,692,952 B1 | 2/2004 | Braff et al. | |
| 6,881,315 B2 | 4/2005 | Iida et al. | |
| 6,881,317 B2 | 4/2005 | Huang et al. | |
| 6,913,697 B2 | 7/2005 | Lopez et al. | |
| 6,949,355 B2 | 9/2005 | Yamanishi et al. | |
| 6,960,449 B2 | 11/2005 | Wang et al. | |
| 7,150,812 B2 | 12/2006 | Huang et al. | |
| 7,276,170 B2 | 10/2007 | Oakey et al. | |
| 7,318,902 B2 | 1/2008 | Oakey et al. | |
| 7,472,794 B2 | 1/2009 | Oakey et al. | |
| 7,682,838 B2 | 3/2010 | Wang et al. | |
| 7,735,652 B2 * | 6/2010 | Inglis ............... | B01L 3/502753 |
| | | | 210/433.1 |
| 7,837,944 B2 | 11/2010 | Auner et al. | |
| 7,846,393 B2 | 12/2010 | Tai et al. | |
| 7,863,012 B2 | 1/2011 | Rao et al. | |
| 7,977,095 B2 | 7/2011 | Bonyhadi et al. | |
| 7,988,840 B2 | 8/2011 | Huang et al. | |

(56)                References Cited

U.S. PATENT DOCUMENTS

| | | | |
|---|---|---|---|
| 7,993,821 B2 | 8/2011 | Chiu et al. |
| 8,008,032 B2 | 8/2011 | Forsyth et al. |
| 8,021,614 B2 | 9/2011 | Huang et al. |
| 8,088,715 B2 | 1/2012 | Bodmer et al. |
| 8,137,912 B2 | 3/2012 | Kapur et al. |
| 8,168,389 B2 | 5/2012 | Shoemaker et al. |
| 8,186,913 B2 | 5/2012 | Toner et al. |
| 8,263,023 B2 | 9/2012 | Le Vot et al. |
| 8,263,404 B2 | 9/2012 | Olken et al. |
| 8,282,799 B2 | 10/2012 | Huang et al. |
| 8,304,230 B2 | 11/2012 | Toner et al. |
| 8,329,422 B2 | 12/2012 | Rao et al. |
| 8,354,075 B1 | 1/2013 | Tai et al. |
| 8,372,579 B2 | 2/2013 | Toner et al. |
| 8,372,584 B2 | 2/2013 | Shoemaker et al. |
| 8,579,117 B2 | 11/2013 | Sturm et al. |
| 8,585,971 B2 | 11/2013 | Huang et al. |
| 8,783,467 B2 | 7/2014 | Loutherback et al. |
| 8,895,298 B2 | 11/2014 | Toner et al. |
| 8,906,682 B2 | 12/2014 | June et al. |
| 8,921,102 B2 | 12/2014 | Fuchs et al. |
| 8,951,484 B2 | 2/2015 | Bersano-Begey et al. |
| 8,986,966 B2 | 3/2015 | Toner et al. |
| 9,017,942 B2 | 4/2015 | Shoemaker et al. |
| 9,034,658 B2 * | 5/2015 | Barber ............. G01N 33/56972 |
| | | 436/518 |
| 9,273,355 B2 | 3/2016 | Shoemaker et al. |
| 9,328,156 B2 | 5/2016 | June et al. |
| 9,347,100 B2 | 5/2016 | Shoemaker et al. |
| 9,427,688 B2 | 8/2016 | Reichenbach |
| 9,610,582 B2 | 4/2017 | Kapur et al. |
| 9,629,877 B2 | 4/2017 | Cooper et al. |
| 9,878,327 B2 | 1/2018 | Smith et al. |
| 9,895,694 B2 | 2/2018 | Kapur et al. |
| 9,956,562 B2 | 5/2018 | Huang et al. |
| 10,324,011 B2 | 6/2019 | D'Silva |
| 10,359,429 B2 | 7/2019 | Forsyth |
| 10,391,491 B2 | 8/2019 | Toner |
| 10,844,353 B2 | 11/2020 | Ward et al. |
| 10,852,220 B2 | 12/2020 | D'Silva et al. |
| 10,976,232 B2 | 4/2021 | Ward et al. |
| 10,988,734 B2 | 4/2021 | Ward et al. |
| 2001/0036624 A1 | 11/2001 | Sumita et al. |
| 2002/0005354 A1 | 1/2002 | Spence et al. |
| 2002/0090741 A1 | 7/2002 | Jurgensen et al. |
| 2002/0110835 A1 | 8/2002 | Kumar |
| 2002/0115163 A1 | 8/2002 | Wang et al. |
| 2002/0119482 A1 | 8/2002 | Nelson et al. |
| 2002/0123078 A1 | 9/2002 | Seul et al. |
| 2002/0164825 A1 | 11/2002 | Chen |
| 2003/0049563 A1 | 3/2003 | Iida et al. |
| 2003/0096405 A1 | 5/2003 | Takayama et al. |
| 2003/0113528 A1 | 6/2003 | Moya |
| 2003/0119077 A1 | 6/2003 | Ts'o et al. |
| 2003/0159999 A1 | 8/2003 | Oakey et al. |
| 2003/0180762 A1 | 9/2003 | Tuma et al. |
| 2004/0018116 A1 | 1/2004 | Desmond et al. |
| 2004/0018611 A1 | 1/2004 | Ward et al. |
| 2004/0019300 A1 | 1/2004 | Leonard |
| 2004/0033515 A1 * | 2/2004 | Cao ................... B01L 3/502707 |
| | | 435/6.12 |
| 2004/0043506 A1 | 3/2004 | Haussecker et al. |
| 2004/0144651 A1 | 7/2004 | Huang et al. |
| 2004/0166555 A1 | 8/2004 | Braff et al. |
| 2004/0224402 A1 | 11/2004 | Bonyhadi et al. |
| 2004/0229349 A1 | 11/2004 | Daridon |
| 2004/0232074 A1 | 11/2004 | Peters et al. |
| 2005/0061962 A1 | 3/2005 | Mueth et al. |
| 2005/0164158 A1 | 7/2005 | Wang et al. |
| 2005/0207940 A1 | 9/2005 | Butler et al. |
| 2005/0266433 A1 | 12/2005 | Kapur et al. |
| 2005/0272103 A1 | 12/2005 | Chen |
| 2005/0282293 A1 | 12/2005 | Cosman et al. |
| 2006/0035386 A1 | 2/2006 | Hattori et al. |
| 2006/0121624 A1 | 6/2006 | Huang et al. |

| | | | |
|---|---|---|---|
| 2006/0128006 A1 | 6/2006 | Gerhardt et al. |
| 2006/0134599 A1 * | 6/2006 | Toner ............... B01L 3/502761 |
| | | 435/4 |
| 2006/0160243 A1 | 7/2006 | Tang et al. |
| 2006/0223178 A1 | 10/2006 | Barber et al. |
| 2006/0252087 A1 | 11/2006 | Tang et al. |
| 2007/0026381 A1 | 2/2007 | Huang et al. |
| 2007/0026413 A1 | 2/2007 | Toner et al. |
| 2007/0026414 A1 | 2/2007 | Fuchs et al. |
| 2007/0026415 A1 | 2/2007 | Fuchs et al. |
| 2007/0026416 A1 | 2/2007 | Fuchs et al. |
| 2007/0026417 A1 | 2/2007 | Fuchs et al. |
| 2007/0026418 A1 | 2/2007 | Fuchs et al. |
| 2007/0026419 A1 | 2/2007 | Fuchs et al. |
| 2007/0026469 A1 | 2/2007 | Fuchs et al. |
| 2007/0042339 A1 | 2/2007 | Toner et al. |
| 2007/0059680 A1 | 3/2007 | Kapur et al. |
| 2007/0059716 A1 * | 3/2007 | Balis ................. B01L 3/502746 |
| | | 435/6.11 |
| 2007/0059718 A1 | 3/2007 | Kapur et al. |
| 2007/0059719 A1 | 3/2007 | Kapur et al. |
| 2007/0059774 A1 | 3/2007 | Kapur et al. |
| 2007/0059781 A1 | 3/2007 | Kapur et al. |
| 2007/0072290 A1 | 3/2007 | Hvichia |
| 2007/0099207 A1 | 5/2007 | Fuchs et al. |
| 2007/0160503 A1 | 7/2007 | Sethu et al. |
| 2007/0172903 A1 | 7/2007 | Toner et al. |
| 2007/0187250 A1 | 8/2007 | Huang et al. |
| 2007/0196820 A1 | 8/2007 | Kapur et al. |
| 2007/0231851 A1 | 10/2007 | Toner et al. |
| 2007/0259424 A1 | 11/2007 | Toner et al. |
| 2007/0264675 A1 | 11/2007 | Toner et al. |
| 2007/0292401 A1 | 12/2007 | Harmon et al. |
| 2008/0070792 A1 | 3/2008 | Stoughton et al. |
| 2008/0090239 A1 | 4/2008 | Shoemaker et al. |
| 2008/0113358 A1 | 5/2008 | Kapur et al. |
| 2008/0124721 A1 | 5/2008 | Kapur et al. |
| 2008/0248499 A1 | 10/2008 | Chiu et al. |
| 2008/0314161 A1 | 12/2008 | Sparks et al. |
| 2009/0136982 A1 | 5/2009 | Tang et al. |
| 2009/0291443 A1 | 11/2009 | Stoughton et al. |
| 2010/0006479 A1 | 1/2010 | Reichenbach |
| 2010/0055758 A1 | 3/2010 | Kapur et al. |
| 2010/0059414 A1 | 3/2010 | Sturm et al. |
| 2010/0066880 A1 | 3/2010 | Sato et al. |
| 2010/0167337 A1 | 7/2010 | Tsinberg et al. |
| 2010/0233694 A1 | 9/2010 | Kopf-Sill |
| 2010/0234674 A1 | 9/2010 | Wheeler et al. |
| 2010/0291572 A1 | 11/2010 | Stoughton et al. |
| 2010/0297733 A1 * | 11/2010 | Lin ......................... B03C 1/288 |
| | | 435/239 |
| 2010/0301171 A1 | 12/2010 | Wood |
| 2010/0326916 A1 | 12/2010 | Wrazel et al. |
| 2011/0003293 A1 | 1/2011 | Stoughton et al. |
| 2011/0070642 A1 | 3/2011 | Cayre |
| 2011/0189650 A1 | 8/2011 | Ayliffe et al. |
| 2011/0212440 A1 | 9/2011 | Viovy et al. |
| 2011/0213288 A1 | 9/2011 | Choi et al. |
| 2011/0294186 A1 | 12/2011 | Fuchs et al. |
| 2011/0306043 A1 | 12/2011 | Fuchs et al. |
| 2012/0006728 A1 | 1/2012 | Huang et al. |
| 2012/0006760 A1 | 1/2012 | Toner et al. |
| 2012/0015835 A1 | 1/2012 | Fuchs et al. |
| 2012/0037544 A1 * | 2/2012 | Lane ................... B01D 21/0042 |
| | | 209/156 |
| 2012/0063971 A1 | 3/2012 | Carlo et al. |
| 2012/0078531 A1 | 3/2012 | Lo et al. |
| 2012/0100521 A1 | 4/2012 | Soper et al. |
| 2012/0100560 A1 | 4/2012 | Searson et al. |
| 2012/0115755 A1 | 5/2012 | Oh et al. |
| 2012/0171667 A1 | 7/2012 | Shoemaker et al. |
| 2012/0178097 A1 | 7/2012 | Tai et al. |
| 2012/0196273 A1 | 8/2012 | Huang et al. |
| 2012/0258459 A1 | 10/2012 | Huang |
| 2012/0258475 A1 | 10/2012 | Tang et al. |
| 2012/0270209 A1 | 10/2012 | Shah et al. |
| 2012/0295246 A1 | 11/2012 | Faustman et al. |
| 2013/0079251 A1 | 3/2013 | Boles et al. |
| 2013/0083315 A1 | 4/2013 | Lo et al. |

(56) References Cited

U.S. PATENT DOCUMENTS

| 2013/0143197 A1 | 6/2013 | Heyneker |
| 2013/0189689 A1 | 7/2013 | Shoemaker et al. |
| 2013/0209988 A1 | 8/2013 | Barber |
| 2013/0210644 A1 | 8/2013 | Stoughton et al. |
| 2013/0260392 A1 | 10/2013 | Forsyth et al. |
| 2013/0288903 A1 | 10/2013 | Kapur et al. |
| 2013/0302796 A1* | 11/2013 | Fuchs .................... B82Y 5/00 |
| | | 435/6.11 |
| 2013/0302797 A1 | 11/2013 | Kopf-Sill et al. |
| 2013/0324418 A1 | 12/2013 | Fuchs et al. |
| 2014/0017776 A1 | 1/2014 | Kopf-Sill |
| 2014/0030788 A1 | 1/2014 | Chen et al. |
| 2014/0051064 A1 | 2/2014 | van den Engh |
| 2014/0093867 A1* | 4/2014 | Burke .................. G01N 1/4077 |
| | | 435/5 |
| 2014/0106975 A1 | 4/2014 | Stoughton et al. |
| 2014/0154703 A1 | 6/2014 | Skelley et al. |
| 2014/0227777 A1* | 8/2014 | Choi ........................ G01N 1/34 |
| | | 435/309.1 |
| 2014/0234986 A1 | 8/2014 | Forsyth et al. |
| 2014/0342375 A1 | 11/2014 | Grisham et al. |
| 2015/0024482 A1 | 1/2015 | Frigault et al. |
| 2015/0025243 A1 | 1/2015 | Mosher et al. |
| 2015/0064153 A1 | 3/2015 | Civin et al. |
| 2015/0232936 A1 | 8/2015 | Shoemaker et al. |
| 2015/0233931 A1 | 8/2015 | Kopf-Sill et al. |
| 2015/0260711 A1 | 9/2015 | Toner et al. |
| 2015/0268244 A1 | 9/2015 | Cho |
| 2015/0299317 A1 | 10/2015 | Orentas et al. |
| 2015/0316555 A1 | 11/2015 | Fuchs et al. |
| 2015/0344956 A1 | 12/2015 | Kapur et al. |
| 2016/0002737 A1 | 1/2016 | Fuchs et al. |
| 2016/0047735 A1 | 2/2016 | Grisham et al. |
| 2016/0081314 A1 | 3/2016 | Thurston et al. |
| 2016/0103044 A1 | 4/2016 | Kopf-Sill |
| 2016/0139012 A1 | 5/2016 | D'Silva et al. |
| 2016/0168539 A1 | 6/2016 | Civin et al. |
| 2016/0244714 A1 | 8/2016 | Spuhler et al. |
| 2016/0339434 A1 | 11/2016 | Toner et al. |
| 2016/0361360 A1 | 12/2016 | Chang et al. |
| 2017/0023578 A1 | 1/2017 | Forsyth et al. |
| 2017/0101680 A1 | 4/2017 | Kopf-Sill et al. |
| 2017/0137515 A1 | 5/2017 | Chang et al. |
| 2017/0166866 A1 | 6/2017 | Lliang et al. |
| 2017/0209864 A1 | 7/2017 | Grisham et al. |
| 2017/0224789 A1 | 8/2017 | Sonavaria et al. |
| 2017/0225166 A1 | 8/2017 | Toner |
| 2017/0248508 A1 | 8/2017 | Ward et al. |
| 2017/0333900 A1 | 11/2017 | Grisham et al. |
| 2018/0038876 A1 | 2/2018 | Arai |
| 2018/0282811 A1 | 10/2018 | Koph-Sill et al. |
| 2019/0071639 A1 | 3/2019 | Ward et al. |
| 2019/0137369 A1 | 5/2019 | D'Silva et al. |
| 2019/0366342 A1 | 12/2019 | Ward et al. |
| 2020/0025656 A1 | 1/2020 | D'Silva et al. |
| 2020/0025657 A1 | 1/2020 | D'Silva et al. |
| 2020/0025669 A1 | 1/2020 | Ward et al. |
| 2020/0056153 A1 | 2/2020 | Ward et al. |
| 2020/0399600 A1 | 12/2020 | Ward et al. |

FOREIGN PATENT DOCUMENTS

| EP | 1425294 B1 | 7/2008 |
| EP | 1585583 B1 | 4/2010 |
| EP | 1597353 B1 | 11/2010 |
| EP | 2201361 B1 | 5/2011 |
| EP | 1984030 B1 | 5/2013 |
| WO | WO-9116452 A1 | 10/1991 |
| WO | WO-9429707 A1 | 12/1994 |
| WO | WO-0135071 A2 | 5/2001 |
| WO | WO-2004029221 A2 | 4/2004 |
| WO | WO-2004029221 A3 | 5/2004 |
| WO | WO-2004037374 A2 | 5/2004 |
| WO | WO-2004037374 A3 | 10/2004 |
| WO | WO-2004113877 A1 | 12/2004 |
| WO | WO-2005047529 A1 | 5/2005 |
| WO | WO-2005049168 A2 | 6/2005 |
| WO | WO-2005061075 A1 | 7/2005 |
| WO | WO-2005049168 A3 | 9/2005 |
| WO | WO-2006037561 A1 | 4/2006 |
| WO | WO-2006078470 A2 | 7/2006 |
| WO | WO-2006078470 A3 | 9/2006 |
| WO | WO-2006108087 A2 | 10/2006 |
| WO | WO-2006108101 A2 | 10/2006 |
| WO | WO-2006133208 A2 | 12/2006 |
| WO | WO-2007/035585 A2 | 3/2007 |
| WO | WO-2007/035586 A2 | 3/2007 |
| WO | WO-2007035498 A2 | 3/2007 |
| WO | WO-2007079229 A2 | 7/2007 |
| WO | WO-2007079250 A2 | 7/2007 |
| WO | WO-2007147018 A1 | 12/2007 |
| WO | WO-2007147074 A2 | 12/2007 |
| WO | WO-2007147076 A2 | 12/2007 |
| WO | WO-2007147079 A2 | 12/2007 |
| WO | WO-2008008515 A2 | 1/2008 |
| WO | WO-2008017871 A1 | 2/2008 |
| WO | WO-2008111990 A1 | 9/2008 |
| WO | WO-2007079229 A3 | 1/2009 |
| WO | WO-2007079250 A3 | 3/2009 |
| WO | WO-2006108101 A3 | 4/2009 |
| WO | WO-2006108087 A3 | 6/2009 |
| WO | WO-2009076560 A2 | 6/2009 |
| WO | WO 2010/011934 | 1/2010 |
| WO | WO-2010124155 A1 | 10/2010 |
| WO | WO-2010129441 A2 | 11/2010 |
| WO | WO-2010144745 A2 | 12/2010 |
| WO | WO-2011119962 A2 | 9/2011 |
| WO | WO 2012/016136 | 2/2012 |
| WO | WO-2012024194 A2 | 2/2012 |
| WO | WO-2012094642 A2 | 7/2012 |
| WO | WO 2014/004577 A1 | 1/2014 |
| WO | WO-2014046621 A1 | 3/2014 |
| WO | WO-2014116183 A1 | 7/2014 |
| WO | WO-2014145075 A2 | 9/2014 |
| WO | WO-2014145152 A2 | 9/2014 |
| WO | WO 2015/084257 | 6/2015 |
| WO | WO 2015/162211 | 10/2015 |
| WO | WO 2015/164745 | 10/2015 |
| WO | WO-2016019393 A1 | 2/2016 |
| WO | WO 2016/073481 | 5/2016 |
| WO | WO 2017/035262 A1 | 3/2017 |
| WO | WO 2017/176764 | 10/2017 |
| WO | WO 2018/080997 | 5/2018 |
| WO | PCT/US2018/047426 | 8/2018 |
| WO | WO 2019/046052 | 3/2019 |
| WO | WO 2019/222049 | 11/2019 |
| WO | WO 2020/014538 | 1/2020 |

OTHER PUBLICATIONS

Loutherback et al, Improved performance of deterministic lateral displacement arrays with triangular posts, Feb. 17, 2010, p. 1-7 (Year: 2010).*

Bargiel, Commercialization of Lateral Displacement Array for Dewatering of Microalgae, May 2009, p. 14-16, 30 (Year: 2009).*

U.S. Appl. No. 60/414,258, filed Apr. 8, 2004 (posted by WIPO), Toner, et al.

International Preliminary Report on Patentability for PCT/US2015/043500; international stage of the present application.

International Search Report for PCT/US2016/048455, completed Oct. 17, 2016; which is related to copending application U.S. Appl. No. 15/595,548.

Written Opinion for PCT/US2016/048455, completed Oct. 17, 2016; which is related to copending application U.S. Appl. No. 15/595,548.

International Preliminary Report on Patentability for PCT/US2016/048455, completed Oct. 17, 2016; which is related to copending application U.S. Appl. No. 15/595,548.

International Preliminary Report on Patentability for PCT/US2014/029866; international stage of copending U.S. Appl. No. 14/774,268, sent Sep. 15, 2015.

(56) References Cited

OTHER PUBLICATIONS

International Preliminary Report on Patentability for PCT/US2014/029736, which is international stage of co-pending U.S. Appl. No. 14/774,260, sent Sep. 15, 2015.

Amended claims filed EP 2014763363.0. which is a European counterpart of co-pending U.S. Appl. No. 14/774,260, filed Apr. 28, 2016.

Supplementary European Search Report for EP 2014763363.0 sent Jul. 1, 2016.

European Search Opinion for EP 2014763363.0 sent Jul. 1, 2016.

Amended claims and Response to EP Search Opinion for EP 2014763363.0 filed May 4, 2017.

Examination Report for EP 2014763363.0, sent Sep. 13, 2017.

Amended Claims and Response to Examination Report for EP 2014763363.0, filed Mar. 20, 2018.

Translation of amended claims filed in China for CN 2014800285714, which is a Chinese counterpart of co-pending U.S. Appl. No. 14/774,260.

Office Action for CN 2014800285714 with English language summary attached to its front, sent May 5, 2017.

Translation of amended claims filed in response to Office Action for CN 2014800285714, filed Oct. 9, 2017.

English translation of Office Action with Response for CN 2014800285714 due May 17, 2018.

Restriction Requirement for co-pending U.S. Appl. No. 14/774,260, mailed Oct. 4, 2017.

Response to Restriction Requirement for co-pending U.S. Appl. No. 14/774,260, filed Dec. 9, 2017.

Amendment to Accompany Response to Restriction Requirement for co-pending U.S. Appl. No. 14/774,260, filed Dec. 9, 2017.

Office Action sent Mar. 6, 2018 for copending U.S. Appl. No. 14/774,260.

Supplementary Examination Report EP 14764615, which is the European counterpart of copending U.S. Appl. No. 14/774,268, mailed Jul. 1, 2016.

European Search Opinion for EP 14764615, mailed Jul. 1, 2016.

Response to European Search Opinion for EP 14764615, filed May 10, 2017.

Amended Claims with Annotations in response to European Search Opinion for EP 14764615, filed May 10, 2017.

Examination Report for EP 14764615, sent Sep. 13, 2017.

Amended Claims and Response to Examination Report for EP 14764615, filed Sep. 23, 2018.

English language translation of First Office Action for CN 201480028570X, which is the Chinese counterpart of copending U.S. Appl. No. 14/774,268, sent Feb. 21, 2017.

Clean copy of claims in response to First Office Action for CN 201480028570X, filed Jul. 5, 2017.

Second Office Action for Chinese application 201480028570X, with English language summary attached to the front of the document, sent Nov. 15, 2017.

Clean copy of amended claims in response to Second Office Action for CN 201480028570X, filed Jan. 30, 2018.

Office Action for co-pending U.S. Appl. No. 14/941,957, mailed Jan. 12, 2017.

Response to Office Action of Jan. 12, 2017 for co-pending U.S. Appl. No. 14/941,957, filed Jul. 1, 2017.

Notice of Non-Compliant Amendment for co-pending U.S. Appl. No. 14/941,957, mailed Oct. 31, 2017.

Response to Notice of Non-Compliant Amendment for co-pending U.S. Appl. No. 14/941,957, filed Dec. 9, 2017.

Best, et al., "RNA-Seq of Tumor-Educated Platelets Enables Blood-Based Pan-Cancer, Multiclass, and Molecular Pathway Cancer Diagnostics," *Cancer Cell* 28:666-676 (Nov. 2015).

Deng, et al., "Manipulation of magnetic microbeads in suspension using micromagnetic systems fabricated with soft lithography," *Applied Physics Letters* 78:1775 (Mar. 2001).

Gluckman, "Current status of umbilical cord blood hematopoietic stem cell transplantation," *Exp. Hematol.* 28:1197-1205 (2000).

Harris, et al., "Single-Molecule DNA Sequencing of a Viral Genome," *Science* 320:106 (Apr. 2008).

Kanwar, et al., "Microfluidic device (ExoChip) for On-Chip isolation, quantification and characterization of circulating exosomes," *Lab Chip* 14(11):1891-1900 (Jun. 2014).

Kwon, et al., "Endothelium." Human Adult Stem Cells. Springer, Dordrecht, 73-89, (2009).

Lee, et al., "Exosomes and microvesicles: extracellular vesicles for genetic information transfer and gene therapy," *Human Molecular Genetics* 21 (rev. issue 1):R125-R134 (Aug. 2012).

Liu, et al., "High throughput capture of circulating tumor cells using an integrated microfluidic system," *Biosensors and Bioelectronics* 47:113-119 (2013).

Margulies, et al., "Genome sequencing in microfabricated high-density picolitre reactors," *Nature* 437:376-380 (Sep. 2005).

Soni, et al., "Progress toward Ultrafast DNA Sequencing Using Solid State Nanopores," *Clin. Chem.* 53:1996-2001 (2007).

Zheng, et al., "Deterministic lateral displacement MEMS device for continuous blood cell separation," Micro Electro Mechanical Systems, 2005. 18th IEEE International Conference.

U.S. Appl. No. 14/774,260, filed Sep. 10, 2015, 2016/0139012 A1, May 19, 2016, D'Silva, et al.

U.S. Appl. No. 14/774,268, filed Sep. 10, 2015, 2016/0047735 A1, Feb. 18, 2016, Grisham, et al.

U.S. Appl. No. 14/941,957, filed Nov. 16, 2015, 2016/0168539 A1, Jun. 16, 2016, Civin, et al.

U.S. Appl. No. 14/995,894, filed Jan. 14, 2016, 2017/0023578 A1, Jan. 26, 2017, Forsyth, et al.

U.S. Appl. No. 15/478,405, filed Apr. 4, 2017, 2017/0333900 A1, Nov. 23, 2017, Grisham, et al.

U.S. Appl. No. 15/595,548, filed May 15, 2017, 2017/0248508 A1, Aug. 31, 2017, Ward, et al.

U.S. Appl. No. 15/870,945, filed Jan. 13, 2018, Kopf-Sill, et al.

European Search Opinion and Search Report for EP 15827324.3, EP counterpart of U.S. Appl. No. 15/329,753, sent Dec. 12, 2017.

Response to European Search Opinion and Search Report for EP 15827324.3, EP counterpart of U.S. Appl. No. 15/329,753, filed Jul. 12, 2018.

Clean copy of amended claims with Response to Search Opinion and Search Report for EP 15827324.3, EP counterpart of U.S. Appl. No. 15/329,753, filed Jul. 12, 2018.

Response to Office Action for co-pending U.S. Appl. No. 14/774,260, filed Jun. 6, 2018.

Amended claims filed in Response to Office Action, filed May 16, 2015; (CN 20140028714; Chinese counterpart of copending U.S. Appl. No. 14/774,260).

Restriction Requirement for copending U.S. Appl. No. 14/774,268, mailed May 21, 2018.

Response to Restriction Requirement for copending U.S. Appl. No. 14/774,268, filed Aug. 21, 2018.

English language summary of Office Action for CN 201480028570X, which is the Chinese counterpart of copending U.S. Appl. No. 14/774,268, sent May 28, 2018.

English translation of clean copy of amended claims filed in response to 3rd Office Action for CN 201480028570X, which is the Chinese counterpart of copending U.S. Appl. No. 14/774,268, filed Aug. 13, 2018.

Office Action for copending U.S. Appl. No. 14/941,957, mailed May 14, 2018.

Response to Office Action for copending U.S. Appl. No. 14/941,957, filed Sep. 12, 2018.

Restriction Requirement for copending U.S. Appl. No. 15/478,405, mailed Jun. 12, 2018.

Response to Restriction Requirement with accompanying amendment attached for copending U.S. Appl. No. 15/478,405, filed Sep. 12, 2018.

Radisic, et al., "Micro- and nanotechnology in cell separation," *International Journal of Nanomedicine* 1(1):3-14 (2006).

Reddy, et al., "Isolation of Stem Cells from Human Umbical Cord Blood," in Vemuri (eds) Stem Cell Assays. Methods in Molecular Biology vol. 407, Human Press, pp. 149-163 (2007).

Yi, et al., "Microfluidics technology for manipulation and analysis of biological cells," *Analytica Chimica Acta* 560:1-23 (2006).

(56) References Cited

OTHER PUBLICATIONS

Notice of Allowance for copending U.S. Appl. No. 14/774,260, mailed Sep. 19, 2018.

U.S. Appl. No. 16/123,056, filed Sep. 6, 2018, D'Silva, et al.

Alessandrino, et al. Adverse events occurring during bone marrow or peripheral blood progenitor cell infusion: analysis of 126 cases. Bone Marrow Transplant. Mar. 1999;23(6):533-7.

Al-Fandi, et al. New design for the separation of microorganisms using microfluidic deterministic lateral displacement. Robotics and Computer-Integrated Manufacturing. 2011; 27(2):237-244.

Alix-Panabieres, et al. Challenges in circulating tumour cell research. Nat Rev Cancer. Sep. 2014;14(9):623-31. doi: 10.1038/nrc3820. Epub Jul. 31, 2014.

Apocell. ApoStream Technology. Available at http://www.apocell. com/ctc-technology-2/apostreamtm-technology. Accessed Nov. 20, 2015.

Barker, et al. Umbilical cord blood transplantation: current state of the art. Curr Opin Oncol. Mar. 2002;14(2):160-4.

Basford, et al. Umbilical cord blood processing using Prepacyte-CB increases haematopoietic progenitor cell availability over conventional Hetastarch separation. Cell Prolif. Dec. 2009;42(6):751-61. doi: 10.1111/j.1365-2184.2009.00646.x. Epub Sep. 15, 2009.

Bauer, J. Advances in cell separation: recent developments in counterflow centrifugal elutriation and continuous flow cell separation. Journal of Chromatography. 1999;722:55-69.

Beech, et al. Sorting cells by size, shape and deformability. Lab Chip. Mar. 21, 2012;12(6):1048-51. doi: 10.1039/c2lc21083e. Epub Feb. 10, 2012.

Beech, et al. Tipping the balance of deterministic lateral displacement devices using dielectrophoresis. Lab Chip. Sep. 21, 2009;9(18):2698-706. doi: 10.1039/b823275j. Epub Jun. 15, 2009.

Bendall, et al. A deep profiler's guide to cytometry. Trends Immunol. Jul. 2012;33(7):323-32. doi: 10.1016/j.it.2012.02.010. Epub Apr. 2, 2012.

Bendall, et al. Single-cell mass cytometry of differential immune and drug responses across a human hematopoietic continuum. Science. May 6, 2011;332(6030):687-96. doi: 10.1126/science. 1198704.

Bowman, et al. Inertia and scaling in deterministic lateral displacement. Biomicrofluidics. Dec. 5, 2013;7(6):64111. doi: 10.1063/1. 4833955. eCollection 2013.

Boyum. Isolation of mononuclear cells and granulocytes from human blood. Isolation of monuclear cells by one centrifugation, and of granulocytes by combining centrifugation and sedimentation at 1 g. Scand J Clin Lab Invest Suppl. 1968;97:77-89.

Boyum. Separation of White Blood Cells. Nature. Nov. 21, 1964;204:793-4.

CDC. Advanced Abstracting: Breast Cancer Stage of Disease (Part 3). Available at http://www.cdc.gov/cancer/npcr/training/nets/module9/nets9_3.pdf. Accessed Apr. 13, 2015.

Chang, et al. A continuous multi-size particle separator using negative dielectrophoretic virtual pillars induced by a planar spot electrode array. Proceedings of the IEEE International Conference on Micro Electro Mechanical Systems (MEMS), Feb. 2007.

Chen, et al. Microfluidic chemical processing with on-chip washing by deterministic lateral displacement arrays with separator walls. Biomicrofluidics. Sep. 9, 2015;9(5):054105. doi: 10.1063/1. 4930863. eCollection 2015.

Chen, et al. Rare cell isolation and analysis in microfluidics. Lab Chip. Feb. 21, 2014;14(4):626-45. doi: 10.1039/c3lc90136j.

Chen, et al. Reduction of Output Contamination in On-chip Chemical Treatment and Washing using Separator Walls in Deterministic Lateral Displacement Arrays. Spring Symp Mat Res Soc; San Francisco, CA Apr. 21-25, 2014.

Chou, et al. Sorting by diffusion: an asymmetric obstacle course for continuous molecular separation. Proc Natl Acad Sci U S A. Nov. 23, 1999;96(24):13762-5.

Chow, et al. Whole blood fixation and permeabilization protocol with red blood cell lysis for flow cytometry of intracellular phosphorylated epitopes in leukocyte subpopulations. Cytometry A. Sep. 2005;67(1):4-17.

Colace, et al. Microfluidics and coagulation biology. Annu Rev Biomed Eng. 2013;15:283-303. doi: 10.1146/annurev-bioeng-071812-152406. Epub May 3, 2013.

Collins, et al. Particle separation using virtual deterministic lateral displacement (vDLD). Lab Chip. May 7, 2014;14(9):1595-603. doi: 10.1039/c3lc51367j. Epub Mar. 18, 2014.

Copelan. Hematopoietic stem-cell transplantation. N Engl J Med. Apr. 27, 2006;354(17):1813-26.

Co-pending U.S. Appl. No. 14/995,894, filed Jan. 14, 2016.

Expired U.S. Appl. No. 62/032,520, filed Aug. 1, 2014.

Expired U.S. Appl. No. 60/414,065, filed Sep. 27, 2002.

Expired U.S. Appl. No. 60/414,102, filed Sep. 27, 2002.

Expired U.S. Appl. No. 60/420,756, filed Oct. 23, 2002.

Expired U.S. Appl. No. 60/478,299, filed Jun. 13, 2003.

Expired U.S. Appl. No. 60/549,610, filed Mar. 3, 2004.

Expired U.S. Appl. No. 60/703,833, filed Jul. 29, 2005.

Expired U.S. Appl. No. 61/799,835, filed Mar. 15, 2013.

Expired U.S. Appl. No. 61/800,222, filed Mar. 15, 2013.

Coulter® Ac·T diff2™. Safety and Performance at a Remarkable Value. Product information. BeckmanCoulter. Accessed Mar. 13, 2014. https://www.beckmancoulter.com/wsrportal/wsrportal.portal?_nfpb=true&_windowLabel=UCM_RENDERER&_urlType=render&wlpUCM_RENDERER_path=%2Fwsr%2Fdiagnostics%2Fclinical-products%2Fhematology%2Fcoulter-act-diff2-hematology-analyzer%2Findex.htm.

Cynvenio Technology. LiquidBiopsy Rare Cell Isolation Platform. Available at http://www.cynvenio.com/technology. Accessed on Nov. 20, 2015.

Davis, et al. Deterministic hydrodynamics: taking blood apart. Proc Natl Acad Sci U S A. Oct. 3, 2006;103(40):14779-84. Epub Sep. 25, 2006.

Davis, J. Microfluidic separation of blood components through deterministic lateral displacement. Ph.D. Thesis, Princeton University, 2008 (http://www.princeton.edu/~sturmlab/theses/Davis-Thesis.pdf).

Department of Transport Merchant Shipping Notice No. M.1214. Recommendations to Prevent Contamination of Ships Freshwater Storage and Distribution Systems. Notice to Shipowners, Masters, Fishing Vessel Skippers, Shipbuilders and Repairers. This notice supersedes Notices Nos. M.410, M.633 and M.901. Department of Transport Marine Directorate London WC1V 6LP Jun. 1986. Available at http://www.octomarine.net/mca_flag_regulations/mca_reg_m-1214_contamination_prevention.php. Accessed on Aug. 3, 2015.

Devendra, et al. Deterministic fractionation of binary suspensions moving past a line of microposts. Microfluidics and Nanofluidics 17(3):519, Apr. 2014.

D'Silva, et al. Inhibition of clot formation in deterministic lateral displacement arrays for processing large volumes of blood for rare cell capture. Lab Chip. May 21, 2015;15(10):2240-7. doi: 10.1039/c4lc01409j.

D'Silva, Joseph. Post Geometry Design for High-Throughput Harvesting of Nucleated Cells from Blood with Minimal Erythrocyte Contamination Using DLD Arrays. Chapter 4 from High-Throughput Microfluidic Capture of Rare Cells from Large Volumes of Blood. Princeton University, Ph.D. dissertation, May 2016, pp. 53-113.

Ernst, et al. Efficacy of High-Dose Bolus Tirofiban Compared to Regular-Dose Glycoprotein IIb/IIIa Inhibitors on Platelet Aggregation Inhibition in Myocardial Infarction Patients Treated with Primary Angioplasty. European Society of Cardiology. Aug. 2003; Abstract 239.

Fiorini, et al. Disposable microfluidic devices: fabrication, function, and application. Biotechniques. Mar. 2005;38(3):429-46.

Flow Cytometry and Sorting Core Facility. One-step fix/perm Protocol. St. Michael's Hospital, Toronto, Ontario, Canada. Accessed Aug. 26, 2014. http://www.stmichaelshospital.com/research/facilities/docs/Protocol1-Onestep-Fix- perm.doc.

Foundation Medicine. Foundation Medicine Initiates Multi-Center Clinical Study Evaluating Its Circulating Tumor DNA (ctDNA)

(56) References Cited

OTHER PUBLICATIONS

Assay in Multiple Tumor Types. Jul. 28, 2015. Available at http://investors.foundationmedicine.com/releasedetail.cfm?releaseid=924086. Accessed Oct. 27, 2015.

Gajkowska, et al. Flow cytometric enumeration of CD34+ hematopoietic stem and progenitor cells in leukapheresis product and bone marrow for clinical transplantation: a comparison of three methods. Folia Histochem Cytobiol. 2006;44(1):53-60.

Geffken, et al. The measurement of fibrinogen in population-based research. Studies on instrumentation and methodology. Arch Pathol Lab Med. Nov. 1994;118(11):1106-9.

Gervais, L. Capillary Microfluidic Chips for Point-of-Care Testing: from Research Tools to Decentralized Medical Diagnostics. Lausanne: EPFL, 2011.

Gluckman, et al. Outcome of cord-blood transplantation from related and unrelated donors. Eurocord Transplant Group and the European Blood and Marrow Transplantation Group. N Engl J Med. Aug. 7, 1997;337(6):373-81.

Gutensohn, et al. Semi-automated flow cytometric analysis of CD34-expressing hematopoietic cells in peripheral blood progenitor cell apheresis products. Transfusion. Nov.-Dec. 1999;39(11-12):1220-6.

Han, et al. Separation of long DNA molecules in a microfabricated entropic trap array. Science. May 12, 2000;288(5468):1026-9.

Hematopoietic Stem Cells . In Stem Cell Information. Bethesda, MD: National Institutes of Health, U.S. Department of Health and Human Services, 2011 [cited Monday, Mar. 10, 2014] Available at< http://stemcells.nih.gov/info/scireport/pages/chapter5.aspx>.

Herault, et al. A rapid single-laser flow cytometric method for discrimination of early apoptotic cells in a heterogenous cell population. Br J Haematol. Mar. 1999;104(3):530-7.

Herold, et al. Lab on a Chip Technology: Biomolecular separation and analysis. (edited) vol. 2. Horizon Scientific Press, 2009.

Hodgkinson, et al. Tumorigenicity and genetic profiling of circulating tumor cells in small-cell lung cancer. Nat Med. Aug. 2014;20(8):897-903. doi: 10.1038/nm.3600. Epub Jun. 1, 2014.

Holm, et al. Separation of parasites from human blood using deterministic lateral displacement. Lab Chip. Apr. 7, 2011;11(7):1326-32. doi: 10.1039/c0lc00560f. Epub Feb. 18, 2011. Supplemental Information.

Holmes, et al. Separation of blood cells with differing deformability using deterministic lateral displacement.Interface Focus. Dec. 6, 2014;4(6):20140011. doi: 10.1098/rsfs.2014.0011.

Huang, et al. A DNA prism for high-speed continuous fractionation of large DNA molecules. Nat Biotechnol. Oct. 2002;20(10):1048-51. Epub Sep. 3, 2002.

Huang, et al. A microfluidics approach for the isolation of nucleated red blood cells (NRBCs) from the peripheral blood of pregnant women. Prenat Diagn. Oct. 2008;28(10):892-9. doi: 10.1002/pd.2079.

Huang, et al. Continuous particle separation through deterministic lateral displacement. Science. May 14, 2004;304(5673):987-90.

Huang, et al. Role of molecular size in ratchet fractionation. Phys Rev Lett. Oct. 21, 2002;89(17):178301. Epub Oct. 4, 2002.

Huh, et al. Gravity-driven microhydrodynamics-based cell sorter (microHYCS) for rapid, inexpensive, and efficient cell separation and size-profiling. 2nd Annual International IEEE-EMBS Special Topic Conference on Microtechnology in Medicine and Biology. Madison, Wisconsin USA; May 2-4, 2002:466-469.

ICellate Cancer Cell Detection. Cancer cell detection system for individualized cancer research and detection. Available at http://www.icellate.se. Accessed Oct. 27, 2015.

Igout, et al. Evaluation of the coulter LH 750 haematology analyzer compared with flow cytometry as the reference method for WBC, platelet and nucleated RBC count. Clin Lab Haematol. Feb. 2004;26(1):1-7.

Inglis, et al. Critical particle size for fractionation by deterministic lateral displacement. Lab Chip. May 2006;6(5):655-8. Epub Mar. 17, 2006.

Inglis, et al. Determining blood cell size using microfluidic hydro-dynamics. J Immunol Methods. Jan. 1, 2008;329(1-2):151-6. Epub Nov. 1, 2007.

Inglis, et al. Scaling deterministic lateral displacement arrays for high throughput and dilution-free enrichment of leukocytes. J. Micromech. Microeng. 2011; 21:054024.

International search report and written opinion dated Jan. 9, 2015 for PCT Application No. US2014/029866.

International search report and written opinion dated Aug. 27, 2014 for PCT Application No. US2014/029736.

International search report and written opinion dated Dec. 29, 2015 for PCT Application No. PCT/US2015/43500.

Jiang, et al. Fractionation by shape in deterministic lateral displacement microfluidic devices. Microfluidics and Nanofluidics. Aug. 2015, vol. 19, Issue 2, pp. 427-434.

Karabacak, et al. Microfluidic, marker-free isolation of circulating tumor cells from blood samples. Nat Protoc. Mar. 2014;9(3):694-710. doi: 10.1038/nprot.2014.044. Epub Feb. 27, 2014.

Kenis, et al. Microfabrication Inside Capillaries Using Multiphase Laminar Flow Patterning. Science. 1999; 285:83-85.

Keung, et al. Cardiac arrhythmia after infusion of cryopreserved stem cells. Bone Marrow Transplant. Sep. 1994;14(3):363-7.

Khodaee, et al. Numerical Simulation of Separation of Circulating Tumor Cells from Blood Stream in Deterministic Lateral Displacement (DLD) Microfluidic Channel. Journal of Mechanics, vol. 32, Issue 04, Aug. 2016, pp. 463-471. Copyright © The Society of Theoretical and Applied Mechanics 2016. Published online: Dec. 21, 2015.

Kruger, et al. Deformability-based red blood cell separation in deterministic lateral displacement devices—A simulation study. Biomicrofluidics. Oct. 13, 2014;8(5):054114. doi: 10.1063/1.4897913. eCollection 2014.

Kurtzberg, et al. Results of the cord blood transplantation (COBLT) study unrelated donor banking program. Transfusion. Jun. 2005;45(6):842-55.

Lasky, et al. In utero or ex utero cord blood collection: which is better? Transfusion. Oct. 2002;42(10):1261-7.

Li, et al. Knock-in of an internal tandem duplication mutation into murine FLT3 confers myeloproliferative disease in a mouse model. Blood. Apr. 1, 2008;111(7):3849-58. doi: 10.1182/blood-2007-08-109942. Epub Feb. 1, 2008.

Liu, et al. Rapid isolation of cancer cells using microfluidic deterministic lateral displacement structure. Biomicrofluidics. Jan. 7, 2013;7(1):11801. doi: 10.1063/1.4774308. eCollection 2013.

Long, et al. Multi-directional sorting modes in deterministic lateral displacement devices. Physical Review E 78, 046304 (2008).

Lotherback, et al. Critical size, dynamic range, and throughput improvements in sorting by deterministic lateral displacement enabled by triangular posts. Presented at the Symposium of the Materials Research Society, San Francisco, CA, Apr. 2009.

Lotherback, et al. Deterministic microfluidic ratchet. Phys Rev Lett. Jan. 30, 2009;102(4):045301. Epub Jan. 26, 2009.

Lotherback, et al. Deterministic separation of cancer cells from blood at 10 mL/min. AIP Adv. Dec. 2012;2(4):42107. Epub Oct. 3, 2012.

Lotherback, et al. Improved performance of deterministic lateral displacement arrays with triangular posts. Microfluid Nanofluid (2010) 9:1143-1149.

Lotherback. Microfluidic devices for high throughput cell sorting and chemical treatment. Princeton University. Dissertation. Nov. 2011.

Lotherback. Parallelized Microfluidic Separations for Large-scale Dewatering of Biofuel Algae. Symp. Mat. Res. Soc., Nov. 29, 2010, Boston, MA. Abstract # S4.18.

Lubbersen, et al. Particle suspension concentration with sparse obstacle arrays in a flow channel. Chemical Engineering and Processing: Process Intensification, 95:90-97, 2015.

Maheswaran, et al. Detection of mutations in EGFR in circulating lung-cancer cells. N Engl J Med. Jul. 24, 2008;359(4):366-77. doi: 10.1056/NEJMoa0800668. Epub Jul. 2, 2008.

Mandy, et al. Flow Cytometry Principles, Chapter 25. In: Vo-Dinh T, editor. Biomedical Photonics Handbook: CRC Press; 2003. p. 1-20.

(56) References Cited

OTHER PUBLICATIONS

Martinez-Lopez, et al. Prognostic value of deep sequencing method for minimal residual disease detection in multiple myeloma. Blood. May 15, 2014;123(20):3073-9. doi: 10.1182/blood-2014-01-550020. Epub Mar. 19, 2014.

Maus, et al. Adoptive immunotherapy for cancer or viruses. Annu Rev Immunol. 2014;32:189-225. doi: 10.1146/annurev-immunol-032713-120136. Epub Jan. 9, 2014.

McGrath, et al. Deterministic lateral displacement for particle separation: a review. Lab Chip. Sep. 30, 2014;14(21):4139-58. doi: 10.1039/c4lc00939h.

MedGadget. Clearbridge BioMedics Launching ClearCell FX System for Capturing Circulating Tumor Cell. Available at http://www.medgadget.com/2014/05/clearbridge-biomedics-launching-clearcell-fx-system-for-capturing-circulating-tumor-cell.html. Accessed on Nov. 20, 2015.

Mikolajczyk, et al. Detection of EpCAM-Negative and Cytokeratin-Negative Circulating Tumor Cells in Peripheral Blood. J Oncol. 2011;2011:252361. doi: 10.1155/2011/252361. Epub Apr. 19, 2011.

Milone, et al. Adverse events after infusions of cryopreserved hematopoietic stem cells depend on non-mononuclear cells in the infused suspension and patient age. Cytotherapy. 2007;9(4):348-55.

Moore, et al. High dimensional flow cytometry comes of age. European Pharmaceutical Review. 2012; 17(4):20-4.

Morton, et al. Crossing microfluidic streamlines to lyse, label and wash cells. Lab Chip. Sep. 2008;8(9):1448-53. doi: 10.1039/b805614e. Epub Jul. 23, 2008.

Nagrath, et al. Isolation of rare circulating tumour cells in cancer patients by microchip technology. Nature. Dec. 20, 2007;450(7173):1235-9.

Oakey et al. Laminar Flow-Based Separations at the Microscale. Biotechnology Progress. 2002; pp. 1439-1442.

Office action dated May 18, 2015 for U.S. Appl. No. 14/212,885.

Office action dated Sep. 2, 2014 for U.S. Appl. No. 13/803,741.

Ozkumur, et al. Inertial Focusing for Tumor Antigen-Dependent and -Independent Sorting of Rare Circulating Tumor Cells. Sci Transl Med. Apr. 3, 2013;5(179):179ra47. doi: 10.1126/scitranslmed.3005616.

Quek, et al. Separation of deformable particles in deterministic lateral displacement devices. Phys Rev E Stat Nonlin Soft Matter Phys. May 2011;83(5 Pt 2):056301. Epub May 2, 2011.

Quirk, W.R. The 2015 Liquid Biopsy Report. Sep. 2015. Piper Jaffray Investment Research.

Ranjan, et al. DLD pillar shape design for efficient separation of spherical and non-spherical bioparticles. Lab Chip. Sep. 30, 2014;14(21):4250-62. doi: 10.1039/c4lc00578c.

ReportLinker. Circulating Tumor Cell (CTC) Diagnostics: Technologies and Global Markets. Available at http://www.reportlinker.com/p02009162-summary/Circulating-Tumor-Cell-CTC-Diagnostics-Technologies-and-Global-Markets.html. Accessed Oct. 2, 2015.

Rocha, et al. Improving outcomes of cord blood transplantation: HLA matching, cell dose and other graft- and transplantation-related factors. Br J Haematol. Oct. 2009;147(2):262-74. doi: 10.1111/j.1365-2141.2009.07883.x.

Rocha, et al. Umbilical cord blood transplantation. Curr Opin Hematol. Nov. 2004;11(6):375-85.

Rubinstein, et al. Outcomes among 562 recipients of placental-blood transplants from unrelated donors. N Engl J Med. Nov. 26, 1998;339(22):1565-77.

Rubinstein, et al. Processing and cryopreservation of placental/umbilical cord blood for unrelated bone marrow reconstitution. Proc Natl Acad Sci U S A. Oct. 24, 1995;92(22):10119-22.

Savage, et al. Functional self-association of von Willebrand factor during platelet adhesion under flow. Proc Natl Acad Sci U S A. Jan. 8, 2002;99(1):425-30. Epub Dec. 26, 2001.

Sollier et al. Size-selective collection of circulating tumor cells using Vortex technology. Lab Chip 14(1):63-77 (2014).

Solves, et al. A new automatic device for routine cord blood banking: critical analysis of different volume reduction methodologies. Cytotherapy. 2009;11(8):1101-7. doi: 10.3109/14653240903253865.

Solves, et al. Comparison between two strategies for umbilical cord blood collection. Bone Marrow Transplant. Feb. 2003;31(4):269-73.

Sommanson. Deterministic lateral separation of cells. Lund University. Master Thesis. 2006.

Spectrolyse blood collection tubes. American Diagnostic Inc. 2010.

Stokstad, Erik. Tests used to ensure ships don't carry deadly cargo draw sharp criticism. Jan. 14, 2015. News.sciencemag.org. Available at http://news.sciencemag.org/biology/2015/01/tests-used-ensure-ships-don-t-carry-deadly-cargo-draw-sharp-criticism. Accessed on Aug. 3, 2015.

Strauss, et al. Abstract P5-10-07: The LiquidBiopsy in metastatic breast cancer (MBC): A novel diagnostic platform for next generation sequencing (NGS) of circulating tumor cells (CTCs). Cancer Research 75, No. 9 Supplement (2015): P5-10.

Stroncek, et al. Adverse reactions in patients transfused with cryopreserved marrow. Transfusion. Jul.-Aug. 1991;31(6):521-6.

Takayama, et al. Patterning Cells and Their Environments Using Multiple Laminar Fluid Flows in Capillary Networks. Proceedings of the National Academy of Sciences of the United States of America. 1999:5545-5548.

Toner, et al. Blood-on-a-Chip. Annu. Rev. Biomed. Eng. 7:77-103, C1-C3 (2005).

TriTest CD3 FITC/CD19 PE/CD45 PerCP Reagent. Informational package insert. BD Biosciences. Aug. 2010.

Tsao, et al. Bonding of thermoplastic polymer microfluidics. Microfluidics and Nanofluidics. Jan. 2009, vol. 6, Issue 1, pp. 1-16.

Turner, et al. Confinement-induced entropic recoil of single DNA molecules in a nanofluidic structure. Phys Rev Lett. Mar. 25, 2002;88(12):128103. Epub Mar. 12, 2002.

U.S. Appl. No. U.S. Appl. No. 14/774,260, filed Sep. 10, 2015.

Van Lochem, et al. Immunophenotypic differentiation patterns of normal hematopoiesis in human bone marrow: reference patterns for age-related changes and disease-induced shifts. Cytometry B Clin Cytom. Jul. 2004;60(1):1-13.

Vona, et al. Isolation by size of epthelieal tumor cells. American Journal of Pathology. 2000; 156:57-63.

Vortex Biosciences. Overview: Cancer and CTCs. Available at http://www.vortexbiosciences.com/overview. Accessed Oct. 27, 2015.

Wagner, et al. Umbilical cord blood transplantation: the first 20 years. Semin Hematol. Jan. 2010;47(1):3-12. doi: 10.1053/j.seminhematol.2009.10.011.

Wang, et al. Single cell analysis: the new frontier in 'omics'. Trends Biotechnol. Jun. 2010;28(6):281-90. doi: 10.1016/j.tibtech.2010.03.002. Epub Apr. 29, 2010.

Wood. Ten-Color Immunophenotyping of Hematopoietic Cells. Current protocols in cytometry. John Wiley & Sons, Inc., 2001.

Yamada, et al. Pinched flow fractionation: continuous size separation of particles utilizing a laminar flow profile in a pinched microchannel. Anal Chem. Sep. 15, 2004;76(18):5465-71.

Yang, et al. Microfluidic device fabrication by thermoplastic hot-embossing. Methods Mol Biol. 2013;949:115-23. doi: 10.1007/978-1-62703-134-9_8.

Ye, et al. Effects of the particle deformability on the critical separation diameter in the deterministic lateral displacement device. Journal of Fluid Mechanics, 743, pp. 60-74 doi:10.1017/jfm.2014.22.

Yu, et al. A microfluidic approach for whole blood leucocyte isolation for leucocyte immunophenotyping by flow cytometry. Poster submitted to CYTO2012 in Apr. 2012. Cited by permission. XXVII Congress of the International Society for Advancement of Cytometry (ISAC) Congress Center Leipzig. Leipzig, Germany. Jun. 23-27, 2012.

Zambelli, et al. Clinical toxicity of cryopreserved circulating progenitor cells infusion. Anticancer Res. Nov.-Dec. 1998;18(6B):4705-8.

(56) References Cited

OTHER PUBLICATIONS

Zeming, et al. Asymmetrical Deterministic Lateral Displacement Gaps for Dual Functions of Enhanced Separation and Throughput of Red Blood Cells. Sci Rep. Mar. 10, 2016;6:22934. doi: 10.1038/srep22934.

Zeming, et al. Rotational separation of non-spherical bioparticles using I-shaped pillar arrays in a microfluidic device. Nat Commun. 2013;4:1625. doi: 10.1038/ncomms2653.

Zenhausern, et al. Fatal cardiac arrhythmia after infusion of dimethyl sulfoxide-cryopreserved hematopoietic stem cells in a patient with severe primary cardiac amyloidosis and end-stage renal failure. Ann Hematol. Sep. 2000;79(9):523-6.

Zhang, et al. Applications of Microfluidics in Stem Cell Biology. Bionanoscience. Dec. 1, 2012;2(4):277-286.

Zhang, et al. Behavior of rigid and deformable particles in deterministic lateral displacement devices with different post shapes. J Chem Phys. Dec. 28, 2015;143(24):243145. doi: 10.1063/1.4937171.

Zhang, et al. Electrospun TiO2 Nanofiber-Based Cell Capture Assay for Detecting Circulating Tumor Cells from Colorectal and Gastric Cancer Patients. Adv Mater. May 22, 2012;24(20):2756-60. doi: 10.1002/adma.201200155. Epub Apr. 23, 2012.

Zhang, et al. Label-free enrichment of functional cardiomyocytes using microfluidic deterministic lateral flow displacement. PLoS One. 2012;7(5):e37619. doi: 10.1371/journal.pone.0037619. Epub May 29, 2012.

Zingsem, et al. Cord blood processing with an automated and functionally closed system. Transfusion. Jun. 2003;43(6):806-13.

Response to Rule 71 Communication for EP 2014764615.2, filed by Applicant Jan. 28, 2019; European counterpart of U.S. Appl. No. 14/774,268.

Second Communication Under Rule 71(3) for EP20 14764615.2, sent by the EPO on Mar. 7, 2019; European counterpart of U.S. Appl. No. 14/774,268.

Amended claims filed for CN 20140028714 in response to the 3rd Office Action filed Jan. 23, 2019; Chinese counterpart of copending U.S. Appl. No. 14/774,260.

Notice of Allowance for CN 201480028570X (in Chinese); Chinese counterpart of copending U.S. Appl. No. 14/774,268.

Notice of Allowance for copending U.S. Appl. No. 14/774,260, mailed Jan. 30, 2019.

Response to Office Action for copending U.S. Appl. No. 14/774,268, filed Apr. 5, 2019.

Response to Office Action for copending U.S. Appl. No. 15/478,405, filed Apr. 5, 2019.

Partial English translation summarizing 3rd Office Action, sent Nov. 5, 2018; (CN 20140028714; Chinese counterpart of U.S. Appl. No. 14/774,260).

Communication from EPO regarding intention to grant and grant text for EP 2014764615 dated Sep. 25, 2018. EP counterpart of copending U.S. Appl. No. 14/774,268.

Request for Continued Examination for copending U.S. Appl. No. 14/774,260, filed Dec. 18, 2018.

Supplemental Amendment for copending U.S. Appl. No. 14/774,260, filed Jan. 1, 2019.

Office Action for copending U.S. Appl. No. 14/774,268, mailed Nov. 13, 2018.

Office Action for copending U.S. Appl. No. 15/478,405, mailed Nov. 19, 2018.

Office Action for copending U.S. Appl. No. 14/941,957, mailed Jan. 7, 2019.

Agrawal, et al., "PDGF upregulates CLEC-2 to induce T regulatory cells," Oncotarget 6(30):28621-28632 (Sep. 2015).

Campos-Gonzalez, et al., "Deterministic Lateral Displacement: The Next Generation Car T-Cell Processing?" SLAS 23(4): (Jan. 2018).

Chiche-Lapierre, et al., "Comparative analysis of Sepax S-100, COBE 2991, and Manual DMSO Removal Techniques From Cryopreserved Hematopoietic Stem Cell Apheresis Product," Cytotherapy 18(6):S47 (2016).

Civin, et al., "Automated Leukocyte Processing by Microfluidic Deterministic Lateral Displacement," Cytometry A 89:1073-1083 (2016).

Couzin-Frankel, et al., "Supply of Promising T-Cell Therapy is Strained," Science 356:1112 (Jun. 2017).

Disilva, J., "Throughout Microfluidic Capture of Rare Cells from Large Volumes of Blood," A Dissertation Presented to the Faculty of Princeton University in Candidacy for the Degree of Doctor of Philosophy, (May 2016).

Feng, et al., "Maximizing particle concentration in deterministic lateral displacement arrays," Biomicrofluidics 11:024121 (published online Apr. 2017).

Fousek, et al., "The Evolution of T-cell Therapies for Solid Malignancies," Clinical Cancer Research 21(5):3384-3392 (Aug. 2015).

Hokland, et al., "The Isopaque-Ficoll Method Re-evaluated: Selective Loss of Autologous Rosette-forming Lymphocytes During Isolation of Mononuclear Cells from Human Peripheral Blood," Scand. J.Immunol. 11(3):353-356 (Mar. 1980).

Johnson, et al., "Driving Gene-engineered T-cell Immunotherapy of Cancer," Cell Res. 27:38-58 (2017).

Koesdjojo, et al., "DLD Microfluidic Purification and Characterization of Intact and Viable Circulating Tumor Cells in Peripheral Blood," AACR Annual Meeting Abstract #3956 (2016).

Kurihara, et al., "Imaging Brain Tumors by Targeting Peptide Radiopharmaceuticals through the Blood-Brain Barrier," Cancer Research 59(24):6159-6163 (Dec. 1999).

Levine, et al., "Global Manufacturing of CAR T-cell Therapy," Mol. Therapy: Meth. Clin. Dev. 4:92-101 (2017).

Li, et al., "Comparison of anti-CD3 and anti-CD28-coated beads with soluble anti-CD3 for expanding Human T-cells: Differing impact on CD8 T-cell phenotype and responsiveness to restimulation," J. Transl. Med. 8:104-118 (2010).

Mahnke, et al., "The who's who of T-cell differentiation: Human memory T-cell subsets," Eur. J. Immunol. 43:2797-2809 (2013).

Marktkamcham, et al., "The Effects of Anti-CD3/CD28 Coated Beads and IL-2 on Expanded T Cell for Immunotherapy," Adv. Clin. Exp. Med. 25:821-828 (2016).

National Cell Manufacturing Consortium. Achieving Large-Scale, Cost-Effective, Reproducible Manufacturing of High Quality Cells. A Technology Roadmap to 20205. (Feb. 2016).

Powell, et al., "Efficient clinical-scale enrichment of lymphocytes for use in adoptive immunotherapy using a modified counterflow centrifugal elutriation program," Cytotherapy 11(7):923-935 (2009).

Sadelain, et al., "Therapeutic T cell engineering," Nature 545:423-431 (May 2017).

Stroncek, et al., "Counter-flow elutriation of clinical peripheral blood mononuclear cell concentrates for the production of dendritic and T cell therapies," J. Transl. Med. 12:241 (2014).

Trickett, et al., "T-cell Stimulation and Expansion Using Anti-CD3/CD28 Beads," J/ Immunol. Meth. 275:251-255 (Apr. 2003).

Vonderheide, et al., "Engineering T cells for cancer: our synthetic future," Immunol. Rev. 257:7-13 (2014).

Wang, et al., "Clinical manufacturing of CAR T cells: a foundation of a promising therapy," Mol. Ther. Oncolytics 3:16015 (2016).

Zhang, et al., "Optimized DNA electroporation for primary human T cell engineering," BMC Biotechnology 18:4 (2018).

Zhu, et al., "Platelets Provoke Distinct Dynamics of Immune Response by Differentially Regulating CD4+ T-cell Proliferation," J. Throm. Haem. 12:1156-1165 (2014).

U.S. Appl. No. 16/108,365, filed Aug. 22, 2018, Ward, et al.

Proposed Text for Grant for EP 14764615.2, sent Mar. 7, 2019; European counterpart of copending U.S. Appl. No. 14/774,268.

Request to file divisional of EP 14764615.2, filed Jun. 26, 2019; European counterpart of copending U.S. Appl. No. 14/774,268.

EPO form for filing of divisional of EP 14764615.2, filed Jun. 26, 2019; European counterpart of copending U.S. Appl. No. 14/774,268.

Specification and claims for divisional of EP 14764615.2, filed Jun. 26, 2019; European counterpart of copending U.S. Appl. No. 14/774,268.

Filing receipt for divisional assigning it EP 19182687.4, generated Jun. 26, 2019; European counterpart of copending U.S. Appl. No. 14/774,268.

(56)  References Cited

OTHER PUBLICATIONS

Translation of Certificate of Invention Patent for Application CN 201480028570X, sent Apr. 9, 2019; Chinese counterpart of copending U.S. Appl. No. 14/774,268.

Claims for Patent for CN 201480028570X, of Apr. 9, 2019; Chinese counterpart of copending U.S. Appl. No. 14/774,268.

Translation of Filing Information for Divisional of CN 201480028570X, sent Apr. 26, 2019; Chinese counterpart of copending U.S. Appl. No. 14/774,268.

Communication Under Rule 71(3) for EP 14 763 363.0, sent May 24, 2019; European counterpart of copending U.S. Appl. No. 14/774,260.

Proposed text for grant for EP 14 763 363.0, sent May 24, 2019; European counterpart of copending U.S. Appl. No. 14/774,260.

First Examination Report for EP 15 827 324.3, sent May 24, 2019; European counterpart of U.S. Appl. No. 15/329,753.

Response to Examination Report for EP 15 827 324.3, filed on Aug. 22, 2019; European counterpart of U.S. Appl. No. 15/329,753.

Amended claims submitted with Response to Examination Report for EP 15 827 324.3, filed on Aug. 22, 2019; European counterpart of U.S. Appl. No. 15/329,753.

Amendment Under 37 CFR 1.312 filed Apr. 21, 2019, for copending U.S. Appl. No. 14/774,260.

Communication sent from the USPTO on Apr. 25, 2019, for copending U.S. Appl. No. 14/774,260.

Issue Notification notifying applicant that patent will issue as U.S. Pat. No. 10,324,011 sent May 29, 2019, for copending U.S. Appl. No. 14/774,260.

Final Rejection mailed May 31, 2019, for copending U.S. Appl. No. 14/774,268.

Response and Amendment Under 37 CFR 1.312 sent to the USPTO on Jul. 3, 2019, for copending U.S. Appl. No. 14/941,957.

Response and Amendment Under 37 CFR 1.312 sent to the USPTO on Aug. 30, 2019, for copending U.S. Appl. No. 15/478,405.

Response to Office Action mailed May 31, 2019, for copending U.S. Appl. No. 14/774,268, filed Sep. 21, 2019.

U.S. Appl. No. 16/343,754, filed Apr. 20, 2019, Ward, et al.

Communication Under Rule 71(3) for EP 15827324.3, sent May 14, 2020; European counterpart of copending U.S. Appl. No. 15/329,753.

Text proposed for Grant for EP 15827324.3, sent May 14, 2020; European counterpart of copending U.S. Appl. No. 15/329,753.

Office Action in Canada for CA 2,942,831, sent Feb. 6, 2020; Canadian counterpart of copending U.S. Appl. No. 14/774,260.

Response to Office Action in Canada for CA 2,942,831, filed Jun. 5, 2020; Canadian counterpart of copending U.S. Appl. No. 14/774,260.

Clean copy of claims filed with Response to Office Action in Canada for CA 2,942,831, filed Jun. 5, 2020; Canadian counterpart of copending U.S. Appl. No. 14/774,260.

Brief English language Summary of Office Action in China for CN 2014800285714, sent Jun. 5, 2020; Chinese counterpart of copending U.S. Appl. No. 14/774,260.

English language copy of claims in CN 2014800285714 at time of Office Action, sent Jun. 5, 2020; Chinese counterpart of copending U.S. Appl. No. 14/774,260.

European Search Report for EP 19199294.0, dated Jan. 8, 2020; European counterpart of copending U.S. Appl. No. 14/774,260.

Claims in EP 19199294.0, filed Jun. 8, 2020, European counterpart of copending U.S. Appl. No. 14/774,260.

Response to Rule 69 Communication for EP 19182687.4, filed May 18, 2020; European counterpart of copending U.S. Appl. No. 14/774,268.

Clean copy of amended claims for EP 19182687.4, filed May 18, 2020; European counterpart of copending U.S. Appl. No. 14/774,268.

Notice of Allowance mailed May 11, 2020 for copending U.S. Appl. No. 16/588,137.

Supplemental Response to Office Action, filed Jul. 6, 2020 for copending U.S. Appl. No. 14/941,957.

Declaration Under 37 CFR 1.132 filed Jul. 6, 2020 for copending U.S. Appl. No. 14/941,957.

Inglis, David, "Microfluidic Devices for Cell Separation," A Dissertation presented to the faculty of Princeton University, Sep. 2007.

Amended claims for CN 2019103452215 filed with Request for Substantive Examination on Jun. 26, 2019; Chinese counterpart of U.S. Appl. No. 14/774,268.

Extended European Search Report EP 19182687.4 dated Oct. 7, 2019; European counterpart of U.S. Appl. No. 14/774,268.

Rule 69 Communication for EP 19182687.4 dated Nov. 25, 2019; European counterpart of U.S. Appl. No. 14/774,268.

Canadian Search Report for CA 2942831 dated Feb. 5, 2019; Canadian counterpart of U.S. Appl. No. 14/774,260.

Second Examination Report for EP 15827324.3 sent Jan. 21, 2020; European counterpart of corresponding U.S. Appl. No. 15/329,753.

Response to Second Examination Report for EP 15827324.3 filed Apr. 6, 2020; European counterpart of corresponding U.S. Appl. No. 15/329,753.

Amended Description filed with the Response to Second Examination Report for EP 15827324.3 filed Apr. 6, 2020; European counterpart of corresponding U.S. Appl. No. 15/329,753.

Amended claims filed with the Response to Second Examination Report for EP 15827324.3 filed Apr. 6, 2020; European counterpart of corresponding U.S. Appl. No. 15/329,753.

Final Office Action mailed Dec. 4, 2019 for copending U.S. Appl. No. 15/478,405.

Non Final Office Action mailed Jan. 2, 2020 for copending U.S. Appl. No. 14/774,268.

Amendment and Response filed Apr. 21, 2020 for copending U.S. Appl. No. 14/774,268.

Final Office Action mailed Oct. 22, 2019 for copending U.S. Appl. No. 14/941,957.

Amendment and Response to Accompany RCE filed Mar. 23, 2020 for copending U.S. Appl. No. 14/941,957.

Restriction Requirement mailed Feb. 12, 2020 for copending U.S. Appl. No. 16/588,137.

Response to Restriction Requirement filed Apr. 10, 2020 for copending U.S. Appl. No. 16/588,137.

Lee, et al., "Continuous medium exchange and optically induced electroporation of cells in an integrated microfluidic system," *Microsystems and Nanoengineering* 1:1-9 (2015).

Song, et al., "Automatic detecting and counting magnetic based-labeled target cells from a suspension in a microfluidic chip," *Electrophoresis* 40:897-905 (2019).

U.S. Appl. No. 16/587,022, filed Sep. 29, 2019, US-2020/0025656 A1, Jan. 23, 2020, D'Silva.

U.S. Appl. No. 16/587,057, filed Sep. 30, 2019, US-2020/0025669 A1, Jan. 23, 2020, Ward.

U.S. Appl. No. 16/588,137, filed Sep. 30, 2019, US-2020/0025657 A1, Jan. 23, 2020, D'Silva.

U.S. Appl. No. 16/662,033, filed Oct. 24, 2019, US-2020/0056153 A1, Feb. 20, 2020, Ward.

U.S. Appl. No. 17/009,797, filed Sep. 2, 2020, Ward.

Response to European Search Report for EP 19199294.0, with clean copy of the claims attached, filed Aug. 10, 2020, European counterpart of U.S. Appl. No. 14/774,260.

Amended claims filed in Response to Chinese Office Action sent Jun. 5, 2020 for CN 201480028714 (counterpart of U.S. Appl. No. 16/123,056 and U.S. Appl. No. 16/123,056) filed on Oct. 20, 2020.

Decision to grant European patent for EP 15827324.3 (counterpart of U.S. Appl. No. 15/329,753) sent on Oct. 1, 2020.

Proposed text for grant for EP 15827324.3 (counterpart of U.S. Appl. No. 15/329,753) sent on Oct. 1, 2020.

Allowed claims for EP 15827324.3 (counterpart of U.S. Appl. No. 15/329,753) sent on Oct. 1, 2020.

Non Final Office for copending U.S. Appl. No. 14/941,957, mailed Sep. 17, 2020.

Restriction Requirement for copending U.S. Appl. No. 16/123,056, mailed Oct. 20, 2020.

Response to Restriction Requirement for copending U.S. Appl. No. 16/123,056, filed Dec. 20, 2020.

Amendment to Accompany Response to Restriction Requirement for copending U.S. Appl. No. 16/123,056, filed Dec. 20, 2020.

Response to Office Action of Sep. 17, 2020 for copending U.S. Appl. No. 14/941,957, filed Jan. 18, 2021.

(56)     References Cited

OTHER PUBLICATIONS

Terminal Disclaimer for copending U.S. Appl. No. 14/941,957, filed Jan. 18, 2021.
Notice of Allowance for copending U.S. Appl. No. 14/941,957, sent Feb. 10, 2021.
Corrected Notice of Allowance for copending U.S. Appl. No. 14/941,957, sent Mar. 18, 2021.
Notice to File Corrected Application Papers for copending U.S. Appl. No. 14/941,957, sent Mar. 30, 2021.
Request for Continued Examination for copending U.S. Appl. No. 14/941,957, filed May 1, 2021.
Amendment to Accompany RCE for copending U.S. Appl. No. 14/941,957, filed May 1, 2021.
Response to Notice to File Corrected Application Papers for copending U.S. Appl. No. 14/941,957, filed May 1, 2021.
Replacement figures for copending U.S. Appl. No. 14/941,957, filed May 1, 2021.
Final Office Action for copending U.S. Appl. No. 14/774,268, mailed Apr. 9, 2021.
Office Action for Canadian application 2,942,831, which is a counterpart of copending U.S. Appl. No. 14/774,260, sent Mar. 12, 2021.
Claims pending in Canadian application 2,942,831 when the Office Action was sent on Mar. 12, 2021.
U.S. Appl. No. 17/192,691, filed Mar. 4, 2021, Ward.

* cited by examiner

NORMALIZED VELOCITY

COMPARISON OF CRITICAL PARTICLE SIZES
BETWEEN CIRCULAR POSTS AND TRIANGULAR POSTS

FIG. 15

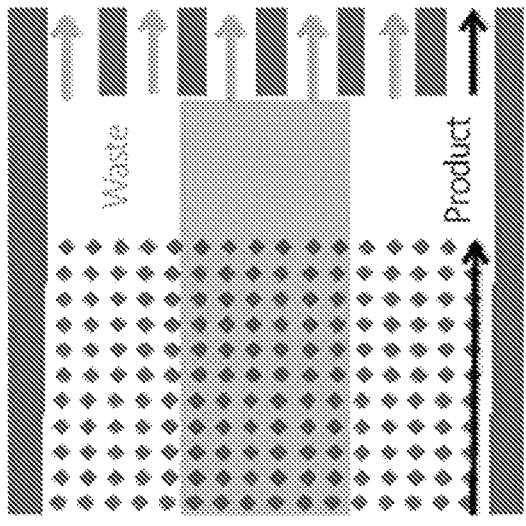
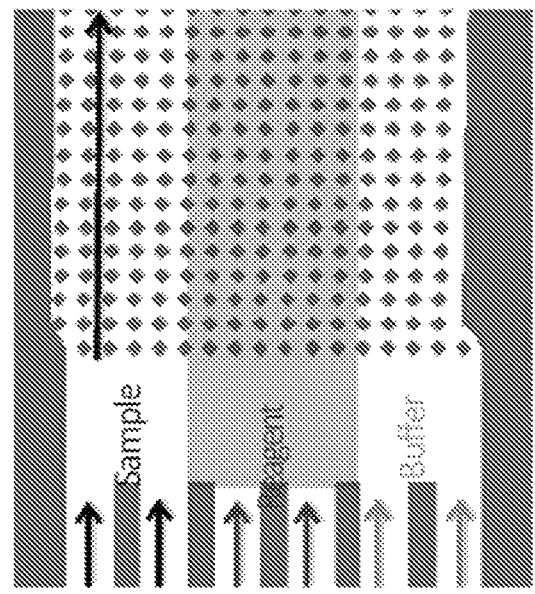
FIG. 19

- Incubation Time $= \dfrac{\text{width of reagent input}}{\text{row shift}\times\text{flow speed}}$

- Limited source diffusion

- $c(x, y, t) = \dfrac{Q}{\sqrt{\pi D x / v_{flow}}} \exp -\left(\dfrac{y}{2\sqrt{D x / v_{flow}}}\right)^2$

FIG. 26
Modified
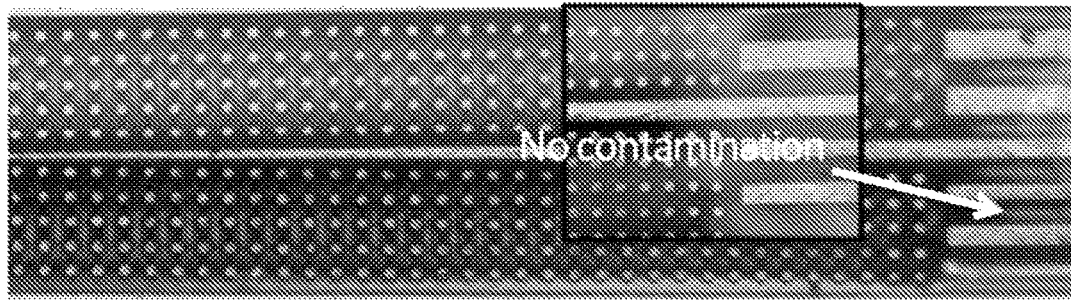
Original
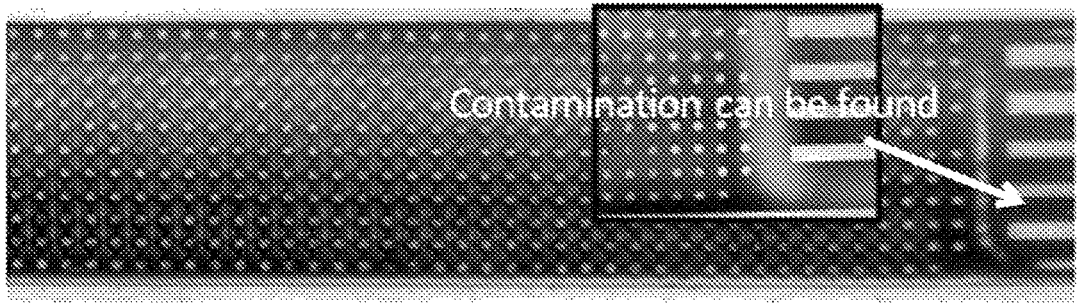

FIG. 29A
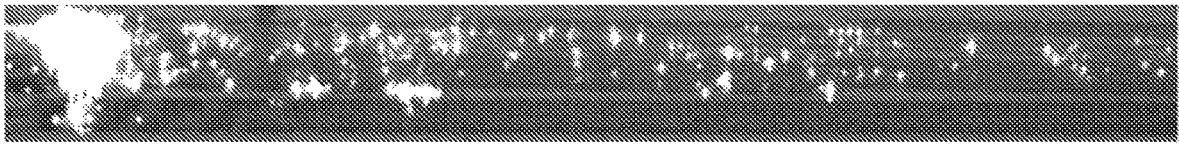
Input region
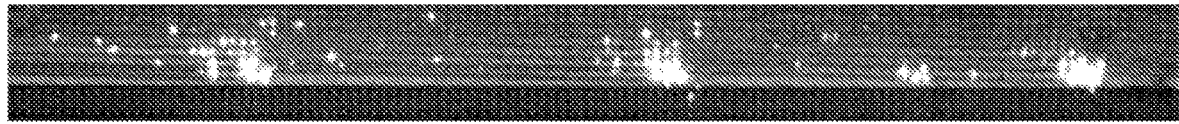
Middle of the chip
Output region FIG. 30
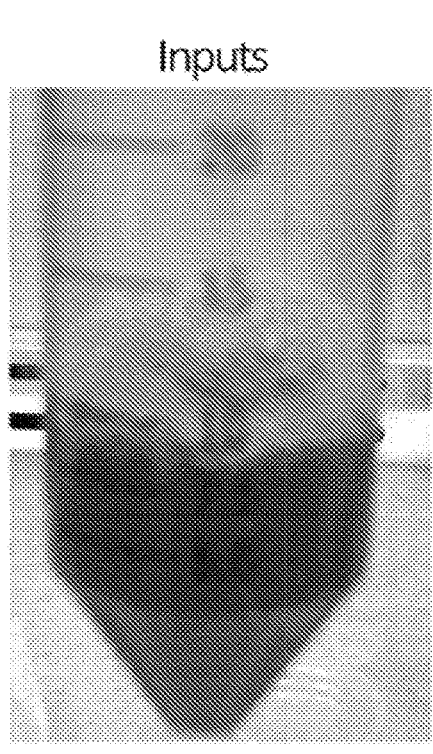
Inputs
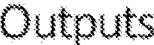
Outputs
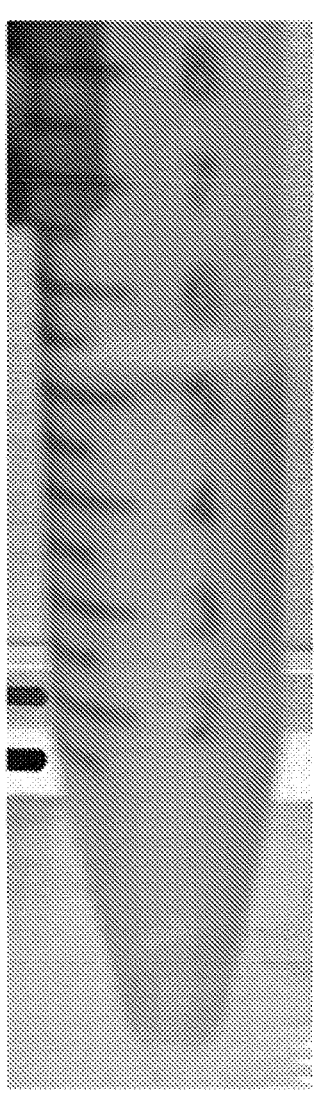

A vertical cleaning stream is introduced to clean the particles trapped in dead zones.

On-chip cleaning stream

DLD Array

Particles and buffer inputs

Product and waste outputs

Wall for fluid confinement

On-chip cleaning stream

DLD Array

Particles and buffer inputs

Product and waste outputs

Wall for fluid confinement

Blocked

FIG. 34B
Before running on-chip cleaning stream          Clogged beads
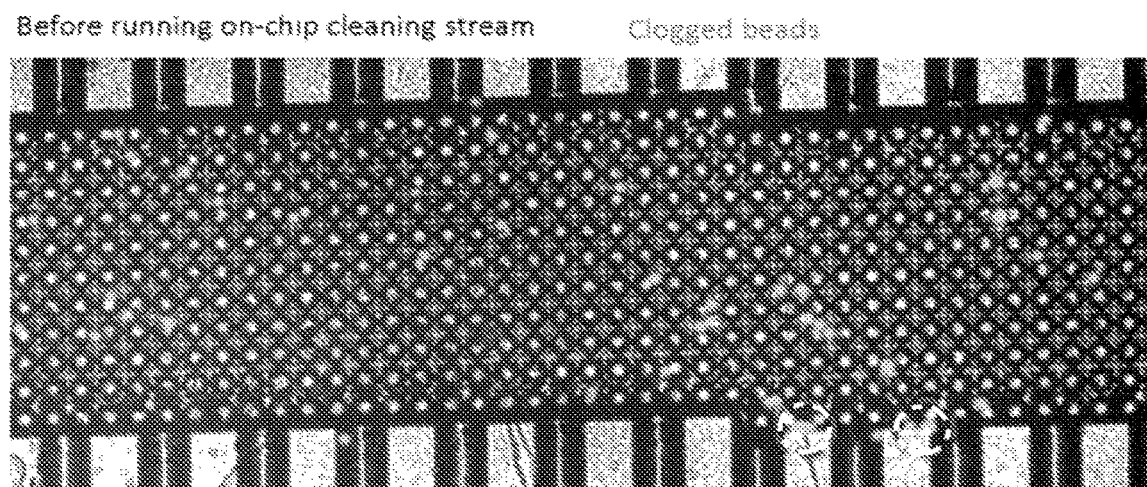
After running on-chip cleaning stream (most clogged beads are cleaned away)
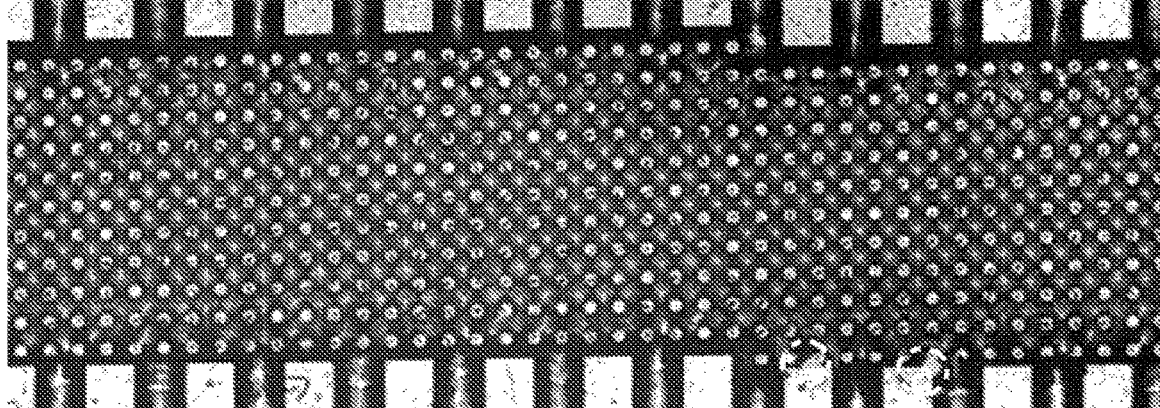

Disposable Cell Separation Module

Waste outlet port
(potentially with safe on-board containment feature)

Product
Outlet port

Buffer
input port

MicroPost Array Chamber

Blood Sample
Input port
(potentially with safe enclosure feature)

Desktop Instrument

Up to 8 cell separation modules,
With up to 10 samples per module

FIG. 44

RBC Fraction Out

WBC Fraction Out

Lane1

Lane2

Buffer IN

Blood IN

Figure 46:
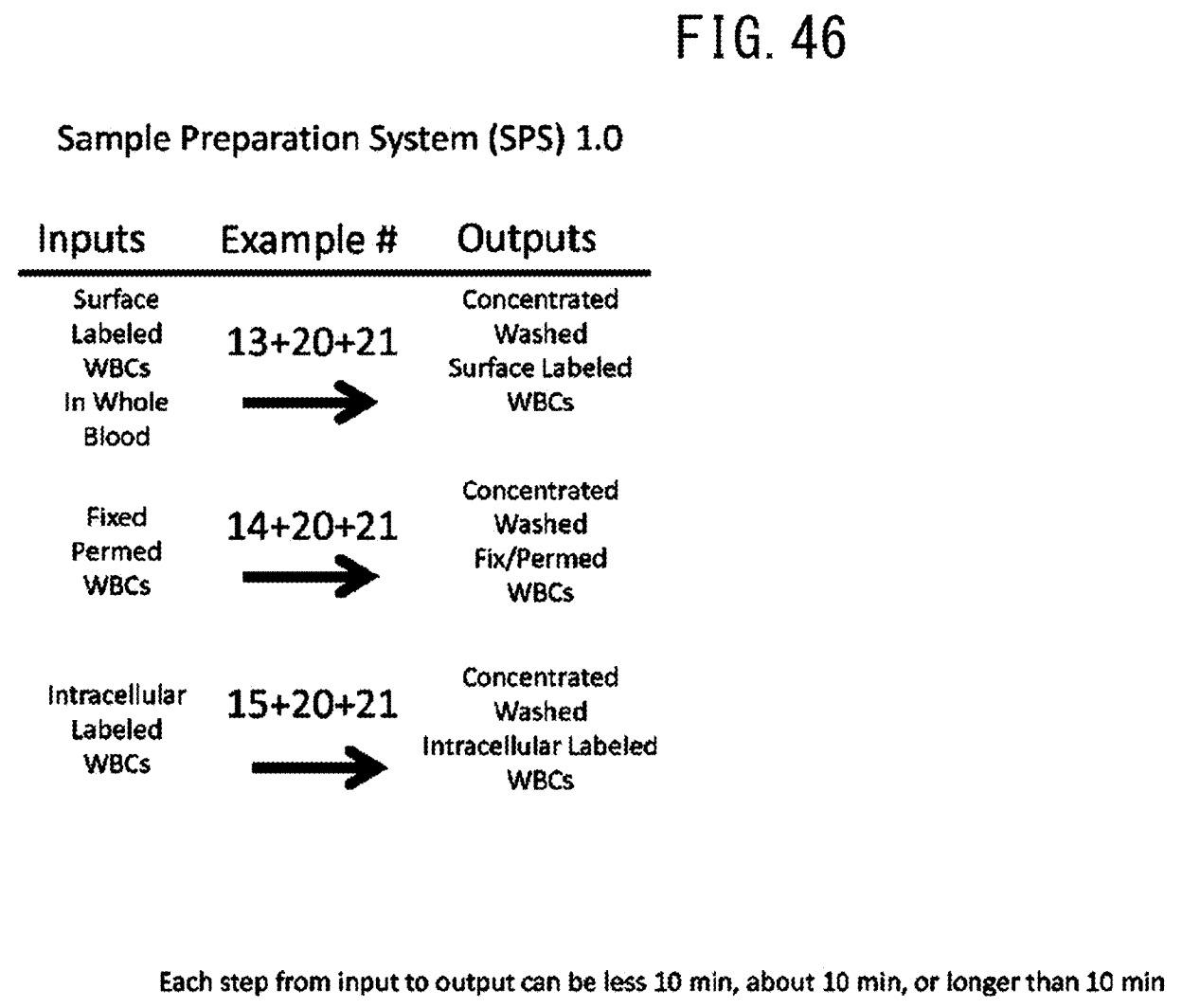

Sample Preparation System (SPS) 1.0

| Inputs | Example # | Outputs |
|--------|-----------|---------|
| Surface Labeled WBCs In Whole Blood | 13+20+21 ⟶ | Concentrated Washed Surface Labeled WBCs |
| Fixed Permed WBCs | 14+20+21 ⟶ | Concentrated Washed Fix/Permed WBCs |
| Intracellular Labeled WBCs | 15+20+21 ⟶ | Concentrated Washed Intracellular Labeled WBCs |

Each step from input to output can be less 10 min, about 10 min, or longer than 10 min

FIG. 47

Sample Preparation System (SPS) 2.0
Car Wash

| Inputs | Example # | Outputs |
|---|---|---|
| Whole Blood | 16+20+21 → | Concentrated Washed Surface Labeled WBCs |
| Surface Labeled WBCs | 17+20+21 → | Concentrated Washed Surface Labeled Fix/Permed WBCs |
| Fixed Permed WBCs | 18+20+21 → | Concentrated Washed Intracellular Labeled WBCs |
| Whole Blood (Surface Stained or Not) | 19+20+21 → | Concentrated & Washed (Surface Stained) Fixed Permed Intracellular Labeled WBCs |

Each step from input to output can be less 10 min, about 10 min, or longer than 10 min

Waste output

Product output

Waste output

Array

Bypass channel

Array

METHODS AND SYSTEMS FOR PROCESSING PARTICLES

CROSS-REFERENCE

This application claims the benefit of U.S. Provisional Patent Application No. 62/032,520, filed on Aug. 1, 2014, and is related to U.S. Provisional Patent Application No. 61/939,044, filed on Feb. 12, 2014, U.S. Provisional Patent Application No. 61/939,070, filed on Feb. 12, 2014, U.S. Provisional Patent Application No. 61/800,222, filed on Mar. 15, 2013, U.S. patent application Ser. No. 14/212,294, filed Mar. 14, 2014, and PCT/US14/29866, filed on Mar. 14, 2014, each of which is herein incorporated by reference in its entirety.

STATEMENT AS TO FEDERALLY SPONSORED RESEARCH

This invention was made with government support under Grant No. CA174121 and Grant No. HL110574 awarded by the National Institutes of Health (NIH). The government has certain rights in the invention.

BACKGROUND

There is a need for improved methods for chemical and/or enzymatic treatment, washing, and isolation of particles (e.g., cells) obtained from samples comprising particles (e.g., cells). There is also a need for improved methods of isolating particles, e.g., cells, from a sample.

SUMMARY

In one aspect, provided herein are methods, systems, and devices for processing particles that can allow automating and simplifying the cell preparation process for particles analysis.

In another aspect, provided herein is a system for processing first particles of at least a predetermined size in a sample, the device comprising: a) a first channel extending from a plurality of inlets to a plurality of outlets, wherein the channel is bounded by a first wall and a second wall opposite from the first wall; b) a first array of obstacles arranged in rows in the channel, wherein each subsequent row of the first array of obstacles is shifted laterally with respect to a previous row, wherein the first array of obstacles is configured to differentially deflect first particles of at least a predetermined size to a first outlet and second particles in the sample of less than the predetermined size to a second outlet, wherein the device is configured such that the first particles are inputted in a first flow stream from a first inlet and are deflected into a second flow stream flowing from a second inlet to the first outlet while being deflected, wherein the second flow stream comprises a reagent; and c) a flow-through incubator channel fluidically connected with the first outlet, wherein the flow-through incubator channel is fluidically connected to a second channel, wherein the second channel is bounded by a first wall and a second wall opposite from the first wall, wherein the second channel comprises a second array of obstacles. In some cases the flow-through incubator channel comprises a serpentine channel. In some cases, the serpentine channel comprises at least 20 turns. In some cases, the serpentine channel comprises a total length of at least 30 mm. In some cases, the serpentine channel comprises at least 20 parallel segments. In some cases, a segment of the at least 20 parallel segments is about 30 mm in length. In some cases, the serpentine channel has a width of at least 100 μm. In some cases, the serpentine channel has a depth of at least 100 μm. In some cases, the flow-through incubator channel is a linear channel. In some cases, wherein the flow-through incubator channel comprises a structure configured to move particles in a flow stream in the flow-through incubator channel relative to the flow stream in the flow-through incubator channel. In some cases, the structure comprises an array of obstacles configured to deflect the particles to a direction that is not parallel to the first flow stream. In some cases, the flow-through incubator channel comprises an inlet configured to introduce a third flow stream in the flow-through incubator channel. In some cases, the reagent comprises a labeling reagent, a fixation agent, a permeabilization reagent, or a washing buffer. In some cases, the system further comprises a balancer configured to balance fluidic resistance of the system, wherein the balancer is fluidically connected to the second outlet. In some cases, the balancer is configured to have a fluidic resistance that is substantially the same as a fluidic resistance through the flow-through incubator. In some cases, the balancer comprises a fluidic pressure control. In some cases, the fluidic pressure control is capable of generating negative pressure in the balancer. In some cases, the flow-through incubator comprises a first serpentine channel, and the balancer comprises a second serpentine channel. In some cases, the second serpentine channel is connected to a third channel comprising an array of obstacles, wherein the third channel is substantially similar to the first channel. In some cases, the first flow stream and the second flow stream are parallel to each other. In some cases, the first channel comprises at least one separator wall oriented parallel to at least one of the flow streams, and the at least one separator wall is configured to delay the flow of deflected particles, wherein the delay serves to substantially increase an amount of time that the deflected particles reside in a flow stream, and/or substantially reduce mixing between the first flow stream and second flow stream. In some cases, the system further comprises an analytical component fluidically connected to the second channel. In some cases, the analytical component is a cell sorter.

In another aspect, provided herein is a system for processing first particles of at least a predetermined size in a sample, the system comprising (1) a microfluidic device, the microfluidic device comprising (A) a channel extending from a plurality of inlets to a plurality of outlets; and (B) a first array of obstacles arranged in rows in the channel, wherein each subsequent row of obstacles is shifted laterally with respect to a previous row, wherein the array of obstacles is configured to differentially deflect first particles of at least a predetermined size to a first outlet and second particles in the sample of less than the predetermined size to a second outlet; and (2) an incubator comprising a first portal fluidically connected with the first outlet of the microfluidic device and a second portal fluidically connected to a second liquid source. In some cases, the incubator is a container. In some cases, the container is a glass vial. In some cases, the system further comprises a flow controller configured to control flow in the microfluidic device or incubator. In some cases, the first portal of the incubator is a first inlet of the incubator and the second portal is a second inlet of the incubator. In some cases, the first portal of the incubator is a first inlet of the incubator and the second portal of the incubator is a first outlet of the incubator. In some cases, the second liquid source comprises a treatment reagent. In some cases, the incubator is configured to agitate a liquid in the incubator. In some cases, the incubator is configured to mix a liquid in the incubator.

In another aspect, provided herein is a device for purifying first particles of at least a predetermined size from a sample, the device comprising an array of obstacles arranged in rows, wherein each subsequent row of obstacles is shifted laterally with respect to a previous row, wherein the array of obstacles differentially deflect first particles of at least a predetermined size to a first outlet and second particles of less than the predetermined size in the sample to a second outlet, wherein surfaces of two adjacent obstacles in a row of the array of obstacles define a gap, wherein a shape of the gap is substantially symmetrically relative to a plane parallel to the direction of flow, wherein the plane is equidistant from the center of the cross-section of each of the two obstacles in the row, wherein the two obstacles defining a gap have a polygonal cross-section, wherein a vertex of each of the two obstacles with the polygonal cross-section points toward each other in a direction substantially perpendicular to a direction of flow of the sample through the array of obstacles. In some cases, the polygonal cross-section is a quadrilateral cross-section. In some cases, the quadrilateral cross-section is a square cross-section.

In another aspect, provided herein is a method for processing first particles of at least a predetermined size in a sample, the method comprising a) providing a sample comprising first particles of at least a predetermined size; b) passing the sample through a channel extending from a plurality of inlets to a plurality of outlets, wherein the channel is bounded by a first wall and a second wall opposite from the first wall, wherein the channel comprises an array of obstacles arranged in rows in the channel, wherein each subsequent row of obstacles is shifted laterally with respect to a previous row, wherein the first particles of at least a predetermined size are differentially deflected to a first outlet, and the device is configured to differentially deflect second particles of at least a predetermined size to a second outlet, wherein the first particles are inputted in a first flow stream from a first inlet and are deflected into a second flow stream flowing from a second inlet to the first outlet while being deflected, wherein the second flow stream comprises a reagent; and c) incubating the deflected first particles with the reagent in a flow-through incubator channel, wherein the flow-through incubator channel is fluidically connected with the first outlet, wherein the flow-through incubator channel is fluidically connected to a second channel, wherein the second channel is bounded by a first wall and a second wall opposite from the first wall, wherein the second channel comprises a second array of obstacles. In some cases, the method further comprises passing the deflected first particles through a third flow stream in the second channel. In some cases, the third flow stream comprises a wash buffer. In some cases, the reagent comprises an antibody. In some cases, the first particles comprise cells. In some cases, the cells comprise white blood cells. In some cases, the deflected first particles are in the flow-through incubator for up to 10 minutes.

In another aspect, provided herein is a method for processing first particles of at least a predetermined size in a sample, the method comprising: a) providing a sample comprising first particles of at least a predetermined size; b) passing the sample through a device comprising a channel extending from a plurality of inlets to a plurality of outlets, wherein the channel comprises array of obstacles arranged in rows in the channel, wherein each subsequent row of obstacles is shifted laterally with respect to a previous row, wherein the first particles of at least a predetermined size are differentially deflected to a first outlet, and wherein the device is configured to differentially deflect second particles of less than a predetermined size to a second outlet; and c) incubating the differentially deflected first particles in an incubator, wherein the incubator comprises a first portal fluidically connected with the first outlet of the microfluidic device and a second portal fluidically connected to a second liquid source. In some cases, the first particles comprise cells. In some cases, the cells comprise white blood cells. In some cases, the deflected first particles are in the incubator for at least 10 minutes.

In another aspect, provided herein is a method for purifying first particles of at least a predetermined size from a sample, the method comprising: a) providing a sample comprising first particles of at least a predetermined size; and b) passing the sample through a device the system comprising an array of obstacles arranged in rows, wherein each subsequent row of obstacles is shifted laterally with respect to a previous row, wherein first particles of at least a predetermined size are differentially deflected to a first outlet, and wherein the device is configured to differentially deflect second particles of less than the predetermined size to a second outlet, wherein surfaces of two adjacent obstacles in a row of the array of obstacles define a gap, wherein a shape of the gap is substantially symmetrically relative to a plane parallel to the direction of flow, wherein the plane is equidistant from the center of the cross-section of each of the two obstacles in the row, wherein the two obstacles defining a gap have a polygonal cross-section, wherein a vertex of each of the two obstacles with the polygonal cross-section points toward each other in a direction substantially perpendicular to a direction of flow of the sample through the array of obstacles. In some cases, a purified product at the first outlet comprises at least 60% of the first particles from the sample. In some cases, a purified product at the first outlet comprises at least 80% of the first particles from the sample. In some cases, the sample further comprises second particles of less than the predetermined size, wherein the second particles of less than the predetermined size are differentially deflected to the second outlet. In some cases, a purified product at the first outlet comprises less than 0.1% of the second particles from the sample. In some cases, a purified product at the first outlet comprises less than 0.01% of the second particles from the sample. In some cases, the sample is whole blood. In some cases, the first particles comprise white blood cells. In some cases, the second particles comprise red blood cells. In some cases, the method further comprises analyzing the first particles using an analytical component. In some cases, the analytical component is a cell sorter. In some cases, the sample is passed a flow rate of about 40 mL/hr.

In another aspect, provided herein is a method for processing first particles of at least a predetermined size, the method comprising: a) providing a sample comprising first particles of at least a predetermined size; b) labeling one or more molecules on a surface of the first particles wherein the labeling of step b) is not performed on the microfluidic device; c) passing the sample through a microfluidic device comprising a channel extending from a plurality of inlets to a plurality of outlets, wherein the channel is bounded by a first wall and a second wall opposite from the first wall, wherein the channel comprises an array of obstacles arranged in rows in the channel, wherein each subsequent row of obstacles is shifted laterally with respect to a previous row, wherein the array of obstacles is configured to differentially deflect the first particles of at least a predetermined size to a first outlet and second particles of less than the predetermined size to a second outlet, wherein the first particles are inputted in a first flow stream from a first inlet and are deflected to flow into a second flow stream flowing from a second inlet to the first outlet while being deflected, wherein the second flow stream comprises a wash buffer; d) fixing the first particles, wherein the fixing is not performed on the microfluidic device; e) permeabilizing the first particles, wherein the permeabilizing is not performed on the microfluidic device; and f) labeling one or more molecules inside the first particles, wherein the labeling is not performed on the microfluidic device, wherein step c is performed between step b) and step d), between step d) and step e), between step e and step f, and/or after step e). In some cases, the first particles are cells. In some cases, the cells are white blood cells. In some cases, the sample is whole blood. In some cases, the channel comprises at least one separator wall oriented parallel to at least one of the flow streams, and the at least one separator wall is configured to delay the flow of deflected first particles, wherein the delay serves to substantially increase an amount of time that the deflected particles reside in a flow stream, and/or substantially reduce mixing between the first flow stream and the second flow stream. In some cases, the method further comprises analyzing the first particles using an analytical component. In some cases, the analytical component is a cell sorter.

In another aspect, provided herein is a method for processing first particles of at least a predetermined size, the method comprising: a) providing a sample comprising first particles of at least a predetermined size; b) passing the sample through a microfluidic device comprising a channel extending from a plurality of inlets to a plurality of outlets, wherein the channel is bounded by a first wall and a second wall opposite from the first wall, wherein the channel comprises an array of obstacles arranged in rows in the channel, wherein each subsequent row of obstacles is shifted laterally with respect to a previous row, wherein the array of obstacles is configured to differentially deflect the first particles of at least a predetermined size to a first outlet and second particles of less than the predetermined size to a second outlet, wherein the first particles are inputted in a first flow stream from a first inlet and are deflected to flow into a first reaction flow stream comprising a reagent that labels a molecule on a surface of the first particles and a second reaction flow stream comprising a wash buffer, wherein the reaction flow streams flow from the plurality of inlets to the plurality of outlets; c) fixing the first particles, wherein the fixing is not performed on the microfluidic device; d) permeabilizing the first particles, wherein the permeabilizing is not performed on the microfluidic device; and e) labeling a molecule inside the first particles, wherein the labeling is not performed on the microfluidic device. In some cases, the particles are cells. In some cases, the particles are white blood cells. In some cases, the sample is whole blood. In some cases, the channel comprises at least one separator wall oriented parallel to at least one of the flow streams, and the at least one separator wall is configured to delay the flow of deflected particles, wherein the delay serves to substantially increase an amount of time that the deflected particles reside in a flow stream, and/or substantially reduce mixing between the first reaction flow stream and the second reaction flow stream. In some cases, the method further comprises analyzing the first particles using an analytical component. In some cases, the analytical component is a cell sorter. In some cases, the method further comprises a washing step on a microfluidic device between step c) and step d), between step d) and step e), and/or after step e).

In another aspect, provided herein is method for processing first particles of at least a predetermined size, the method comprising: a) providing a sample comprising first particles of at least a predetermined size; b) labeling a molecule on a surface of the first particles; c) passing the sample through a microfluidic device comprising a channel extending from a plurality of inlets to a plurality of outlets, wherein the channel is bounded by a first wall and a second wall opposite from the first wall, wherein the channel comprises an array of obstacles arranged in rows in the channel, wherein each subsequent row of obstacles is shifted laterally with respect to a previous row, wherein the array of obstacles is configured to differentially deflect the first particles of at least a predetermined size to a first outlet and second particles of less than the predetermined size to a second outlet, wherein the first particles are inputted in a first flow stream from a first inlet and are deflected to flow into a first reaction flow stream comprising a fixation reagent and a permeabilization reagent and the second reaction flow stream comprising a wash buffer, and d) labeling a molecule inside the first particles, wherein the labeling a molecule inside the first particles is not performed on the microfluidic device, wherein the labeling a molecule on the surface of the first particles is not performed on a microfluidic device. In some cases, the particles are cells. In some cases, the cells are white blood cells. In some cases, the sample is whole blood. In some cases, the channel comprises at least one separator wall oriented parallel to at least one of the flow streams, and the at least one separator wall is configured to delay the flow of deflected particles, wherein the delay serves to substantially increase an amount of time that the deflected particles reside in a flow stream, and/or substantially reduce mixing between the first reaction flow stream and the second reaction flow stream. In some cases, the method further comprises analyzing the first particles using an analytical component. In some cases, the analytical component is a cell sorter. In some cases, a wash step is performed after step d) on a microfluidic device.

In another aspect, provided herein is a method for processing first particles of at least a predetermined size, the method comprising: a) providing a sample comprising first particles of at least a predetermined size; b) labeling a molecule on a surface of the first particles; c) fixing the first particles; d) permeabilizing the first particles; and e) passing the sample through a microfluidic device comprising a channel extending from a plurality of inlets to a plurality of outlets, wherein the channel is bounded by a first wall and a second wall opposite from the first wall, wherein the channel comprises an array of obstacles arranged in rows in the channel, wherein each subsequent row of obstacles is shifted laterally with respect to a previous row, wherein the array of obstacles is configured to differentially deflect the first particles of at least a predetermined size to a first outlet and second particles of less than the predetermined size to a second outlet, wherein the first particles are inputted in a first flow stream from a first inlet and are deflected to flow through a first reaction flow comprising a reagent that labels a molecule inside the first particles and a second reaction flow stream comprising a washing buffer, wherein the labeling the molecule on a surface is not performed on the microfluidic device, wherein the fixing is not performed on the microfluidic device, and wherein the permeabilizing is not performed on the microfluidic device. In some cases, the particles are cells. In some cases, the cells are white blood cells. In some cases, the sample is whole blood. In some cases, the channel comprises at least one separator wall oriented parallel to at least one of the flow streams, and the at least one separator wall is configured to delay the flow of deflected particles, wherein the delay serves to substantially increase an amount of time that the deflected particles reside in a flow stream, and/or substantially reduce mixing between the first reaction flow stream and the second reaction flow stream. In some cases, the method further comprises analyzing the first particles using an analytical component. In some cases, the analytical component is a cell sorter.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

In FIG. 2C, small arrows indicate the direction of the fluid along the particle path; the particles generally follow the fluid direction when the fluid flow direction is left-to-right and generally follow the array direction when the fluid flow direction is right-to-left.

FIG. 15 is a graph comparing the critical size characteristics of round and triangular posts.

FIG. 19 shows input and output views of a multi-steam "car wash" DLD array for multiple sequential chemical and/or enzymatic processing.

FIG. 26 shows a comparison of contamination in the output portion of a "car wash" DLD array with (Modified) and without (Original) opposing separator walls.

FIG. 29A shows views of areas of potential clogging in the input, middle and output portions of the array of obstacles in the DLD array of FIG. 28 following flowing a blood sample through the DLD array shown in FIG. 28.

FIG. 30 shows the inputs and outputs of running a blood sample through any of the "car wash" DLD arrays as provided herein.

FIGS. 27A and B) and without (Ver. 1 chip; FIG. 19) a pair of opposing separator walls.

FIG. 34B shows a portion of the DLD array following the bump mode before the cleaning mode (top) and after the cleaning mode (bottom).

FIG. 44 illustrates a DLD chip in a manifold as described herein.

FIG. 45 shows a schematic depicting changes in conventional sample preparation protocol and time through the use of DLD devices as described herein. Sample preparation time can be reduced from about 2 to 3 hours to less than 20 minutes.

FIG. 46 illustrates a products for sample preparation system utilizing the DLD devices as described herein.

FIG. 47 illustrates a products for sample preparation system utilizing the DLD devices as described herein.

FIG. 48A: the schematic of the wall-separated DLD array design for on-chip cell processing and washing. Target cells (following path P1 and P2) are processed, and washed in a continuous fluidic flow. Separator walls reduce the diffusion of the treatment chemical, indicated by red shading, to minimize the contamination in the product output. FIG. 48B: the schematic of detailed DLD array design (d=18 μm, g=18 μm, and ε=1.36°), and cell motion in this DLD array. Cells smaller than a critical size will follow the stream line in an average straight direction (small cell, black arrow), while cells larger than the critical size will bump at posts following the tilted axis of the array (target cell, red arrow). FIG. 48C: Schematic of the manifold setup. FIG. 48D: Schematic of experimental setup for on-chip cell processing.

FIG. 52A shows middle region of the wall-separated DLD array where the leukocytes are passing through the R6G stream and close to entering into the washing stream (region "B" in FIG. 50B). FIG. 52B shows labeled leukocytes in the output channel with negligible fluorescence background. The inset of FIG. 52B shows vials of collected product and waste outputs, showing low red blood cell level in the product.

FIGS. 53A-C show purification of white blood cells (WBCs) with obstacles with different cross-sectional shapes in a DLD array. FIG. 53A shows the WBC yield and red blood cell (RBC) contamination obtained using obstacles with different cross-sectional shapes at about 40 mL/hr. The "X" represents a quarter circle. Orientation of flow is from top to bottom. FIG. 53B shows inertial effects of assymetric triangular, diamond and circular obstacles. The flow is in the y-direction; the x-velocity is the lateral velocity due to inertial effects. y=0 is the gap (narrowest point), negative y-values are upstream in the direction of the flow, and positive y-values are downstream in the direction of the flow. FIG. 53C shows a comparison of shear forces generated by circular and diamond obstacles. Flow is from top to bottom.

FIG. 54A shows an exemplary flow-through incubator connecting two DLD arrays. FIG. 54B shows an exemplary fluidic resistance balancer connected to a DLD array connected to a flow-through incubator connected to a second DLD array.

FIG. 56 illustrates an outlet from a DLD array; the fluidic resistance ratio between the product output and the waste output is 3:1. The volume ratio of the product output and the waste output is 1:3.

FIG. 58 illustrates a fluidic resistance ratio between the product output and the waste output of a DLD array is 6:1. The volume ratio of the product output and the waste output is 1:6.

DETAILED DESCRIPTION

I. Overview

Figure 1:
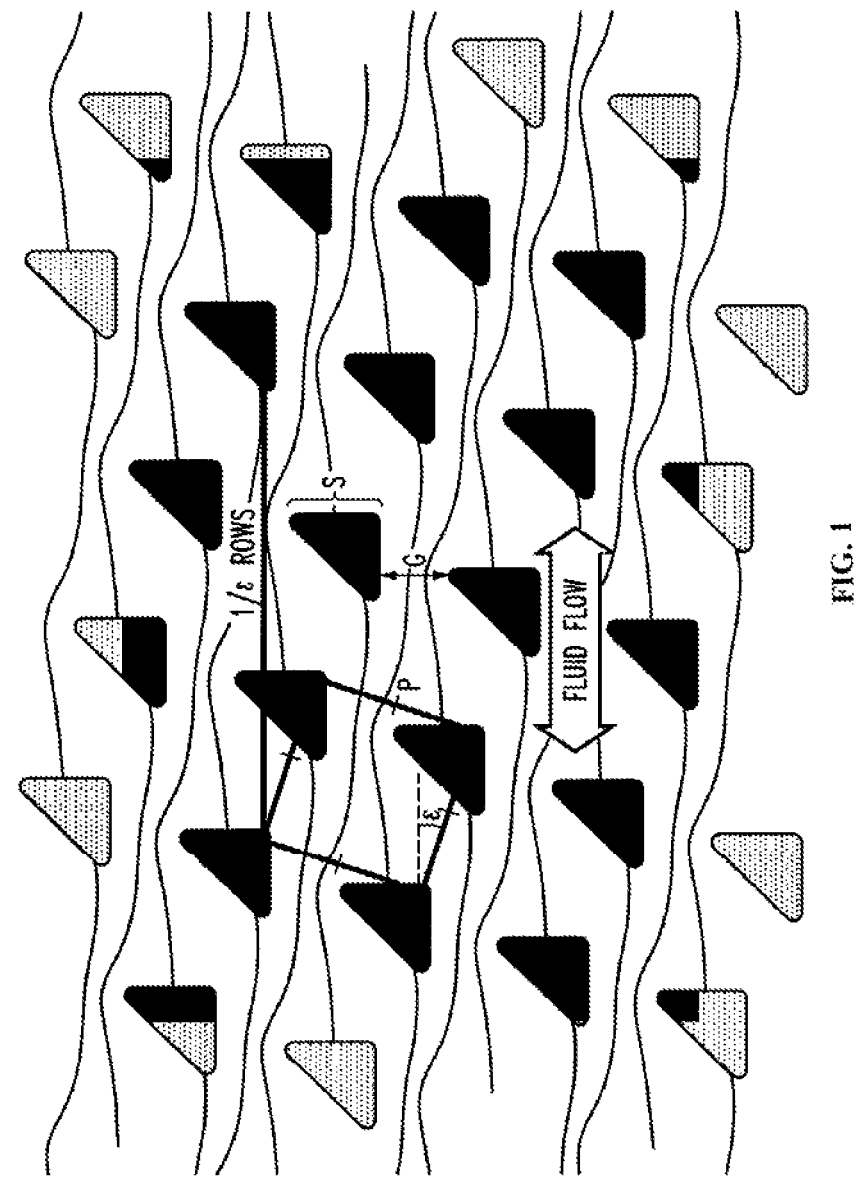
FIG. 1 is a schematic diagram of cross-section of a "bump array" device having right triangularly-shaped obstacles disposed in a microfluidic channel. In the figure, fluid flow alternates between the right-to-left and left-to-right directions, as indicated by the double-headed arrow marked, "Fluid Flow." In this array, right triangular posts are disposed in a square lattice arrangement that is tilted with respect directions of fluid flow. The tilt angle $\epsilon$ (epsilon) is chosen so the device is periodic. In this embodiment, a tilt angle of 18.4 degrees (1/3 radian) makes the device periodic after three rows. The gap between posts is denoted G with triangle side length S and array pitch P. Streamlines are shown extending between the posts, dividing the fluid flow between the posts into three regions ("stream tubes") of equal volumetric flow.

Provided herein are methods, compositions, devices, systems, and kits for chemical processing, purification, isolation, and/or concentration of particles. In some cases, the chemical processing, purification, isolation, and/or concentration of particles can be high-throughput. The chemical processing, purification, isolation, and/or concentration of particles can involve separating particles based on size, e.g., flowing a sample through an array of obstacles, e.g., a deterministic lateral displacement (DLD) array. Devices for separating particles based on size and/or using DLD are described, e.g., in U.S. Pat. Nos. 7,150,812, 7,318,902, 7,472,794, 7,735,652, 7,988,840, 8,021,614, 8,282,799, 8,304,230, 8,579,117, and PCT Publication No. WO2012094642, which are herein incorporated by reference in their entireties. In some cases, the high-throughput methods comprise flow rates of at least 1 mL/min, at least 5 mL/min, at least 10 mL/min or at least 20 mL/min. In some cases, devices described herein can process less than 1 ml, at least 10 mL, at least 100 mL, or at least 300 mL of sample.

Provided herein are methods, systems, and devices (e.g., DLD chips) for automating and simplifying the cell preparation process for cell analysis (e.g., flow cytometric analysis or cell sorting). A multi-step manual cell processing procedure for flow cytometry is shown in the first column of FIG. 42. The DLD chips described herein can allow automation and combination of these steps. The methods, systems and devices provided herein can replace the manual wash steps involving centrifugation and resuspension, as well as the red blood cells (RBC) lysis step and all the manual handling steps associated with surface and intracellular labeling and fixation/permeabilization (fixation/permeabilization). In some cases, DLD chips are used in junction with off-chip procedures to process cells. The methods, systems and devices can also reduce the starting sample size (e.g., to no greater than about 100 μL whole blood). In some cases, the conventional wash steps can be replaced with an on-chip process that purifies ("harvests") white blood cells (WBCs) without centrifugation from a mixture of monoclonal antibodies (Mab) and other labels, fixation/permeabilization reagents, and red blood cells (RBCs).

In one aspect, the methods, systems and devices herein can be used to perform one or more cell processing steps on a microfluidic chip. Performing the steps on the microfluidic chip can reduce the handling time and cost. In some cases, a washing and/or concentration step can be performed on a microfluidic chip. In some cases, a fixation/permeabilization step, a cell surface labeling step and an intracellular labeling step can be performed individually or in any combination on a microfluidic chip. In some case, any of the above mentioned steps, or combination thereof, can be performed in combination with a washing/concentration on a microfluidic chip. For example, a fixation/permeabilization step and a washing/concentration step can be performed on a microfluidic chip. In another example, a cell-surface labeling step and a washing/concentration step can be performed on a microfluidic chip. In another example, an intracellular labeling step and a washing/concentration step can be performed on a microfluidic chip.

In another aspect, any of the microfluidic chips or combination thereof can be used together with any off-chip methods for processing cells. In some cases, one or more of the cell processing steps can be performed on one or more microfluidic chips, and the other cell processing steps can be performed using any off-chip methods. In some cases, all the cell processing steps can be performed on a microfluidic chip. For example, all of the surface labeling, fixation, permeabilization, intracellular labeling, and associated wash steps can be integrated into a single "car wash" chip herein. Combination of the cell processing steps on microfluidic can reduce handling time and cost, and can result in additional product chips and processes. In some cases, provided herein is a system for processing particles in a sample, the system comprising: a microfluidic component, wherein the microfluidic component comprises a channel extending from a plurality of inlets to a plurality of outlets, wherein the channel is bounded by a first wall and a second wall opposite from the first wall; and an array of obstacles, wherein the first array of obstacles deflects the particles through a series of flow streams flowing from the plurality of inlets to the plurality of outlets, wherein the particles are deflected toward the second wall when flowing from the inlets to the outlets, and wherein the plurality of flow streams comprise two flow streams selected from the group consisting of a flow stream comprising a labeling agent, a flow stream comprising a fixation agent and a permeabilization agent, and a flow stream comprising a washing buffer, and a non-microfluidic component.

In another aspect, methods, devices and systems for prolonging the incubation time of cells in a solution are provided herein. In some cases, provided herein includes a system for prolonging contact time of particles with a solution comprising a reaction agent, the system comprising a flow-through incubator, wherein the flow-through incubator is fluidically connected, e.g., a channel comprising a DLD array, wherein the particles flow from the channel to the flow-through incubator in a flow stream, and wherein the flow stream comprises the solution comprising the reaction agent. In some cases, the flow-through incubator can be a component on a microfluidic chip for processing cells. In some cases, the device and methods can prolong the distance the cells travel in a solution, so that the cells can keep contact with the solution for longer time without reducing the flow rate in the system. In some cases, the flow-through incubator can be a channel on a microfluidic chip, e.g., a serpentine channel. In some cases, the flow-through incubator can be an off-chip device. In some cases, the flow-through incubator can be an off-chip container. In some cases, an off-chip container is fluidically connected to a channel comprising a DLD array.

In another aspect, the flow-through incubator can be used in combination with any of the microfluidic chips provided herein to prolong the contact time of cells with a solution. In some cases, provided herein is a system for processing first particles of at least a predetermined size in a sample, the device comprising: a channel extending from a plurality of inlets to a plurality of outlets, wherein the channel is bounded by a first wall and a second wall opposite from the first wall; a first array of obstacles arranged in rows in the channel, wherein each subsequent row of the first array of obstacles is shifted laterally with respect to a previous row, wherein the first array of obstacles is configured to differentially deflect first particles of at least a predetermined size to a first outlet and second particles in the sample of less than the predetermined size to a second outlet, wherein the device is configured such that the first particles are inputted in a first flow stream from a first inlet and are deflected into a second flow stream flowing from a second inlet to the first outlet while being deflected toward the second wall, wherein the second flow stream comprises a reagent; and a flow-through incubator fluidically connected with the first outlet, wherein the flow-through incubator comprises a channel.

In another aspect, an off-chip incubator can be used with any of the microfluidic chips to prolong the contacting time of cells with a solution. In some cases, provided herein includes a system for processing first particles of at least a predetermined size in a sample, the system comprising: a device comprising a channel extending from a plurality of inlets to a plurality of outlets; a first array of obstacles arranged in rows in the channel, wherein each subsequent row of obstacles is shifted laterally with respect to a previous row, wherein the array of obstacles is configured to differentially deflect first particles of at least a predetermined size to a first outlet and second particles in the sample of less than the predetermined size to a second outlet; and an incubator fluidically connected with the first outlet.

In another aspect, provided herein also include methods and devices for purifying a first types of cells in a sample comprising the first types of cells. The sample can comprise a second type of cells. Such methods and devices can be configured to achieve a high yield of the first types of cells. The methods and devices can be configured to achieve a low contamination of the second types of cells. In some cases, such devices can comprise an array of obstacles with certain cross-sectional shapes. For example, at least one of the obstacles can have a quadrilateral cross-sectional shape (e.g., diamond shape). Provided herein is a system for purifying first particles from a sample, the system comprising: an array of obstacles arranged in rows, wherein each subsequent row of obstacles is shifted laterally with respect to a previous row, wherein the array of obstacles is configured to differentially deflect first particles of at least a predetermined size to a first outlet and second particles of less than the predetermined size in the sample to a second outlet, wherein surfaces of two of the obstacles define a respective gap, wherein the respective gap is substantially symmetrically oriented about a plane that extends through the center of the respective gap and that is parallel to a direction of flow of the sample through the array of obstacles, wherein each of the two obstacles defining a respective gap has a polygonal cross-section, wherein a vertex of each of the two obstacles with the polygonal cross-section points to a direction substantially parallel to the direction of flow of the sample through the array of obstacles.

In another aspect, provided herein is a DLD device, the device comprising at least three sets of arrays of obstacles arranged in rows, wherein the gap size between obstacles in the second array is smaller than the gap size between obstacles in the first array, and wherein the gap size of the obstacles in the third array is smaller than the gap size between obstacles in the second array, wherein the length of the third array is about 1.2 cm.

Figure 57:
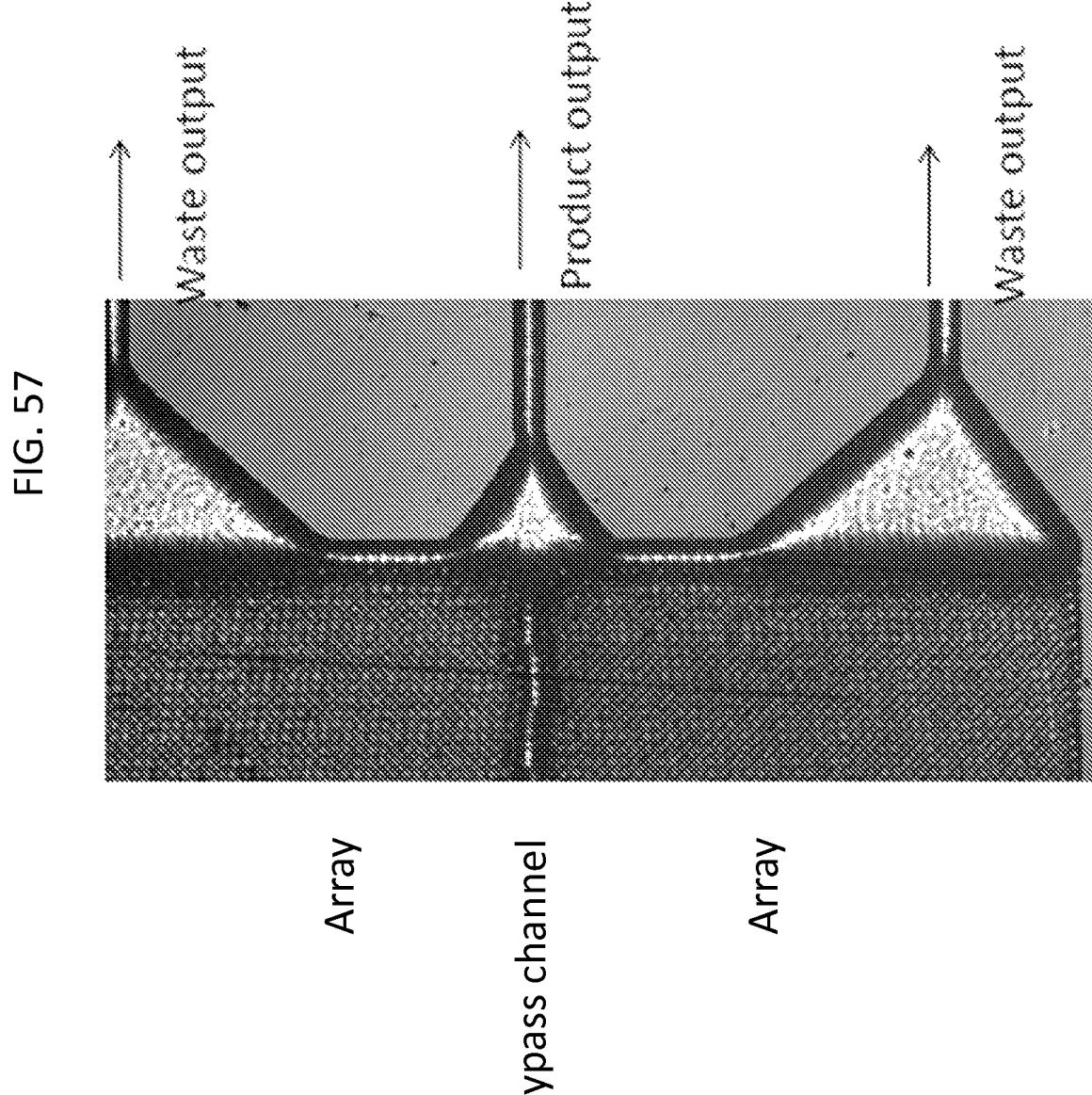
FIG. 57 illustrates a fluidic resistance ratio between the product output and the waste output of a DLD array is 3:1. The volume ratio of the product output and the waste output is 1:3.
Figure 58:
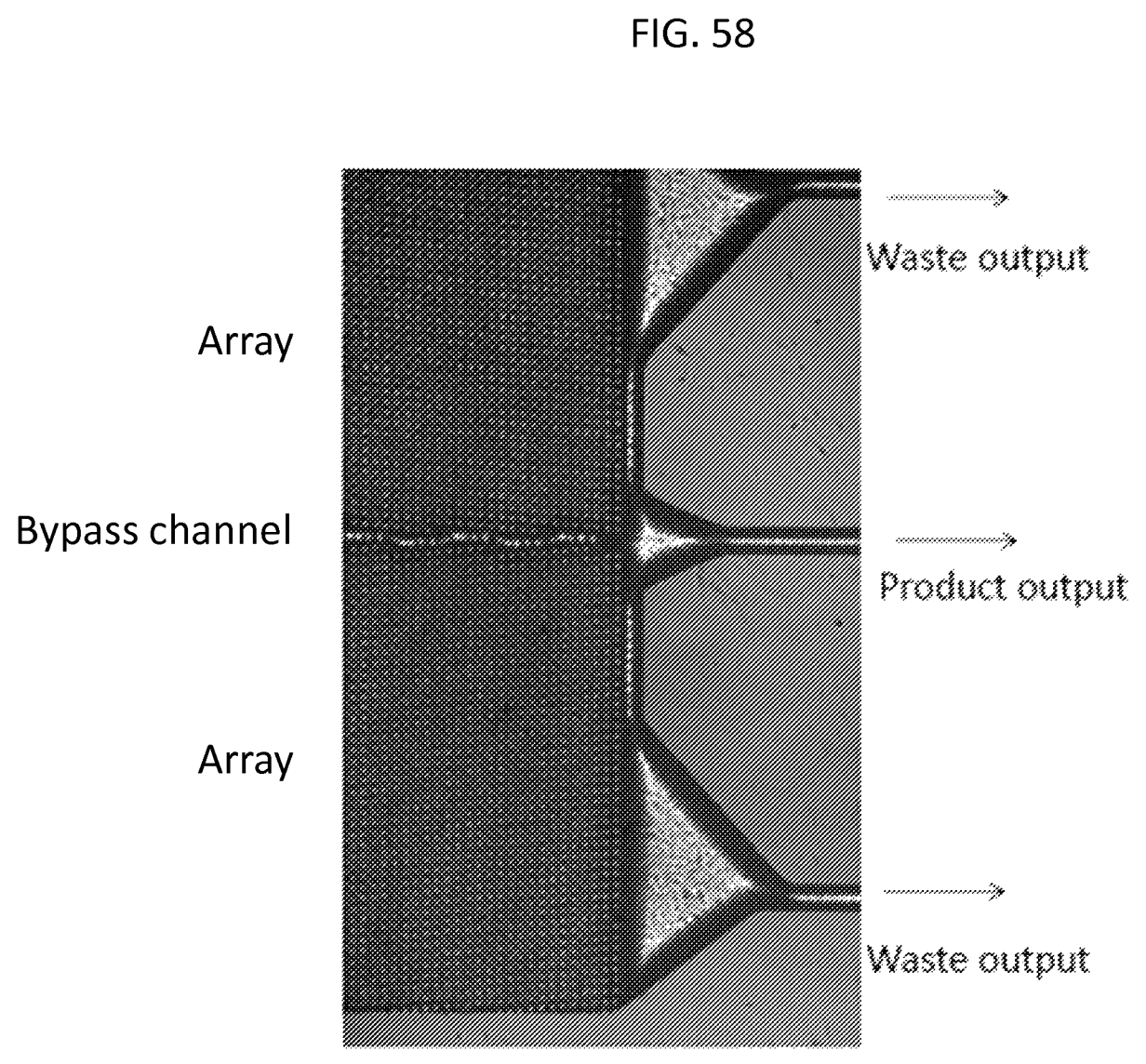

In another aspect, provided herein is a mirrored DLD comprising a bypass channel configured to flow into a product output channel, wherein the volume of the product channel at the base of the DLD array is about 1/3, 1/6, or 1/7 the volume of a waste collection channel at the base of the DLD array (see, e.g., FIG. 57 and FIG. 58).

In one aspect, a device for processing, purifying, and concentrating particles is provided herein, wherein the device comprises a channel extending from a plurality of inlets to a plurality of outlets, and wherein the channel is bounded by a first wall and a second wall opposite from the first wall; and an array of obstacles disposed within the channel configured to deflect particles toward the second wall when the particles are flowed from the inlets to the outlets. The device can be configured such that particles in a fluid sample are inputted into at least one of the plurality of inlets and particles of a predetermined size in the fluid sample are deflected through a series of parallel flow streams flowing from the plurality of inlets to the plurality of outlets while also being deflected toward the second wall. In some cases, the series of parallel flow streams comprises at least four flow streams comprising a reagent. The reagents can be the same or different reagents.

In another aspect, a device is provided herein, the device comprising a channel extending from a plurality of inlets to a plurality of outlets, wherein the channel is bounded by a first wall and a second wall opposite from the first wall, and wherein the device is configured to flow a plurality of flow streams from the plurality of inlets to the plurality of outlets, wherein the plurality of flow streams flow parallel to each other; and an array of obstacles disposed within the channel configured to deflect particles toward the second wall when the particles are flowed from the inlets to the outlets, wherein the array of obstacles comprises at least one separator wall oriented parallel to flow of the plurality of flow streams and the first and second walls. The device can be configured wherein particles introduced into an sample inlet near the first wall pass through the plurality of flow streams while being deflected toward the second wall, and wherein the at least one separator wall is configured to delay the flow of deflected particles toward the second wall, wherein the delay serves to substantially increase an amount of time that deflected particles reside in a flow stream, and/or substantially reduce mixing between parallel flow streams.

In another aspect, a device is provided herein, the device comprising a channel extending from at least one inlet to a plurality of outlets, wherein the channel is bounded by a first wall and a second wall opposite from the first wall; and an array of obstacles disposed within the channel configured to deflect particles in a stream comprising particles toward the second wall when the stream comprising particles is flowed from the at least one inlet to the plurality of outlets. The device is configured wherein the first wall comprises a plurality of inlets adapted to flow a fluid towards a plurality of outlets in the second wall, wherein the direction of the flow of the fluid is perpendicular to flow of the stream comprising the particles and wherein the flow of the fluid is configured to remove any particles that have become clogged in the array of obstacles following movement of the particles toward the second wall.

In another aspect, a method for labeling cells is provided, the method comprising providing a sample comprising cells, processing the sample comprising cells, wherein the processing comprises introducing the sample comprising cells into a sample inlet of a device comprising an array of obstacles, and passing the sample through the array of obstacles, wherein the array of obstacles comprises a plurality of parallel flow streams flowing through the array of obstacles, wherein the passing comprises flowing cells from the sample from the sample inlet through the plurality of parallel flow streams, wherein at least one of the plurality of parallel flow streams comprises a labeling reagent, at least one of the plurality of parallel flow streams comprises a fixation agent, at least one of the plurality of parallel flow streams comprises a permeabilization agent, and at least one of the plurality of parallel flow streams comprises a wash buffer, whereby the passing the sample through the array of obstacles serves to label the cells while also simultaneously separating the cells by size; and harvesting labeled cells of a predetermined size from one of a plurality of outlets of the device.

In another aspect, a method for processing leukocytes for molecular diagnostic testing is provided, the method comprising labeling and harvesting the leukocytes from a sample using a microfluidic device, wherein the yield of labeled cells is at least 85% and the viability of the labeled cells is at least 90%.

In another aspect, methods are provided herein for processing particles in a sample using the microfluidic device and the flow-through incubator disclosed herein. Such methods can allow the particles to be incubated with a reaction agent for a sufficient time without reducing the flow rate in the microfluidic device. Methods provided herein can comprise passing particles in a sample through a system comprising any microfluidic chips and any incubator provided herein. In some cases, provided herein includes a method for processing first particles of at least a predetermined size in a sample, the method comprising: providing a sample comprising first particles of at least a predetermined size, and optionally, second particles of less than the predetermined size; passing the sample through a system, wherein the system comprises a channel extending from a plurality of inlets to a plurality of outlets, wherein the channel is bounded by a first wall and a second wall opposite from the first wall; an array of obstacles arranged in rows in the channel, wherein each subsequent row of obstacles is shifted laterally with respect to a previous row, wherein the array of obstacles is configured to differentially deflect first particles to a first outlet and the second particles to a second outlet, wherein the device is configured such that the first particles are inputted in a first flow stream from a first inlet and are deflected into a second flow stream flowing from a second inlet to the first outlet while being deflected toward the second wall, wherein the second flow stream comprises a reagent; and a flow-through incubator fluidically connected with the first outlet, wherein the flow-through incubator comprises a channel.

In another aspect, also provided herein are methods for purifying a group of particles from a sample. In some cases, the methods comprising passing the sample through an array of obstacles with certain cross-sectional shapes, e.g., a quadrilateral shape. Such obstacles can have enhanced displacement effect of the obstacles (e.g., due to increased inertial effect) and can reduce the deformation of the particles. Thus the particles can be purified from the sample with a high yield and low contamination from other components in the sample. Provided herein is a method for purifying first particles of at least a predetermined size from a sample, the method comprising: providing a sample comprising first particles of at least a predetermined size, and optionally, second particles of less than the predetermined size; passing the sample through an array of obstacles arranged in rows, wherein each subsequent row of obstacles is shifted laterally with respect to a previous row, wherein the array of obstacles is configured to differentially deflect first particles to a first outlet and second particles to a second outlet, wherein surfaces of two of the obstacles define a respective gap, wherein the respective gap is substantially symmetrically oriented about a plane that extends through the center of the respective gap and that is parallel to a direction of flow of the sample through the array of obstacles, wherein each of the two obstacles defining a respective gap has a polygonal cross-section, wherein a vertex of each of the two obstacles with the polygonal cross-section points to a direction substantially parallel to the direction of flow of the sample through the array of obstacles.

In another aspect, methods are provided herein to process particles in a sample using one or more microfluidic chips and one or more off-chip devices. Such combinations can provide flexible procedures for processing the particles. In some cases, provided herein includes a method for processing first particles of at least a predetermined size, the method comprising: providing a sample comprising first particles of at least a predetermined size, and optionally, second particles of less than the predetermined size; passing the sample through a microfluidic device, system, wherein the system comprises a channel extending from a plurality of inlets to a plurality of outlets, wherein the channel is bounded by a first wall and a second wall opposite from the first wall; an array of obstacles arranged in rows in the channel, wherein each subsequent row of obstacles is shifted laterally with respect to a previous row, wherein the array of obstacles is configured to differentially deflect the first particles to a first outlet and the second particles to a second outlet, wherein the device is configured such that the first particles are inputted in a first flow stream from a first inlet and are deflected to flow through one or more reaction flow streams flowing from the plurality of inlets to the plurality of outlets, wherein the one or more of reaction flow streams comprise a reaction flow stream comprising a labeling reagent, a reaction flow stream comprising a fixation agent, a reaction flow stream comprising a permeabilization agent, and a reaction flow stream comprising a washing buffer, or any combination thereof; passing the sample through a non-microfluidic device, wherein the non-microfluidic device comprises a solution comprising a reagent, wherein the reagent is selected from the group of a labeling reagent, a fixation agent, a permeabilization reagent, or a washing buffer.

In another aspect, methods are provided for prolonging time of particles in a solution comprising a reaction agent when the particles are passing from a reservoir comprising the solution. In some cases, one of the methods can comprise passing the particles from the reservoir on a microfluidic device through a flow-through incubator, wherein the flow-through incubator is fluidically connected with the reservoir, and wherein the particles are in the solution when passing through the flow-through incubator.

In some cases, one of the methods can comprise: providing a sample comprising particles; introducing the sample into a microfluidic device, wherein the microfluidic device comprises an array of obstacles, a plurality of inlets, and a plurality of outlets, and wherein the particles are inputted into at least one of the plurality of inlets; passing the particles through the array of obstacles, wherein the particles are deflected through a series of flow streams flowing from the plurality of inlets to the plurality of outlets, and wherein the plurality of flow streams comprise two flow streams selected from the group consisting a flow stream comprising a labeling reagent, a flow stream comprising a fixation agent, a flow stream comprising a permeabilization agent, and a flow stream comprising a washing buffer, and passing the particles through a flow-through incubator, wherein the flow-through incubator is fluidically connected with the array of obstacles, thereby prolonging the time the particles are in at least one of the flow streams.

In another aspect, a system for processing and analyzing particles is provided, the system comprising a plurality of reservoirs, wherein at least one of the reservoirs comprises a sample comprising particles, and at least one of the reservoirs comprises a reagent; a device, wherein the device is in fluid communication with each of the plurality of reservoirs, and wherein the device is adapted to process particles from the sample comprising particles, wherein the processing comprises flowing the sample comprising particles from the reservoir comprising the sample into an input of a device, and passing the particles through the device, wherein the passing comprises flowing the particles from the input through a plurality of parallel flow streams within the device, wherein at least one of the parallel flow streams comprises a reagent which flows from at least one of the plurality of reservoirs, and wherein the device comprises an array of obstacles, whereby the passing the particles through the device serves to process the particles as well as separate the particles by size; and an analytical device in fluid communication with at least one of a plurality of outlet ports of the device, wherein the analytical device is configured to perform an analysis of particles processed by the device.

Microfluidic processes known as Deterministic Lateral Displacement (DLD) can remove cells from a flow of fluid, on the basis of their size (2). As a mixture of fluid and particles flows through an array of microposts, in which the micropost axis can be tilted at a small angle of a few degrees from the direction of the fluid flow, particles above a certain critical size (such as leukocytes) can "bump" off the posts to flow in a direction along the tilted array axis (hence the device can be referred to as a "bump array"). Smaller particles and dissolved molecules, such as red blood cells, monoclonal antibodies (Mabs), and chemical reagents (e.g., fixatives, enzymes, permeabilization agents) can flow straight ahead, on average, with or in the fluid stream. Thus, after travelling across the microfluidic chip, the larger cells can be flowed out of and away from the fluid stream of the original input mixture and can be collected separately. The process can be used to remove a range of objects from an input fluid, ranging from large DNA oligomers (~100 kpb) to *E. coli* and other bacteria, platelets, erythrocytes and leukocytes (2, 4, 5). The critical size determining which path the cells or other objects follow can be controlled by the design of the micropost array (e.g. post size and shape, gaps between posts, axis tilt angle) (6). Cells or particles several times larger than the critical size that determines bumping (i.e. cell harvest) can flow through the device without clogging. In some cases, the operating conditions (e.g. chip loading, flow rates, output collection) can be automated.

A cell processing method described herein can recover all subsets of leukocytes in >90% yield. The methods and devices can be a research, clinical, and/or commercial tool that can replace the current standard centrifugal wash/concentrate steps that can be commonplace in research and clinical laboratories. The use of the cell processing procedure is not be restricted to flow cytometry and/or to leukocytes.

The tests to quantify the numbers and functional states of key leukocyte types from blood samples can offer enhanced precision and personalization of clinical diagnosis, prognosis, and treatment response. For example, labeling of >30 cell surface and intracellular target molecules can assess signaling pathway status of multiple types of normal leukocytes vs. leukemia cells simultaneously, by multi-parameter flow cytometry or atomic mass spectrometry (1). Stem cells or infected cells can be analyzed similarly. Cells can be analyzed by next generation sequencing. However, current procedures to process blood leukocytes can be expensive, time-consuming, repetitive, and human operator-dependent; and can have low cell yields and can require considerable human expertise.

Conventionally, combined surface membrane and intracellular labeling of blood leukocytes can require lysing erythrocytes to harvest the leukocyte population (Lysis); incubating with fluorescent monoclonal antibodies (Mabs) against cell surface leukocyte lineage/stage or cancer markers (Surface Labeling); performing a fixation/permeabilization (Fixation/permeabilization) step; and incubating with reagents (e.g. tagged Mabs, nucleic acids, dyes) that can bind to intracellular (cytoplasmic and nuclear) molecules (Intracellular Labeling). Following each of these 4 steps, one or more Wash/Concentrate steps can be required, currently involving centrifugation and resuspension of the cell pellet. Leukocyte yield can be ~80-90% in each Wash/Concentrate step, so overall yield can be <50% after multiple washes.

Described herein are methods, compositions, devices, system and/or kits utilizing Deterministic Lateral Displacement (DLD) microfluidic technology (2) to replace each of the Wash/Concentrate Steps. In some cases, a leukocyte harvesting and a Wash/Concentrate step is combined into a single step, thereby avoiding lysis and further streamlining workflow. Thus, a multi-step, labor-intensive process taking up to a half-day can be replaced by a high yield, low cost process that takes <1 hr and can have less or minimal operator-dependent steps. In some cases, the multiple sequential steps can be performed to harvest, label, and wash/concentrate leukocytes in a "Car Wash" approach on a single microchip, inputting whole blood and outputting labeled cells for downstream applications (e.g., flow cytometry or mass spectrometry analysis).

The Deterministic Lateral Displacement (DLD) separation described here can outperform standard centrifugal procedures. Provided herein are microfluidic devices, compositions, systems, kits, and methods to wash and concentrate leukocytes rapidly, at low cost, with increased cell yield, and with improved reproducibility. Microfluidic DLD systems can be designed and fabricated to remove and concentrate leukocytes or spiked leukemia cells from a stream containing Mabs used for the Labeling steps or from the solution used for a Fixation/permeabilization step. Volumes of 0.1-1 ml can be processed in <5-10 minutes (e.g., by an automated process). In some cases, >90% yield and 90% viability of leukocytes and removal of >99% unbound fluorescent or Fixation/permeabilization reagents with no skewing of sub-populations is achieved.

In some cases, an erythrocyte lysis step and subsequent centrifugal Wash/Concentrate step is replaced by a DLD microfluidic step. In some cases, the DLD microfluidic step is a single DLD microfluidic step.

As described herein, leukocytes can be labeled in whole blood (healthy and leukemia samples), and then a DLD microfluidic process can isolate, purify, and/or concentrate the Mab-labeled leukocytes from the mixture of blood and excess free Mab. In some cases, >99% erythrocyte depletion is achieved.

The devices, methods, compositions, and/or kits can prepare leukocytes (including leukemia cells in blood) for flow cytometry. In some cases, the devices, methods, compositions, systems, and/or kits provided herein are a general replacement for centrifugation in preparative procedures for diverse tests to be performed on samples. The diverse tests can be any test or downstream application as described herein. The samples can be any sample as provided herein (e.g., on blood leukocytes).

II. Particles

In some cases, a particle that can be chemically and/or enzymatically processed or treated, purified, isolated, and/or concentrated using methods, compositions, devices, systems, and/or kits described herein can be a cell, cellular fragment, or nucleic acid. In some cases, a particle is not a cell, cellular fragment, or nucleic acid, e.g., a particle is a bead.

A. Blood Components

In some cases, a particle is a blood component. In some cases, methods, compositions, devices, systems, and/or kits described herein can be used to process (e.g., chemically and/or enzymatically process or treat), purify or separate blood components, e.g., for blood banking. In some cases, a blood component comprises a platelet, red blood cell (erythrocyte), white blood cell (e.g, granulocytes, e.g, neutrophil, basophil, or eosinophil, or agranulocyte, e.g., lymphocyte, monocyte, or macrophage). In some cases, methods described herein can be used for leukocyte depletion from red blood cells or platelets (e.g., to replace leukocyte filters in processing of blood products for transfusion of patients). In some cases, methods described herein can be used for in-line leukocyte or platelet isolation (e.g., to replace centrifugal apheresis). In some cases, methods, compositions, devices, systems, and/or kits described herein can be used to deplete erythrocytes from a blood sample, e.g., an umbilical cord blood sample.

In some cases, a cell is a dendritic cell. In some cases, a cell is any cell of the innate or adaptive immune system.

B. Leukocytes (White Blood Cells)

In some cases, a cell processed (e.g., chemically and/or enzymatically processed or treated), purified, isolated, and/or concentrated using methods, compositions, devices, systems, and/or kits described herein is a leukocyte (white blood cell). A leukocyte can be, e.g, a neutrophil, eosinophil, basophil, lymphocyte, or monocyte. A leukocyte can be, e.g, a granulocyte or agranulocyte. In some cases, a granulocyte is a neutrophil, basophil, or eosinophil. In some cases, an agranulocyte is a lymphocyte, monocyte, or macrophage. A lymphocyte can be, e.g., a B-cell or a T-cell. A T-cell can be, e.g., a CD4+ T helper cell (e.g, $T_H1$, $T_H2$, $T_H3$, $T_H17$, $T_H9$, or $T_{FH}$), a CD8+ cytotoxic T-cell, a γδ T cell, a regulatory (suppressor) T-cell, a Natural Killer T (NKT) cell, an or antigen-specific T-cell, e.g., memory T cell, e.g., central memory T-cells, $T_{EM}$ cells, or $T_{EMRA}$ cell. In some cases, a lymphocyte is a Natural Killer (NK) cell. A B-cell can be a plasma B-cell, a memory B-cell, a B-1 cell, a B-2 cell, a marginal-zone B-cell, a follicular B-cell, or a regulatory B-cell. In some cases, a cell is a regulatory macrophage. In some cases, a cell is a plasmacytoid dendritic cell (pDC). In some cases, a cell is myeloid-derived suppressor cells (MD-SCs). In some cases, a cell is a megakarocyte.

In some cases, a leukocyte (white blood cell) can be identified by one or more cell surface markers. In some cases, a leukocyte (white blood cell) can be identified through the use of binding agents (e.g., antibodies, antibody fragments, probes, etc. as provided herein) to one or more cell surface markers (e.g., detecting the presence and/or absence of a label associated with the binding agent). The cell surface marker on a leukocyte (human or mouse) can be a transmembrane protein. The transmembrane protein can be a glycoprotein. In some cases, a transmembrane glycoprotein used to identify a leukocyte (e.g., human or mouse) is a cluster of differentiation (CD) transmembrane glycoprotein. The binding agent can comprise a label as provided herein. The label as provided herein can be detectable (e.g., fluorescence, etc.) The CD protein can be CD1a, 1b, 1c, 1d, 2, 3, 4, 5, 8, 10, 11a, 11b, 11c, 13, 14, 15, 16/32, 19, 20, 21/35 (CR2/CR1), 22, 23, 25, 26, 31, 33, 38, 39, 40, 44, 45RB, 45RA, 45R/B220, 49b (pan-NK cells), 49d, 52, 53, 54, 57, 62L, 63, 64, 66b, 68, 69, 70, 73, 79a (Igα), 79b (Igβ), 80, 83, 85g/ILT7, 86, 88, 93, 94, 103, 105 (Endoglin), 107a, 107 (Mac3), 114, 115, 117, 119, 122, 123, 124, 127, 129, 134, 137(4-1BB), 138 (Syndecan-1), 158 (Kir), 161, 163, 183, 184 (CXCR4), 191, 193 (CCR3), 194 (CCR4), 195, 195 (CCR5), 197, 197 (CCR7), w198 (CCR8), 203c, 205/Dec-205, 207 (Langerin), 209DC-SIGN), 223, 244 (2B4), 252 (OX40L), 267, 268 (BAFF-R), 273 (B7-DC, PD-L2), 278 (ICOS), 279/PD-1, 282 (TLR2), 289 (TLR9), 284 (TLR4), 294, 303, 304, 305, 314 (NKG2D), 319 (CRACC), 328 (Siglec-7), or 335 (NKp46). A leukocyte (white blood cell) cell surface marker can be, e.g., surface IgM, IgD, DC Marker (33D1), F4/80, CMKLR-1, HLA-DR, Siglex H, MHC Class II, LAP (TGF-b), GITR, GARP, FR4, CTLA-4, TRANCE, TNF-β, TNF-α, Tim-3, LT-βR, IL-18R, CCR1, TGF-β, IL-R, CCR6, CCR4, CRTH2, IFN-γR, Tim-1, Vα24-Jα18 TCR (iNKT), Ly108, Ly49, CD56 (NCAM), TCR-α/β, TCR-γ/δ, CXCR1, CXCR2, GR-1, JAML, TLR2, CCR2, Ly-6C, Ly-6G, F4/80, VEGFR1, C3AR, FcεRIα, Galectin-9, MRP-14, Siglec-8, Siglec-10. TLR4, IgE, GITRL, HLA-DR, ILT-3, Mac-2 (Galectin-3). CMKLR-1, or DC Marker (33D1).

In some cases, a leukocyte (white blood cell) can be identified by one or more intracellular markers. A leukocyte (white blood cell) intracellular marker can be, e.g., Pax-5, Helios, FoxP3, GM-CSF, IL-2, IFN-γ, T-bet, IL-21, IL-17A, IL-17F, IL-22, RORγt, RORα, STAT3, IL-10, IL-13, IL-5, IL-4, IL-6, GATA3, c-Maf, Granzyme B, Perforin, or Granulysin.

In some cases, the devices, method, compositions, systems, and/or kits provided herein can be used to differentiate between mature and immature B and T cells. As provided herein, differentiation or identification of the presence (e.g., positive), absence (e.g., negative) and/or a combination thereof a marker as provided herein can be determined through the use of a binding agent specific for or directed to or against the marker (e.g., cell surface and/or intracellular). The binding agent can be any binding agent known in the art (e.g., antibody, antibody fragment, probe (e.g., nucleic acid probe), etc.). The binding agent can comprise a label as provided herein. The label as provided herein can be detectable (e.g., fluorescence, etc.). Differentiation between mature and immature T cells can be performed by identifying the presence (e.g., positive), absence (e.g., negative) and/or a combination thereof of CD3, 4, 8, 25, 44, 117, 127, and TCR-α/β, TCR-γ/δ markers (e.g., detecting the presence and/or absence of a label associated with a binding agent). Differentiation between mature and immature Treg cells can be performed by identifying the presence (e.g., positive), absence (e.g., negative) and/or a combination thereof of CD3, 4, 8, 25, 40, 44, 45RA, 45RB, 62L, 117, 127, 134 (OX40), 137 (4-1BB), 197, 199 (CCR9), 223 (LAG-3), Integrin α4, Integrin β7, 304 (Neuropilin), 357(GITR), CTLA-4, Foxp3, GARP, IL-10, IL-15Rα, LAP (TGFβ) and TCR-α/β markers. Differentiation between mature and immature mouse B cells can be performed by identifying the presence (e.g., positive), absence (e.g., negative) and/or a combination thereof of CD2, 11b, 16/32. 19, 21/35, 23, 22, 24 (HAS), 43, 45R (B220), 93 (AA4.1), 117, 127, BP-1, cμ, sμ, λ5, IgD, IgM, markers. Differentiation between mature and immature human B cells can be performed by identifying the presence (e.g., positive), absence (e.g., negative) and/or a combination thereof of CD9, 19, 20, 23, 24 (HSA), 27, 28, 31, 34, 38, 40, 45R (B220), 95 (FAS), 150 (SLAM), 184 (CXCR4), IgD, IgM, IgA, IgG markers. Differentiation between mature and immature human or mouse dendritic cells can be performed by identifying the presence (e.g., positive), absence (e.g., negative) and/or a combination thereof of CD3, 11b, 11c, 14, 16, 19, 34, 49b, 68, 80, 86, 107b (Mac-3), 115, 117, 123, 127, 135, 303 (BDCA-2), CXCR1, F4/80, Ly6C, Ly6G, Gr-1, MHC II, NKp46, Sca-1, Ter119, iNOS, TNFα, markers. Differentiation between mature and immature human or mouse monocytes/macrophages can be performed by identifying the presence (e.g., positive), absence (e.g., negative) and/or a combination thereof of CD3, 11b, 11c, 13, 14, 16, 19, 33, 34, 43, 45, 62L, 68, 115, 117, 123, 127, 135, 163, 204, 206, CCR2, CCR5, CX3CR1, F4/80, LysA/E, Tie-2, Lys6B.2, Ly6C, Ly6G, Gr-1, MHC II, NKp46, Sca-1, Ter119, or VEGFR1 markers. Differentiation between mature and immature human and mouse macrophage subclasses can be performed by the presence (e.g., positive), absence (e.g., negative) and/or a combination thereof of a number of proteins including CD14, CD11b, 16, 32, 51/61. 64, 68, 86, 121a, 121b, 124, 150, 163, 181, 182, 206, 210, 215, CCLs 1, 2, 3, 4, 5, 8, 15, 16, 18, 20, 24, CCR2, CCR7, CXCLs, 8, 9, 10, 11, 13, 16, IFNγ, IL-RA, IL-1β, IL-6, IL-10, IL-12, IL-15, IL-23, iNOS, Ly6C, MHC II (human and mouse), TNF-α, Dectin-1, FcεR1α, Lectins, RAGE, Scavenger Receptor, Arginase, or LAP (TGFβ) markers.

In some cases, the devices, method, compositions, systems, and/or kits provided herein can be used to differentiate between or identify subsets of leukocytes (white blood cells). Differentiation or identification of subsets of leukocytes (white blood cells) can be through treating a sample comprising particles (e.g., leukocytes) with one or more binding agents as described herein specific for or directed to or against one or more of the markers (e.g., cell surface or intracellular markers). The binding agent can comprise a label as provided herein. The label as provided herein can be detectable (e.g., fluorescence, etc.) Subsets of leukocytes (white blood cells) can be differentiated from other leukocytes through identifying the presence (e.g., positive), absence (e.g., negative), and/or combinations of leukocyte-type specific intracellular markers (e.g., detecting the presence and/or absence of a label associated with a binding agent). Subsets of leukocytes (white blood cells) can be differentiated from other leukocytes through identifying the presence (e.g., positive), absence (e.g., negative), and/or combinations of leukocyte-type specific markers. For example, Th2 cells can be identified by the transcription factor GATA3 and the cytokines: IL-4, IL-5, IL-6, IL-10, and IL-13. Th17 cells can be identified by intracellular RORγt and STAT3 and production of cytokines: IL-17A, IL-17F, IL-21 and IL-22. Th1 cells can be identified by the transcription factor T-bet and cytokines: IL-2, IFN-γ, and TNF. A megakaryocyte can be identified by GM-CSF, IL-3, IL-6, IL-11, chemokines (SDF-1; FGF-4), and erythropoietin. NK can be identified by the presence (e.g., positive), absence (e.g., negative) and/or a combination thereof of cell surface markers CD16 (FcγRIII) and CD56 in humans, NK1.1 or NK1.2 in C57BL/6 mice, while they do not express T-cell antigen receptors (TCR) or Pan T marker CD3 or immunoglobulins (Ig) B cell receptors, which are found on T and B cells. Up to 80% of human NK cells can express CD8. They are distinct from Natural Killer T cells, which can express CD3. In humans, pDCs express the surface markers CD123, BDCA-2(CD303) and BDCA-4(CD304), but do not express CD11c or CD14, which distinguishes them from conventional dendritic cells or monocytes, respectively. Mouse pDC express CD11c, B220, BST-2 (mPDCA) and Siglec-H and are negative for CD11b. T regulatory cells can be characterized or identified by the presence (e.g., positive), absence (e.g., negative) and/or a combination thereof of CD4, CD25, and Foxp3, while lacking CD127. CD4+Foxp3+ regulatory T cells have been referred to as "naturally-occurring" regulatory T cells to distinguish them from "suppressor" T cell populations that are generated in vitro. While other variants of suppressive T cells do exist, such as CD8 suppressor cells, Th3 and Tr-1 cells, Tregs are classically defined as CD4+CD25+FOXP3+ cells. Macrophages can be identified by specific expression of a number of proteins including CD14, CD11b, F4/80 (mice)/EMR1 (human), MAC-1/MAC-3 and CD68. Myeloid-derived suppressor cells (MDSCs) are a heterogeneous population of cells that have potent T cell-suppressive function, characterized by an activated state with increased production of reactive oxygen and nitrogen species, and arginase 1. In mice, MDSCs can be identified by CD11b+GR1+, while in humans, MDSCs can be identified by LIN-HLA-DR-CD33+ or CD11b+CD14−CD33+. Th17 cells can be identified using cell surface markers for CD4, CD161 and CCR6.

C. Stem Cells

In some cases, a cell processed (e.g., chemically or enzymatically processed or treated), purified, isolated, and/or concentrated using methods, compositions, devices, systems, and/or kits described herein is a stem cell. In some cases, the stem cell is an adult stem cell (somatic stem cell). In some cases, an adult stem cell is a hematopoietic stem cell (HSC) or hematopoietic progenitor cell (HPC). In some cases, a HSC is from bone marrow (e.g., bone marrow of pelvis, femur, or sternum). In some cases, an HSC is in a cord blood sample, e.g., umbilical cord blood. In some cases, an HSC is from placenta. In some cases, granulocyte-colony stimulating factor (G-CSF) is administered to a subject; G-CSF can induce HSCs to leave bone marrow and circulate in blood vessels. In some cases, an HSC is in peripheral blood (e.g., G-CSF mobilized adult peripheral blood). In some cases, a stem cell is a long-term stem cell or a short-term progenitor cell. In some cases, stem cells are used for ex vivo expansion, and the products of ex vivo expansion are purified using methods and devices described herein. In some cases, a stem cell is derived from adipose tissue (adipose-derived stem cells (ASCs)). In some cases, stem cells are derived from a collengase digest of adipose tissue.

In some cases, a HSC (e.g., undifferentiated HSC) can be identified by one or more cell surface markers. In some cases, characterizing or identifying a HSC (e.g., undifferentiated HSC) comprises identifying the presence (e.g., positive), absence (e.g., negative), and/or combinations of one or more cell surface markers. The identifying can be through treating a sample comprising particles (e.g., HSCs) with one or more binding agents as described herein specific for or directed to or against one or more of the markers (e.g., cell surface). The binding agent can comprise a label as provided herein. The label as provided herein can be detectable (e.g., fluorescence, etc.). The identification can be through identifying the presence (e.g., positive), absence (e.g., negative), and/or combinations of the markers (e.g., detecting the presence and/or absence of a label associated with a binding agent). The marker can be a cell surface or an intracellular marker. The binding agent can be any binding agent known in the art (e.g., antibody, antibody fragment, probe (e.g., nucleic acid probe), etc.). A cell surface marker on a HSC can be a cluster of differentiation (CD) transmembrane glycoprotein. The CD can be CD 10, 31, 34, 38, 44, 45, 59, 84, 90, 93 (C1Rqp), 105 (Endoglin), 110, 111, 117 (c-Kit), 133, 135 (Flk-2), 150 (SLAM), 184 (CXCR4), 202b (Tie2/Tek), 243 9MDR-1), 271 (NGFR), 309 (VEGFR2), 338. A cell surface marker on a HSC can be a Hematopoietic Stem Cell Marker, VEGF Receptor 2, CXCR4, Angiotensin Converting Enzyme 1, BCRP/ABCG2, Ly-6A/E (Sca-1). A human HSC cell surface marker can be, e.g., CD34+, CD59+*, Thy1$^+$, CD38$^{low/-}$, C-kit$^{-/low}$, or lin$^-$. A mouse HSC cell surface marker can be, e.g., CD34low/−, SCA-1+, Thy1$^{+/low}$, CD38+, C-kit+, or lin−. An intracellular marker can be e.g., ATF2, GATA1, GATA2, GFI1, or RUNX1/AML1.

An HSC can give rise to blood cells, e.g., red blood cells, B lymphocytes, T lymphocytes, natural killer cells, neutrophils, basophils, eosinophils, monocytes, and macrophages.

An adult stem cell (somatic stem cell) can be an HSC, a mesenchymal stem cell, a neural stem cell, an epithelial stem cell, or a skin stem cell. In some cases, a stem cell is a mesenchymal stem cell. A mesenchymal stem cell can give rise to, e.g., bone cells (osteocytes), cartilage cells (chondrocytes), fat cells (adipocytes), and other kinds of connective tissue cells such as those in tendons.

In some cases, a stem cell is neural stem cell. A neural stem cell can be found in a brain. A neural stem cell can give rise to, e.g., nerve cells (neurons) and two categories of non-neuronal cells, e.g., astrocytes and oligodendrocytes. In some cases, the devices, method, compositions, systems, and/or kits provided herein can be used to identify a neural stem cell. Identification of a neural stem cell can be through treating a sample comprising particles (e.g., neural stem cell) with one or more binding agents as described herein specific for or directed to or against one or more markers (e.g., cell surface or intracellular markers) expressed by neural stem cells. The binding agent can comprise a label as provided herein. The label as provided herein can be detectable (e.g., fluorescence, etc.). The identification can be through identifying the presence (e.g., positive), absence (e.g., negative), and/or combinations of the markers (e.g., detecting the presence and/or absence of a label associated with a binding agent). The markers can be cell surface markers, e.g., CD 15, 24, or 184. The markers can be intracellular markers, e.g., Nestin, Pax6, Sox1, or Sox2.

In some cases, a stem cell is an intestinal epithelial stem cell. An intestinal epithelial stem cell can line the digestive tract and can occur in deep crypts. An intestinal epithelial stem cell can give rise to absorptive cells, goblet cells, paneth cells, and/or enteroendocrine cells. In some cases, the devices, method, compositions, systems, and/or kits provided herein can be used to identify an intestinal epithelial stem cell. Identification of an intestinal epithelial cell can be through treating a sample comprising particles (e.g., an intestinal epithelial stem cell) with one or more binding agents as described herein specific for or directed to or against one or more markers (e.g., cell surface or intracellular markers) expressed by an intestinal epithelial stem cells. The binding agent can comprise a label as provided herein. The label as provided herein can be detectable (e.g., fluorescence, etc.). The identification can be through identifying the presence (e.g., positive), absence (e.g., negative), and/or combinations of the markers (e.g., detecting the presence and/or absence of a label associated with a binding agent). The markers can be cell surface or intracellular markers known in the art. The markers can be, e.g., CD 44, ICAM-1/CD54, CD34, Lrig1, Lgr5, Bmi1, Tert, or Hopx.

In some cases, a stem cell is skin stem cell. A skin stem cell can occur in the basal layer of epidermis and at the base of hair follicles. An epidermal stem cell can give rise to keratinocytes, which can migrate to the surface of the skin and form a protective layer. Follicular stem cells can give rise to both the hair follicle and to the epidermis. In some cases, the devices, method, compositions, systems, and/or kits provided herein can be used to identify a skin stem cell. Identification of a skin stem cell can be through treating a sample comprising particles (e.g., skin stem cell) with one or more binding agents as described herein specific for or directed to or against one or more markers (e.g., cell surface or intracellular markers) expressed by skin stem cells. The binding agent can comprise a label as provided herein. The label as provided herein can be detectable (e.g., fluorescence, etc.). The identification can be through identifying the presence (e.g., positive), absence (e.g., negative), and/or combinations of the markers (e.g., detecting the presence and/or absence of a label associated with a binding agent). The markers can be cell surface or intracellular markers known in the art. The markers can be, e.g., CD 34, K15, Nestin, Follistatin, p63, Integrin alpha 6, Tenascin C, EGFR, IGFR, Delta 1, TBRII, or Frizzled factors.

In some cases, a stem cell is an embryonic stem (ES) cell. An embryonic stem cell can be derived from embryos that develop from an egg that has been fertilized in vitro. In some cases, an embryonic stem is a human embryonic stem cell. In some cases, a stem cell is an induced pluripotent stem cell (iPSC). An iPSC can be a somatic cell that is genetically reprogrammed to an embryonic stem cell-like state. In some cases, a stem cell is an undifferentiated stem cell. In some cases, a stem cell is cancer stem cell. In some cases, the devices, method, compositions, systems, and/or kits provided herein can be used to identify an ES cell. Identification of an ES cell can be through treating a sample comprising particles (e.g., ES cell) with one or more binding agents as described herein specific for or directed to or against one or more markers (e.g., cell surface or intracellular markers)

expressed by ES cells. The binding agent can comprise a label as provided herein. The label as provided herein can be detectable (e.g., fluorescence, etc.). The identification can be through identifying the presence (e.g., positive), absence (e.g., negative), and/or combinations of the markers (e.g., detecting the presence and/or absence of a label associated with a binding agent). The markers can be cell surface markers, e.g., CD 9, 15 (SSEA-1), 49f, 24, 29, 324, 338, SSEA-3, SSEA-4, SSEA-5, TRA-1-81, TRA-1-60, TRA-2-49, or TRA-2-54. The markers can be an intracellular marker, e.g., c-Myc, Nanog, FOXD3, OCT3/4. Stat-3, or Sox2.

In some cases, the devices, method, compositions, systems, and/or kits provided herein can be used to identify a mesenchymal stem cell. Identification of a mesenchymal stem cell can be through treating a sample comprising particles (e.g., mesenchymal stem cell) with one or more binding agents as described herein specific for or directed to or against one or more markers (e.g., cell surface or intracellular markers) expressed by mesenchymal stem cells. The binding agent can comprise a label as provided herein. The label as provided herein can be detectable (e.g., fluorescence, etc.). The identification can be through identifying the presence (e.g., positive), absence (e.g., negative), and/or combinations of the markers (e.g., detecting the presence and/or absence of a label associated with a binding agent). The markers can be cell surface markers, e.g., CD 10, 13, 29, 31, 44, 45RO, 49a, 49e, 51, 54, 56, 73, 90, 105 (Endoglin), 106 (VCAM-1), 117 (c-kit), 166 (ALCAM), 349 (Frizzled-9), TfR, BMPRs-IA, IB, and II, N-cadherin, SSEA-4, STRO-1, Sca-1/Ly6, PDGF R alpha, HLA class I, Carcino Embryonic Antigen, Integrin 5α, Integrin β1, p75, NGF Receptor, Sprouty 2, or TNAP. The markers can be intracellular markers, e.g., Bone alkaline phosphatase, dbx2, Flightless 1, KLF5, Spi1, Tafazzin, nucleotstemin, or vimentin.

D. Other Particles

In some cases, a particle that can be processed (e.g., chemically and/or enzymatically processed or treated), purified, isolated, and/or concentrated using methods, compositions, devices, systems, and/or kits described herein can be a cancer cell, a circulating tumor cell (CTC), an epithelial cell, a circulating endothelial cell (CEC), a circulating stem cell (CSC), or cancer stem cells. In some cases, a particle is a bone marrow cell, progenitor cell foam cell, fetal cell, mesenchymal cell, circulating epithelial cell, circulating endometrial cell, trophoblast, immune system cell (host or graft), connective tissue cell, bacterium, fungus, virus, protozoan, algae, or plant cell. In some cases, a particle is a microparticle.

In some cases, a particle is a cellular fragment. In some cases, a cellular fragment is a protein. In some cases, a protein is an antibody, or antibody fragment. In some cases, a cellular fragment is a T-cell receptor. In some cases, a protein is an immunoglobulin. In some cases, a particle is a polypeptide.

In some cases, a particle is a rare cell, e.g., a cell type with an abundance of less than 1000 in a one mL sample, e.g., circulating tumor cells (CTCs), circulating fetal cells, stem cells, or cells infected by a virus or parasite. If sample is a water sample, a rare cell can be a pathogenic bacterium or cell infected with a virus.

In some cases, a cellular fragment is a nucleic acid. A nucleic acid can be, e.g., DNA or RNA. DNA can be genomic DNA, mitochondrial DNA, and/or cell-free DNA. RNA can be, e.g., messenger RNA (mRNA), ribosomal RNA (rRNA), transfer RNA (tRNA), signal recognition particle RNA, small nuclear RNA, small nucleoar RNA, SmY RNA, small cajal body-specific RNA, telomerase RNA, spliced leader RNA, antisense RNA, CRISPR RNA, long noncoding RNA (long ncRNA), microRNA (miRNA), short interfering RNA (siRNA), short hairpin RNA (shRNA), trans-acting siRNA, repeat associated siRNA, and/or cell-free RNA. In some cases, a nucleic acid is double stranded. In some cases, a nucleic acid is single stranded. In some cases, a nucleic acid comprises one or two overhangs. In some cases, a nucleic acid comprises a 5' overhang. In some cases, a nucleic acid comprises a 3' overhang. In some cases, the nucleic acid comprises "high molecular weight" nucleic acid. In some cases, a nucleic acid is a low molecular weight nucleic acid. In some cases, the nucleic acid is intranuclear, intracellular, or extracellular.

The term "polynucleotide", "nucleic acid", or grammatical equivalents, can refer to two or more nucleotides covalently linked together. A nucleic acid described herein can contain phosphodiester bonds, although in some cases, as outlined below (for example in the construction of primers and probes such as label probes), nucleic acid analogs are included that can have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid (also referred to herein as "PNA") backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with bicyclic structures including locked nucleic acids (also referred to herein as "LNA"), Koshkin et al., J. Am. Chem. Soc. 120.13252 3 (1998); positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169 176). Several nucleic acid analogs are described in Rawls, C & E News Jun. 2, 1997 page 35. "Locked nucleic acids" are also included within the definition of nucleic acid analogs. LNAs can be a class of nucleic acid analogues in which the ribose ring is "locked" by a methylene bridge connecting the 2'-O atom with the 4'-C atom. All of these references are hereby expressly incorporated by reference.

These modifications of the ribose-phosphate backbone can be done to increase the stability and half-life of such molecules in physiological environments. For example, PNA:DNA and LNA-DNA hybrids can exhibit higher stability and thus can be used in some embodiments. Nucleic acids can be single stranded or double stranded, as specified, or contain portions of both double stranded or single stranded sequence. Depending on the application, the nucleic acids can be DNA (including, e.g., genomic DNA, mitochondrial DNA, and cDNA), RNA (including, e.g., mRNA and rRNA) or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

In some cases, a cellular fragment is a membrane, cellular organelle, nucleosome, exosome, or nucleus. In some cases, a cellular fragment is a mitochondria, rough endoplasmic reticulum, ribosome, smooth endoplasmic reticulum, chloroplast, golgi apparatus, golgi body, glycoprotein, glycolipid, cisternae, liposome, peroxisome, glyoxysome, centriole, cytoskeleton, lysosome, cilia, flagellum, contractile vacuole, vesicle, nuclear envelope, vacuole, cell membrane, microtubule, nucleolus, plasma membrane, or chromatin.

One or more particles described herein can be in a sample. In some cases, one or more different types of particles described herein can be in a sample.

E. Particle Sizes

In some cases, a particle processed (e.g., chemically processed or treated), purified, isolated, and/or concentrated using methods, compositions, devices, systems, and/or kits described herein has a predetermined particle size (or critical particle size). In some cases, particles with a size at least that of a predetermined particle size are directed to a first outlet in a device, whereas particles less than a predetermined are directed to a second outlet in a device. In some cases, particle size is a diameter of a particle.

In some cases, a particle size is at least 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15, 5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1000 μm.

In some cases, a particle size is about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15, 5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1000 μm.

In some cases, a particle size is less than 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15, 5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1000 μm.

In some cases, a particle size is about 0.1 to about 1 μm, about 1 to about 5 μm, about 5 to about 10 μm, about 10 to about 15 μm, about 10 to about 20 μm, about 10 to about 25 μm, about 15 to about 25 μm, about 20 to about 30 μm, about 30 to about 40 μm, about 40 to about 50 μm, about 50 to about 60 μm, about 60 to about 70 μm, about 70 to about 80 μm, about 80 to about 90 μm, or about 90 to about 100 μm, about 100 to about 200 μm, about 200 to about 300 μm, about 300 to about 400 μm, about 400 to about 500 μm, about 500 to about 600 μm, or about 500 to about 1000 μm.

In some cases, where a particle is polynucleotide, the polynucleotide comprises at least 2, 5, 10, 20, 30, 40, 50, 60, 70, 80, 90, 100, 150, 200, 250, 300, 350, 400, 450, 500, 600, 700, 800, 900, 1000, 1500, 2000, 3000, 4000, 5000, 6000, 7000, 8000, 9000, 10,000, 20,000, 30,000, 40,000, 50,000, 60,000, 70,000, 80,000, 90,000, or 100,000 bases.

In some cases, where a particle is a polynucleotide, the polynucleotide comprises about 2, 5, 10, 20, 30, 40, 50, 60, 70, 80, 90, 100, 150, 200, 250, 300, 350, 400, 450, 500, 600, 700, 800, 900, 1000, 1500, 2000, 3000, 4000, 5000, 6000, 7000, 8000, 9000, 10,000, 20,000, 30,000, 40,000, 50,000, 60,000, 70,000, 80,000, 90,000, 100,000, 500,000, 1,000, 000, 5,000,000, or 10,000,000 bases. In some cases, a polynucleotide is a whole chromosome. In some cases, a polynucleotide is a human chromosome 1, 2, 3, 4, 5, 6, 7, 8, 9, 10, 11, 12, 13, 14, 15, 16, 17, 18, 19, 20, 21, 22, X or Y.

In some cases, where a particle is a polynucleotide, the polynucleotide comprises less than 2, 5, 10, 20, 30, 40, 50, 60, 70, 80, 90, 100, 150, 200, 250, 300, 350, 400, 450, 500, 600, 700, 800, 900, 1000, 1500, 2000, 3000, 4000, 5000, 6000, 7000, 8000, 9000, 10,000, 20,000, 30,000, 40,000, 50,000, 60,000, 70,000, 80,000, 90,000, 100,000, 500,000, 1,000,000, 5,000,000, or 10,000,000 bases.

In some cases, a polynucleotide comprises about 10 to about 100 bases, about 50 to about 100 bases, about 100 to about 200 bases, about 500 to about 1000 bases, about 1000 to about 2000 bases, about 2000 to about 5000 bases, about 5000 to about 10,000 bases, about 10,000 to about 50,000 bases, or about 50,000 to about 100,000 bases.

III. Samples

Particles from samples can be processed (e.g., chemically or enzymatically processed or treated), purified, isolated, and/or concentrated using the methods, compositions, devices, systems, and/or kits described herein.

A. Types of Samples

In some cases, a sample is a biological sample. In some case, the biological sample is blood. The blood sample can be, e.g., peripheral blood, maternal blood, G-CSF mobilized adult peripheral blood, or cord blood. Cord blood can be, e.g., umbilical cord blood, or placental cord blood.

In some cases, a biological sample is serum, plasma, sweat, tears, ear flow, sputum, synovial fluid, lymph, bone marrow suspension, urine, saliva, semen, vaginal flow or secretion, cerebrospinal fluid, feces, cervical lavage, sebum, semen, prostatic fluid, Cowper's fluid, pre-ejaculatory fluid, female ejaculate, brain fluid (e.g., cerebrospinal fluid), ascites, milk (e.g., breast milk), cerumen, secretions of the respiratory, intestinal or genitourinary tract, broncheoalveolar lavage fluid, amniotic fluid, aqueous humor, and water samples). A sample can be fluids into which cells have been introduced (for example, culture media and liquefied tissue samples). A sample can be a lysate. A biological sample can be hair, cyst fluid, pleural fluid, peritoneal fluid, pericardial fluid, lymph, chyme, chyle, bile, interstitial fluid, menses, pus, sebum, mucosal secretion, stool water, pancreatic juice, lavage fluid from sinus cavities, bronchopulmonary aspirate, or blastocyl cavity fluid. A biological sample can be a tissue sample or biopsy. A fluid sample from an organism or one that has been solubilized can be at least 1, 2, 3, 4, 5, 6, 7, 7.5, 8, 9, 10, 20, 50, 75, 100, 200, 500, 1000 or 1500 mL.

In some cases, a biological sample is from an animal, e.g., human, mouse, rat, cat, dog, cow, chicken, donkey, rabbit, chimpanzee, gorilla, orangutan, horse, guinea pig, pig, or rhesus monkey.

In some cases, a biological sample is from a plant. In some cases, a biological sample comprises a plant.

In some cases, a biological sample is from a fungus. In some cases, a biological sample comprises a fungus.

In some cases, a sample comprises leukocytes and erythrocytes.

In some cases, a sample comprises cells. In some cases, a sample comprises dead cells, and/or debris. The methods, compositions, devices, systems, and/or kits described herein can be used for size-based removal of debris and/or dead cells from a sample comprising cells. In some cases, the methods, compositions, devices, systems, and/or kits described herein can be used for cell wash procedures. In some cases, the sample is a cell culture sample. In some cases, the methods, compositions, devices, systems, and/or kits described herein can be used to process (e.g., chemically and/or enzymatically process or treat), isolate, purify, and/or concentrate cells from other components in a cell culture sample, e.g., medium, growth factors, etc.

In some cases, a sample comprises a buffer. The buffer can be free or substantially free of a reagent. In some cases, the methods, compositions, devices, systems, and/or kits described herein can be used for buffer/medium exchange.

In some cases, a sample comprises enzyme digested adipose tissue. In some cases, the enzyme digested adipose tissue is a source for autologous progenitor cells. In some cases, the methods, compositions, devices, systems, and/or kits described herein can be used to clean-up enzyme (e.g. collagenase) digested adipose tissue as a source for autologous progenitor cells, e.g., purify stem cells from the enzyme digested adipose tissue.

In some cases, a sample comprises cancer cells from tumors. In some cases, the methods, compositions, devices, systems, and/or kits described herein can be used to process (e.g., chemically process or treat), isolate, purify, and/or concentrate cancer cells from tumors.

In some cases, a sample comprises infiltrating or stromal host cells from a tumor. In some cases, the methods, compositions, devices, systems, and/or kits described herein can be used to process (e.g., chemically and/or enzymatically process or treat), isolate, purify, and/or concentrate infiltrating cells or stromal host cells from a tumor. For example, tumor-infiltrating lymphocytes can be white blood cells that have left the bloodstream and migrated to a tumor. Stromal cells can be connective tissue. Stromal cells can provide an extracellular matrix on which tumors can grow.

In some cases, a sample is an industrial sample. In some cases, the methods, compositions, devices, systems, and/or kits described herein can be used to process (e.g., chemically and/or enzymatically process or treat), isolate, purify, and/or concentrate particles in an industrial sample.

In some cases, a sample comprises algae, yeast, bacteria, or a virus. In some cases, methods, compositions, devices, systems, and/or kits described herein can be used to process (e.g., chemically and/or enzymatically process or treat), isolate, purify, and/or concentrate algae, yeast, bacteria, and/or a virus. For example, a sample with yeast can be a beer production sample. Methods, compositions, devices, systems, and/or kits described herein can be used to process (e.g., chemically and/or enzymatically process or treat), isolate, purify, and/or concentrate yeast from the sample from a beer production sample.

In some cases, a sample comprises an antibody. In some cases, methods, compositions, devices, systems, and/or kits described herein can be used to process (e.g., chemically and/or enzymatically process or treat), isolate, purify, and/or concentrate and antibody from a sample comprising an antibody.

In some cases, a sample comprises plants, mitochondria, lentivirus, exosomes, or dividing cells. Methods, compositions, devices, systems, and/or kits described herein can be used to process (e.g., chemically and/or enzymatically process or treat), isolate, purify, and/or concentrate plants, mitochondria, lentivirus, exosomes, or dividing cells from the sample.

In some cases, a sample comprises cells at different stages in the cell cycle, G0 (Gap 0/Resting), G1 (Gap 1), S (Synthesis), M (Mitosis), or G2 (Gap 2). Cells can have different sizes at different stages of the cell cycle. In some cases, the methods and devices described herein are used to separate cells at different stages of the cell cycle.

In some cases, a sample is from a body of water. A body of water can be, e.g., from a creek, pond, river, ocean, lake, sea, puddle, stream canal, wetland, marsh, reservoir, harbor, bay, artificial lake, barachois, basin, bayou, beck, bight, billabong, boil, brook, burn, channel, cove, draw, estuary, firth, fjord, glacier, gulf, inlet, kettle, kill, lagoon, loch, mangrove swamp, Mediterranean sea, mere, mill pond, moat, oxbow lake, phytotelma, pool (swimming pool, reflecting pool), pothole, rapid, roadstead, run, salt marsh, sea loch, sea lough, source, spring, strait, stream, subglacial, lake, swamp, tarn, tide pool, vernal pool, wash, or wetland. A water sample can be a ballast tank washing, e.g., from a transport vessel (see, e.g., //news.sciencemag.org/biology/2015/01/tests-used-ensure-ships-don-t-carry-deadly-cargo-draw-sharp-criticism).

In some cases, a sample is from a bioterror attack. In some cases, a sample from a bioterror attack comprises a virus, e.g., smallpox virus or influenza virus. In some cases, a sample from a bioterror attack comprises anthrax. In some cases, a sample from a bioterror attack comprises more than one type of infective agent.

In some cases, the methods described herein are used purify viruses from cells, e.g., a lentivirus. Examples of lentivirus include human immunodeficiency virus (HIV), simian immunodeficiency virus, feline immunodeficiency virus, puma lentivirus, equine infectious anemia virus, bovine immunodeficiency virus, caprine arthritis encephalitis virus, or Visna virus. In some cases, a virus can be purified away from cells and/or cellular debris.

In some cases, a sample is from a hospital or other medical health care facility. In some cases, a sample is from a wastewater treatment facility. In some cases, a sample is from an algal biofuel production facility. In some cases, a sample is from a brewery. In some cases, a sample is from a public water system. In some cases, a sample is from a sewage system.

In some cases, a sample is from a chemical spill. In some cases, a sample is from a mine, e.g., coal mine. In some cases, a sample is an archeological sample. In some cases, a sample is a forensic sample.

In some cases, the erythrocytes in samples are not lysed. In some cases, erythrocytes in samples are lysed.

In some cases, a sample comprises one or more labels. In some cases, a sample comprises at least 2, 3, 4, 5, 6, 7, 8, 9, 10, 11, 12, 13, 14, 15, 16, 17, 18, 19, or 20 different labels. In some cases, a label is an antibody, antibody fragment, dye, stain (e.g., ethidium bromide), nucleic acid adapter, radioactive particle, fluorescent particle, oligonucleotide, probe, or fluorescently-labeled probe. In some cases, a label is bound, linked, or conjugated to an antibody, antibody fragment, dye, stain (e.g., ethidium bromide), nucleic acid adapter, radioactive particle, fluorescent particle, oligonucleotide, probe, or fluorescently-labeled probe. In some cases, a device, method, composition, system, and/or kit as provided herein process a particle (e.g., cell) such that the particle (e.g., cell) comprises a first label and a second label. The first and second label can be different labels. The first label can be bound, conjugated, or linked to a binding agent as provided herein directed to a marker of the surface of the particle (e.g. cell surface marker), while the second label can be bound, conjugated, or linked to binding agent as provided herein directed to a marker in the interior of the particle (e.g., intracellular marker). The label can be any label as provided herein.

In some cases, a sample comprises an enzyme, e.g., a restriction enzyme, kinase (e.g., DNA kinase (e.g., T4 polynucleotide kinase), protein kinase, e.g., serine kinase, threonine kinase, tyrosine kinase), DNase, RNase, phosphatase, ligase (e.g., RNA ligase, DNA ligase), horseradish peroxidase (HRP), alkaline phosphatase (AP), glucose oxidase, polymerase (e.g., DNA polymerase (e.g., thermostable DNA polymerase, Taq polymerase) RNA polymerase), terminal deoxynucleotidyl transferase, reverse transcriptase (e.g., viral reverse-transcriptase, non-viral reverse transcriptase), telomerase, methylase, or topoisomerase. In some cases, methods and/or device used herein can be used to separate a label or enzyme from another component of a sample, e.g., a polynucleotide or cell.

B. Number of Particles/Numbers of Different Types of Particles in a Sample

A sample can comprise one or more first particles. In some cases, a sample can comprise at least 1, 2, 3, 4, 5, 6, 7, 8, 9, 10, 50, 100, 500, 1000, 10,000, 100,000, 1,000,000, 10,000,000, 100,000,000, 1,000,000,000, 10,000,000,000, 100,000,000,000, or 1,000,000,000,000 first particles. A sample can comprise about 1, 2, 3, 4, 5, 6, 7, 8, 9, 10, 50, 100, 500, 1000, 10,000, 100,000, 1,000,000, 10,000,000, 100,000,000, 1,000,000,000, 10,000,000,000, 100,000,000,000, or 1,000,000,000,000 first particles. In some cases, a sample comprises about 10 to about 100 first particles, about 5 to about 10 first particles, about 10 to about 50 first particles, about 50 to about 100 first particles, about 100 to about 1000 first particles, about 1000 to about 10,000 first particles, about 10,000 to about 100,000 first particles, about 100,000 to about 1,000,000 first particles, about 1,000,000 to about 10,000,000 first particles, about 10,000,000 to about 100,000,000 first particles, about 100,000,000 to about 1,000,000,000 first particles, about 1,000,000,000 to about 10,000,000,000 first particles, about 10,000,000,000 to about 100,000,000,000 first particles, or about 100,000,000,000 to about 1,000,000,000,000 first particles.

In some cases, a sample comprises at least 1, 2, 3, 4, 5, 6, 7, 8, 9, 10, 50, 100, 500, 1000, 10,000, 100,000, 1,000,000, 10,000,000, 100,000,000, 1,000,000,000, 10,000,000,000, 100,000,000,000, or 1,000,000,000,000 total particles. A sample can comprise about 1, 2, 3, 4, 5, 6, 7, 8, 9, 10, 50, 100, 500, 1000, 10,000, 100,000, 1,000,000, 10,000,000, 100,000,000, 1,000,000,000, 10,000,000,000, 100,000,000,000, or 1,000,000,000,000 first particles, In some cases, a sample comprises about 10 to about 100 total particles, about 5 to about 10 total particles, about 10 to about 50 total particles, about 50 to about 100 total particles, or about 100 to about 1000 total particles, about 1000 to about 10,000 total particles, about 10,000 to about 100,000 total particles, about 100,000 to about 1,000,000 total particles, about 1,000,000 to about 10,000,000 total particles, about 10,000,000 to about 100,000,000 total particles, about 100,000,000 to about 1,000,000,000 total particles, about 1,000,000,000 to about 10,000,000,000 total particles, about 10,000,000,000 to about 100,000,000,000 total particles, or about 100,000,000,000 to about 1,000,000,000,000 total particles.

A sample can comprise one or more different types of particles. A sample can comprise at least 1, 2, 3, 4, 5, 6, 7, 8, 9, 10, 50, 100, 500, 1000, 10,000, 100,000, 1,000,000, 10,000,000, 100,000,000, 1,000,000,000, 10,000,000,000, 100,000,000,000, or 1,000,000,000,000 different types of particles. A sample can comprise about 1, 2, 3, 4, 5, 6, 7, 8, 9, 10, 50, 100, 500, 1000, 10,000, 100,000, 1,000,000, 10,000,000, 100,000,000, 1,000,000,000, 10,000,000,000, 100,000,000,000, or 1,000,000,000,000 different types of particles. In some cases, a sample comprises about 10 to about 100 different types of particles, about 5 to about 10 different types of particles, about 10 to about 50 different types of particles, about 50 to about 100 different types of particles, or about 100 to about 1000 different types of particles, about 1000 to about 10,000 different types of particles, about 10,000 to about 100,000 different types of particles, about 100,000 to about 1,000,000 different types of particles, about 1,000,000 to about 10,000,000 different types of particles, about 10,000,000 to about 100,000,000 different types of particles, about 100,000,000 to about 1,000,000,000 different types of particles, about 1,000,000,000 to about 10,000,000,000 different types of particles, about 10,000,000,000 to about 100,000,000,000 different types of particles, or about 100,000,000,000 to about 1,000,000,000,000 different types of particles.

C. Ratio of First and Second Particles in a Sample

In some cases, a sample comprises a first particle and a second particle. A sample can comprise only one type of particle, e.g., a particle of less than a predetermined size or a particle of at least a predetermined size. In some cases, the ratio of the abundance of the first particle to the second particle in the sample is less than 1:1, 1:10, 1:100, 1:1000, 1:10,000, 1:100,000, 1:1,000,000, 1:10,000,000, 1:100,000,000, or 1:1,000,000,000. In some cases, the ratio of the abundance of the first particle to the second particle in the sample is greater than 1:1, 1:10, 1:100, 1:1000, 1:10,000, 1:100,000, 1:1,000,000, 1:10,000,000, 1:100,000,000, or 1:1,000,000,000. In some cases, the ratio of the abundance of the first particle to the second particle in the sample is about 1:1, 1:10, 1:100, 1:1000, 1:10,000, 1:100,000, or 1:1,000,000, 1:10,000,000, 1:100,000,000, or 1:1,000,000,000.

In some cases, a sample comprises a rare cell type. In some cases, the ratio of the abundance of the rare cell type to the abundance of cells of one or more other cell types in a sample is about 1:100, 1:1000, 1:10,000, 1:100,000, 1:1,000,000, 1:10,000,000, 1:100,000,000, or 1:1,000,000,000. In some cases the ratio of abundance of cells of the rare cell type to the abundance of cells of one or more other cell types is less than 1:100, 1:1000, 1:10,000, 1:100,000, 1:1,000,000, 1:10,000,000, 1:100,000,000, or 1:1,000,000,000.

D. Sample Dilution

In some cases, a sample is diluted. In some cases, a sample, e.g., a blood sample, is diluted before it is applied to a device described herein. A sample can be diluted, e.g., in order to prevent clogging of a device described herein. In some cases, a sample is diluted after being passed through a device described herein.

A sample can be diluted at least 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87. 88, 89, 90, 91, 92, 93, 94, 95, 96, 97, 98, 99, 100, 125, 150, 175, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or 3000, 4000, 5000, 6000, 7000, 8000, 9000, or 10,000-fold.

In some cases, a sample is diluted about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87. 88, 89, 90, 91, 92, 93, 94, 95, 96, 97, 98, 99, 100, 125, 150, 175, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or 3000, 4000, 5000, 6000, 7000, 8000, 9000, or 10,000-fold.

A sample can be diluted, e.g., by adding water, buffer, and/or other fluid to the sample. In some cases, a sample is diluted by adding an additive.

E. Clogging and Sample Additives

Disclosed herein are methods for processing large volumes of blood with deterministic lateral displacement arrays, e.g., for isolation of rare cells. In some cases, the disclosed methods can be used to extract circulating tumor cells from large volumes (~100 mL) of whole blood of cancer patients, or, e.g., to extract stem cells from large volumes of umbilical cord blood. The disclosed methods are also useful for general processing of blood using DLD arrays.

In some cases, deterministic lateral displacement (DLD) arrays are used to extract rare cells from hundreds of microliters of blood. Using the disclosed methods, DLD arrays can be used to extract rare cells from hundreds of milliliters of blood. The "robustness" of the technique against clogging and fouling for lower throughputs for other blood applications is also improved.

In some cases, a process for reducing clogging comprises a combination of four techniques: 1) increase in the concentration of the calcium-chelating anti-coagulant EDTA from, e.g., 1 mM to, e.g., 5 mM; 2) add a direct thrombin inhibitor, e.g., PPACK at a concentration of, e.g., 40 µM; 3) increase in the flow velocity 10×; and 4) a 3× increase in the dilution of blood. In some cases, only one technique is performed. In some cases, two or more of the techniques are performed.

In some cases, a kit is provided comprising a calcium-chelating agent and a thrombin inhibitor. In some cases, the kit comprises EDTA and PPACK.

Using blood with fluorescently stained leukocytes, the level of clogging can be measured as a function of the volume of blood that had passed through the DLD array. Employing the disclosed approach, ~100 mL of blood can pass through the DLD array before clogging using a combination of the four methods above, compared to a few hundred microliters previously.

The combination of EDTA and PPACK can be used as a running buffer for dilution of the blood in preparation for processing of the blood with DLD arrays.

The references listed herein are also part of the application and are incorporated by reference in their entirety as if fully set forth herein.

Deterministic lateral displacement arrays can be used to capture leukocytes and circulating tumor cells from blood with high enrichment and at high flow rates.

In some cases, the volume of blood that can be processed with these devices is limited due to clogging of the micro-post (obstacle) array. In some cases, by removing platelets from blood before putting the blood in the arrays, platelets can be identified as a dominant contributor to clogging. For example, running leukocytes alone can lead to far less clogging than running blood. In some cases, a biological mechanism causing clogging can be disabled, which can yield at least a 40-fold reduction in clogging. In some cases, higher flow rates and greater dilution of blood can be used to achieve a further reduction in clogging of a micro-post array.

The physiological conditions in devices comprising an array of obstacles (high shear, rapid repeated acceleration and deceleration) can be different from those found in typical situations involving blood clotting studies.

Clogging of a micro-post (obstacle) array can be caused by one or both of two complementary, mutually dependent processes involved in hemostasis: coagulation and platelet activation, which lead to a clot. In some cases, clots (which then can trap leukocytes) can cause the clogging.

Figure 35:
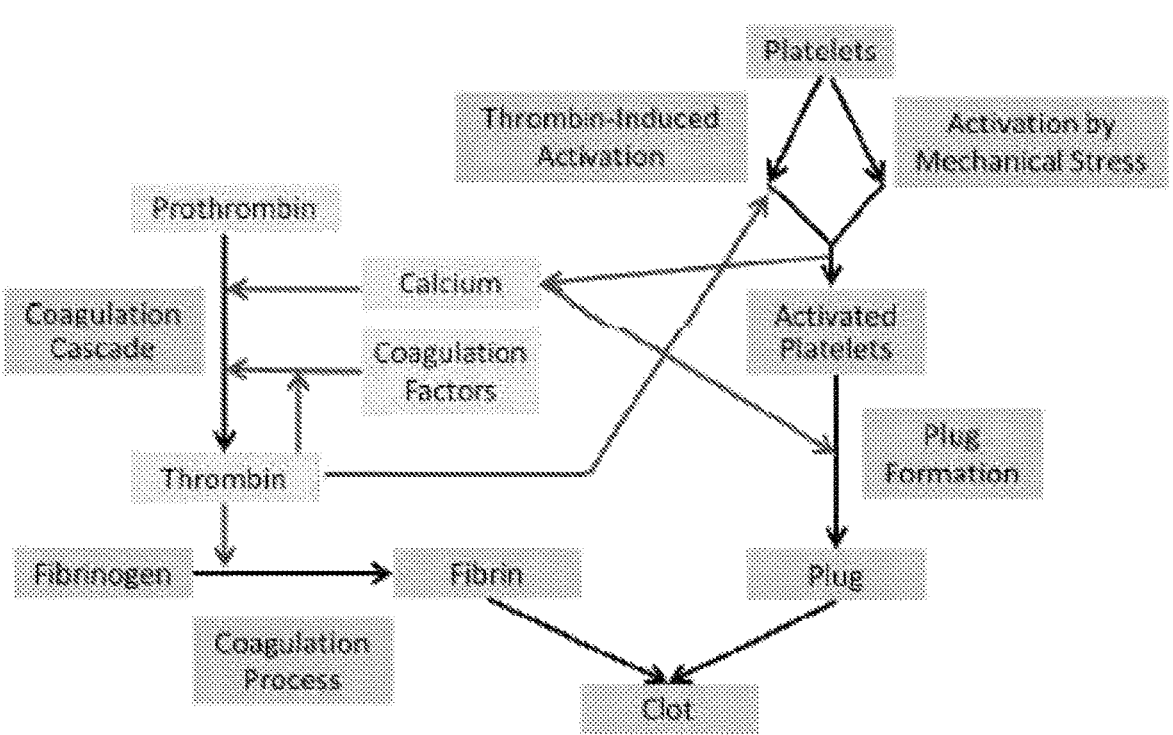
FIG. 35 shows a simplified diagram of process by which platelet-induced clogging of a DLD array as provided herein can occur.

FIG. 35 illustrates a simplified view of possible ways in which these two processes can interact to cause clogging as well as underlying mechanisms which can be attacked to disable these mechanisms. The cycle may be initiated by mechanical stress on the platelets from shear forces as the platelets pass between the posts in a micro-post array, or their rapid acceleration and deceleration caused by a micro-array structure.

Coagulation-related processes are on the left side of the diagram, and the platelet processes are on the right side of the diagram. They can inter-relate through thrombin and calcium pathways and dependencies. In some cases, both the thrombin and the calcium pathways/dependencies can be addressed for maximum effectiveness.

In some cases, high flow rate and dilution both lead to an increase in the maximum throughput of whole blood before significant clogging can occur.

In some cases, a dominant clogging mechanism is the activity of calcium-dependent integrins on platelet surfaces, the interaction of which can lead to aggregation of platelets. In some cases, calcium-dependent integrins are one of the dominant contributors to platelet-induced clogging. In some cases, increasing the concentration of EDTA from 1 mM to 5 mM can result in an 8-fold reduction in clogging. In some cases, acid citrate dextrose (ACD), like EDTA, chelates calcium in blood plasma, has a similar effect. The chelation of calcium can also reduce the coagulation pathways (on the left of the diagram).

In some cases, a dominant clogging mechanism is due to thrombin effects, e.g., thrombin-induced platelet activation. Thrombin can catalyze the conversion of fibrinogen into fibrin as a part of a coagulation cascade. In some cases, thrombin is a potent platelet-activating agonist. Heparin can be effective in reducing clogging—it can reduce the formation of thrombin.

In some cases, a calcium chelator can be combined with a thrombin inhibitor. In some cases, inhibiting thrombin with the direct thrombin inhibitor PPACK can achieve a further 5-fold reduction in clogging on top of that achieved with a 5 mM concentration of EDTA.

Figure 36:
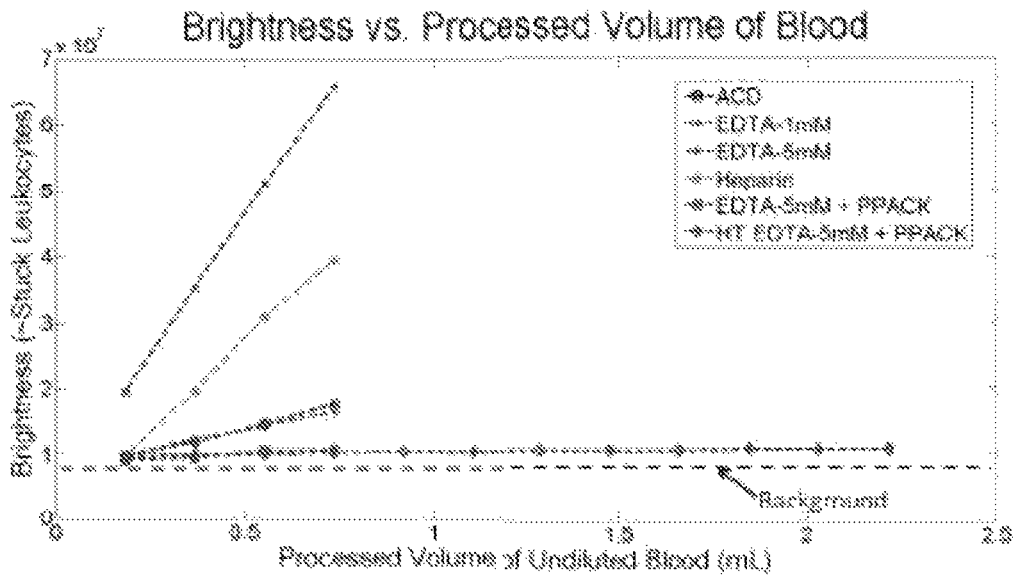
FIG. 36 shows the results of experiments identifying calcium-dependent integrins and thrombin-induced platelet activation as the dominant contributors to platelet-induced clogging of DLD arrays as provided herein. The x-axis shows the volume of blood that has been processed through the array, while the y-axis shows the fluorescence of leukocytes stuck or clogged in the array. Diluted blood was actually processed, but this x-axis represents the amount of undiluted blood that was used before dilution and which flowed through the array, which had 40 micron triangular posts and a gap width of 27 microns.

FIG. 36 shows these results for the case of an array with 40 um triangular posts with 27 um gaps for leukocyte separation from blood.

Deterministic lateral displacement (DLD) arrays have been used to concentrate circulating tumor cells (CTCs) in diluted whole blood at flow rates as high as 10 mL/min with capture efficiencies exceeding 85% (K. Loutherback et al., AIP Advances, 2012). In some cases, the equivalent volume of undiluted blood that can be processed is limited to 0.3 mL per DLD array due to clogging of the array. Since the concentration of CTCs can be as low as 1-10 cells/mL in clinical samples, increasing the volume of blood that can be processed with DLD arrays can allow for collection of sufficient numbers of CTCs for biological experiments or clinical diagnostic studies. Furthermore, by bumping large cells, such as CTCs, into a buffer stream, DLD arrays can be used to harvest CTCs free of the background of smaller particles, such as leukocytes, erythrocytes, and platelets present in blood or, free of plasma, resulting in a highly enriched or concentrated product (see e.g., J. A. Davis, et al., PNAS, 2006).

In some cases, two biological mechanisms can cause clogging of the array, and these two mechanisms can be inhibited. In some cases, shear-induced platelet aggregation is only a minor contributor to clogging of the array. In some cases, by comparing the reduction in clogging achieved by the calcium-chelating anticoagulants EDTA and ACD to that achieved by the indirect thrombin inhibitor heparin as well as by measuring the EDTA concentration-dependent reduction in clogging, activity of calcium-dependent integrins as a dominant contributor to clogging can be identified. In some cases, combining EDTA with the direct thrombin inhibitor PPACK can be used to identify thrombin-induced platelet activation as the second dominant mechanism contributing to clogging. Using a combination of EDTA and PPACK, a 40-fold decrease in clogging of the array can be demonstrated, which can allow a commensurate increase in the volume of blood processed. Based on data in a single-channel device (2 mm wide), we can expect a complete chip to be able to process >100 mL quantities of blood in 30 minutes without significant clogging. Finally, in some cases, the glycoprotein 11b/Illa integrin complex, which is activated by shear forces, can be inhibited using the glycoprotein 11b/Illa inhibitor tirofiban to show that shear-induced platelet aggregation plays only a minor role in clogging of the array.

In some cases, a sample can comprise one or more additives. In some cases, a chelating agent is added to a sample. In some cases, the chelating agent comprises a calcium-chelating agent. In some cases, the chelating agent comprises acetylacetone, aerobactin, aminoethyletha-nolamine, aminopolycarboxylic acid, ATMP, BAPTA, BDTH2, benzotriazole, Bipyridine, 2,2'-Bipyridine, 4,4'-Bipyridine, 1,2-Bis(dimethylarsino)benzene, 1,2-Bis(dim-ethylphosphino)ethane, 1,2-Bis(diphenylphosphino)ethane, Catechol, Chelex 100, Citric acid, Corrole, Crown ether, 18-Crown-6, Cryptand, 2.2.2-Cryptand, Cyclen, Defera-sirox, Deferiprone, Deferoxamine, Dexrazoxane, Trans-1,2-Diaminocyclohexane, 1,2-Diaminopropane, Dibenzoyl-methane, Diethylenetriamine, Diglyme, 2,3-Dihydroxybenzoic acid, Dimercaprol, 2,3-Dimercapto-1-propanesulfonic acid, Dimercaptosuccinic acid, Dimethylglyoxime, DIOP, Diphenylethylenediamine, DOTA, DOTA-TATE, DTPMP, EDDH, EDDS, EDTMP, EGTA, 1,2-Ethanedithiol, Ethylenediamine, Ethylenediami-netetraacetic acid (EDTA), Etidronic acid, Extended por-phyrins, Ferrichrome, Fluo-4, Fura-2, Gluconic acid, Gly-oxal-bis(mesitylimine), Hexafluoroacetylacetone, Homocitric acid, Iminodiacetic acid, Indo-1, Metal acety-lacetonates, Metal dithiolene complex, Metallacrown, Nitrilotriacetic acid, Pendetide, Penicillamine, Pentetic acid, Phanephos, Phenanthroline, O-Phenylenediamine, Phospho-nate, Phytochelatin, Polyaspartic acid, Porphin, Porphyrin, 3-Pyridylnicotinamide, 4-Pyridylnicotinamide, Sodium diethyldithiocarbamate, Sodium polyaspartate, Terpyridine, Tetramethylethylenediamine, Tetraphenylporphyrin, 1,4,7-Triazacyclononane, Triethylenetetramine, Triphos, Triso-dium citrate, or 1,4,7-Trithiacyclononane. In some cases, the one or more additives is Kolliphor®, e.g., Kolliphor® P 188 (Poly(ethylene glycol)-block-poly(propylene glycol)-block-poly(ethylene glycol). In some cases, the one or more additives comprise Kolliphor® ELP, EL, RH 40, CS12, CS20, CS B, CS S, CS A, CS L, TPGS, PS 60, PS 80, HS15, P 407, P 237, or P 338. The concentration of a Kolliphor can be about 0.5%, 1%, 1.5%, 2%, 3%, 4%, or 5%. For example, Kolliphor® can be Sigma K4894-500g or Sigma P5556.

In some cases, the sample, e.g., a blood sample, is collected in a tube comprising $K_2EDTA$ or $K_3EDTA$.

In some cases, the sample comprises an agent that reduces the activity of calcium-dependent integrins. In some cases, the sample comprises an agent that reduces calcium depen-dent thrombin formation.

In some cases, an agent that chelates calcium comprises acid citrate dextrose (ACD). The final concentration of ACD in a sample, e.g., a blood sample, can be 10%.

In some cases, the chelating agent is EDTA. In some cases, the calcium chelating agent is EDTA. In some cases, the final concentration of the chelating agent in the sample is at least 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, or 20 mM. In some cases, the final concentration of EDTA in the sample is at least 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, or 25 mM. In some cases, the concen-tration of EDTA is about 2 mM to about 7 mM, or about 3 mM to about 6 mM.

In some cases, one or more thrombin inhibitors are added to a sample, e.g., a blood sample. In some cases, a thrombin inhibitor is a direct thrombin inhibitor. In some cases, a direct thrombin inhibitor is a bivalent thrombin inhibitor. In some cases, a direct thrombin inhibitor is a univalent throm-bin inhibitor. In some cases, a direct thrombin inhibitor is an allosteric inhibitor. A bivalent direct thrombin inhibitor can be hirudin, bivalirudin, lepirudin, or desirudin. A univalent direct thrombin inhibitor can be argatroban, melagatran, ximelagatran, or dabigatran. An allosteric direct thrombin inhibitor can be a DNA aptamer, benzofuran dimer, benzo-furan trimer, or polymeric lignin. In some cases, a direct thrombin inhibitor is PPACK (D-Phe-Pro-Arg-CMK).

In some cases, the thrombin inhibitor is PPACK (D-Phe-Pro-Arg-CMK), benzamidine hydrochloride, p-APMSF, p-APMSF hydrochloride, TLCK hydrochloride, uPA inhibi-tor, PPACK dihydrochloride, or PPACK dihydrochloride biotinylated. In some cases, Heparin is a thrombin inhibitor.

In some cases, the final concentration of the thrombin inhibitor, e.g., direct thrombin inhibitor in a sample is at least 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 250, 300, 350, or 400 μM. In some cases, a final concentration a thrombin inhibitor in a sample is about 30 to about 50 μM, or about 20 to about 60 μM.

In some cases, the final concentration of PPACK in a sample is at least 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 250, 300, 350, or 400 μM. In some cases, a final concentration of PPACK in a sample is about 30 to about 50 μM, or about 20 to about 60 μM.

In some cases, a chelating agent and a thrombin inhibitor are added to a sample. In some cases, a calcium chelating agent and a thrombin inhibitor are added to a sample. In some cases, a chelating agent and a thrombin inhibitor are added to a sample, and the sample is diluted at least 3 fold.

In some cases, a sample comprises EDTA and PPACK. In some cases, a sample comprises EDTA at a concentration of about 5 mM and PPACK at a concentration of about 40 μM. In some cases, a blood sample comprises EDTA at a concentration of about 5 mM and PPACK at a concentration of about 40 μM In some cases, a blood sample is diluted about 3 fold, and the diluted blood sample comprises EDTA and PPACK. In some cases, a blood sample is diluted about 3 fold, and the diluted blood sample comprises EDTA at a concentration of about 5 mM and PPACK at a concentration of about 40 μM.

In some cases, a sample, e.g., a blood sample, comprises one or more additives, e.g., sodium fluoride (NaF), Heparin, EDTA, or sodium citrate. In some cases, an additive is an anticoagulant or antiplatelet agent, e.g., clopidogrel, prasugrel, ticagrelor, ticlopidine, argatroban, bivalirudin, dalteparin, enoxaparin, fondaparinux, heparin, heparin lock flush, lepirudin, anagrelide, apixaban, aspirin, aspirin/dipyridamole, cilostazol, dabigatran, dipyridamole, batroxobin, hementin, rivaroxaban, warfarin, or urokinase. In some cases, an anticoagulant is an antithrombic, fibrinolytic, or thrombolytic.

In some cases, whole blood is diluted with 1×PBS with 2 mM EDTA and 0.5% BSA. In some cases, clogging in the device and systems herein can be reduced or prevented by reducing the volume of the sample introduced into the devices and systems. For example, clogging can be reduced or prevented by reducing the sample volume to no greater than 150, 140, 130, 100, 90, 80, 70, 60, 50, 40, 30, 20, 10, or 1 μL. In some cases, the sample introduced into a device or system can have a volume no greater than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150

μL. In a particular case, the sample introduced into the devices and systems can have a volume no greater than 100 μL.

F. Sample Volumes

Samples can be applied to devices described herein, e.g., devices with ordered arrays of obstacles, e.g., deterministic lateral displacement (DLD) devices. The volume of sample that can be applied to a device and/or processed by a device can be at least 0.01, 0.02, 0.03, 0.04, 0.05, 0.06, 0.7, 0.08, 0.09, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15, 5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87. 88, 89, 90, 91, 92, 93, 94, 95, 96, 97, 98, 99, 100, 125, 150, 175, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or 3000 mL.

The volume of sample that can be applied to a device and/or processed by a device can be less than 0.01, 0.02, 0.03, 0.04, 0.05, 0.06, 0.7, 0.08, 0.09, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15, 5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87. 88, 89, 90, 91, 92, 93, 94, 95, 96, 97, 98, 99, 100, 125, 150, 175, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or 3000 mL. In some cases, the volume of sample that can be applied to a device and/or processed by a device can be no greater than 150 μL. For example, the volume of sample that can be applied to a device and/or processed by a device can be no greater than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150 μL. In a particular case, the volume of sample that can be applied to a device and/or processed by a device can be no greater than 100 μL.

The volume of sample that can be applied to a device and/or processed by a device can be about 0.01, 0.02, 0.03, 0.04, 0.05, 0.06, 0.7, 0.08, 0.09, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87. 88, 89, 90, 91, 92, 93, 94, 95, 96, 97, 98, 99, 100, 125, 150, 175, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or 3000 mL. In some cases, the volume of sample that can be applied to a device and/or processed by a device can be about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150 µL. In a particular case, the volume of sample that can be applied to a device and/or processed by a device can be about 100 µL.

The volume of sample that can be applied to device and/or processed by a device can be about 0.1 to about 1 mL, about 1 to about 10 mL, about 10 mL to about 20 mL, about 10 mL to about 50 mL, about 10 mL to about 100 mL, about 20 mL to about 100 mL, about 100 mL to about 300 mL, about 100 mL to about 1000 mL, about 100 mL to about 500 mL, or about 100 mL to about 3000 mL.

G. Concentration of Particles in a Sample

In some cases, a concentration of first particles, second particles, or total particles in a sample is about 1, 5, 10, 50, 100, 500, 1000, $10^4$, $10^5$, $10^6$, $10^7$, $10^8$, $10^9$, $10^{10}$, or $10^{11}$ per mL of sample.

In some cases, a concentration of first particles, second particles, or total particles in a sample is less than 1, 5, 10, 50, 100, 500, 1000, $10^4$, $10^5$, $10^6$, $10^7$, $10^8$, $10^9$, $10^{10}$, or $10^{11}$ per mL of sample.

In some cases, a concentration of first particles, second particles, or total particles in a sample is at least 1, 5, 10, 50, 100, 500, 1000, $10^4$, $10^5$, $10^6$, $10^7$, $10^8$, $10^9$, $10^{10}$, or $10^{11}$ per mL of sample.

IV. Devices

Exemplary devices for separating particles based on size are described, e.g., in U.S. Pat. Nos. 7,150,812, 7,318,902, 7,472,794, 7,735,652, 7,988,840, 8,021,614, 8,282,799, 8,304,230, 8,579,117, and PCT Publication No. WO2012094642, which are herein incorporated by reference in their entireties. Particles and samples described herein can be applied to devices described herein for size-based separation, e.g., high throughput size based separation.

The disclosure relates generally to the field of separation of particles such as spheres, cells, viruses, and molecules. The disclosure relates to separation of particles based on their flow behavior in a fluid-filled field of obstacles in which advective transport of particles by a moving fluid overwhelms the effects of diffusive particle transport.

Separation of particles by size or mass can be a fundamental analytical and preparative technique in biology, medicine, chemistry, and industry. Methods include gel electrophoresis, field-flow fractionation, sedimentation and size exclusion chromatography. Separation of particles and charged biopolymers has been described using arrays of obstacles through particles pass under the influence of fluid flow or an applied electrical field. Separation of particles by these obstacle-array devices can be mediated by interactions among the biopolymers and the obstacles and by the flow behavior of fluid passing between the obstacles.

A variety of microfabricated sieving matrices have been disclosed for separating particles (Chou et. al., 1999, Proc. Natl. Acad. Sci. 96:13762; Han, et al., 2000, Science 288:

1026; Huang et al., 2002, Nat. Biotechnol. 20:1048; Turner et al., 2002, Phys. Rev. Lett. 88(12):128103; Huang et al., 2002, Phys. Rev. Lett. 89:178301; U.S. Pat. Nos. 5,427,663; 7,150,812; 6,881,317). These matrices can depend on accurate fabrication of small features (e.g., posts, or obstacles in a microfluidic channel). The accuracy with which small features can be fabricated can be limited in all microfabrication methods, especially as feature size decreases. The strength and rigidity of materials in which small features of fabricated can also limit the practical usefulness of the fabricated device. Furthermore, the small size of the gaps between obstacles in such matrices can render the matrices susceptible to clogging by particles too large to fit between the obstacles. Micrometer- and nanometer-scale manufacturing can also require state-of-the-art fabrication techniques, and devices fabricated using such methods can have high cost.

Bump array (also known as "obstacle array") devices have been described, and their basic operation is explained, for example in U.S. Pat. No. 7,150,812, which is incorporated herein by reference in its entirety. Referring to FIGS. 3 and 4 of U.S. Pat. No. 7,150,812, a bump array can operate essentially by segregating particles passing through an array (generally, a periodically-ordered array) of obstacles, with segregation occurring between particles that follow an "array direction" that is offset from the direction of bulk fluid flow or from the direction of an applied field.

Figure 8:
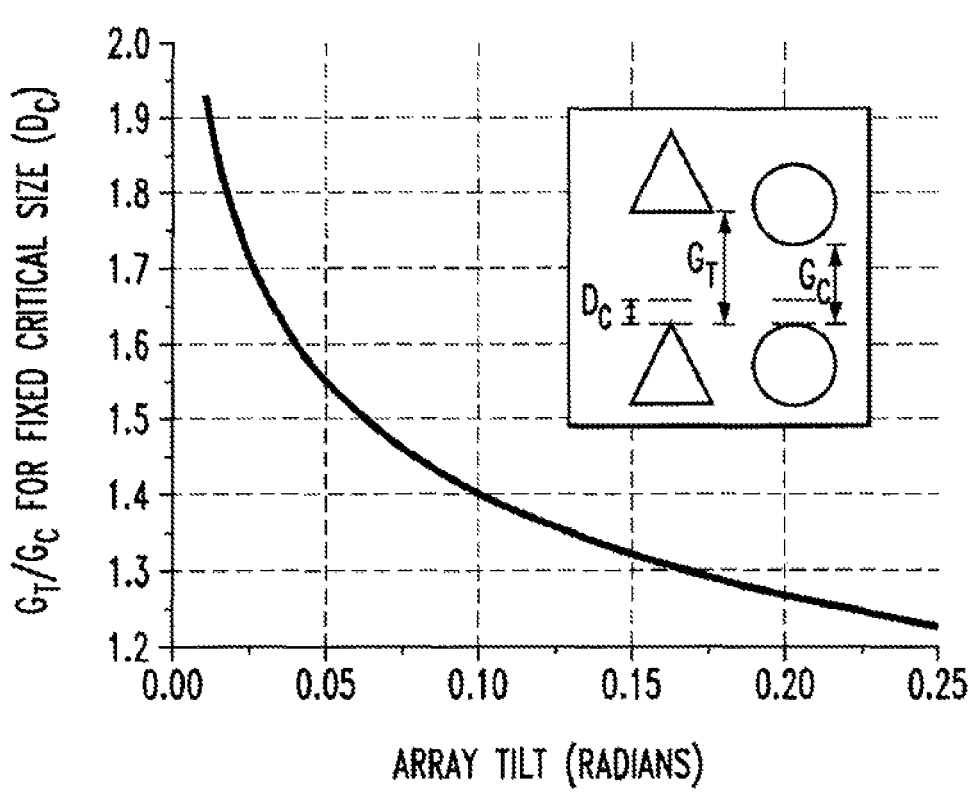
FIG. 8 is a graph illustrating the effect of the tilt angle ("Array Tilt" in FIG. 8) on gap length G. $G_T$ refers to the gap length between triangular posts, and $G_C$ refers to the gap length between round posts.

At the level of flow between two adjacent obstacles under conditions of relatively low Reynold's number, fluid flow can occur in a laminar fashion. Considering the volumetric flow between two obstacles in hypothetical layers (e.g., modeling the flow by considering multiple adjacent stream tubes of equal volumetric flow between the obstacles, as shown in FIG. 8 of U.S. Pat. No. 7,150,812), the likelihood that fluid in a layer will pass on one side or the other of the next (i.e., downstream) obstacle can be calculable by standard methods (see, e.g., Inglis et al., 2006, Lab Chip 6:655-658). For an ordered array of obstacles offset from the direction of bulk fluid flow, the arrangement of the obstacles can define an array direction corresponding to the direction in which the majority of fluid layers between two obstacles travels. A minority of fluid layers can travel around the downstream obstacle in a direction other than the array direction.

The path that a particle passing between the two obstacles can take can depend on the flow of the fluid in the layers occupied by the particle. Conceptually, for a particle having a size equal to one of the hypothetical fluid layers described in the preceding paragraph, the particle can follow the path of the fluid layer in which it occurs, unless it diffuses to a different layer. For particles larger than a single fluid layer, the particle can take the path corresponding to the majority of the fluid layers acting upon it. Particles having a size greater than twice the sum of the thicknesses of the minority of layers that travel around a downstream obstacle in the direction other than the array direction can be acted upon by more fluid layers moving in the array direction, meaning that such particles will travel in the array direction. This concept is also illustrated in FIGS. 5-11 of U.S. Pat. No. 7,150,812. Thus, there can be a "critical size" for particles passing between two obstacles in such an array, such that particles having a size greater to that critical size can travel in the array direction, rather than in the direction of bulk fluid flow and particles having a size less than the critical size can travel in the direction of bulk fluid flow. Particles having a size precisely equal to the critical size can have an equal chance of flowing in either of the two directions. By operating such a device at a high Peclet number (i.e., such that advective particle transport by fluid layers greatly outweighs diffusive particle between layers), the effects of diffusion of particles between fluid layers can be ignored.

A. Bump Arrays

Described herein are ways of structuring and operating obstacle arrays for separating particles. In some obstacle arrays, obstacles have shapes and are arranged such that the profile of fluid flow through gaps between adjacent obstacles is symmetrical about the center line of the gap. The geometry of the adjacent obstacles can be such that the portions of the obstacles defining the gap are symmetrical about the axis of the gap that extends in the direction of bulk fluid flow. The velocity or volumetric profile of fluid flow through such gaps can be approximately parabolic across the gap, with fluid velocity and flux being zero at the surface of each obstacle defining the gap (assuming no-slip flow conditions) and reaches a maximum value at the center point of the gap. The profile being parabolic, a fluid layer of a given width adjacent to one of the obstacles defining the gap can contain an equal proportion of fluid flux as a fluid layer of the same width adjacent the other obstacle that defines the gap meaning that the critical size of particles that are 'bumped' during passage through the gap is equal regardless of which obstacle the particle travels near.

In some cases, particle size-segregating performance of an obstacle array can be improved by shaping and disposing the obstacles such that the portions of adjacent obstacles that deflect fluid flow into a gap between obstacles are not symmetrical about the axis of the gap that extends in the direction of bulk fluid flow. Such lack of flow symmetry into the gap can lead to a non-symmetrical fluid flow profile within the gap. Concentration of fluid flow toward one side of a gap (i.e., a consequence of the non-symmetrical fluid flow profile through the gap) can reduce the critical size of particles that are induced to travel in the array direction, rather than in the direction of bulk fluid flow. This can be so because the non-symmetry of the flow profile can cause differences between the width of the flow layer adjacent to one obstacle that contains a selected proportion of fluid flux through the gap and the width of the flow layer that contains the same proportion of fluid flux and that is adjacent the other obstacle that defines the gap. The different widths of the fluid layers adjacent to obstacles define a gap that exhibits two different critical particle sizes. A particle traversing the gap can be bumped (i.e., travel in the array direction, rather than the bulk fluid flow direction) if it exceeds the critical size of the fluid layer in which it is carried. Thus, it is possible for a particle traversing a gap having a non-symmetrical flow profile to be bumped if the particle travels in the fluid layer adjacent to one obstacle, but to be not-bumped if it travels in the fluid layer adjacent to the other obstacle defining the gap.

Particles traversing an obstacle array pass through multiple gaps between obstacles, and have multiple opportunities to be bumped. When a particle traverses a gap having a non-symmetrical flow profile, the particle can be bumped if the size of the particle exceeds the (different) critical sizes defined by the flow layers adjacent to the two obstacles defining the gap. However, the particle can sometimes be bumped if the size of the particle exceeds the critical size defined by the flow layer adjacent to one of the two obstacles, but does not exceed the critical size defined by the flow layer adjacent to the other obstacle. In some cases, particles that do not exceed the critical size defined by the flow layer adjacent to either of the obstacles cannot be bumped. There are at least two implications that follow from this observation.

First, in an obstacle array in which the obstacles define gaps having a non-symmetrical flow profile, particles having a size that exceeds the smaller of the two critical sizes defined by the flow layers adjacent to the obstacles can be separated from particles having a size smaller than that smaller critical size The critical size defined by a gap can be decreased by altering the symmetry of flow through the gap without necessarily decreasing the size of the gap ("G" in FIG. 1). Decreasing gap size can increase the cost and difficulty of producing the array. Conversely, for a given critical size, the size of the gap defining that critical size can be increased by altering the symmetry of flow through the gap. Because smaller gaps are more likely to clog than larger ones, this arrangement can improve the operability of the arrays, allowing greater throughput and lower likelihood of clogging.

Second, in an obstacle array in which the obstacles define gaps having a non-symmetrical flow profile, particles can be separated into three populations: i) particles having a size smaller than either of the critical sizes defined by the flow layers adjacent to the obstacles; ii) particles having a size intermediate between the two critical sizes defined by the flow layers adjacent to the obstacles; and iii) particles having a size larger than either of the critical sizes defined by the flow layers adjacent to the obstacles.

In another aspect, decreasing the roundness of edges of obstacles that define gaps can improve the particle size-segregating performance of an obstacle array. By way of example, arrays of obstacles having a triangular cross-section with sharp vertices can exhibit a lower critical particle size than do arrays of identically-sized and -spaced triangular obstacles having rounded vertices.

Thus, by sharpening the edges of obstacles defining gaps in an obstacle array, the critical size of particles deflected in the array direction under the influence of bulk fluid flow can be decreased without necessarily reducing the size of the obstacles. Conversely, obstacles having sharper edges can be spaced farther apart than, but still yield particle segregation properties equivalent to, identically-sized obstacles having less sharp edges.

In yet another aspect, shaping the obstacles in an obstacle array in such a way that the geometry of the obstacles encountered by fluid flowing through the array in one direction differs (and defines a different critical particle size) from the geometry of the obstacles encountered by fluid flowing through the array in a second direction. For example, fluid flowing through the array illustrated in FIG. 1 in a left-to-right direction encounters and flows around the rounded vertices of the right triangular posts of the array (in this flow direction, the profile of fluid flow through the gaps is asymmetric about the axis of the gaps). However, fluid flowing through the same array in a right-to-left direction encounters and flows around the flat edges of the right triangular posts of the array (in this flow direction, the profile of fluid flow through the gaps is symmetric about the axis of the gaps, being essentially parabolic).

B. Bump Arrays Having Gas with Asymmetrical Flow Profiles

Described herein are bump array devices that are useful for segregating particles by size. In one embodiment, a device includes a body defining a microfluidic flow channel for containing fluid flow. An array of obstacles is disposed within the flow channel, such that fluid flowing through the channel flows around the obstacles. The obstacles extend across the flow channel, generally being either fixed to, integral with, or abutting the surface of the flow channel at each end of the obstacle.

The obstacles can be arranged in rows and columns, in such a configuration that the rows define an array direction that differs from the direction of fluid flow in the flow channel by a tilt angle (ε) that has a magnitude greater than zero. The maximum operable value of ε can be 1/3 radian. The value of ε can be 1/5 radian or less, and a value of 1/10 radian can be suitable in various embodiments of the arrays described herein. The obstacles that are in columns define gaps between themselves, and fluid flowing through the flow channel is able to pass between these gaps, in a direction that is generally transverse with respect to the columns (i.e., generally perpendicular to the long axis of the obstacles in the column and generally perpendicular to a plane extending through the obstacles in the column).

The obstacles can have shapes so that the surfaces (upstream of, downstream of, or bridging the gap, relative to the direction of bulk fluid flow) of two obstacles defining a gap are asymmetrically oriented about the plane that extends through the center of the gap and that is parallel to the direction of bulk fluid flow through the channel. That is, the portions of the two obstacles can cause asymmetric fluid flow through the gap. The result can be that the velocity profile of fluid flow through the gap is asymmetrically oriented about the plane. As a result of this, the critical particle size for particles passing through the gap adjacent to one of the obstacles can be different than the critical particle size for particles passing through the gap adjacent to the other of the obstacles.

A device can be made from any of the materials from which micro- and nano-scale fluid handling devices are typically fabricated, including silicon, glasses, plastics, and hybrid materials. The flow channel can be constructed using two or more pieces which, when assembled, form a closed cavity (preferably one having orifices for adding or withdrawing fluids) having the obstacles disposed within it. The obstacles can be fabricated on one or more pieces that are assembled to form the flow channel, or they can be fabricated in the form of an insert that is sandwiched between two or more pieces that define the boundaries of the flow channel. Materials and methods for fabricating such devices are known in the art.

In some cases, the flow channel can be formed between two parallel, substantially planar surfaces, with the obstacles formed in one of the two surfaces (e.g., by etching the surface to remove material that originally surrounded the non-etched portions that remain as obstacles). The obstacles can have a substantially constant cross-section along their length, it being recognized that techniques used to fabricate the obstacles can limit the uniformity of the cross section.

The obstacles can be solid bodies that extend across the flow channel, in some cases from one face of the flow channel to an opposite face of the flow channel. Where an obstacle is integral with (or an extension of) one of the faces of the flow channel at one end of the obstacle, the other end of the obstacle can be sealed to or pressed against the opposite face of the flow channel A small space (preferably too small to accommodate any of particles of interest for an intended use) can be tolerable between one end of an obstacle and a face of the flow channel, provided the space does not adversely affect the structural stability of the obstacle or the relevant flow properties of the device. In some embodiments described herein, obstacles are defined by a cross-sectional shape (e.g., round or triangular). Methods of imparting a shape to an obstacle formed from a monolithic material are well known (e.g., photolithography and various micromachining techniques) and substantially any such techniques may be used to fabricate the obstacles described herein. The sizes of the gaps, obstacles, and other features of the arrays described herein depend on the identity and size of the particles to be handled and separated in the device, as described elsewhere herein. Typical dimensions are on the order of micrometers or hundreds of nanometers, but larger and smaller dimensions are possible, subject to the limitations of fabrication techniques.

As described herein, certain advantages can be realized by forming obstacles having sharp (i.e., non-rounded) edges, especially at the narrowest part of a gap between two obstacles. In order to take advantage of the benefits of sharp edges, a skilled artisan will recognize that certain microfabrication techniques can be preferable to others for forming such edges. Sharpness of edges can be described in any of a number of ways. By way of example, the radius of curvature of an edge (e.g., the vertex of a triangular post) can be measured or estimated and that radius can be compared with a characteristic dimension of the obstacle (e.g., the shorter side adjacent the vertex of a triangular, square, or rectangular post, or the radius of a round post having a pointed section). Sharpness can be described, for example, as a ratio of the radius of curvature to the characteristic dimension. Using equilateral triangular posts as an example, suitable ratios include those not greater than 0.25, and preferably not greater than 0.2.

In some cases, the number of obstacles that occur in an array is not critical, but the obstacles can be sufficiently numerous that the particle-separating properties of the arrays that are described herein can be realized. In some cases, the precise layout and shape of the array is not critical. In view of the disclosures described herein, a skilled artisan in this field is able to design the layout and number of obstacles necessary to make bump arrays capable of separating particles, taking into account the sizes and identities of particles to be separated, the volume of fluid in which the particles to be separated are contained, the strength and rigidity of the materials used to fabricate the array, the pressure capacity of fluid handling devices to be used with the array, and other ordinary design features.

The obstacles can generally be organized into rows and columns (use of the terms rows and columns does not mean or imply that the rows and columns are perpendicular to one another). Obstacles that are generally aligned in a direction transverse to fluid flow in the flow channel can be referred to as obstacles in a column. Obstacles adjacent to one another in a column can define a gap through which fluid flows. Obstacles in adjacent columns can be offset from one another by a degree characterized by a tilt angle, designated ε (epsilon). Thus, for several columns adjacent to one another (i.e., several columns of obstacles that are passed consecutively by fluid flow in a single direction generally transverse to the columns), corresponding obstacles in the columns can be offset from one another such that the corresponding obstacles form a row of obstacles that extends at the angle ε relative to the direction of fluid flow past the columns. The tilt angle can be selected and the columns can be spaced apart from each other such that 1/ε (when ε is expressed in radians) is an integer, and the columns of obstacles repeat periodically. The obstacles in a single column can also be offset from one another by the same or a different tilt angle. By way of example, the rows and columns can be arranged at an angle of 90 degrees with respect to one another, with both the rows and the columns tilted, relative to the direction of bulk fluid flow through the flow channel, at the same angle of $\epsilon$.

One or more portions of two obstacles that define a gap can be shaped in such a way that the portions of the obstacles that are upstream from, downstream from, or bridging (or some combination of these, with reference to the direction of bulk fluid flow through the flow channel) the narrowest portion of the gap between the obstacles are asymmetrical about the plane that bisects the gap and is parallel to the direction of bulk fluid flow. Both for simplicity of fabrication and to aid modeling of array behavior, all obstacles in an array can be identical in size and shape, although this need not be the case. In some cases, all obstacles in an array are not identical in shape. Furthermore, arrays having portions in which obstacles are identical to one another within a single portion, but different from obstacles in other portions can be made.

Asymmetry in one or more portions of one or both of the obstacles defining a gap can lead to increased fluid flow on one side or the other of the gap. A particle can be bumped upon passage through a gap only if the particle exceeds the critical particle size corresponding to the gap. The critical particle size can be determined by the density of fluid flux near the boundaries of the gap (i.e., the edges of the obstacles that define the gap). Increased fluid flow on one side of a gap (i.e., against one of the two obstacles defining the narrowest portion of the gap) can intensify flux density near that side, reducing the size of the particle that will be bumped upon passage through that side of the gap.

In one embodiment of the device, the shape of each of multiple obstacles in a column can be substantially identical and symmetrical about the plane that bisects each of the multiple obstacles. That is, for any one column of obstacles, the geometry encountered by particles traveling in fluid flowing through the gaps between the obstacles in the column can be identical when the fluid is traveling in a first direction and when the fluid is travelling in a second direction that is separated from the first direction by 180 degrees (i.e., flow in the opposite direction).

The geometry encountered by particles traveling in fluid flowing through the gaps between the obstacles in the column can be different when the fluid is traveling in a first direction from the geometry encountered when the fluid is travelling in a second direction that is different from the first direction by 90-180 degrees. In this embodiment, fluid flow can, for example, be oscillated between the two flow directions, and the particles in the fluid can encounter the different obstacle geometry. If these geometrical differences can result in different fluid profiles through the gaps (compare the panels in FIG. 6B, for example), then the gap can exhibit different critical particle sizes in the two directions. If a gap exhibits different critical sizes for flow in the two directions, then the populations of particles that will be bumped upon passing through the gap can differ depending on the direction of flow. This difference in the populations bumped in the two directions can be used to effect segregation of the differently-acting particles.

For example, consider a gap that exhibits a first critical size for bulk fluid flow in one direction, but exhibits a different critical size for bulk fluid flow in a second direction. For fluid flow in the first direction, particles having a size greater than the first critical size can be bumped, and particles having a size less than the first critical size cannot be bumped. Similarly, for fluid flow in the second direction, particles having a size greater than the second critical size can be bumped, and particles having a size less than the second critical size cannot be bumped. If flow is oscillated between the first and second directions, then particles having a size larger than both the first and the second critical sizes can be bumped in both directions. Similarly, particles having a size smaller than both the first and the second critical sizes cannot be bumped in either direction. For these two populations of particles, flow oscillations of approximately equal quantities in both directions can leave these particles substantially at their initial position. However, particles having a size intermediate between the two critical sizes can be bumped when bulk fluid flow is in one direction, but cannot be bumped when bulk fluid flow is in the other direction. Thus, when flow oscillations of approximately equal quantities in both directions are performed, these particles cannot be left in their initial position, but can instead have been displaced from that original position by an amount equal to (the size of an obstacle+the gap distance G)×(the number of oscillations). In this way, these particles (the ones having a size intermediate between the two critical sizes) can be segregated from the other particles with which they were initially intermixed.

When the first and second directions differ by 180 degrees (i.e., the flows are in opposite directions), the particles having a size intermediate between the two critical sizes can be displaced at an angle of 90 degrees relative to the direction of oscillating flow.

The behavior of particles in a bump array is not a function of the absolute direction in which the particles (or the fluid in which they are suspended) move, but rather can be a function of the array geometry that the particles encounter. As an alternative to operating a bump array with alternating flow between first and second directions, the same particle-displacing effects can be obtained using flow only in the first direction by increasing the size of the array by two times the number of oscillations, maintaining one portion of the array in its original arrangement, but altering the second portion of the array such that the geometry of the array is identical to the geometry encountered by particles in fluid moving in the second direction in the original array (even though the fluid moves in the first direction only). Using the array illustrated in FIG. 1 by way of example, the same displacement effects on particles can be obtained by two oscillations of flow in this array (i.e., two units of flow left-to-right and two units of flow right-to-left) as can be obtained by four units of left-to-right flow through an array having four times the (left-to-right) length of the array in FIG. 1, so long as two lengths of the array are arranged as shown in FIG. 1 and two lengths of the array are arranged as the mirror image (left-to-right) of the array shown in FIG. 1.

Described herein in a microfluidic device designed to separate objects on the basis of physical size. The objects can be cells, biomolecules, inorganic beads, or other objects of round or other shape. Typical sizes fractionated can range from 100 nanometers to 50 micrometers; smaller or larger sizes can be fractionated. Use of these arrays can involve continuous flows in one direction, and particles can be separated from the flow direction by an angle which is a monotonic function of their size.

By changing the shape of the posts from circles to a shape that is asymmetric about an axis parallel to the fluid flow, functionalities may be added:

1. The critical particle size for bumping may be different depending on which direction a particle moves through the array. This has been experimentally verified with right triangular posts, and extends to arbitrary shapes that are asymmetric about the flow axis.

2. With such designs, the angle of displacement from the fluid flow of particles may be designed not to be monotonic—e.g. peaked at a certain particle size.

Such bump arrays have multiple uses, including all of the uses for which bump arrays were previously known.

The device can be used to separate particles in a selected size band out of a mixture by deterministic lateral displacement. The mechanism for separation can be the same as the bump array, but it can work under oscillatory flow (AC conditions; i.e., bulk fluid flow alternating between two directions) rather than continuous flow (DC conditions; i.e., bulk fluid flow in only a single direction). Under oscillatory flow, particles of a given size range can be separated perpendicularly from an input stream (perpendicular to the alternating flow axis when the alternating flows differ in direction by 180 degrees) without any net displacement of the bulk fluid or net displacement of particles outside the desired range. Thus, by injecting a sample including particles of the given range into an obstacle array and thereafter alternating fluid flow through the obstacle array in opposite directions (i.e., in directions separated from one another by 180 degrees), particles that exceed the critical size in one flow direction but do not exceed the critical size in the other flow direction can be separated from other particles in the sample by the bumping induced by the array. Such particles can be bumped (and follow the array direction) when fluid flows in one direction, but are not bumped (and follow the bulk fluid flow direction) when fluid flows in the opposite direction. Particles that do not exceed the critical size in either flow direction will not be bumped by the array (i.e., will follow the bulk fluid in both directions), and will remain with the sample bolus. Particles that exceed the critical size in both flow directions will be bumped by the array (i.e., will follow the array direction) when fluid flows in one direction, and are also bumped (i.e., will follow the array direction in the opposite direction) when fluid flows in the opposite direction, and will therefore remain with the sample bolus.

Critical particle size can depend on direction of fluid flow. Intermediate sized particles can be made to ratchet up a device under oscillatory flow.

Second, in a continuous flow mode, particles of a desired size can be induced to move to one side of a fluid stream, and particles above or below that size to the other side or not displaced at all. Thus collection of desired particles can be easier. In conventional devices, particles above a desired range are also displaced from the fluid flow to the same side of the flow, so separating the desired from undesired larger ones can be harder. In this embodiment, obstacles defining different critical sizes for fluid flow in opposite directions are employed in two configurations that are mirror images of one another. For example, with reference to FIG. 1, such an array would include right triangular posts arranged as shown in FIG. 1 (i.e., hypotenuse sloping from lower right to upper left and the tilt angle ε extending from the horizontal toward the bottom of the figure) and would also include right triangular posts arranged as they would appear in a mirror held perpendicularly at the right or left side of the array shown in FIG. 1 (i.e., right triangular posts having their hypotenuse sloping from upper right to lower left and the tilt angle ε extending from the horizontal toward the top of the figure). Particle separation achieved by bulk fluid flow in a single direction (i.e., either from left-to-right or right-to-left) through such an array would be equivalent to back-and-forth flow through the array illustrated in FIG. 1. Particles in the selected size range can be bumped toward the top of the array (as shown in FIG. 1), while particles having larger or smaller sizes can remain at the vertical level at which they enter the array (assuming approximately equal numbers of obstacles in each of the two configurations are encountered).

Reduction in critical particle size as a ratio of gap, compared to circular posts, can occur when particles bump off sharp edges. This can allow larger separation angle without fear of clogging the device faster separations.

These developments can reduce the necessary chip area compared to a continuous flow bump array.

A device described herein can be a microfabricated post array constructed using standard photolithography. A single mask layer can be etched into silicon or used to make a template for PDMS molding. Usually, post arrays can be sealed with a PDMS coated cover slip to provide closed channels Oscillatory flow operation can require more complicated fluid control drivers and interfaces than continuous flow operation.

Figure 11:
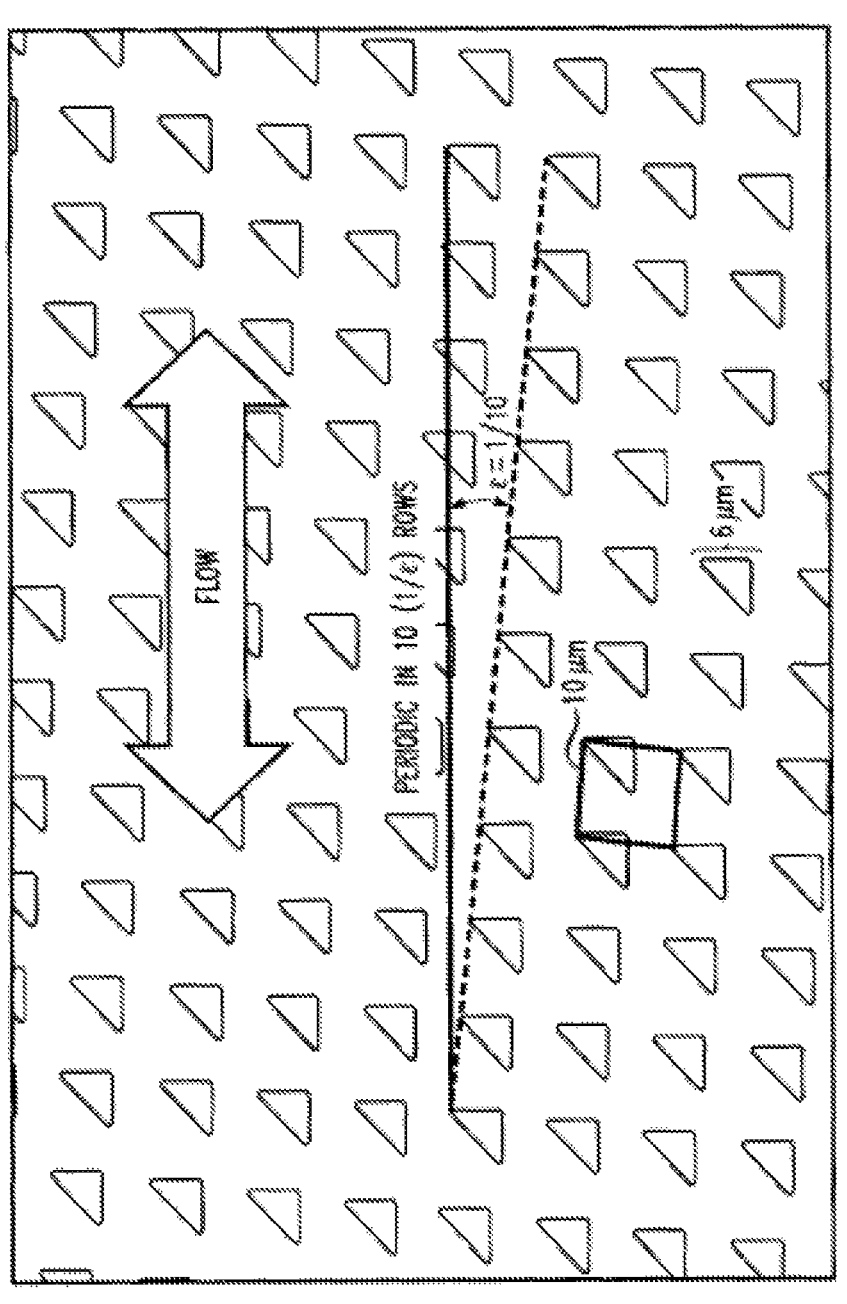
FIG. 11 is an image of an array constructed as described herein.

FIG. 11 is a scanning electron microscope image of posts in an obstacle array of a type described herein. Right isosceles triangular posts, 6 microns on a side, were placed on a square lattice with spacing of 10 microns, giving a gap of approximately 4 microns. The square lattice was tilted 5.71 degrees (0.1 radians) with respect to the device sidewalls to provide necessary asymmetry. Fluid flows along the horizontal axis.

In FIG. 1, the total fluid flux through each gap can be divided into $n=1/\epsilon'$ flow streams (stream tubes), where n is a whole number. Each flow stream can carry equal fluid flux, shown schematically in FIG. 1 for n=3. The stream tubes can be separated by stall lines, each stall line beginning and ending on a post. The stream tubes shift their positions cyclically so that after n rows each streamline returns to its initial position within the gap.

The width of the stream closest a post can determine the critical particle size. If the particle's radius is smaller than the width of the stream, then the particle's trajectory can be undisturbed by the posts and travel in the same direction of the flow. If the particle's radius is larger than the width of the closest stream, then it can be displaced across the stall line and it's trajectory can follow the tilted axis of the array (i.e., the array direction).

The width of the stream closest to the post can be determined by assuming that the velocity profile through a gap is parabolic—the case for fully-developed flow in a rectangular channel. Since each stream can carry equal flux and there are n streams, integration can be done over the flow profile such that the flux through a stream of width Dc/2 (Dc is the critical diameter of a particle) closest to the post is equal to the total flux through the gap divided by n. That is, the integral from 0 to Dc/2 of u(x) dx (u being a function of flux at any position x within the gap) being equal to 1/n times the integral of u(x) dx over the entire gap.

Thus, the critical particle size can be determined from the flow profile. For the case of circular posts, a parabolic flow profile can closely approximates the flow profile through the gap and the critical particle size can be determined analytically.

Figure 4A:
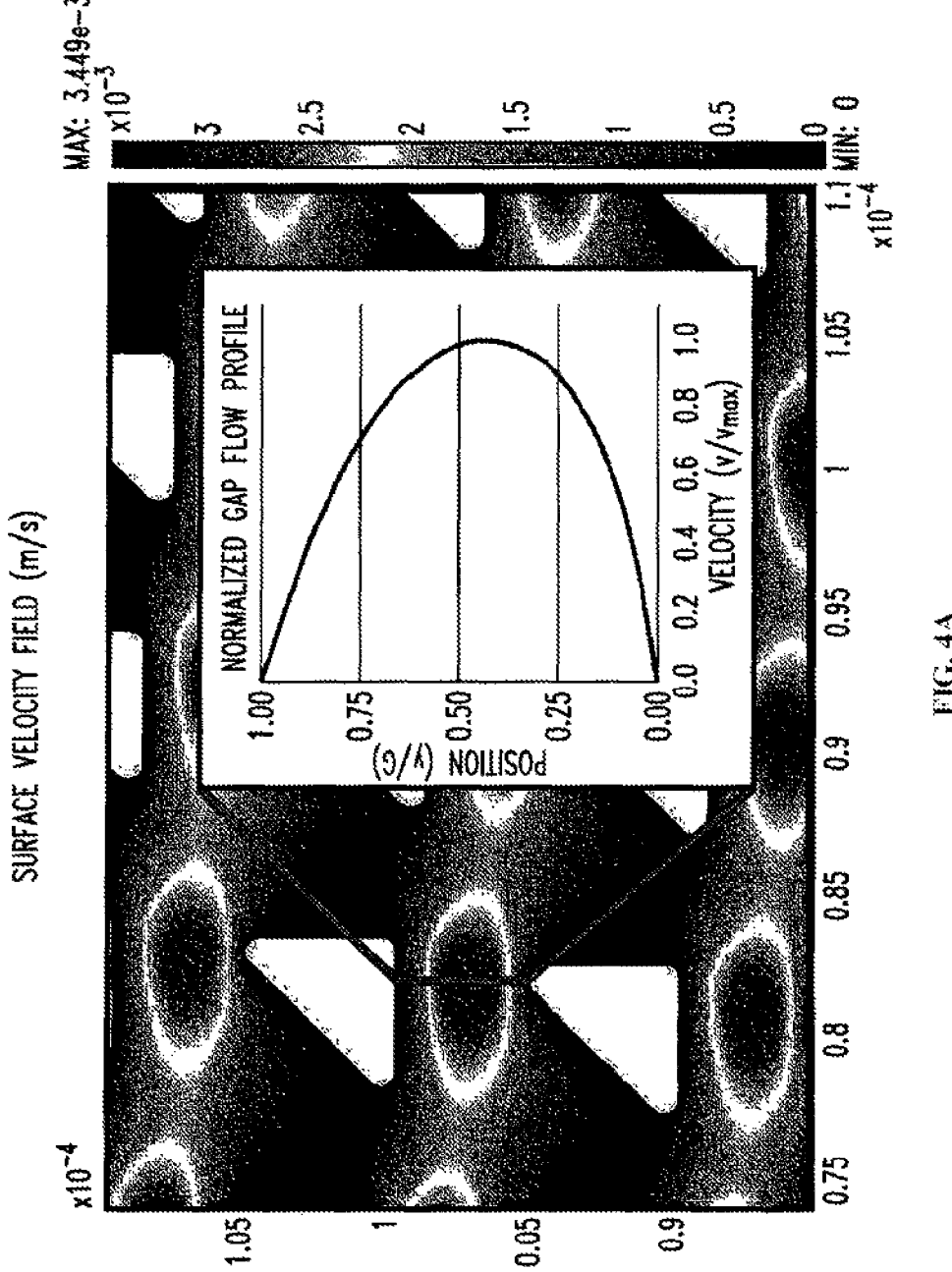
FIG. 4A is a graph showing simulated normalized velocity flow between two right triangular posts.

FIG. 4A shows a numerical simulation of flow profile for an array of triangular posts. In some cases, it cannot be assumed that the flow profile through triangular posts is parabolic because of the broken symmetry. Therefore, flow profile through gap of triangular posts was extracted from numerical simulation (program—COMSOL) of flow through an array with same size and spacing as devices actually made.

Figure 4B:
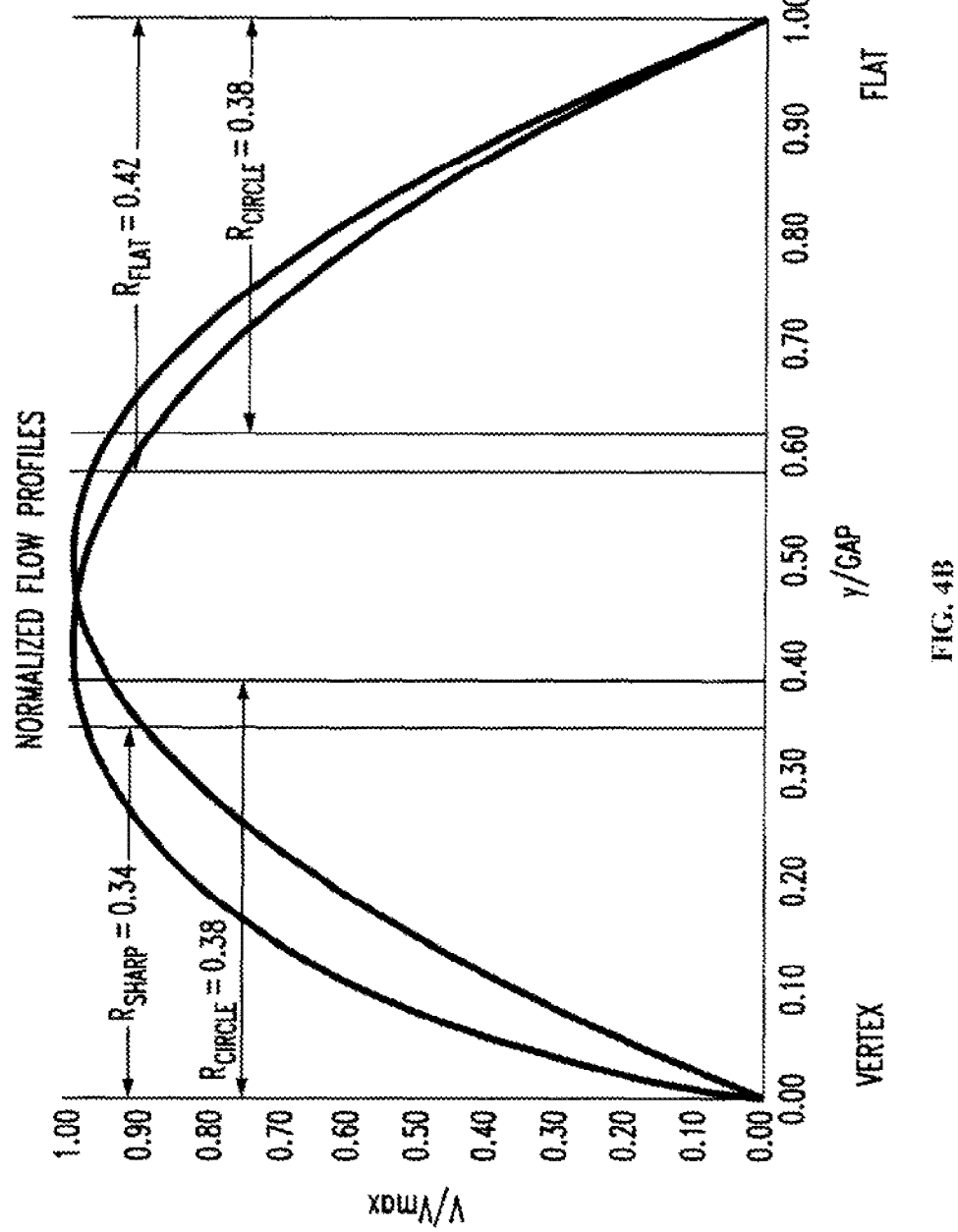
FIG. 4B is a graph showing normalized velocity profiles through gaps between round obstacles (curve that is symmetrical about Y/Gap=0.5) and right triangularly-shaped obstacles in an array of the type shown in FIG. 1 ($\epsilon$=1/3 radian). In these profiles, vertical lines delineate the areas under each curve into thirds, representing three stream tubes of equal volumetric flow. The curve for the round obstacles demonstrates that one third of the volumetric flow between round obstacles occurs in a stream tube that is adjacent to either obstacle and has a width that is 38% of the gap width. The curve for the triangular obstacles demonstrates that one third of the volumetric flow between triangular obstacles occurs in a stream tube that is adjacent to the flat side of one of the two triangular obstacles and has a width that is 42% of the gap width and that an additional one third occurs in a stream tube that is adjacent to the sharp side of the pair of triangular obstacles and has a width that is 34% of the gap width.

FIG. 4B illustrates a comparison of velocity flow profiles between circular and triangular posts. Normalized velocity profiles through gap between triangular and circular posts are shown. As shown, the flow profile for the triangle posts is asymmetric about the center of the gap; more fluid flows along the vertex of the triangle than along the flat edge.

Figure 12:
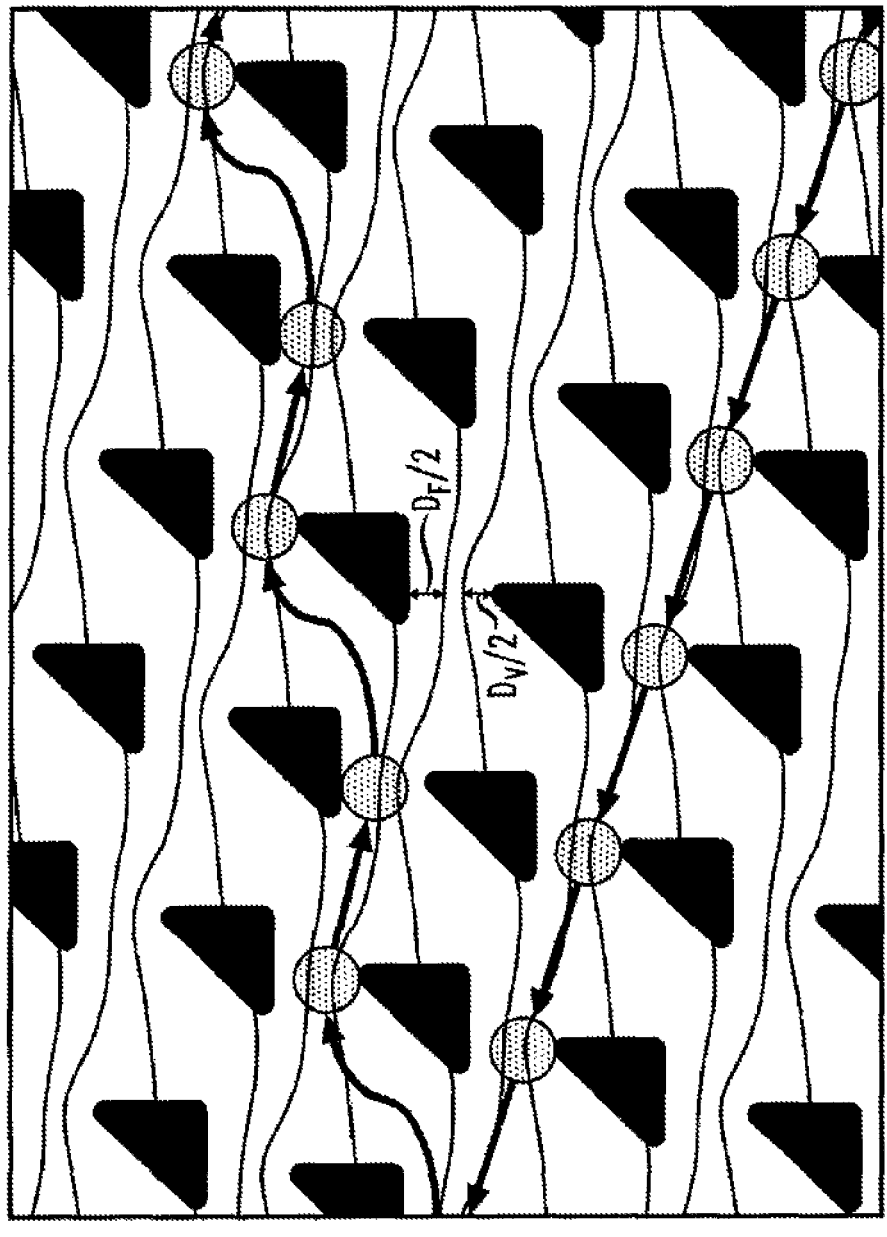
FIG. 12 illustrates particle motion in a ratchet bump array of the type described herein.
Figure 13:
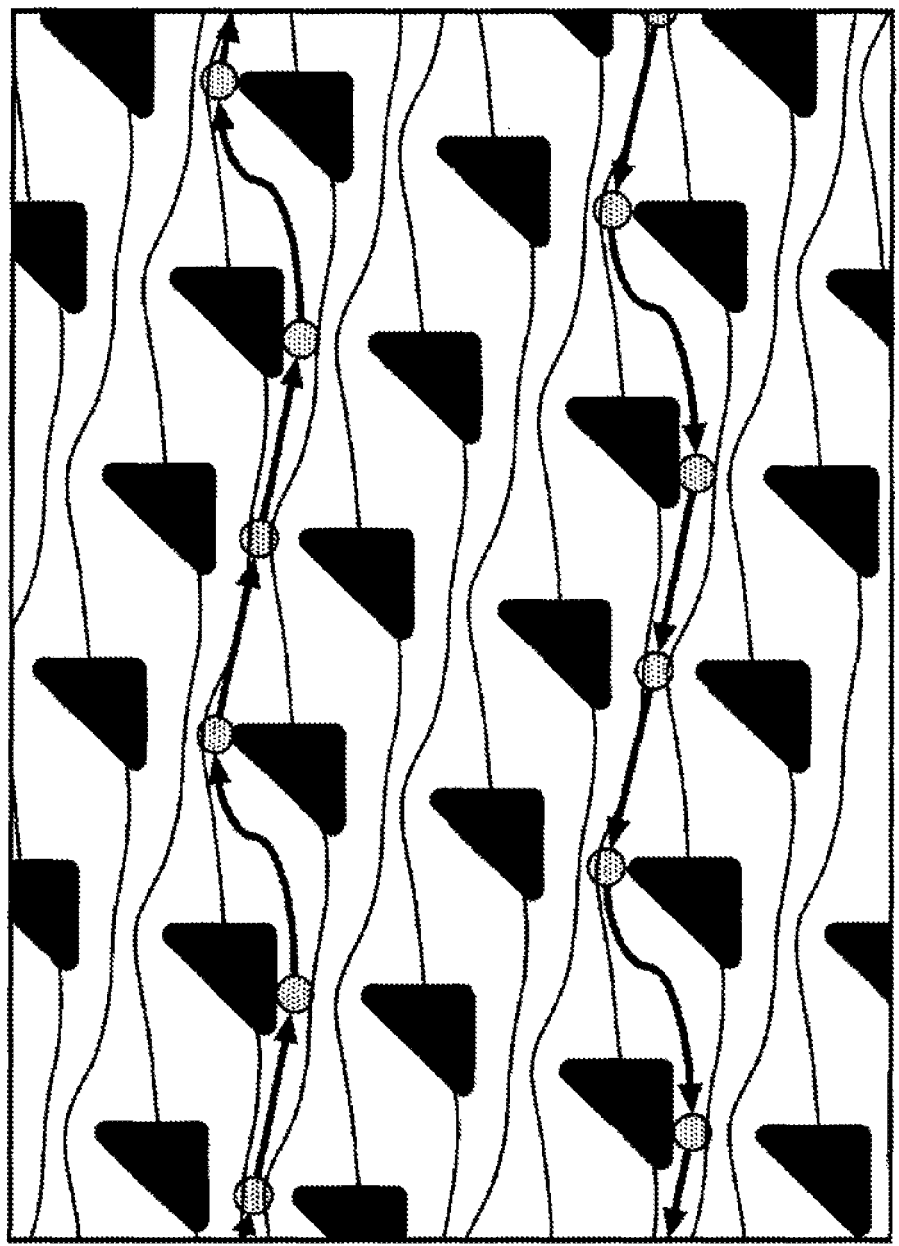
FIG. 13 illustrates particle motion in a ratchet bump array of the type described herein.
Figure 14:
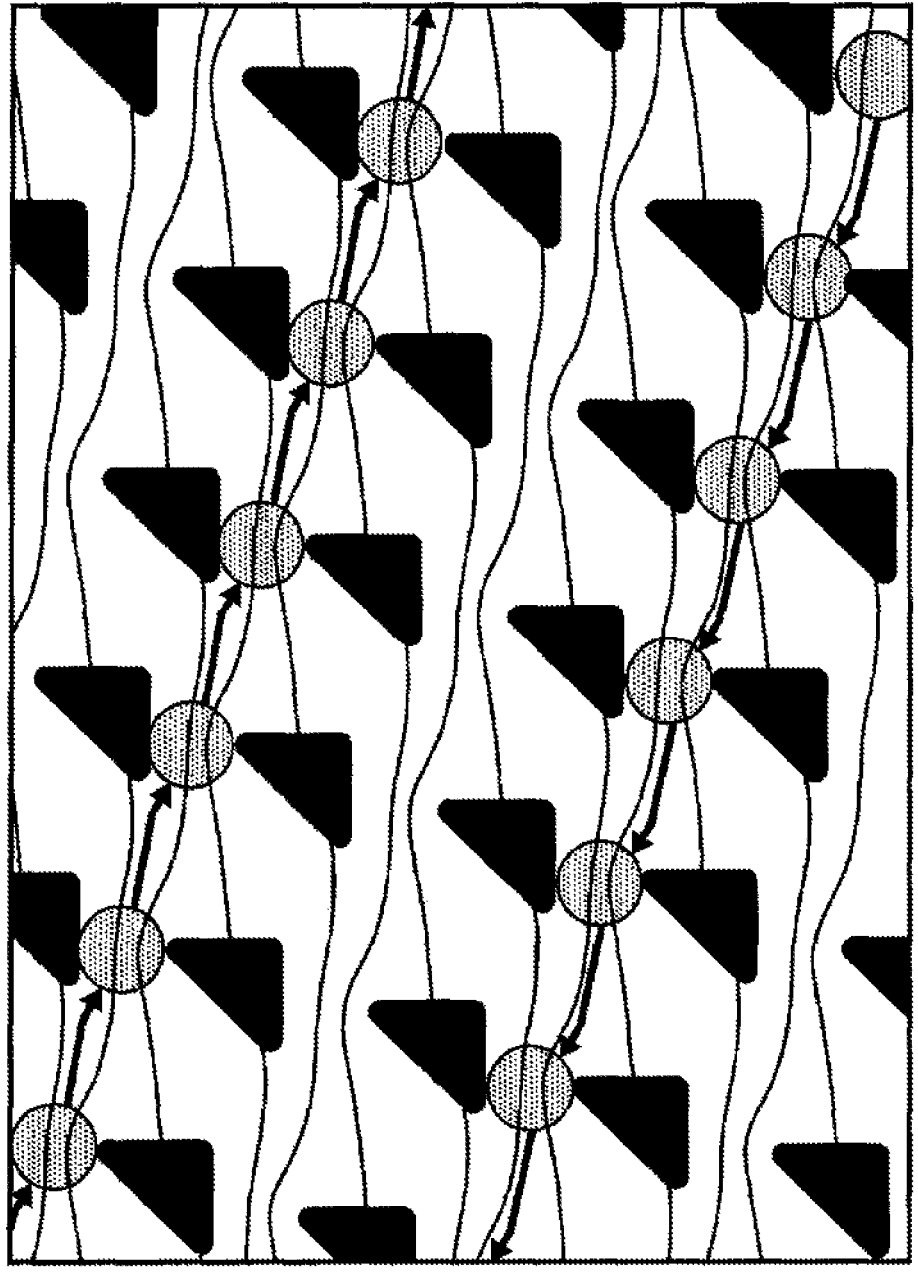
FIG. 14 illustrates particle motion in a ratchet bump array of the type described herein.

FIGS. 12-14 illustrate particle motion in a ratchet bump array of a type described herein. When particles move through the array, the side of the post they interact with depends on which direction they are moving in the array. In this case, when the particles are moving from right-to-left, they bump off the flat edge of the triangular posts. When the particles are moving from left-to-right, they bump off the sharp vertex of the triangular posts. Thus, since the flow profile is asymmetric, it cannot be expected that particles follow the same trajectory when travelling in both directions through the array.

Figure 15:
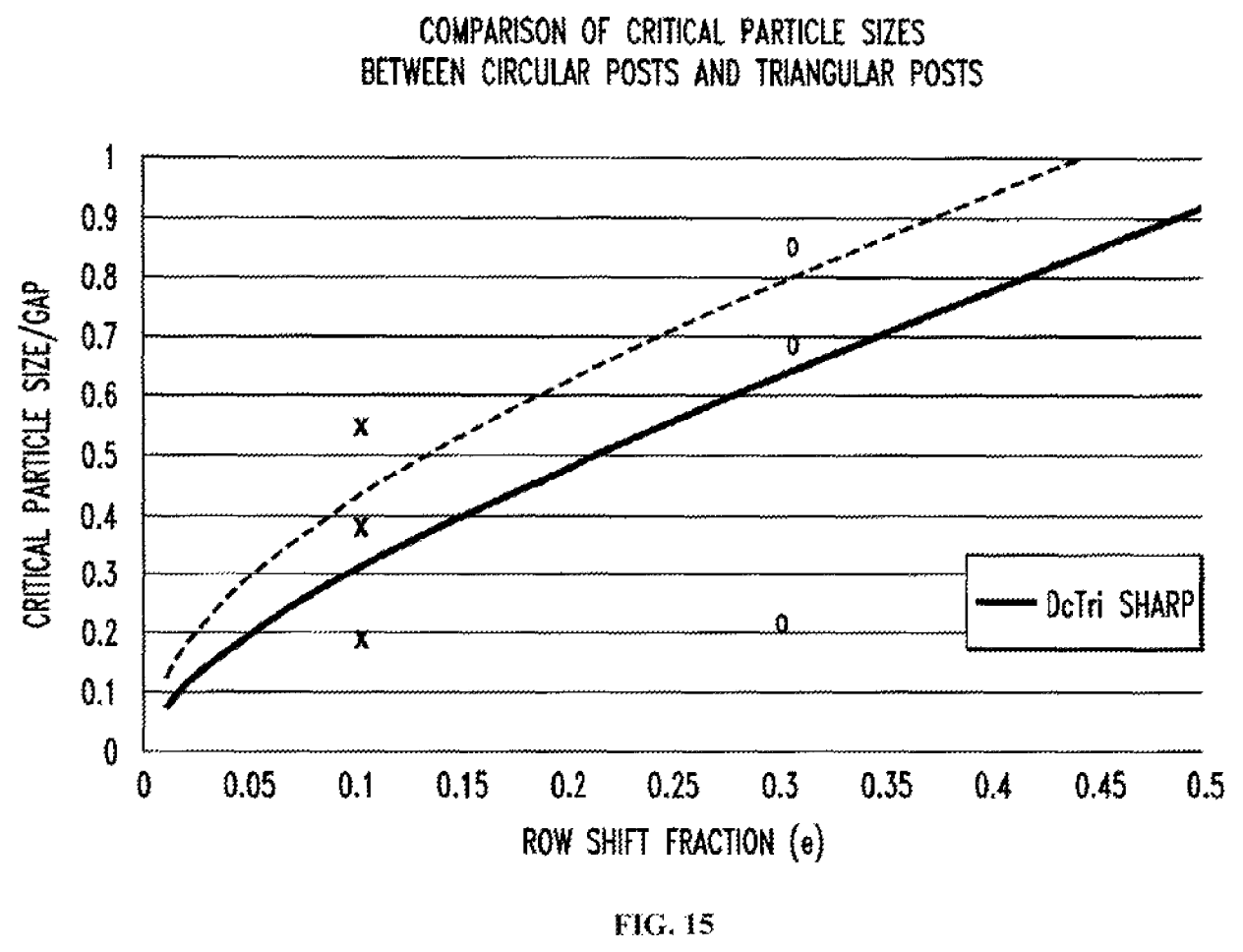

Critical Particle Size for Triangular Posts—Employing the same kind of analysis described in the Inglis et al., 2006, Lab Chip 6:655-658, integratation can occur over the flow profile to find the width of characteristic streams. However, since the flow profile is asymmetric about the center of the gap, the stream width, and hence the critical particle size can be different depending on which side is examined. As shown in FIG. 4B, the result of the asymmetry introduced by the triangular posts is that the critical particle size can be different depending on which side of the triangular obstacle particles interact with. If they are moving along the sharp vertex, then the critical particle size can be smaller than if they are moving along the flat edge. Critical particle size versus array angle ($\epsilon$) are plotted in FIG. 15 compared to circular posts. The critical particle size for bumping along the sharp vertex of the triangle can be substantially smaller than for that of circular posts or the flat edge. This can allow higher angles of separation to be used without fear of clogging the devices. When the particle diameter is larger than the gap size (G in FIG. 1), there can be substantial risk that the array will become clogged if particle density is high.

Figure 3A:
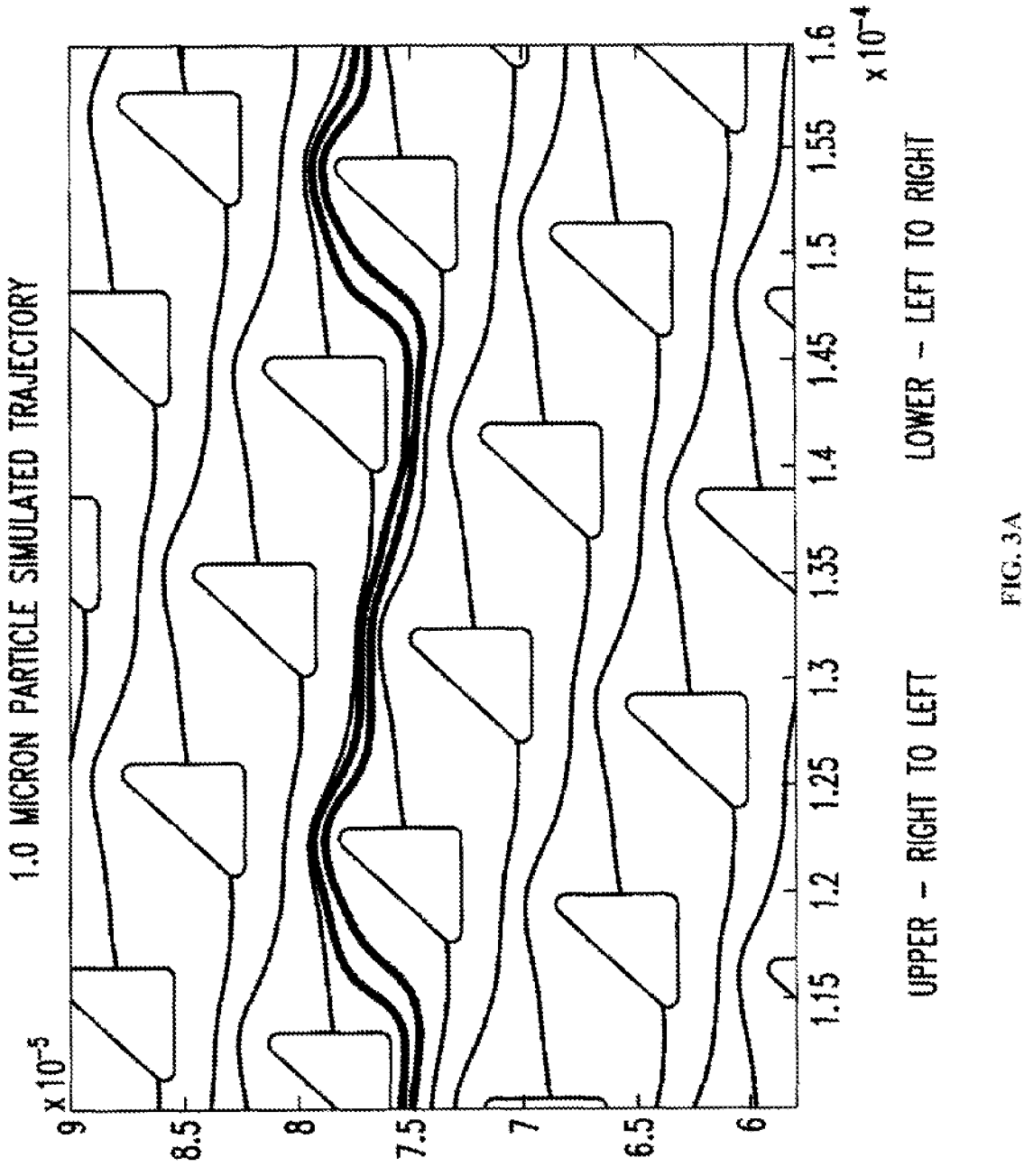
FIG. 3A shows simulated trajectories of 1.0-micrometer diameter particles moving through an array of right triangular posts disposed in a microfluidic flow channel in which fluid flow alternates between the right-to-left and left-to-right directions.
Figure 3B:
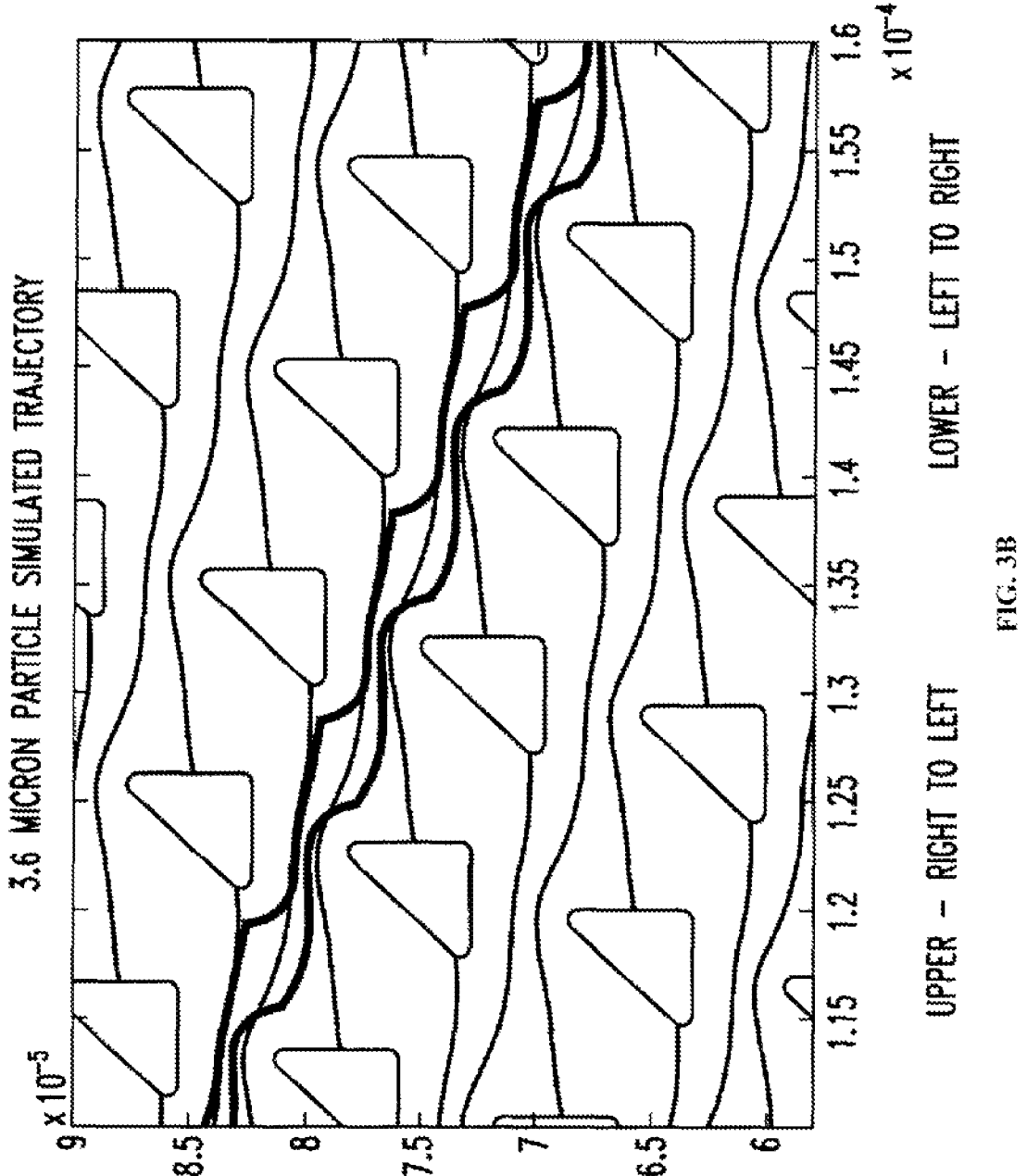
FIG. 3B shows simulated trajectories of 3.6-micrometer diameter particles moving through an array of right triangular posts disposed in a microfluidic flow channel in which fluid flow alternates between the right-to-left and left to-right directions.
Figure 3C:
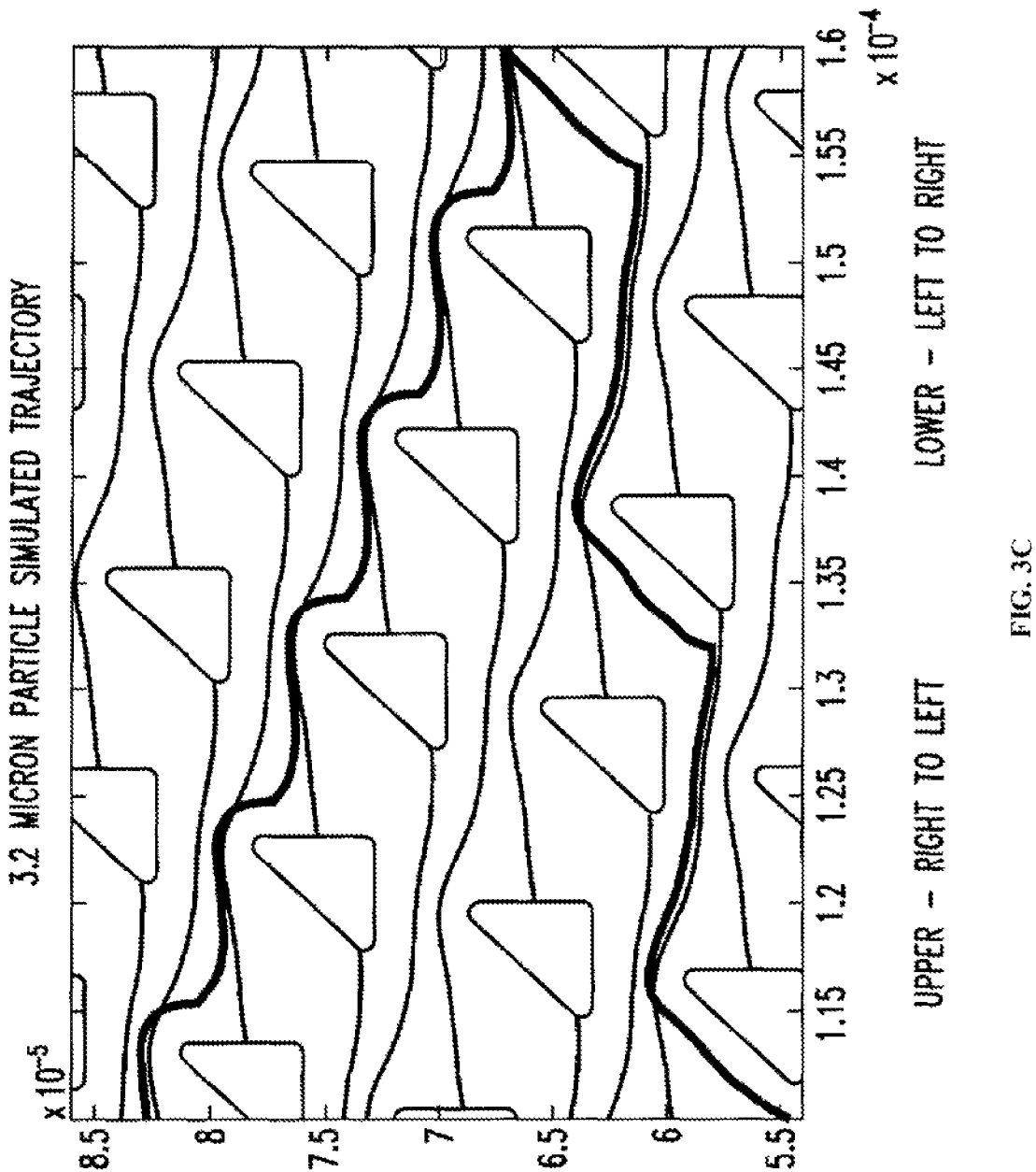
FIG. 3C shows simulated trajectories of 3.2-micrometer diameter particles moving through an array of right triangular posts disposed in a microfluidic flow channel in which fluid flow alternates between the right-to-left and left to-right directions. In these diagrams, the 1.0-micrometer diameter particles are smaller than the critical size of the array in both fluid flow directions, the 3.6-micrometer diameter particles are larger than the critical size of the array in both fluid flow directions, and the 3.2-micrometer diameter particles are smaller than the critical size of the array in one (right-to-left) flow direction, but larger than the critical size of the array in the other (left-to-right) flow direction.

FIGS. 3A-3C illustrate representative particle behavior in a ratchet bump array. For a device constructed as shown in FIG. 11, three representative particles were chosen for this illustration. One particle (illustrated in FIG. 3B) was chosen larger than both critical particle sizes (i.e., larger than the critical particle sizes defined by right-to-left and left-to right fluid flows). One particle (illustrated in FIG. 3A) was chosen that was smaller than both critical particle sizes. Finally, one particle (illustrated in FIG. 3C) was chosen in the interme-diate range i.e., smaller than the critical particle size ($D_F$ in FIG. 12) along the flat edge, but larger than the critical particle size ($D_V$ in FIG. 12) along the sharp edge. These figures illustrate the behavior of particles that were put into the device and their trajectory under oscillatory flow was observed.

Large Particle (FIG. 3B): Since the particle is larger than the critical particle size along both edges, it follows the array tilt axis (E) in both directions and shows no net displacement under oscillatory flow.

Small Particle (FIG. 3A): Since the particle is smaller than the critical particle size along both edges, it follows the fluid trajectory in both directions and shows no net displacement.

Intermediate Particle (FIG. 3C): When the particle moves to the right, it bumps off the flat edge of the triangular posts. Since it is smaller than the critical particle size ($D_F$), it follows the fluid trajectory. When the particle moves to the left, it bumps off the sharp vertex of the triangular posts. Since it is larger than the critical particle size on this side ($D_V$), it follows the array tilt axis and is displaced upward. As shown, under oscillatory flow, particles in the interme-diate range are displaced perpendicular to the direction of the flow. After three cycles of moving back and forth, the bulk fluid has not been displaced, but the particle has moved over 200 microns.

If all three particle types were mixed and placed in a single array under oscillatory flow (i.e., fluid flow oscillating between the right-to-left and left-to-right directions), the intermediate particles would be displaced toward the top of these figures while the small and large particles would have no net motion.

In FIGS. 12-14, representations of intermediate, small, and large particles (respectively) were overlaid on top of numerical simulation of stream tubes to show motion of particles more clearly. n=1/$\epsilon$ was chosen to be 3 to allow periodicity to be seen more easily.

When intermediate particles (FIG. 12) travel along the sharp edge, they bump as can be expected. However, when the particles travel along the flat edge, their motion can be different from that of the small particles. When they perform their characteristic zig to continue in the same direction as the fluid, they are too large to stay in that stream that is close to the sharp vertex and they are displaced across the first stall line. The result is that their motion is periodic in two rows instead of three. With any other tilt angle, the motion can be similar and the periodicity is n−1. The result of this n−1 periodicity is that the intermediate sized particles are actu-ally displaced against the axis tilt angle. Thus a mixture of large, small and intermediate particles will be separated into three streams. Small particles will go straight through (see FIG. 13). Large particles will follow the array tilt axis (see FIG. 14). Intermediate particles will follow a separate path that is dependent on the post geometry.

The applications for which devices described herein are useful include the same ones described in the Huang patent (U.S. Pat. No. 7,150,812): biotechnology and other micro-fluidic operations involving particle separation.

Continuous-flow fractionation of small particles in a liquid based on their size in a micropost "bump array" by deterministic lateral displacement was demonstrated previ-ously (e.g., Huang et al., 2004, Science 304:987-990). A ratchet bump array described herein can possess all the same advantages of the previous work, but can add two new functionalities:

First, the devices can be used to separate particles in a selected size band out of a mixture by deterministic lateral displacement under oscillatory flow (AC conditions) rather than continuous flow (DC conditions). Under oscillatory flow, particles of a given size range can be separated perpendicularly from an input stream (perpendicular to the AC flow axis) without any net displacement of the bulk fluid or particles outside the desired range.

Second, in continuous flow mode, the device can exhibit trimodal behavior. Particles of a desired size range can be induced to move to one side of a fluid stream, and particles above or below that size to the other side or not displaced at all. Thus collection of these desired particles may be easier. In conventional devices, the devices were bimodal and all particles above a desired size range are displaced from the fluid flow to the same side of the flow, so separating the desired from undesired larger ones can require multiple stages whereas the ratchet bump array can require only one.

As used herein, each of the following terms can have the meaning associated with it in this section.

The terms "bump array" and "obstacle array" are used synonymously herein and can describe an ordered array of obstacles that are disposed in a flow channel through which a particle-bearing fluid can be passed.

A "substantially planar" surface can be a surface that has been made about as flat as a surface can be made in view of the fabrication techniques used to obtain a flat surface. In some cases, no fabrication technique will yield a perfectly flat surface. So long as non-flat portions of a surface do not significantly alter the behavior of fluids and particles moving at or near the surface, the surface can be considered substantially planar.

In a bump array device, "fluid flow" and "bulk fluid flow" can be used synonymously to refer to the macroscopic movement of fluid in a general direction across an obstacle array. These terms do not take into account the temporary displacements of fluid streams for fluid to move around an obstacle in order for the fluid to continue to move in the general direction. In some cases, the bulk fluid flow across an obstacle array as provided herein comprises two or more fluid streams flowing from an input or inlet portion or area of the array to an output or outlet portion or area of the array. Each of the two or more fluid streams can flow parallel to each other. The two or more fluid streams can be comprised of the same or different components. The components can be any buffer or reagent described herein or known in the art. In some cases, 2, 3, 4, 5, 6, 7, 8, 9, 10, 11, 12, 13, 14, 15, 16, 17, 18, 19, or 20 fluid streams flow in parallel from an input or inlet portion or area of an array as provided herein to an output or outlet portion or area of the array. Fluid stream can also be referred to as a "stream tube".

In a bump array device, the tilt angle $\epsilon$ can be the angle between the direction of bulk fluid flow and the direction defined by alignment of rows of sequential (in the direction of bulk fluid flow) obstacles in the array. This angle is illustrated in FIGS. 1, 6, and 11, for example.

In a bump array device, the "array direction" can be a direction defined by the alignment of rows of sequential (in the direction of bulk fluid flow) obstacles in the array.

A "critical size" or "predetermined size" of particles passing through an obstacle array can be a parameter that describes the size limit of particles that are able to follow the laminar flow of fluid nearest one side of a gap through which the particles are travelling when flow of that fluid diverges from the majority of fluid flow through the gap. Particles larger than the critical size can be 'bumped' from the flow path of the fluid nearest that side of the gap into the flow path of the majority of the fluid flowing through the gap. In a bump array device, such a particle can be displaced by the distance of (the size of one obstacle+the size of the gap between obstacles) upon passing through the gap and encountering the downstream column of obstacles, while particles having sizes lower than the critical size (or predetermined size) will not necessarily be so displaced. When a profile of fluid flow through a gap is symmetrical about the plane that bisects the gap in the direction of bulk fluid flow, the critical size can be identical for both sides of the gap; however when the profile is asymmetrical, the critical sizes of the two sides of the gap can differ. When assessing a non-spherical particle, its size can be considered to be the spherical exclusion volume swept out by rotation of the particle about a center of gravity in a fluid, at least for particles moving rapidly in solution. The size characteristics of non-spherical particles can be determined empirically using a variety of known methods, and such determinations can be used in selecting or designing appropriate obstacle arrays for use as described herein. Calculation, measurement, and estimation of exclusion volumes for particles of all sorts are well known.

A particle can be "bumped" in a bump array if, upon passing through a gap and encountering a downstream obstacle, the particle's overall trajectory follows the array direction of the bump array (i.e., travels at the tilt angle $\epsilon$ relative to bulk fluid flow). A particle is not bumped if its overall trajectory follows the direction of bulk fluid flow under those circumstances. Conceptually, if flow through a gap is visualized as being composed of multiple individual layers of fluid (i.e., stream tubes, if thought of in a cross-section of fluid flowing through the gap), a particle can be "bumped" if the particle is displaced by a post out of its incident flow tube into an adjacent flow tube as it traverses a gap bounded by the post.

"The direction of bulk fluid flow" in an obstacle array device can refer to the average (e.g., macroscopic) direction of fluid flow through the device (i.e., ignoring local flow deviations necessitated by flow around obstacles in the fluid channel)

C. A Deterministic Microfluidic Ratchet

This example describes a microfluidic device in which the trajectory of particles within a certain size range varies with the direction the particles move through the device. This ratcheting effect can be produced by employing triangular rather than the conventional circular posts or microposts or obstacles in a deterministic lateral displacement (DLD) device where an array of posts selectively displaces particles as they move through the array. This effect can then be used to demonstrate a fractionation technique where particles can be separated from a fluid plug without any net motion of the original fluid plug. The underlying mechanism of this method can be based on an asymmetric fluid velocity distribution through the gap between posts.

Microfluidic devices, such as those used in "lab on a chip" applications, can operate at low Reynolds number ("low" Reynolds number refers to Reynolds number not greater than 1, and preferably smaller, such as 0.1, $10^{-3}$, or smaller). In this regime, the fluid flow through an arbitrary geometry can be considered to be time-invariant reversing the applied pressure gradient that drives the fluid will reverse the flow field because inertial effects are negligible. At high Peclet number ("high" Peclet number can refer to Peclet number greater than 1, and preferably much greater, such as 10, 100, or more), this can be extended to say that diffusive effects can be ignored and objects in the fluid will deterministically flow along a stream tube unless some other interaction, such as displacement by steric repulsion from a channel wall, disrupts their path and moves them to an adjacent stream tube. The degree to which the particle trajectory can be shifted from its original path can depend directly on its size; larger particles can be displaced farther than smaller particles and can consequently follow different stream tubes as they progress through the device. This phenomenon, which can be called deterministic lateral displacement (DLD), has been used in several schemes to perform microscale particle separations.

A "bump array" can be a microfluidic device that relies on deterministic lateral displacement (DLD) to separate particles with high resolution. This device can rely on asymmetric bifurcation of fluid streams in a post array that is tilted at an angle $\epsilon$ (epsilon; typically on the order of 0.1 radians) with respect to the direction of the overall fluid flow. The fluid flowing through a gap splits around a post in the next row, with $1/\epsilon$ of the fluid going through the gap on one side of the next post, while the other $\epsilon$ of fluid goes around the other side of the next post. As a result, the fluid motion can be characterized by $1/\epsilon$ streams that cycle through positions in the gap, but travel straight on average. If a particle suspended in the fluid is small compared to the width of a stream in a gap, the posts will not affect it as it moves through the array and it can travel straight with the fluid flow. However, if the particle is large relative to the width of a stream, it can be displaced into an adjacent stream when the stream it occupies is nearest a post as it moves through a gap. Because of the cyclical way the stream can move through gaps, this displacement or "bump" can occur at every row and the particle can travel at an angle with respect to the fluid and other small particles. With a sufficiently long device, significant separation can be obtained between large and small particles.

Figure 2:
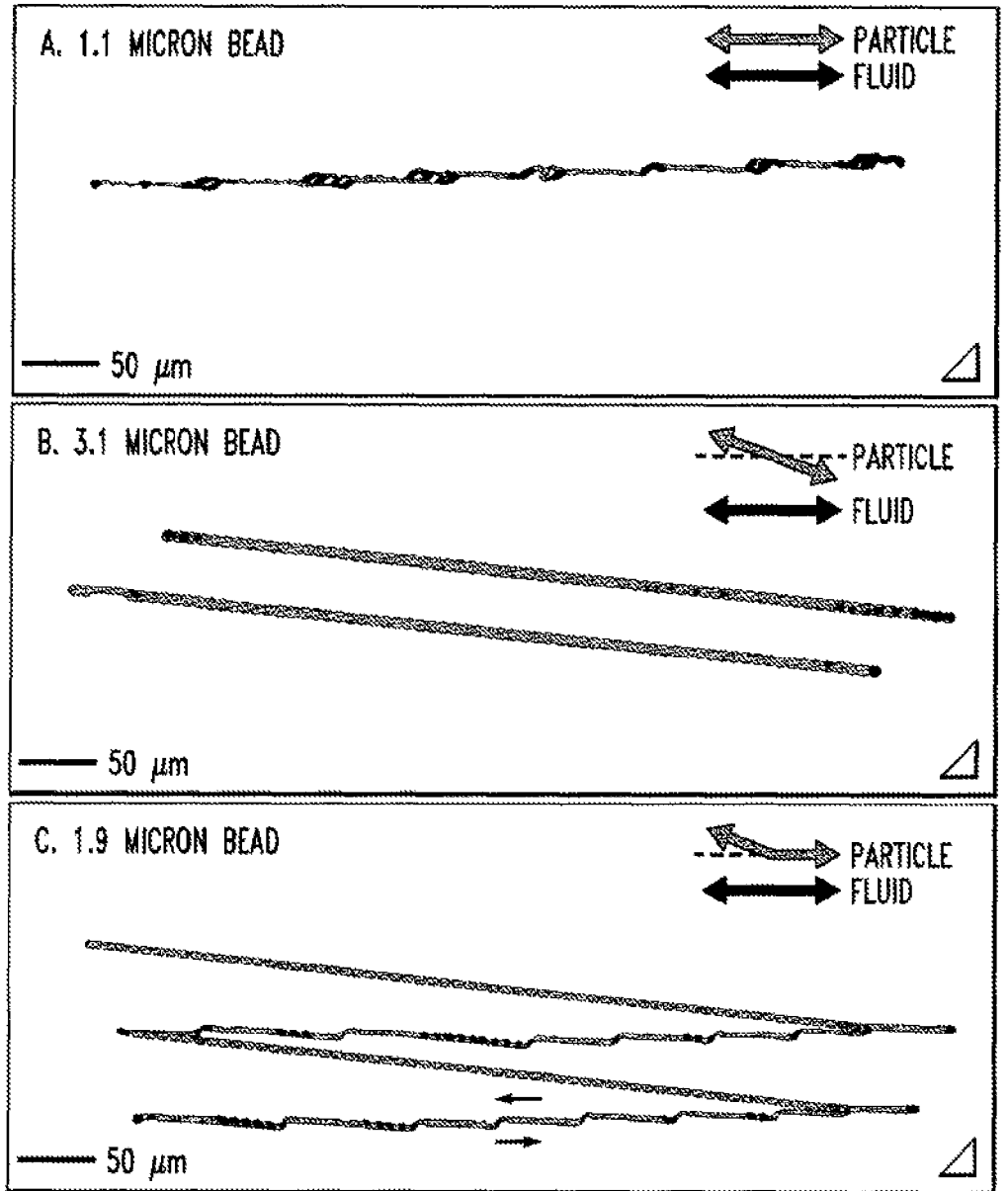
FIGS. 2A, 2B, and 2C, shows the trajectories of spherical polystyrene beads of three different sizes in an array of the type shown in FIG. 1 as the direction of fluid flow is cycled back and forth twice. The orientation of the right triangular posts is denoted in the lower right of each figure. Right isosceles triangles are 6 microns on a side with post to post separation of 10 microns and a tilt angle of 5.71 degrees (0.1 radian). Particle sizes are 1.1 microns in FIG. 2A, 3.1 microns in FIG. 2B, and 1.9 microns in FIG. 2C. Particles shown in FIGS. 2A and 2B retrace their paths when the direction of the fluid is switched, with the particles in FIG. 2A generally following the fluid direction in each fluid flow direction and the particles in FIG. 2B generally following the array direction in each fluid flow direction. By contrast, the trajectory of the particles shown in FIG. 2C varies with the direction of the fluid flow.

FIG. 2A shows a fluorescent time-lapse image of a small particle (1.1 micron diameter polystyrene bead) flowing through such an array at a typical speed of 100 microns/sec. As the particle moves forward, it takes many small steps parallel to the array axis as it moves through, followed by one larger step perpendicular to the motion of the fluid (in what we refer to as "zig-zag mode"), so that the overall motion is to follow the plug of fluid which originally contained the particle. In taking the image of FIG. 2A, the fluid flow was cycled back and forth (by reversing the pressure) twice. The particle retraced its path, as expected from flows at low Reynolds and high Peclet number in a deterministic device not relying on diffusion.

FIG. 2B shows a similar image but for a larger particle (3.1 microns). In this case the particle clearly follows the array axis (i.e., travels in the array direction) and not the fluid flow. Because the particle is displaced from its flow path by the posts in each row, this can be referred to as "bumping mode." This difference in flow direction as a function of particle size can be exploited to make fractionation devices for polystyrene beads as well as biological particles. As in FIG. 2A, the time lapse image shows the path of the particle over two cycles of flowing forward and back, and again the path of the particles is reversible (i.e., the particles end up where they began).

FIG. 2C shows the same experiment in the same array for a particle of intermediate size (1.9 microns). The results are very different from those shown if FIGS. 2A and 2B. This particle "zig-zags" when going to the right (i.e., moving from left-to-right) to follow the fluid flow but "bumps" when going to the left to follow the post array axis. Its path is not reversed when the fluid flow direction is reversed, with the net result that such particles are separated from a plug of fluid in a perpendicular direction when the fluid is subjected to an oscillatory flow.

The displacement of a particle off of a post can be an inherently irreversible interaction, but particle trajectories in a circular post bump array are ostensibly reversible because of symmetry. There is no controversy in this statement for small particles which follow the fluid because the fluid flow must be reversible in the low Reynolds number regime (typical Re 10e-3 for fluid velocity 100 microns/sec and length scale 10 microns). However, large particles do not follow the fluid; instead, they are displaced off posts by steric repulsion so even though the fluid can reverse direction, the trajectory of particles which interact with the posts will not necessarily be reversible unless their interaction with the posts is symmetric with the direction of the fluid. In the schematic in FIG. 3A, particles moving to the left are displaced downward by the top row of posts while particles moving to the right are displaced the same amount by the bottom row of posts. However, if the image is rotated 180 degrees, which is analogous to switching the direction of the fluid, the situation is exactly switched, so the result must be the same in either direction. This rotation works because both the lattice points and post shape are invariant under 180 degree rotation. As a result, both large and small particles in bump array with circular posts can retrace their steps if the flow is switched back and forth.

Numerical simulations showed that the velocity profile through a gap between triangular posts was shifted towards the side of the gap with the vertex. The fluid velocity profile through a gap between posts depends strongly on the local geometry at the gap. For the case of the triangular posts presented here, where there is a sharp vertex on the bottom and a flat edge on the top, a significant deviation from the parabolic flow profile used to describe pressure-driven flow through circular posts should be expected. FIG. 4A shows a numerical simulation of the fluid velocity in an array like that used to produce the particle trajectories in FIG. 2, along with a cross section of the velocity profile across the gap. The line was placed across the smallest spacing between posts to correspond with the narrowest stream widths where crossing stall lines is most likely to occur. The vertices of the triangle were rounded off with a curvature of 500 nm to approximate the rounding off of a sharp point that results from optical lithography. It was found that the flow profile was invariant under changes in the array tilt so this flow profile can be assumed to be the general flow profile for triangular posts arranged in this way.

FIG. 4B shows a comparison between the flow profiles of triangular and circular posts. For round posts, the profile is nearly parabolic as expected for Poiseuille flow through an infinitely long one-dimensional channel. For triangular posts, however, the flow profile is biased towards the sharp triangular corner pointing up into the flow stream. In other words, the streams bunch closer together near this vertex and the critical particle size for a particle to be bumped across a stall line is smaller than it would be for an array with the same gap size but with round obstacles. Along the flat edge, the opposite is true. Because the fluid travels preferentially along the vertex, the width of the stream along the flat edge is wider than for circular posts. The effect of the triangular posts is to create two separate critical particle sizes, one for moving along the vertex of the triangle and another for moving along the flat edge. Therefore, particles in between these two critical particle sizes can exhibit different behavior depending on which direction they are moving through the array. To show this, a technique used by Inglis et al., 2006, Lab Chip 6:655-658 was employed to estimate the critical particle size for circular posts by using the extracted velocity profile instead of the parabola assumed for circular posts.

Figure 5:
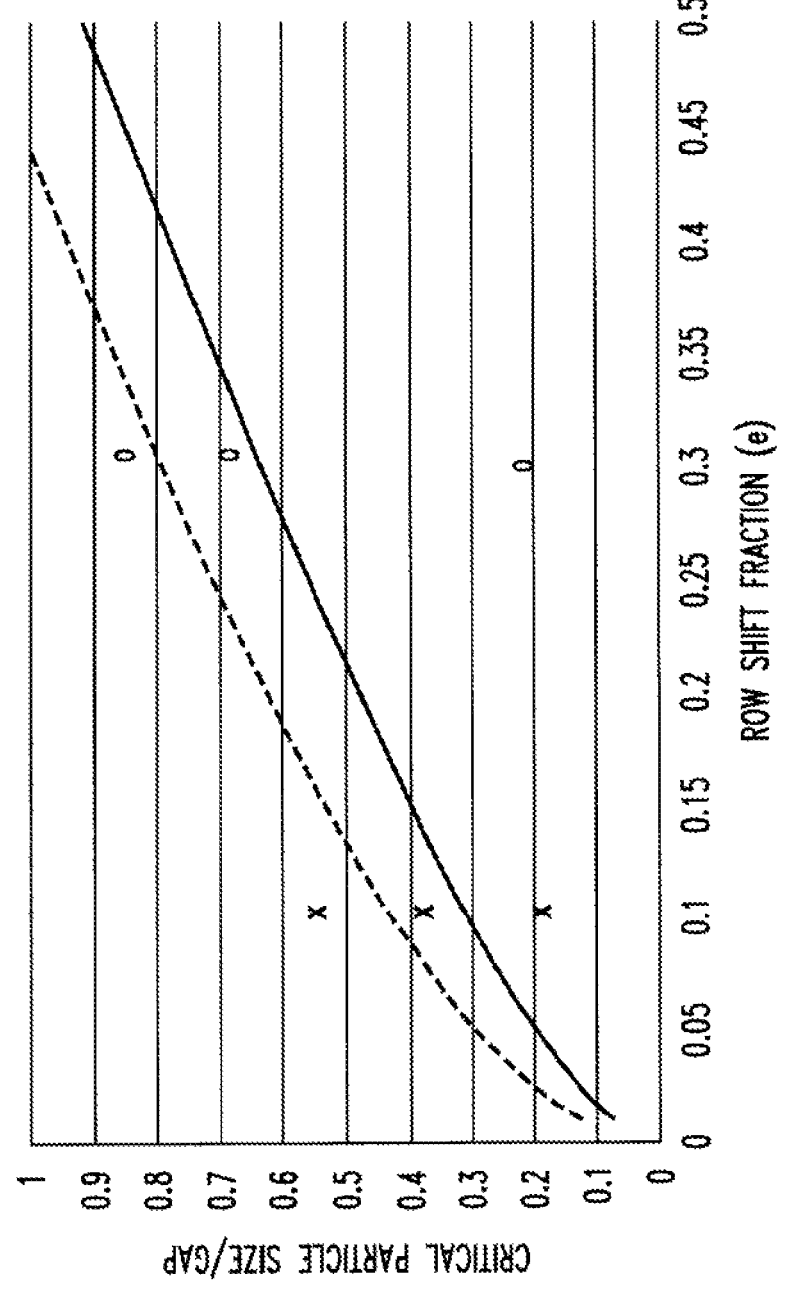
FIG. 5 is a graph of predicted critical diameter versus the array tilt angle ($\epsilon$) for arrays of triangular (lower line) and circular (upper line) obstacles.

FIG. 5 shows this calculation of the critical particle size as a ratio of the gap for the vertex and flat of the triangle as well as for circular posts versus array tilt angle. The particles shown in figure two are shown as circles on the plot. They show good agreement with the predicted behavior. The 1.1 micron bead is smaller than both critical particle sizes so it travels with the fluid in both directions and shows no net displacement when the fluid direction is cycled. The 3.1 micron particle is bigger than both critical particle sizes so it is displaced along the array axis in both directions and shows no net displacement when the fluid direction is cycled. The 1.9 micron particle is in between the two critical particle sizes so it travels with the fluid when it moves along the flat edge of the triangle and with the array axis when it moves along the vertex of the triangle. As a result, it shows a net displacement when the fluid flow is cycled. This is characteristic of a ratcheting behavior. With no net displacement of the fluid, particles in the intermediate range of an array show a net displacement after several fluid flow oscillations. This ratchet differs from other ratchets in that the ratcheting motion does not occur along the axis of the applied force corresponding to fluid flow in either direction. Rather, it is perpendicular to the motion of the fluid.

In another aspect, the DLD chip-based cell processing systems and devices as provided herein can recover all subsets of WBCs from whole blood with >90% yield without the need for a separate RBC lysis step. The use of this new DLD chip-based cell processing method as provided herein can be applicable to many research and diagnostic assays that require single-cell analysis or rare cell isolation, including flow cytometry, mass cytometry, single cell genomics, proteomics, metabolomics and a wide range of new techniques under development. The methods, systems and devices herein can be a research, clinical, and commercial innovation that can productively disrupt cell processing and can replace the current standard centrifugal wash steps that are ubiquitous in research and clinical laboratories.

In another aspect, the microfluidic DLD chip process, which can harvest cells from a flow of fluid on the basis of size. A mixture of fluid and particles flows through an array of microposts, in which the micropost axis can be tilted at a small angle of a few degrees from the direction of the fluid flow. Particles above a certain critical size (in our case, WBCs) can "bump" off the posts to flow in a direction along the tilted array axis (hence the device can be referred to as a "bump array;" FIG. 17) Smaller particles and dissolved molecules, such as red blood cells (RBCs), platelets, soluble and particulate serum constituents, Mabs, and chemical reagents can flow straight ahead, on average, with the fluid stream. Thus, after travelling across the microfluidic chip, the larger cells can have flowed out of and away from the fluid stream of the original input mixture and can be collected separately. The process has been used to remove a range of objects from an input fluid, ranging from large DNA oligomers (~100 kpb) to *E. coli* and other bacteria, platelets, RBCs and WBCs. The critical size determining which path the cells or other objects follow can be controlled by the design of the micropost array (e.g., post size and shape, gaps between posts, axis tilt angle). This is not a sieve process: cells or particles several times larger than the critical size that determines bumping (e.g., cells to be harvested) can flow through the device without clogging. The continuous flow nature of DLD can offer the potential for high throughput without degrading resolution for a low-cost, reproducible approach to wash WBCs that have been labeled for flow cytometry.

D. Bump Array Employing Triangular Posts

This example describes microfluidic arrays which sort particles based on size according to the deterministic lateral displacement (DLD) method, by using triangular posts instead of round or circular posts. When triangular posts are used rather than round posts, and the triangular posts are properly oriented (i.e., such that the surfaces defining the gap are asymmetric), the critical size is decreased for a given gap size between the posts. This is because the different post geometry on either side of the gap causes an asymmetric flow profile through the gap, with flux shifting towards the vertex of the triangle. This shift in fluid flux reduces the width of the stream that determines the critical particle size. In this example, both experiment and modeling are used to show that changing the post shape from circular to triangular results in several practical advantages over similar arrays with circular posts including increased dynamic range and throughput.

Figure 6A:
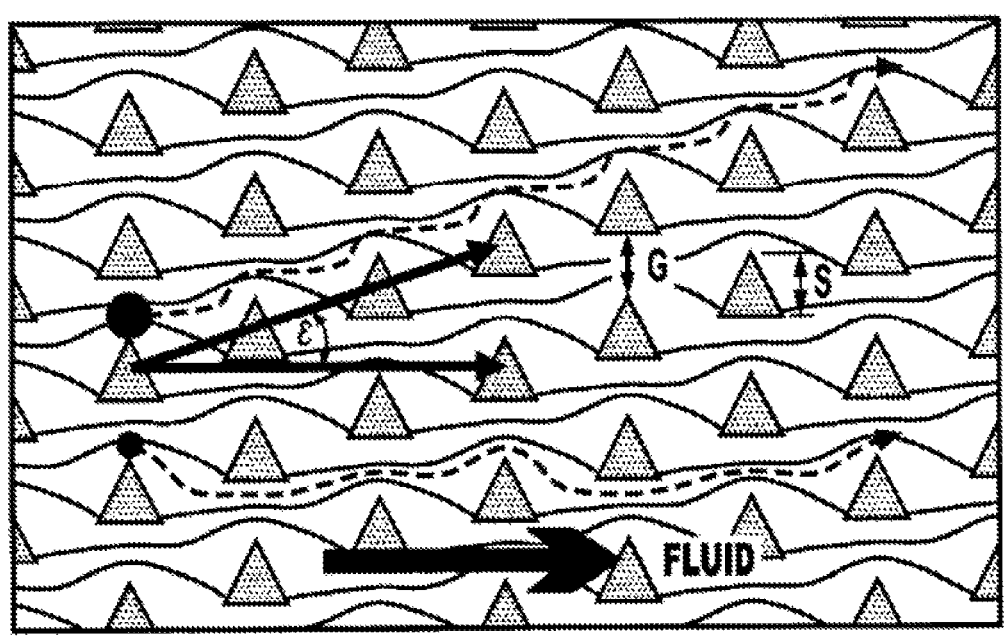
FIG. 6A is a schematic diagram of cross-section of a "bump array" device having equilateral triangularly-shaped obstacles disposed in a microfluidic channel In the figure, fluid flows in the left-to-right direction, as indicated by the arrow marked, "Fluid." In this array, equilateral triangular posts are disposed in a parallelogram lattice arrangement that is tilted with respect to the directions of fluid flow. Other lattice arrangements (e.g., square, rectangular, trapezoidal, hexagonal, etc. lattices) can also be used. The tilt angle $\epsilon$ (epsilon) is chosen so the device is periodic. In this embodiment, a tilt angle of 18.4 degrees (1/3 radian) makes the device periodic after three rows. The tilt angle $\epsilon$ also represents the angle by which the array direction is offset from the fluid flow direction. The gap between posts is denoted G with equilateral triangle side length S. Streamlines are shown extending between the posts, dividing the fluid flow between the posts into three regions ("stream tubes") of equal volumetric flow. A relatively large particle (having a size greater than the critical size for the array) follows the array tilt angle when fluid flow is in the direction shown. A relatively small particle (having a size smaller than the critical size for the array) follows the direction of fluid flow.

Deterministic lateral displacement can be a size-based particle separation technique that relies on selective displacement of particles by an array of obstacles disposed in a flowing fluid. FIG. 6A illustrates a schematic of the relevant array parameters and important features of the devices described in this example. The obstacle array is composed of columns of posts in which each adjacent column is offset a small distance with respect to larger channel walls that dictate the direction of bulk fluid flow ("FLUID" in FIG. 6A). In this case, the posts are equilateral triangles with side length S (contrary to FIG. 6A, S is the side length, not the distance from a vertex of the triangle to the base opposite that vertex). This offset produces an array where an axis along which the obstacles are situated is situated at a tilt angle $\epsilon$ with respect to the direction of fluid flow. The tilt angle is selected such that the array is periodic after $1/\epsilon$ rows. In this case, the fluid flowing through gaps between posts (length of gap is designated G in FIG. 6A) can be partitioned into an integer number of stream tubes delineated by stagnation streamlines. Constrained by the periodicity and the direction of average fluid flow, each of these stream tubes carries an equal volumetric flux.

Particles suspended in the fluid exhibit one of two behaviors depending on their size relative to the width of stream tube nearest to the post as they move through a gap. Unperturbed by other effects, particles can roughly follow the stream tubes in the fluid flow. This behavior can be observed for particles having radii narrower than the stream tube width. These particles, shown as the lower particle and dotted trajectory in FIG. 6A, are not affected by the posts and weave through the array while remain within the bounds of a single stream. As a result, they travel on average in the same direction as the bulk fluid flow. Particles having radii larger than the stream tube width, denoted as the upper particle and dotted trajectory in FIG. 6A, do not fit within a single stream tube as they travel through the gap. Those larger particles are deterministically displaced by the post across the stagnation streamline into the adjacent stream tube. Because of the way the stream tubes cycle through their position in the gap, this displacement will occur at every column of posts and the larger particle will travel along the array axis (i.e., in the array direction, which differs from the bulk fluid direction by the tilt $angle_E$). This binary behavior leads us to describe a critical size which separates these two behaviors. As the particles to be separated are most frequently described by their diameter, we denote the critical size as twice the width of the stream tube nearest to the post in the gap between posts.

Figure 6B:
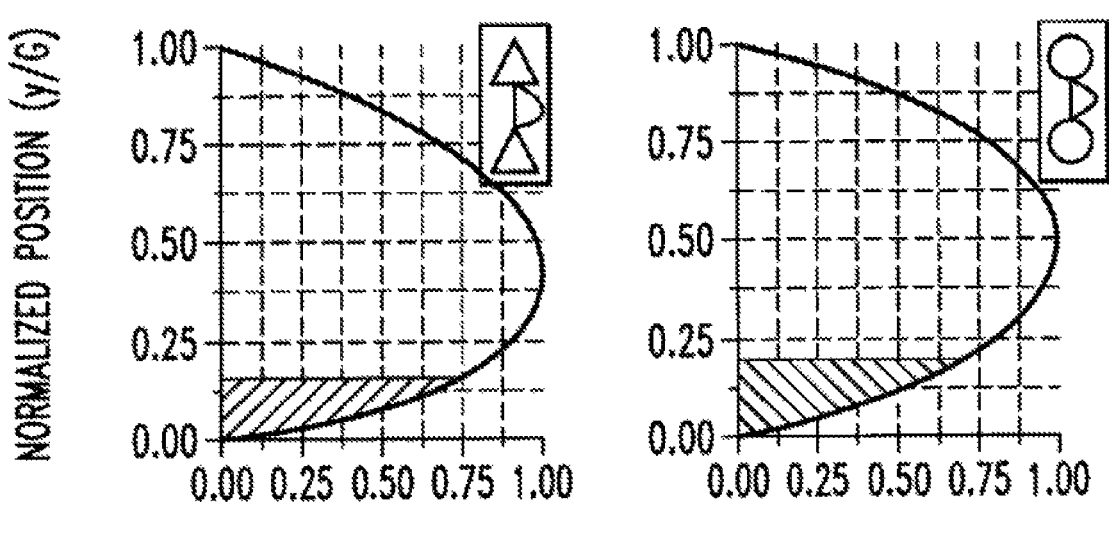
FIG. 6B is a comparison of normalized velocity flow between two equilateral triangular posts (left panel) and normalized velocity flow between two circular posts (right panel). The shaded portions represent an equal proportion of area-under-the-curve, demonstrating that the critical radius for particles flowing past the point of the triangle is significantly smaller (<15% gap width) than the critical radius for particles flowing past the round post (>20% gap width).

Changing the post shape can have a strong effect on the critical particle size by changing the shape of the flow profile through the gap. Alterations to the flow profile alter the width of the stream tubes nearest the posts that define a gap. Because critical particle size can be directly related to these widths, alteration to the flow profile within a gap also alters the critical size(s) defined by the gap. By changing the cross-sectional shape of the posts from a circular shape to equilateral triangles, an asymmetry can be created in the flow profile through the gap that shifts more fluid flux towards the triangle vertex, as shown in FIG. 6B. This results in different stream tube widths at the top (adjacent the flat edge of a triangular post) and bottom (adjacent the vertex of a triangular post) of the gap and gives the array two distinct critical particle sizes.

The shift in flux towards the vertex of the triangle can lead to a reduced stream tube width along this edge and hence can reduce the critical particle size corresponding to that stream tube and edge, relative to a similar array with circular posts. This is demonstrated in the two panels of FIG. 6B, which shows numerically simulated flow profiles across the gaps. The two flow profiles, normalized to the width of the gap between posts and the maximum velocity, are plotted side by side for comparison. The fluid constituting the first stream tube for tilt angle $\epsilon=1/10$ has been shaded to emphasize the difference in stream width, decreasing from about 20% of the gap bounded by circular posts to about 15% of the gap bounded by triangular posts. This shift is central to the reduction in critical particle size behavior exhibited by devices with triangular posts. The shifted flow profile created by triangular posts can be used to create a deterministic microfluidic ratchet. In the information discussed in this example, the focus is on improvement to continuous flow particle separation devices and the deterministic lateral displacement of particles within them that are enabled by changing the post shape.

Figure 7:
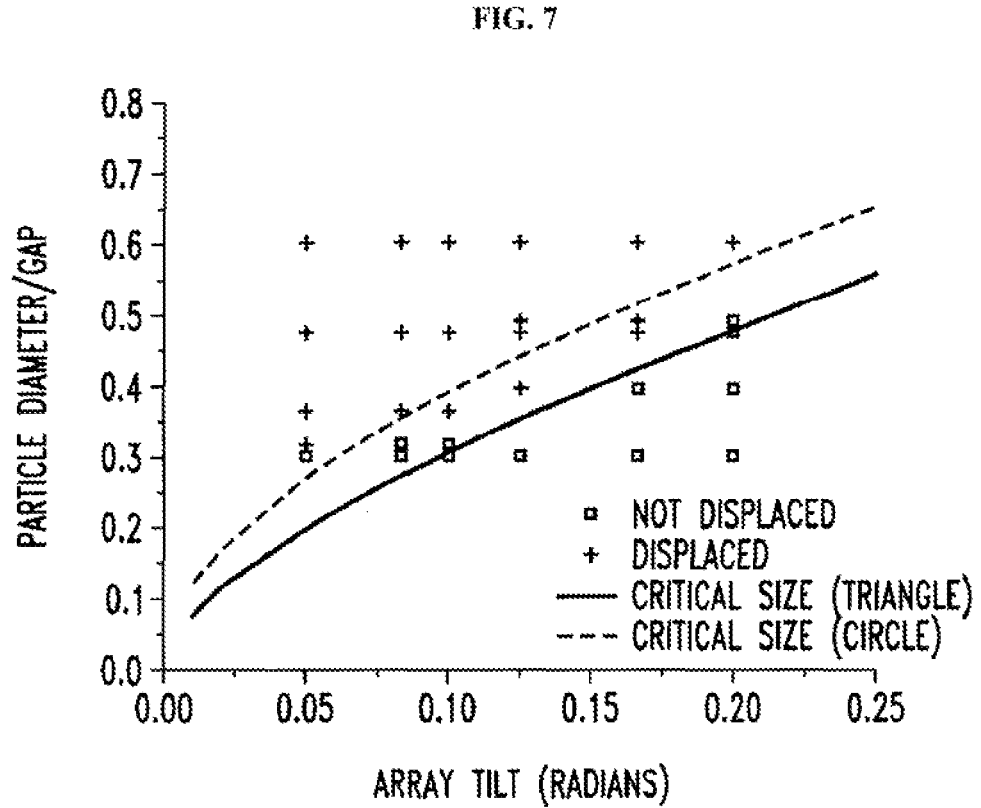
FIG. 7 is a graph illustrating hypothetical and experimental effects of the tilt angle ("Array Tilt" in FIG. 7) on particle displacement.

The reduction in critical particle size enabled by triangular posts was characterized by examining the behavior of fluorescent beads of in arrays with various amounts of array tilt and comparing the results to theoretically predictions. FIG. 7 shows observed particle behavior (displaced by the array or not displaced by the array) normalized to the gap size versus array tilt as well as predicted critical particle sizes using the method described by Inglis et al., 2006, Lab Chip 6:655-658. The lines in FIG. 7 represent the predicted critical particle size for a given tilt angle the solid line representing predictions for arrays with triangular posts and the dotted line representing predictions for arrays with round posts. Particles above the line are expected to be displaced by the array, particles below the line are not expected to be displaced. The data demonstrated that there is reasonable agreement with the predicted behavior for higher tilt angles while there is some deviation at the shallower tilt angles, especially at a tilt angle $\epsilon$ of 1/20 radians. This deviation could be caused by the flow through the array not being completely horizontal, which will have a large affect at shallower array tilts, or because of rounding of the triangular post edges, which will be discussed later in this example.

The predicted particle behavior for circular posts, signified by the dotted line, has been added as a comparison. For any practical tilt angle (between 1/5 and 1/100), the critical size in an array with triangular posts can be substantially smaller than the critical size in a similar array with circular posts, the difference amounting to up to 10% of the gap for the steeper tilt angles. These properties allow smaller particles to be separated by an array of triangular posts than can be separated by an array of round posts having the same gap spacing. These properties also mean that the gap spacing for triangular posts that is necessary to separate particles of a selected size is larger than the corresponding gap spacing for round posts that would be necessary to separate the same particles.

In either case, a reduced critical particle size as a fraction of the gap can be useful in reducing clogging in the array. In some cases, biological samples contain species with a broad range of sizes. In some cases, filtering or multiple separation stages can be used to ensure that an array continues to function. Using triangular posts allows one to increase the size of the gap for a given critical particle size and reduce the chances that the array will clog. FIG. 8 illustrates how much larger the gap between posts can be made as a function of the array tilt. Plotted as a ratio of the two gaps for a fixed critical particle size, a minimum 20% improvement can be seen with increasing gap size as the tilt is reduced, with a ratio of 1.25 for a tilt angle of 1/4 and a ratio of 1.94 for a tilt angle of 1/100. Thus, shallower tilt angles can facilitate use of larger gaps at the cost of a smaller separation angle and increased array size. However, larger gaps can provide another benefit in terms of increased array throughput.

A throughput comparison between an array with triangular and circular posts showed a substantial increase in average velocity for a given pressure drop in the array with triangular posts. Arrays with triangular posts or with circular posts were constructed with nearly identical characteristics. They each had the same overall channel width and length, depth, tilt angle (1/10), and post size (the diameters of round posts were equal to the side lengths of the equilateral triangular posts). The single variation was the gap between posts, which was designed and verified with numerical simulation to give a critical particle diameter of approximately 3.2 microns for both arrays. Those numerical simulations indicated that the critical particle diameter was achieved using a gap of 10.5 microns in arrays with triangular posts and a gap of 8.3 microns in arrays with circular posts.

The trajectories of 500 nanometer fluorescent beads were recorded with an electron multiplying charged coupled device (EMCCD) camera capturing video at 10 frames per second and then analyzed using MATLAB™ software for a given pressure gradient across the array.

Small particles that would not be displaced (i.e., bumped) by the array were chosen so they would sample each of the flow streams evenly and provide an accurate representation of the overall average fluid velocity.

Figure 9:
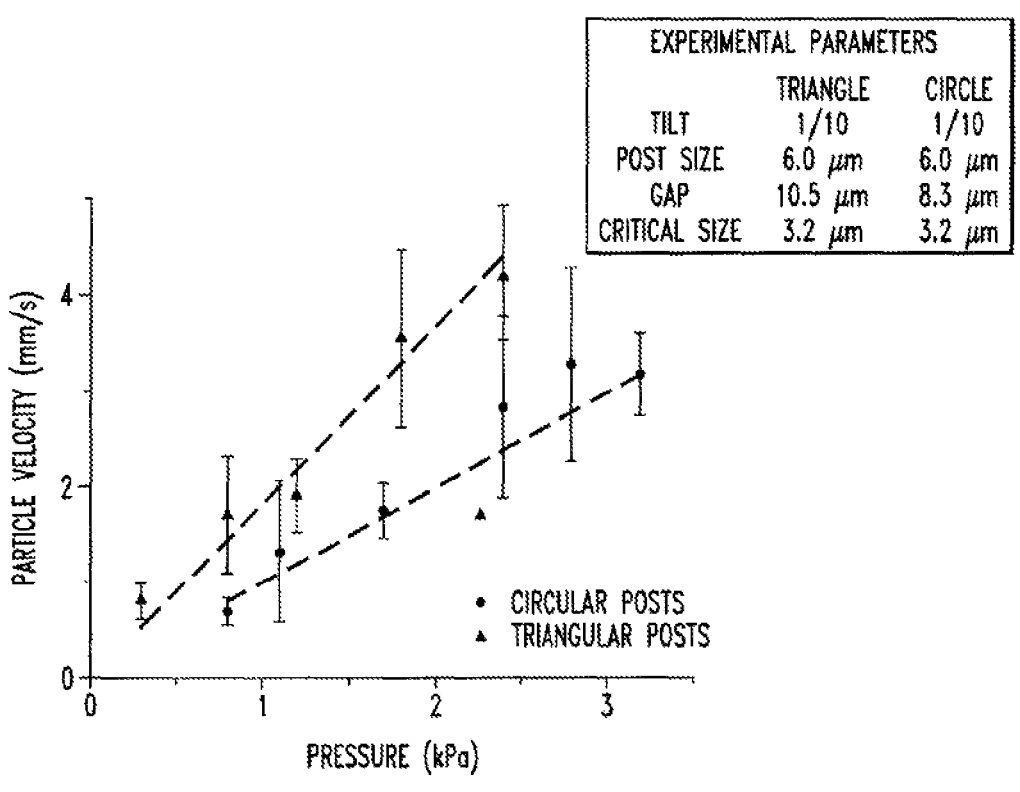
FIG. 9 is a graph illustrating the effect of applied pressure on particle velocity in bump arrays having triangular posts (data shown as triangles) and bump arrays having circular posts (data shown as circles).

The average particle velocities are plotted in FIG. 9 as a function of pressure gradient along with a weighted linear fit. The fitted lines demonstrate that particles in the triangular post array moved much faster. The upper range of pressures was limited by the field of view of the microscope and the capture speed of the camera. Beyond several kPa in pressure, the particles traversed the entire field of view within one or two frames of the video and no accurate estimate of velocity could be made. However, since the Reynolds number in these experiments is on the order of $10^{-2}$, the linear fit can safely be extended into the tens of kPa range to match the expected linear relationship between velocity and pressure that is seen for low Reynolds number flows. The posts need not be triangular in cross-section. Posts having other (square, oblong, or irregular) cross-sectional profiles can also be used, so long as the shape of the obstacles causes the gap to be asymmetric.

Comparing the slopes of the two linear fits in FIG. 9, it can be seen that particles in the array with triangular posts traveled 85% faster on average than those in an array with circular posts. This result agrees with numerical simulation performed with COMSOL™ software that showed that the average velocity for was 82% faster for triangular posts. The mechanism behind these findings can be understood by drawing an analogy to Poiseuille flow between two parallel plates, where the average velocity for a fixed pressure gradient is proportional to the smallest distance between the plates squared. The analogy is not exact because the confining structure is an array of posts instead of two parallel plates, but underscores the benefits of increasing the width of the gap, where just a few microns yields a substantial increase in throughput.

Figure 10:
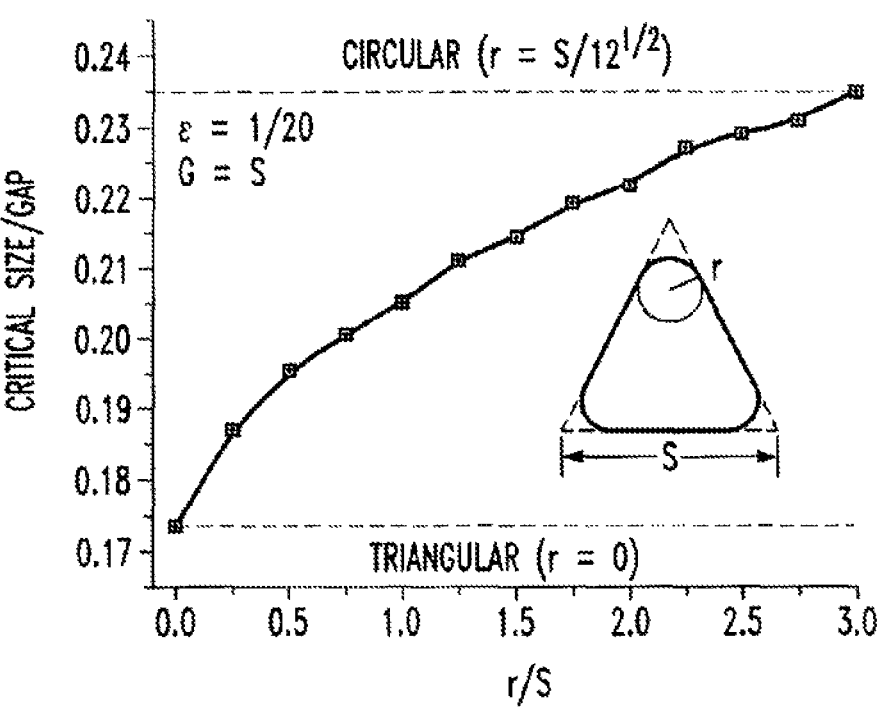
FIG. 10 is a graph illustrating the effect of obstacle edge roundness (expressed as r/S) on the critical size exhibited on the side of a gap bounded by the edge.

The gains achieved by changing the post shape are degraded if care is not taken to maintain sharp post vertices. FIG. 10 shows the effect of rounding triangular post edges on the critical particle size. An array with 10 micron posts, 10 micron gaps between posts, and tilt angle of 1/3o was simulated using COMSOL™ software, with the vertices rounded to various radii of curvature ranging from none $(r=0)$ to complete rounding where the final shape is a circle $(r=S/12^{1/2})$. Flow profiles across the gaps were extracted for each rounding and the critical size for the given tilt was calculated using previously stated methods. As shown in FIG. 10, there is a dramatic increase in the critical particle size as the post shape transitions from triangular to circular. Starting at 0.174 G when the post is completely triangular (i.e., r=0), critical particle size increases 35% to 0.235 G when the post is completely circular (r=S/12$^{1/2}$). The transition suggests that if a fabrication process that produces an undesirable vertex rounding, using larger posts (increasing S) will help to maintain the decreased critical particle size that results from using triangular posts.

This observation also helps to explain the deviation from expected behavior observed for some of the fluorescent beads in FIG. 7. SEM images of the posts show vertex rounding (r/S) of 0.118±0.006, which corresponds to an increase in the critical particle size from 0.93 microns to 1.12 microns.

When purifying a plurality of particles by passing them through an array of obstacles, the yield of the desired particles can be regulated by adjusting the cross-sectional shape of the obstacles. In some cases, adjusting the cross-sectional shape of obstacles can increase the yield of the desired particles. In some cases, the shape of obstacles can affect the level of deformation of particles flowing through the obstacles. Particles undergoing deformation can have low yield after they pass through the obstacles (see e.g., FIG. 53A). Thus, obstacles with cross-sectional shapes that cause low level of the deformation can increase the yield of the particles. In some cases, the cross-sectional shape of obstacles can create inertial effects that result in extra lateral displacement when particles flowing through the obstacles. The inertial effect can result in better separation of particles of different sizes in a sample.

The methods and devices for purifying the particles can comprise an array of obstacles with cross-sections that have one or more vertexes. Obstacles of such shapes can create less shear force to the flowing through particles compared with obstacles with smooth shapes, such as round. In some cases, the cross-sectional shape of the obstacles can be polygonal, e.g., quadrilateral. Non-limiting of quadrilateral include a cyclic quadrilateral, square, kite, parallelogram, rhombus, Lozeng, rhomboid, rectangle, tangential quadrilateral, trapezoid, trapezium, or isososceles trapezoid. The quadrilateral can have at least one angle between 87° and 93°. For example, the shape of the obstacles can be square.

The gaps of the obstacles can also affect the shear force of the obstacles for particles flowing through the obstacles. A respective gap can be defined by the surface of two obstacles. In some cases, the respective gap can be substantially symmetrically oriented about a plane that extends through the center of the respective gap and that is parallel to a direction of flow of the sample through the array of obstacles. In some cases, the respective gap can be asymmetrically oriented about a plane that extends through the center of the respective gap and that is parallel to a direction of flow of the sample through the array of obstacles.

In some cases, methods taking advantage of obstacles with optimized cross-sectional shapes can be used to isolate a first types of particles in a sample comprising the first types of particles and a second type of particles, thereby purifying the first type of particles from the sample. Provided herein includes a method for separating a first group of particles and a second group particles in a sample comprising the first group of particles and the second group particles, the method comprising: (a) passing the sample through an array of obstacles, thereby obtaining a product. In some cases, the cross-sectional shape of the obstacles can be quadrilateral, e.g., a cyclic quadrilateral, square, kite, parallelogram, rhombus, Lozeng, rhomboid, rectangle, tangential quadrilateral, trapezoid, trapezium, or isososceles trapezoid. In some cases, the gap between the particles is symmetrical, and the two obstacles forming the gap have vertices that point at one another across the gap. The cross-sectional shape of the obstacle can be any shape that has a vertex in the gap that yields a symmetrical gap, e.g., quadrilateral, hexagon, octagon, decagon, etc.

Such methods and devices can be configured to achieve a high yield of the first types of cells and a low contamination of the second types of cells in the purified product. In some cases, the yield of the first group of particles (e.g., the desired particles) can be at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. In some cases, the yield of the first group of particles (e.g., the desired particles) can be 100%. In some cases, the contamination of the second group of particles (e.g., the non-desired particles) can be less than 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.005%, or 0.001%. In some cases, the second group of particles does not exist in the purified product. In some cases, the purified product can comprise at least 80% of the first group of particles and less than 0.01% of the second group of particles.

E. "Car Wash" Device

In one aspect, the devices, methods, compositions, and kits provided herein replace chemical or reagent treatment and/or manual wash/concentrate steps present in many techniques known in the art. The devices provided herein can replace any procedures requiring centrifugation known in the art. In some cases, the devices, methods, compositions, and kits provided herein replace the labeling (e.g., cell surface and/or intracellular), and wash/concentrate steps used to process samples comprising cells. The processed cells can then be used for research and/or clinical diagnostic testing. In some cases, the devices, methods, compositions, and kits provided herein replace the labeling (e.g., cell surface and/or intracellular), wash/concentrate, and/or erythrocyte lysis steps used to process blood samples for use in research and clinical diagnostic testing. The clinical and diagnostic testing can be used for cancer, infectious and inflammatory diseases and/or many other diseases. In some cases, the devices, methods, compositions, and kits provided herein replace the lysis, enzymatic treatment(s), cloning, and/or wash/concentrate steps used to process samples comprising cells from cells to nucleic acid libraries. The nucleic acid libraries can be used in sequencing. The sequencing can be any Next Generation sequencing method or platform known in the art. The methods provided herein can be automated reagent-free microfluidic processes that can effectively harvest, wash and concentrate particles (e.g., cells) in several minutes, with high yield, high reproducibility, and low cost. The particles can be any of the cells provided herein. In some case, the particles are stem cells, leukocytes and/or leukemia cells.

Figure 17A:
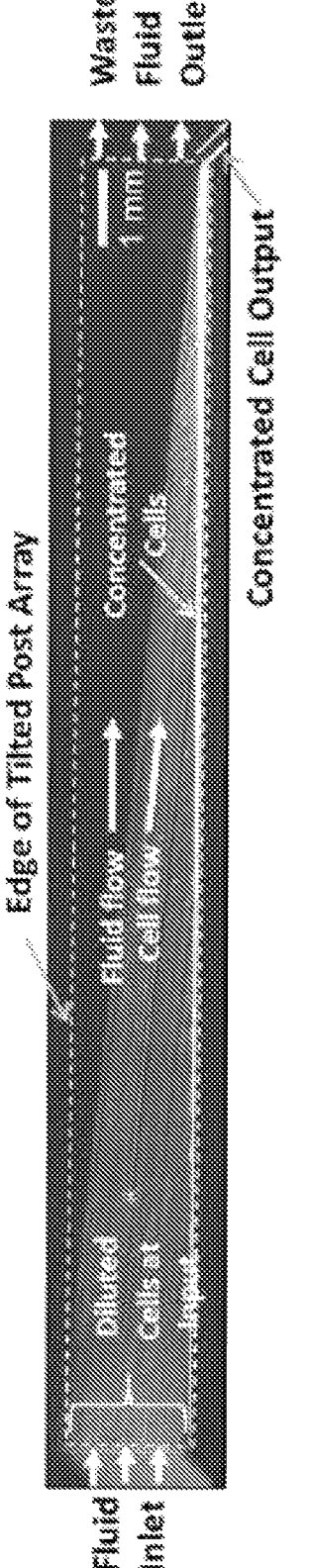
FIG. 17A shows a DLD array designed to "bump" E. coli (>1 μm size). Top view: an example of DLD mechanism showing uniform input of fluorescent (white) E. coli bacteria in a tilted post array being bumped downwards at an angle to the fluid flow, to become highly concentrated against the lower array wall and then collected, while fluid moves horizontally.
Figures 17B, 17C:
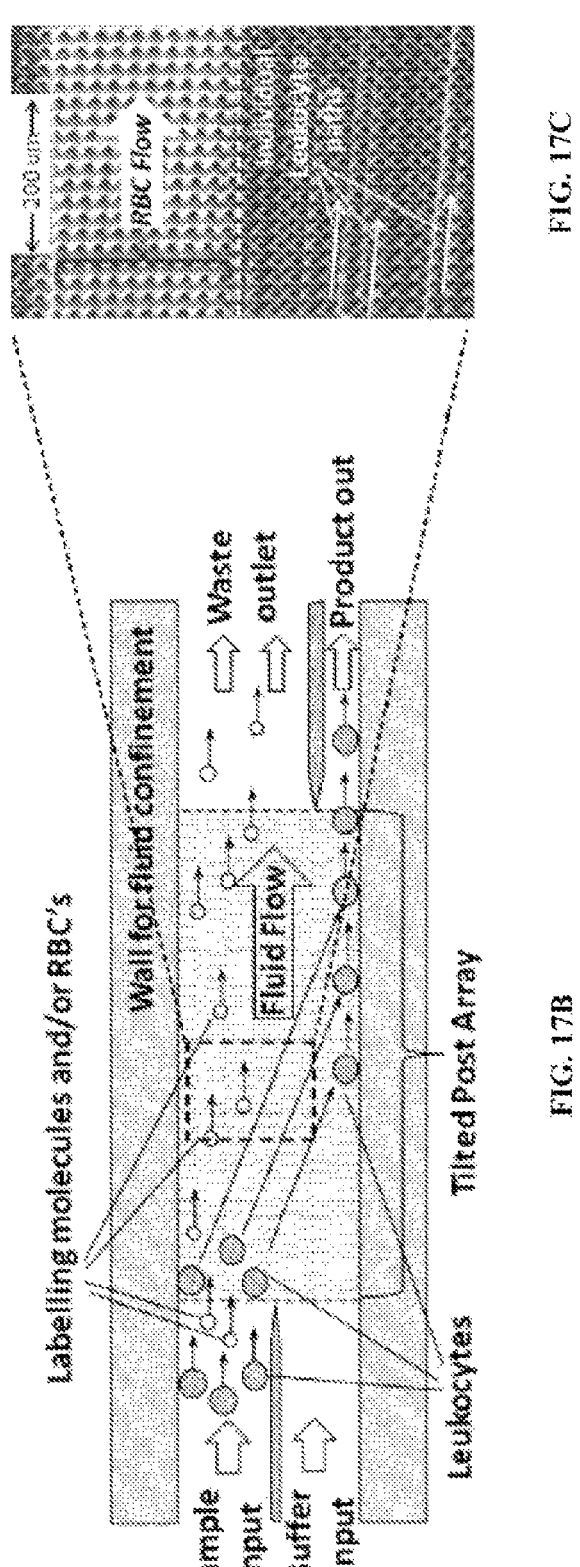
FIG. 17B shows a DLD array having a first stream comprising a sample stream, and a second stream comprising a buffer. Schematic view: Washing of WBCs by extension of FIG. 17A by adding an input buffer stream. Only WBCs (larger than RBCs) move down to the buffer stream and lower wall.
FIG. 17C shows a time lapse image of leukocytes being concentrated and harvested from a DLD array similar to the DLD array shown in FIG. 17B. Time-lapse image of WBCs (blue from nuclear stain) being harvested out of a stream of whole blood (reddish/white) moving left to right using a chip with design as in FIG. 17B.

As shown in FIG. 17B, a "car wash" device as provided herein can comprise two inlets (FIG. 17B; 'sample' and 'buffer') which are configured to flow two separate fluids from an input area of a device to an output area of the device. In FIG. 17B, the two fluids are flowed in a laminar parallel manner across the device to two outlets in an outlet portion of the device, wherein the laminar flowing fluids are present as non-mixing streams or stream-tubes. As also shown in FIG. 17B, the fluids flowing across the device from the input area to the output area encounter an array of obstacle there between. The array of obstacles can be a DLD array (tilted post array in FIG. 17B) as provided herein. The array can be configured to separate particles in the laminar, parallel flowing streams based on size in a deterministic manner as described herein. Particles larger than the critical size of the DLD array can be "bumped" as described herein toward the 'bottom' of the DLD array and be subsequently flowed toward and harvested from an outlet (product out portion of FIG. 17B). As shown in FIG. 17B, the two inlets are separated from each other by a wall. In some cases, a wall separating adjacent inlets in a multi-inlet car wash device as provided herein extends into the interior of a channel comprising the inlets, DLD array, and outlets until the wall encounters or abuts an edge of the DLD array. The edge of the DLD array can be the edge closest or nearest to the inlets. As shown in FIG. 17B, the edge of the DLD array is perpendicular to the wall separating the inlets. As shown in FIG. 17B, the two outlets are separated from each other by a wall. As shown in FIG. 17B, the wall separating adjacent outlets in a 'car wash' device as provided herein can extend from an edge of the DLD array nearest to the outlets to the end of the channel, wherein the edge of the DLD array is perpendicular to the wall separating the outlets. Based on the principles of DLD as described herein, particles (e.g., cells, nucleic acids, reagents such as antibodies, probes, etc.) above a critical size will flow in the direction of bulk fluid flow and exit the device in one outlet (waste output on FIG. 17B), while particles (e.g., cells, nucleic acids, etc.) above the critical size exit the device from a second or separate outlet (product out in FIG. 17B). As shown in FIG. 17B, a 'car wash' device as provided herein is used to wash white blood cells (e.g., leukocytes) in a sample comprising binding agents comprising labels (e.g., labeling molecules) and smaller cells {e.g., RBCs). As can be seen, the sample is flowed from the input area across the DLD array to the output area, wherein upon entering the tilted post array, the white blood cells are bumped from the sample flow stream into the parallel buffer flow stream, while the binding agents comprising labels (e.g., labeling molecules) and RBCs remain in the sample stream. The white blood cells can then be harvested from the product outlet essentially washed and purified from the labeling molecules and RBCs (FIG. 17C).

As shown in FIG. 19, a "car wash" device as provided herein can comprise a plurality of inlets and a plurality of outlets with an array of obstacles there between (e.g., tilted post array in FIG. 19). The plurality of inlets can be more than two inlets. The plurality of outlets can be more than two outlets. The device can comprise a channel bounded by a first wall and a second wall, wherein the second wall opposes the first wall, and wherein the first and second walls are configured to confine fluids flowing there between. The device can further comprise a plurality of inlets between the first and second wall. As shown in FIG. 19, the inlets can be adjacent to each other and can be separated by a wall. The separator walls between adjacent inlets can extend into the channel for a distance. The distance can be to the nearest perpendicular edge of the DLD array. The channel can be configured to flow a plurality of fluids in streams from the plurality of inlets across the DLD array to the plurality of outlets. The streams can be flowed in a parallel, laminar manner, wherein adjacent flowing streams ('flow streams' or 'streamtubes') experience minimal (e.g., due to limited diffusion), no or substantially no mixing between the adjacent flow streams. In some cases, a particle (e.g., cell) can move at an angle to the parallel flow streams by the action of deterministic lateral displacement (DLD). In some cases, cells are introduced without a processing chemical or enzymatic reagent, moved into a flow stream comprising said chemical or enzymatic reagent by DLD, and then out of the stream into a stream comprising a clean (i.e., reagent-free) buffer, and then out of a product outlet, already washed. The DLD array between the plurality of inlets and outlets can be any DLD array as provided herein. In some cases, the DLD array comprises round microposts. In some cases, the DLD array comprises triangular microposts. In some cases, the DLD comprises both round and triangular microposts. The microposts can have any of the dimensions as provided herein. The fluid streams can be flowed through the channel at any of the flow rates as provided herein. In some cases, a car wash device as provided herein is configured to be high-throughput, wherein fluid streams are flowed at high flow speeds (e.g., at least 1 ml/min). In some cases, a car wash device as provided herein is configured to or adapted to be high-throughput, wherein a volume of sample for running through the device is greater than a 100 mls. FIG. 19 shows a device comprising 3 inlets in the input area of a device comprising a DLD array. The 3 inlets are configured to flow 3 flow streams parallel to each other. A first flow stream comprises a sample, wherein the sample comprises particles, a second flow stream comprises a reagent, and a third flow stream comprises a wash buffer. The device is configured such that the sample is inputted into the inlets nearest a first boundary wall and particles within the sample are deflected toward a second, opposing boundary wall as the particles move through the DLD array, whereby the particles within the sample are separated by size in a deterministic manner. Particles within the sample above a critical size of the DLD array can be deflected toward the second wall, while particles below the critical size can flow through the DLD array in the direction of the flow streams. In FIG. 19, particles within the sample stream deflected toward the second wall pass through the reagent stream, and then the buffer flow stream, wherein a reagent within the reagent flow stream can react with the particles as they pass through the reagent stream, and wherein the reagent can be washed off or removed from the particles as they flow through the subsequent buffer flow stream. As shown in FIG. 19, the particles deflected toward the second wall can be concentrated as they encounter the second wall, and can be subsequently flow through and harvested from one (e.g., product in FIG. 19) of the plurality of outlets in the output area of the device, while particles not deflected toward the second wall as well as reagent from the reagent stream flows through one or more outlets of the plurality of outlets that are separate from the product outlet (waste outlet in FIG. 19). The deflected particles collected from a device as provided can be free or substantially free of reagents following flow of the particles through a reagent stream in a multi-stream, 'car wash' device as provided herein.

Figure 18A:
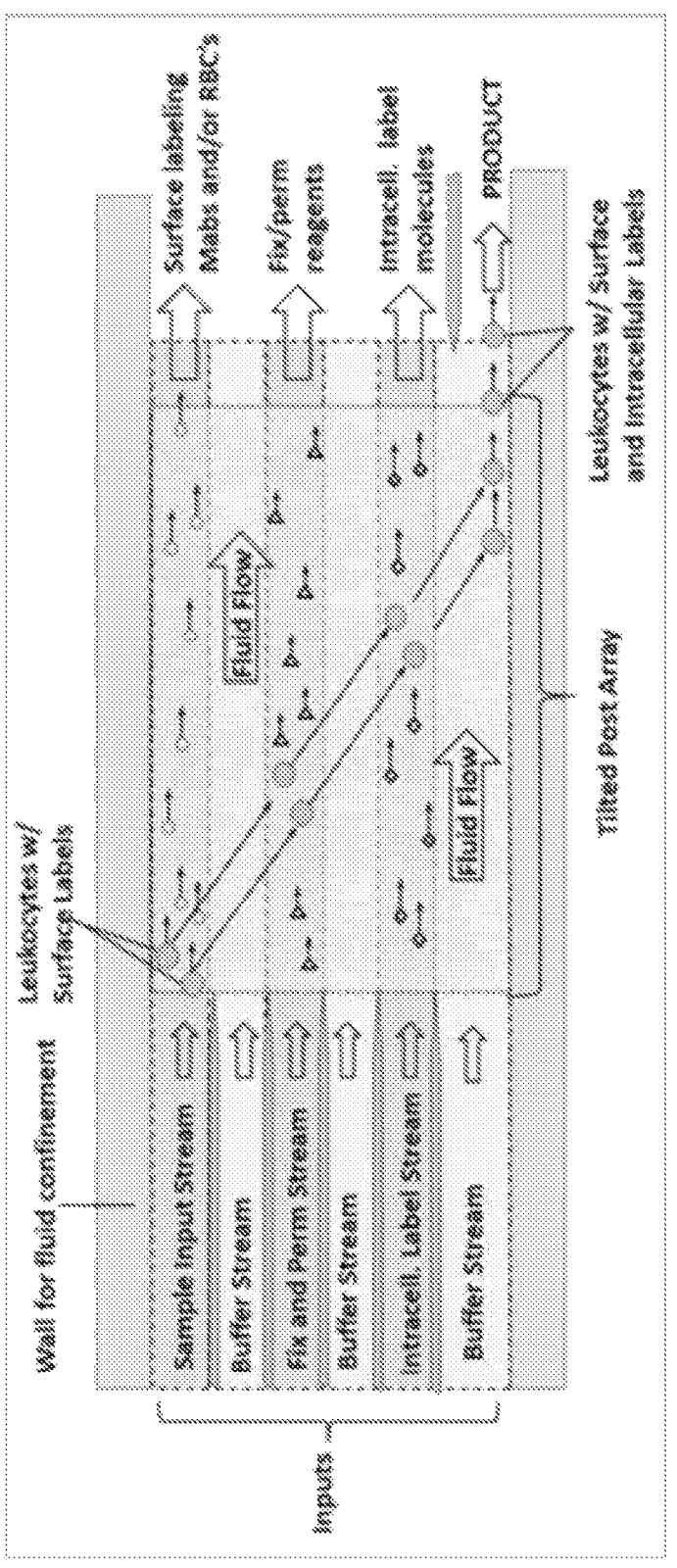
FIG. 18A shows a multi-stream "car wash" chip for multiple sequential chemical processing. Schematic view of car wash concept for multiple sequential chemical processing on-chip for cellular preparation. A single continuous-flow process combines all steps in FIG. 42 into a single chip.

FIG. 18A shows an embodiment of a 'car wash' device as described herein. The device in FIG. 18A comprises a plurality of inlets and a plurality of outlets with an array of obstacles (tilted post array in FIG. 18A) disposed there between. The plurality of inlets can be configured to flow a plurality of flow streams toward the plurality of outlets, wherein the plurality of flow streams each comprises a separate fluid. In FIG. 18A, the channel comprises 6 inlets configured to flow six separate flow streams in laminar, flow streams across a tilted post array toward 2 outlets, a product outlet, and a waste outlet. A first flow stream comprises a sample comprising particles, a second stream comprises a buffer, a third stream comprises a fix and permeabilization stream, a fourth stream comprises a buffer, a fifth stream comprises an intracellular label stream, and a sixth stream comprises a buffer. In some cases, a multi-stream device as described herein comprises a plurality of parallel flow streams flowing from an input portion of the device to an output portion of the device, wherein at least 4 of the flow streams comprise a reagent. The at least 4 flow streams comprising a reagent can comprise the same and/or different reagent. In some cases, each of the flow streams comprising a reagent is bounded by two parallel flow streams, each of which carries a buffer. The buffer can be a wash buffer. A device as depicted in FIG. 18A can be configured to deflect particles (e.g., leukocytes in a sample comprising leukocytes and RBCs, e.g., blood) of a predetermined size (e.g., above a critical size of the tilted post array) from the sample stream through the subsequent five parallel flow streams in series (e.g., sample→buffer→fixation/permeabilization→buffer-→intracell. Label→buffer in FIG. 18A). The buffer streams can serve to wash reagents adsorbed non-specifically (i.e., weakly) to the particles (e.g., cells) and unbound reagents from the preceding adjacent flow stream from the environment of the particles deflected through the streams. The buffer stream can remove or substantially remove non-specifically bound and unbound reagent from a particle as well as from the stream comprising the particles. As shown in FIG. 18A, a waste outlet can have a width that is greater than the width of the product outlet. The waste outlet in FIG. 18A comprises reagents (e.g., surface labeling Mabs, fixation/permeabilization reagents, and intracellular binding agents comprising a label as well as undesired particles, e.g., RBCs, below the critical size of the tilted post array).

Some or all of the washing steps in flow cytometric WBCs processing can be replaced with a microfluidic DLD chip process that can increase yield and automation, and reduce time, variability and cost. Washing steps during cell processing for flow cytometry, which may be performed after surface labeling, fixation/permeabilization, and intracellular labeling, can be associated with variability, cell loss, and cost (based mainly on labor required). The desired WBCs can be moved at an angle to the flow direction, defined by the post geometry, from the input stream to the product output. By running the fluid at modest flow speeds (few mm/s, coupled with the length of a DLD array of about 3-5 cm), cells can move from the chip input to the chip output in about 30 s or less. In such a short time, with proper design there can be little chance of unwanted smaller components, which are not bumped, from moving to the product output stream by random diffusion. This leads to effective washing in just one pass through the chip.

Figure 42:
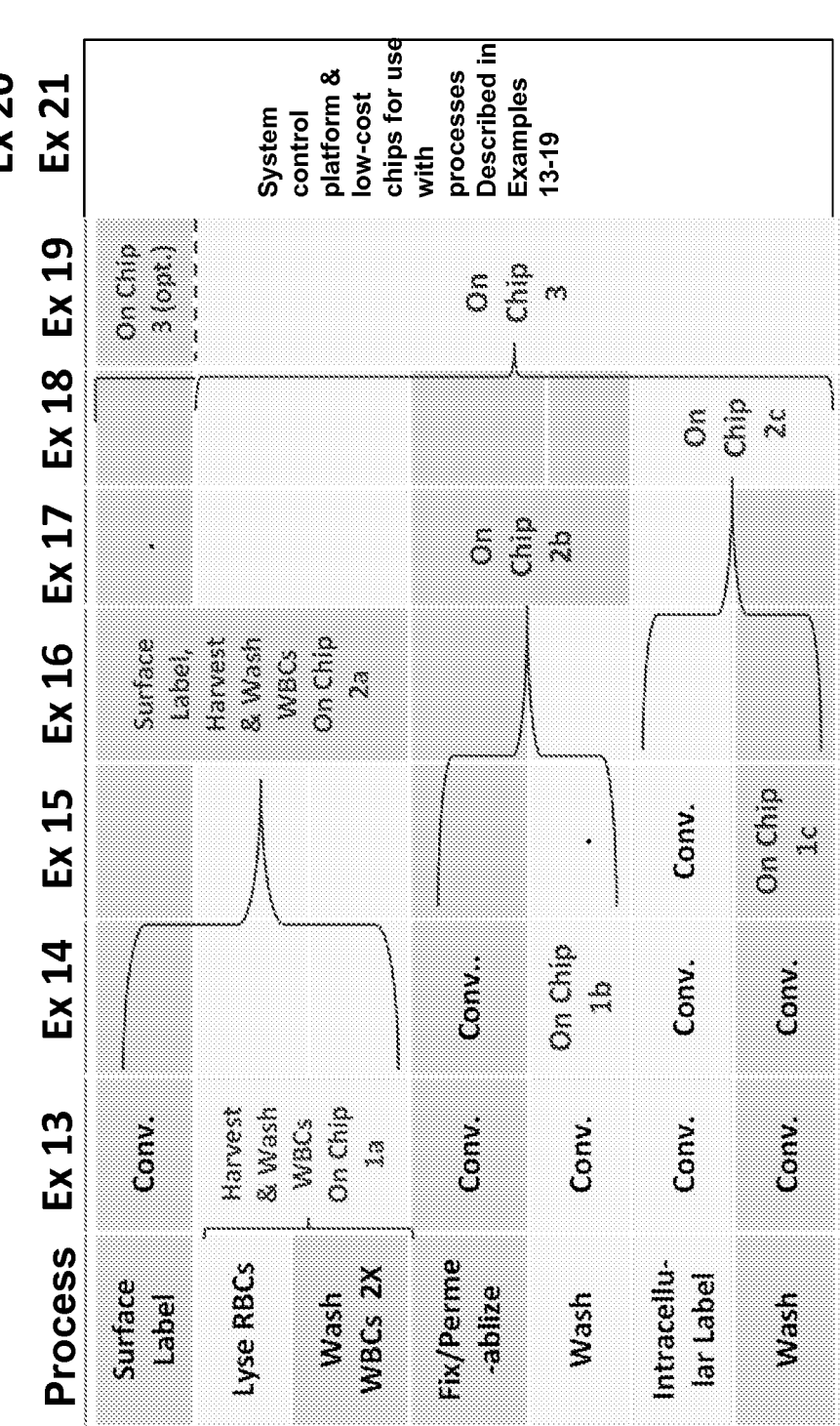
FIG. 42 illustrates conventional methods (left/1$^{st}$ column) for processing cells (e.g., leukocytes) and four embodiments of the methods described herein (vertically down the second through vertically down the right columns).

One or more of the surface labeling, fixation, permeabilization, intracellular labeling steps can be performed on a microfluidic chip provided herein. In some cases, one or more of these steps can be combined with one or more washing steps on the same chip (FIG. 42). In some cases, this can be accomplished by adding another input onto the DLD chip for infusion of the labels or the fixation/permeabilization reagents. Making these procedures into on-chip processes may further reduce cost and time and improve test repeatability and robustness. In some cases, particles can be surface labeled and then washed on the same chip. In some cases, particles can be fixed and/or permeabilize, and then washed on the same chip. In some cases, particle can be intracellularly labeled and then washed on the same chip. In some cases, particles can be surface labeled, washed, fixed and/or permeabilize, and then washed on the same chip. In some cases, particles can be fixed and/or permeabilize, washed, intracellularly labeled, and then washed on the same chip. In some cases, particles can be surface labeled, washed, fixed and/or permeabilized, washed, intracellularly labeled, and then washed on the same chip.

The chips and processing protocols can be developed in an iterative process to provide combinations with different/increasing capabilities (FIG. 42). The capabilities of the platform device can be developed synchronously.

The microfluidic chips performing different cell processing steps can be used together with one or more off-chip processing steps. In some cases, cells can be surface labeled and washed on a microfluidic chip, fixed and/or permeabilize by any off-chip methods. In some cases, cells can be surface labeled by any off-chip methods, and then fixed/permeabilized and washed on a microfluidic chip. In some cases, cells can be fixed and/or permeabilize and washed on a microfluidic chip performing fixation/permeabilization and washing of cells, and then intracellularly labeled by any off-chip methods. In some cases, cells can be fixed/permeabilized and washed by any off-chip methods, and then intracellularly labeled and washed on a microfluidic chip. In some cases, cells can be surface labeled and washed by any off-chip methods, and then fixed and/or permeabilize, washed, intracellularly labeled, and washed on a microfluidic chip. In some cases, cells can be surface labeled and washed on a microfluidic chip, and then fixed and/or permeabilize, washed, intracellularly labeled, and washed by any off-chip methods. In some cases, cells can be surface labeled, washed, fixed and/or permeabilize, and washed by any off-chip methods, and then intracellularly labeled and washed on a microfluidic chip. In some cases, cells can be surface labeled, washed, fixed and/or permeabilized and washed on a microfluidic chip, and then intracellularly labeled by any off-chip methods.

The microfluidic chips performing different cell processing steps can be used together for cell processing. In some cases, cells can be surface labeled and washed on a first microfluidic chip, and fixed and/or permeabilized and washed on a second microfluidic chip. In some cases, cells can be fixed and/or permeabilized and washed on a first microfluidic chip, and intracellularly labeled and washed on a second microfluidic chip. In some cases, cells can be surface labeled and washed on a first microfluidic chip, fixed and/or permeabilized, and washed on a second microfluidic chip, and intracellularly labeled and washed on a third microfluidic chip. In some cases, cells can be surface labeled and washed on a first microfluidic chip, fixed and/or permeabilized and washed by any off-chip methods, and intracellularly labeled and washed on a second microfluidic chip.

Figure 45:
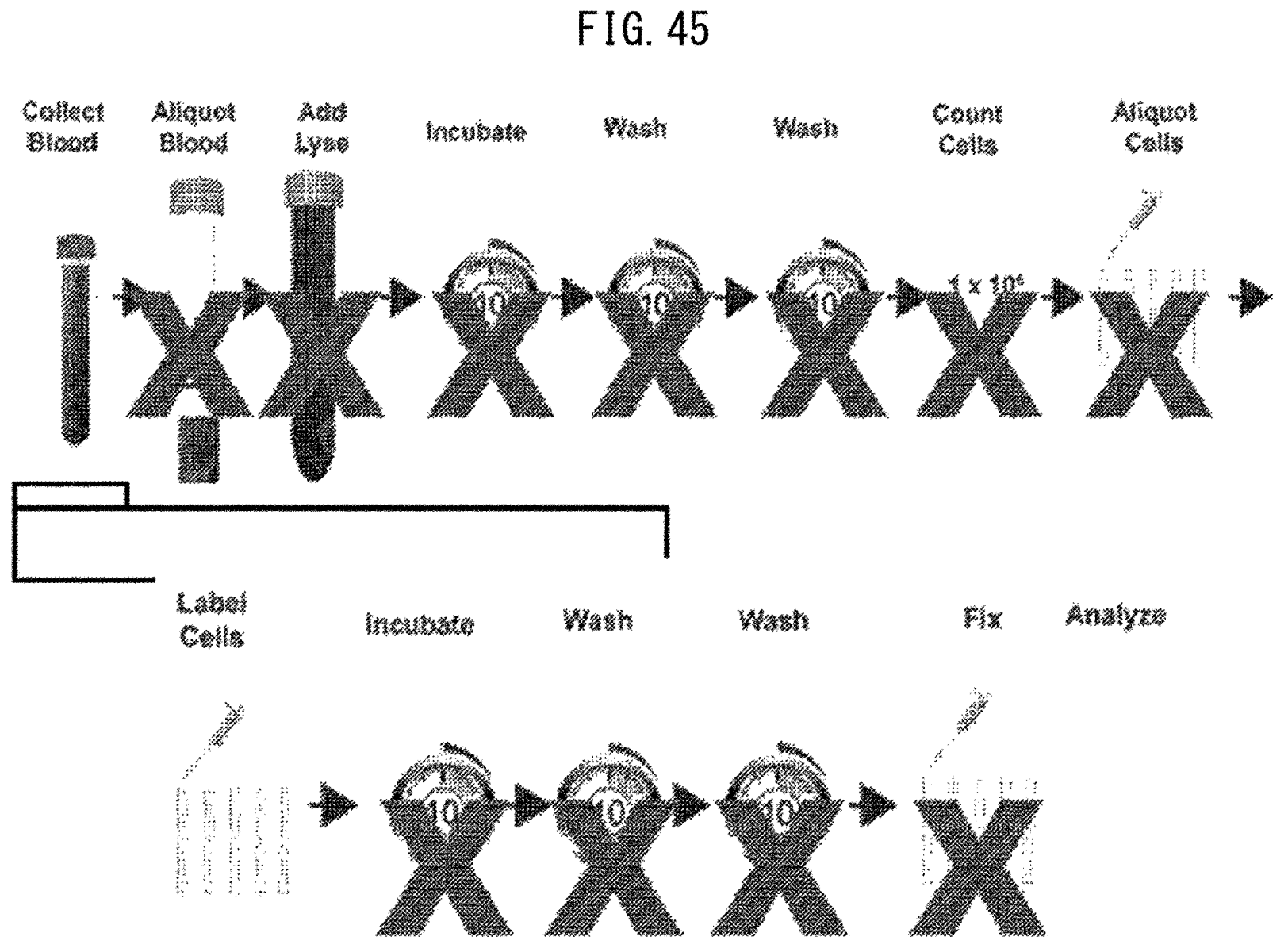

As FIG. 45 depicts, depending on the sample preparation methodology used, multiple sequential steps can be used, each with one or more wash (spin, decant, resuspend) steps, resulting in cell loss and low productivity. The Xs show the steps that can be eliminated by the devices, methods, and systems described herein. Typically, after each washing step the cell yield can be ~80-90% of the starting number of cells, and thus after the several sequential washing steps in a process, the overall cell yield can drop to ~50%.

Methods and devices provided herein can generate uniform, surface and intracellularly labeled WBC preparations quickly and at low cost.

A technique that does not involve a wash step can have free fluorescent Mabs that can create an increase in the standard deviation of both background and signal fluorescence of cells, which can affect assay sensitivity and precision. Cell fragments, platelets and other debris generated from the use of a lysing step can create several flow cytometric artifacts, such as damage to WBCs that interfere with and decrease the quality of the analysis. These factors may be manageable in normal blood samples. In patient samples, such as samples containing leukemia or cancer cells, the malignant cells may be highly sensitive to hypotonic lysis reagents, and overall sample quality can be lower (e.g. resulting dead cells can nonspecifically bind fluorescent Mab and thus give false positives and/or raise background levels). Handling and manipulation of cells can be injurious to fragile WBCs, potentially perturbing the results, and can expose the laboratory worker to biohazardous materials and aerosols.

Described herein are systems, methods, and devices to replace most of the steps associated with WBC processing for flow cytometry with automated microfluidic DLD chip-based processes that can perform all Surface Labeling, Fix/Perm, Intracellular Labeling, and Washing steps with >90% WBC yield from 10 ul of blood in under 10 minutes. The approach described herein can begin by enriching the WBC population from human blood by gently removing RBCs, platelets, and other particulates without introducing debris or other contaminants into the prep. The enrichment process described herein can yield >90% of starting WBCs while maintaining cell ratios. In some cases, as cells pass through the DLD chip, reagents can be introduced in a stream to label the WBCs, or prepare the WBCs to be stained with either a surface or intracellular label. Unbound Mabs, other labels, dyes, fix/perm reagents, and other undesired contaminants of the labeled WBCs can be removed by gently bathing the cells in buffer during passage through the DLD chip without the need for potentially WBC-damaging centrifugation, pipetting, and resuspension.

Approaches described herein can provides significant benefits for clinical and research laboratories: automated workflows can provide gentle and uniform processing of cells, rapid turnaround time, and enriched WBC samples that have can high viability, purity and viability. This cam lead to high quality results downstream and cost/efficiency gains for the labs.

The methods, systems, and devices described herein can focus specifically on preparation of WBCs for flow cytometry. This technology may also have broad applicability for downstream analytical techniques beyond flow cytometry, such as DNA- and RNA-based tests for cancer and other diseases (e.g. gene expression profiling of leukemia cells using microarrays and next generation DNA sequencing), and rare cell detection (e.g. stem cells, circulating tumor cells or minimal residual disease) where it may similarly improve cell recovery, simplify processing, and improve test quality and efficiency.

The microfluidic chip-based processing systems described herein can also be adapted to process cells other than human blood WBCs (e.g. erythroid cells, platelets and other cells from bone marrow, other body fluids, and solid tumors) opening up new realms of possibilities for commercialization of this technology in research and clinical diagnostics.

Larger starting samples which can be problematic for pediatric and anemic patients, patients requiring multiple blood tests or undergoing therapy, as well as in small animal studies (e.g. <10 ul samples from mice can be used, sparing the animal, allowing longitudinal studies of e.g. pharmacokinetics, cancer mutations). Pediatric patients with myleodysplastic syndrome (MDS) or others presenting with hematological neoplasms or undergoing therapy can often present with very low WBC counts. The chips described herein can mitigate this clinical sampling problem.

The accurate, sensitive, multiplexed detection of biomarker proteins, DNA or RNA, can be used for personalized cancer diagnostics. Bead-based assays (BBAs) can measure a variety of soluble and intracellular proteins, including cytokines, chemokines, growth factors, and phosphorylated cell signaling proteins using flow cytometry. ELISA or Western Blot can offer one reaction per sample, where the value in BBAs can be in the ability to multiplex several reactions on each bead. Magnetic beads have also been used frequently in immunoassays. The chip described herein can be configured to prep samples for all of these types of BBAs.

Leukemia/lymphoma diagnostics and staging, or assessing minimal residual disease (MRD) can require high end capabilities and expertise. Technologies that can standardize and simplify high complexity manipulations of samples can increase utilization and drive the availability of this testing beyond reference laboratories or large medical centers into smaller, more distributed venues, closer to the patient. Also, the technology described herein can have the potential to accelerate adoption of flow cytometric testing in developing and resource-poor countries.

Sample prep approaches described herein can improve inputs for flow cytometry by provided standardized samples with gentle, uniform processing, no selective cell loss, and accommodation of small, medium and large sample sizes. Sample prep approaches described herein can provide better lab economics, e.g., faster time to result, less technical expertise required can lower result in a mean lower cost, automation can mean less hands-on time and more productivity, and less reagents can mean lower cost. Sample prep approaches can be broadly applicable, for example, for cell enrichment for myriad downstream applications (e.g., flow cytometry, mass cytometry, DNA/RNA assays, rare cell assays, functional assays, can process many different cell types (e.g., blood, BM, body fluids), and can support other technology platforms (e.g. magnetic and bead-based assays). Sample prep approaches can offer broader market access (e.g., simpler techniques can drive testing nearer the patient, simpler, lower cost techniques can favor technology diffusion into developing countries, simpler lower cost techniques can drive new application development, and standardization can drive new clinical application development.

Newer targeted antineoplastic agents can require accompanying diagnostic monitoring of individual patients to precisely choose the best drugs and to determine and adjust the dose and schedule of the given drugs based on early response. Antineoplastic immunotherapies are emerging that focus on either cancer mutation-specific vulnerabilities of cancer cells involved in anti-cancer responsiveness of the immune system. Patients in clinical studies or undergoing these types of treatments can require extensive flow cytometric testing to assess their status in order to qualify them for treatment and to assess/monitor treatment efficacy. Standardization of sample inputs for these exciting emerging therapeutic modalities may be imperative.

F. "Car Wash" Device with Separator Walls

A multi-stream (e.g., 'car wash') device as provided herein can further comprise a mechanism to reduce mixing between laminar, parallel flowing fluids or flow streams. Mixing between parallel flow streams can occur over time, which can contaminate the output of a device as provided herein. As such, a tradeoff can exist between long processing times that can be required for some chemical or enzymatic streams and having low contamination in a final output of a car wash device as provided herein. For example, incubation times for fixation and/or permeabilization can be ~10 min, while labeling with a labeling agent (e.g., antibodies, probes) can be ~5 min. In comparison, Table 1 shows diffusion coefficients of some reagents.

TABLE 1

| Diffusion Coefficients of Common Reagents | | |
|---|---|---|
| Reagents | Diffusion Coefficient (in water) | Functionality |
| Monoclonal Anitbodies (mAbs) | $10^{-7}$-$10^{-8}$ cm$^2$/sec | Surface Labeling |
| RBC lysis buffer | N/A | Lysis |
| Paraformaldehyde (PFA) | $\sim$$10^{-8}$ cm$^2$/sec | Fixation |
| Ethanol | $10^{-5}$ cm$^2$/sec | Fixation |
| Methanol | $10^{-5}$ cm$^2$/sec | Fixation and permeabilization |
| Acetone | $10^{-5}$ cm$^2$/sec | Fixation and permeabilization |
| Saponin | $\sim$$10^{-6}$ cm$^2$/sec | Permeabilization |
| Triton X-100 | $\sim$$10^{-6}$ cm$^2$/sec | Permeabilization |
| Tween 20 | $\sim$$10^{-7}$ cm$^2$/sec | Permeabilization |

Figure 22:
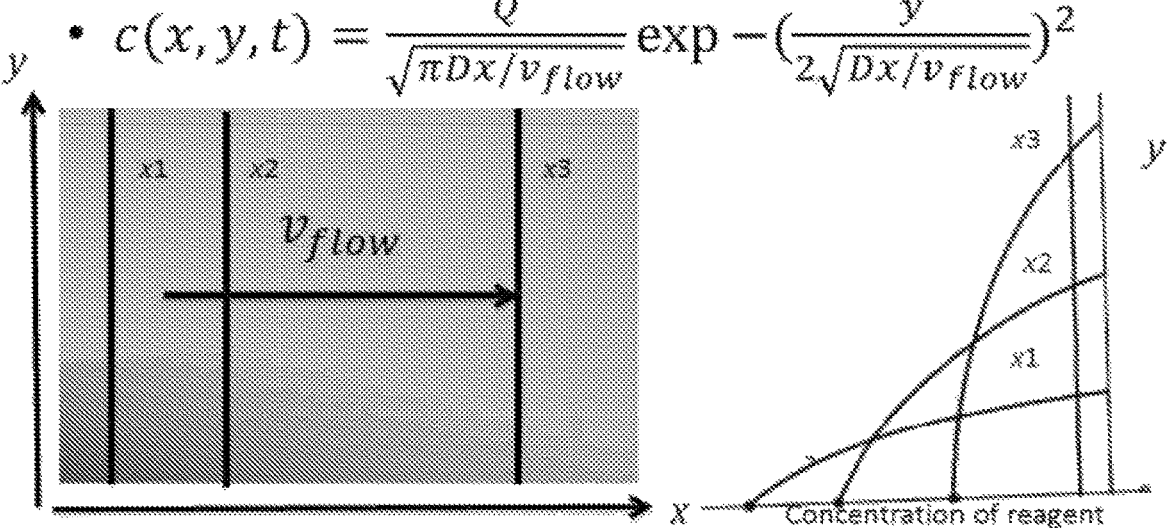
FIG. 22 shows a schematic of a model of incubation time and limited source diffusion.
Figure 24A:
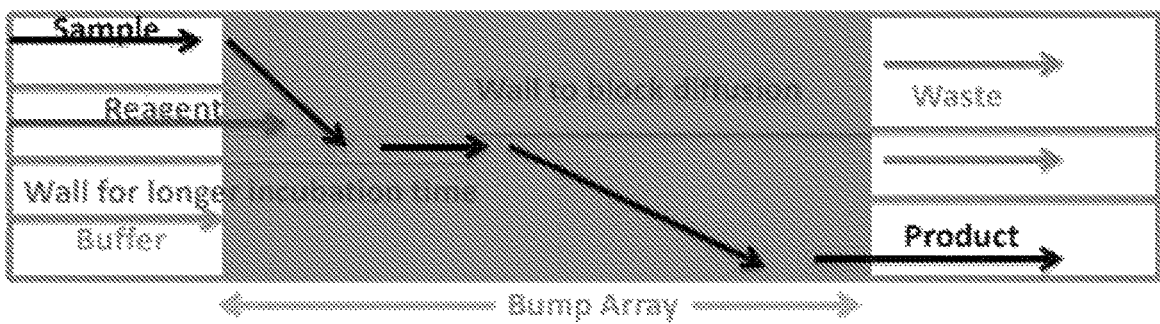
FIG. 24A shows a model of "car wash" chip comprising a sample stream, reagent stream, and buffer stream further comprising a pair of opposing separator walls that extend into the interior of the bump array and separate the reagent stream from the buffer stream.
Figure 32:
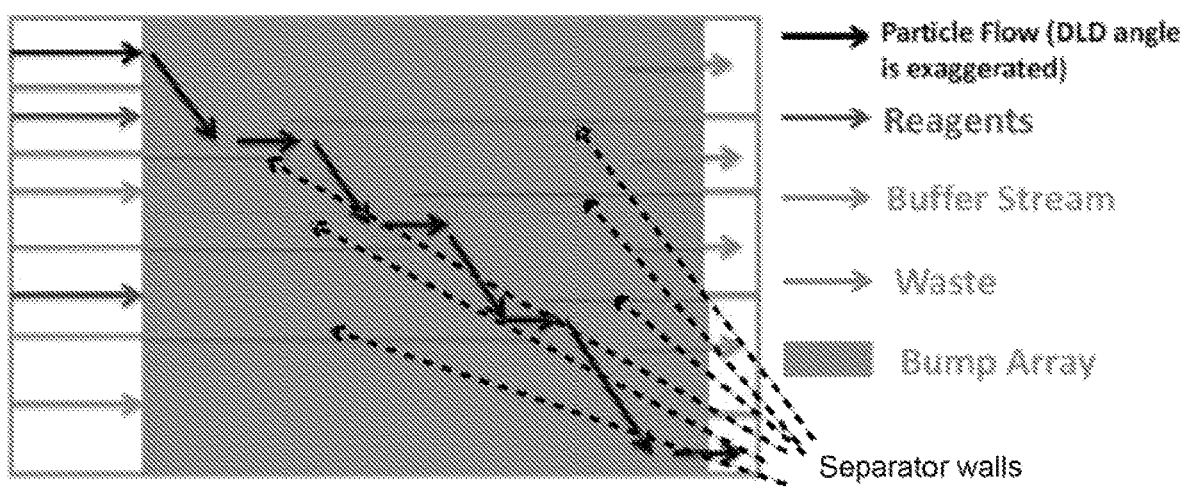
FIG. 32 shows a model of a "car wash" chip comprising a sample stream, two reagent streams, and two buffer streams further comprising three pairs of opposing separator walls that extend into the interior of the bump array and separate the reagent streams from the buffer streams.

Reagents with relatively small diffusion coefficients (e.g. methanol), can diffuse into adjacent streams even with short incubation times, which can lead to a significant percentage of the reagent(s) entering a product stream as can be predicted by a limited source diffusion model (FIG. 22). In some cases, particle flow angle can be adjusted with respect to the horizontal flow streams. In some cases, a separator wall is used to separate adjacent flow streams in a device as provided herein. In some cases, a multi-stream device as provided herein comprises one or more separator walls. In some cases, a multi-stream device as provided herein comprises a plurality of separator walls. The separator walls can be in pairs. In some cases, one of the pair of separator walls extends from an input portion of a channel comprising the pair of separator walls, while the other of the pair extends from an outlet portion of the channel. In some cases, a separator wall or pair of separator walls are parallel to the stream flow and do not interfere with the stream flow patterns. The pair of separator walls can be opposing. As shown in FIGS. 24A and B, the pair of separator walls can be staggered with respect to each other, whereby one of the pair is closer to a first wall that bounds the channel, while the other of the pair is closer to a second wall that bounds the channel. In some cases, a pair of separator walls comprises a gap between separator walls in the pair of separator walls (e.g., FIGS. 24A and B). The gap can comprise a width such that particles can pass through the gap. In some cases, a multi-stream device as provided herein comprises a plurality of separator wall pairs (e.g., FIG. 32). As depicted in FIG. 32, each of the pair of separator walls can be staggered and can comprise a gap between the pair that is configured to allow particles being deflected through an array of obstacles (e.g., DLD array) to pass between the pair of separator walls. In some cases, a separator wall or pair of separator walls is placed between a reagent stream (e.g., chemical or enzyme) and an adjacent buffer (e.g., wash buffer) stream.

A separator wall or pair of separator walls in a device as provided herein can serve to substantially increase the amount of time a particle resides in a flow stream (e.g., reagent). The increase in time a particle resides in a flow stream can be increased by at least, at most, less than, more than, or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% of the time a particle would spend in a flow stream (e.g., reagent flow stream) in a device as provided herein that does not comprise a separator wall or pair of separator walls.

A separator wall or pair of separator walls can serve to substantially limit or block the diffusion of a reagent (e.g., chemical and/or enzymatic) to an adjacent flow stream in a multi-stream (e.g., car wash) device as provided herein. The diffusion can be limited by at least, at most, less than, more than, or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

In some cases, a flow stream in a multi-stream (e.g., car wash) device as provided herein comprises a lysis reagent. In some cases, a lysis reagent comprises a detergent. In some cases, a detergent comprises Triton X-100, SDS, CHAPs, or Tween-20.

In some cases, a flow stream in a multi-stream (e.g., car wash) device as provided herein comprises a buffer. The buffer can be a wash buffer. The buffer can be F108. N-(2-Acetamido)-2-aminoethanesulfonic acid (ACES); N-(2-Acetamido)iminodiacetic acid (ADA); Magnesium acetate; Sodium acetate; Trizma® base; 2-Amino-2-methyl-1-propanol (AMP); Aminoacetic acid; Aminoethanoic acid; 2-Amino-2-methyl-1,3-propanediol (AMPD); Ammonium phosphate monobasic; Ammonium sodium phosphate dibasic tetrahydrate; Ammonium sodium phosphate dibasic tetrahydrate; Ammonium bicarbonate; Ammonium phosphate monobasic; Sodium 5,5-diethylbarbiturate; N,N-Bis(2-hydroxyethyl)-2-aminoethanesulfonic acid (BES); Bis(2-hydroxyethyl)amine, 2,2'-Iminodiethanol (Diethanolamine); 2-Bis(2-hydroxyethyl)amino-2-(hydroxymethyl)-1,3-propanediol; Bis(2-hydroxyethyl)amino-tris(hydroxymethyl) methane; N,N-Bis(2-hydroxyethyl)glycine; N,N-Bis(2-hydroxyethyl)taurine; 2,2-Bis(hydroxymethyl)-2,2',2"-nitrilotriethanol; BIS-TRIS; Calcium acetate hydrate; Calcium carbonate; Calcium citrate tribasic tetrahydrate; Calcium formate; CAPS; N-(Carbamoylmethyl)-2-aminoethanesulfonic acid; -(Carbamoylmethylamino)ethanesulfonic acid; N-(Carbamoylmethyl)iminodiacetic acid; N-(Carbamoylmethyl)taurine; CHES; Citric acid; 3-(Cyclohexylamino)-1-propanesulfonic acid; MOPS; HEPES; Imidazole; HEPPS; Formic acid; Glycine; EPPS; Edetate disodium salt dehydrate; Magnesium acetate; Lithium acetate; Oxalic acid; Phosphate buffered saline; Piperazine; PIPES; Potassium bicarbonate; Potassium carbonate; Potassium chloride; lithium chloride; Potassium phosphate; propionic acid; Sodium acetate; Sodium bicarbonate; Sodium carbonate; Sodium citrate; Sodium phosphate; Sodium tetraborate; STE buffer solution; STET buffer solution; TRIS buffered saline; TRIS-EDTA buffer solution; Sodium pyrophosphate tetrabasic; Trizma® carbonate; Trizma® hydrochloride; Trizma® maleate; TRIS NaCl Tween 20; Triethanolamine; Trizma® acetate; and/or TAPS.

In some cases, a flow stream in a multi-stream (e.g., car wash) device as provided herein comprises a reagent. The reagent can be a chemical or enzymatic reagent. The reagent can be a fixative, permeabilization agent, enzyme, cleavage agent, cytotoxic agent, small molecule, drug moiety, chemotherapeutic agent or a combination or mixture thereof.

In some cases, the reagent is a fixative. The fixative can be formaldehyde, gluteraldehyde, methylalcohol, and/or ethylalcohol. The fixative can be phosphate buffered formalin; formal calcium; formal saline; zinc formalin (unbuffered); Zenker's fixative; Helly's fixative; B-5 fixative; Bouin's solution; Hollande's; Gendre's solution; Clarke's solution; Carnoy's solution; Methacarn; Alcoholic formalin; and/or formol acetic alcohol.

In some cases, the reagent is a permeabilization agent. The permeabilization agent can be detergents, alcohols (methylalcohol), membrane disrupting toxics like digitonin, melittin, and/or saponin. The detergents can be 2-aminoethyl methan thiosulfonate hydrobromide, CHAPS, CHAPSO, digitonin, lithium dodecyl sulfate, n-dodecyl-beta-D-malto-pyranoside, n-octyl-beta-d-glucopyranoside, NDSB-195, NDSB-201, NDSB-211, NDSB-221, NDSB-256, NONI-DET-P40, Pluronic F68, Pluronic F-127, MTSES, Tween-20, Tween-80, Tween-40, sodium dodecyl sulfate (SDS), Triton X-100, Triton X-114, MTSET, sulfobetaine-10, sulfo-betaine-12, or sulfobetaine-14, Igepal® CA-630, or n-do-decyl-β-D-maltoside (DDM).

In some cases, the reagent comprises a binding agent. A reagent comprising a binding agent can also be referred to as a labeling agent. The labeling agent can be any labeling agent known in the art. The labeling agent can be a cell surface labeling agent. The labeling agent can be an intra-cellular labeling agent. The labeling agent can be antibodies, antibody fragments, nucleic acid probes, aptamers, molecu-lar beacons, and/or enzyme substrates. The binding agent can be an antibody, antibody fragment, a nucleic acid (e.g., probe), aptamer, small molecule, or molecular beacon. The antibody can be a primary or secondary antibody. The term "antibody" herein can be used in the broadest sense and specifically covers monoclonal antibodies, polyclonal anti-bodies, multispecific antibodies, and antibody fragments so long as they exhibit the desired biological activity. The term "multispecific antibody" can be used in the broadest sense and specifically covers an antibody comprising an antigen-binding domain that has polyepitopic specificity (i.e., is capable of specifically binding to two, or more, different epitopes on one biological molecule or is capable of spe-cifically binding to epitopes on two, or more, different biological molecules). One specific example of an antigen-binding domain is a $V_H V_L$ unit comprised of a heavy chain variable domain ($V_H$) and a light chain variable domain ($V_L$). Such multispecific antibodies can include, but are not limited to, full length antibodies, antibodies having two or more $V_L$ and $V_H$ domains, antibody fragments such as Fab, Fv, dsFv, scFV, diabodies, bispecific diabodies and triabod-ies, antibody fragments that have been linked covalently or non-covalently. A "bispecific antibody" can be a multispe-cific antibody comprising an antigen-binding domain that can be capable of specifically binding to two different epitopes on one biological molecule or can be capable of specifically binding to epitopes on two different biological molecules. The bispecific antibody can also be referred to as having "dual specificity" or as being "dual specific". In some cases, the binding reagent is a nucleic acid probe, wherein the nucleic acid probe comprises one or nucleotides com-prising a label incorporated into the nucleic acid probe. The nucleic acid probe can be comprise DNA, RNA, or a combination thereof. The labeled nucleotides can be labeled with Alexa Fluor® dyes. Other fluorescent labels on nucleo-tides for use in nucleic acid probes can be, but are not limited to, Diethylaminocoumarin (DEAC), Cyanine 3 (Cy3), Cya-nine 5 (Cy5), Fluorescein (FITC), Lissamine, R110, R6G, Tetramethylrhodamine (TAMRA) and Texas Red. The labeled nucleotides can be labeled with a hapten. The hapten label can be, but are not limited to Amino-digoxigenin (DIG), Biotin, Dinitrophenyl (DNP) and Fluorescein (FITC). The labeled nucleotides can comprise a radioactive label. For example, radioactive labeled nucleotides can include, but are not limited to, $^{33}P$, $^{32}P$, $^{35}S$, $^{3}H$ and $^{14}C$ nucleotides. In some cases, the binding agent binds or is directed to or against a cell surface marker. The cell surface marker can be any cell surface marker as provided herein. In some cases, the binding agent binds or directed to or against an intracellular marker. The intracellular marker can be any intracellular marker as provided herein. In some cases, a device as provided herein is adapted to flow a reagent flow stream comprising a binding agent, wherein the binding agent binds a cell surface marker. In some cases, a device as provided herein is adapted to flow a reagent flow stream comprising a binding agent, wherein the binding agent binds an intracellular marker. In some cases, a device as provided herein is adapted to flow a plurality of flow streams, wherein at least one of the flow streams comprises a binding agent that binds a cell surface marker, and at least one of the flow streams comprises a binding agent that binds an intracellular marker. In some cases, a device as provided herein com-prises a plurality of flow streams, wherein at least of the flow streams comprises a reagent, wherein the reagent is a binding agent, and wherein at least of the flow streams comprises a reagent that is not a binding agent. The reagent that is not binding agent can be an enzyme, a fixative, a permeabilization agent or a combination or mixture thereof.

In some cases, the reagent comprises an enzyme. In some cases, the reagent comprises a plurality of enzymes. In some cases, a device as provided herein comprises a plurality of flow streams, wherein at least of the flow streams comprises a reagent, wherein the reagent is an enzyme. In some cases, a device as provided herein comprises a plurality of flow streams, wherein at least of the flow streams comprises a reagent, wherein the reagent is an enzyme, and wherein at least of the flow streams comprises a reagent that is not an enzyme. The reagent that is not an enzyme can be a binding agent, a fixative, a permeabilization agent or a combination or mixture thereof. In some cases, a device as provided herein comprises a plurality of flow streams, wherein more than one of the flow streams comprises a reagent, wherein the reagent in each of the more than one flow streams is an enzyme, wherein the enzyme in each of the more than one flow streams comprises the same or different enzyme. In some cases, a device as provided herein is adapted to flow a plurality of flow streams, wherein at least one of the flow streams comprises a binding agent that binds a cell surface marker, at least one of the flow streams comprises a binding agent that binds an intracellular marker, and at least one of the flow streams comprises an enzyme. The enzyme can be a restriction enzyme, protease, polymerase, ligase, nuclease, endonuclease, exonuclease, phosphatase, methylase, topoi-somerase or a combination or mixture thereof. The poly-merase can be any polymerase known in the art. The polymerase can be a DNA dependent DNA Polymerase. Examples of DNA-dependent DNA polymerase include, but are not limited to, Klenow polymerase, with or without 3'-exonuclease, Bst DNA polymerase, Bca polymerase, .phi.29 DNA polymerase, Vent polymerase, Deep Vent poly-merase, Taq polymerase, T4 polymerase, and E. coli DNA polymerase 1, derivatives thereof, or mixture of poly-merases. In some cases, the polymerase does not comprise a 5'-exonuclease activity. In other cases, the polymerase comprises 5' exonuclease activity. The polymerase can be a RNA dependent DNA Polymerase or reverse transcriptase (RT). Examples of RTs include, but are not limited to, Moloney murine leukemia virus (M-MLV) reverse tran-scriptase, human immunodeficiency virus (HIV) reverse transcriptase, rous sarcoma virus (RSV) reverse transcriptase, avian myeloblastosis virus (AMV) reverse transcriptase, rous associated virus (RAV) reverse transcriptase, and myeloblastosis associated virus (MAV) reverse transcriptase or other avian sarcoma-leukosis virus (ASLV) reverse transcriptases, and modified RTs derived therefrom. Exonuclease can be, but are not limited to exonuclease 1, exonuclease 7 or a combination or mixture thereof. Endonucleases can be, for example, but not limited to mung bean endonuclease or S1 endonuclease or a combination or mixture thereof.

In some cases, the reagent comprises a label. In some cases, the reagent comprises a binding agent, wherein the binding agent comprises a label. In some cases, the reagent comprises an enzyme, wherein the enzyme comprises a label. The label can be conjugated, bound or linked to a reagent as provided herein. The label can refer to any atom or molecule known in the art that can be used to provide a detectable and/or quantifiable effect. The label can be attached to a nucleic acid or protein (e.g., antibody, antibody fragment, and/or enzyme.). In some cases, the label provides a quantifiable effect. In some cases, the label provides a detectable and quantifiable effect. Labels can include but are not limited to dyes; radiolabels such as $^{32}$P; binding moieties such as biotin; haptens such as digoxgenin; luminogenic, phosphorescent or fluorogenic moieties; mass tags; and fluorescent dyes alone or in combination with moieties that can suppress or shift emission spectra by fluorescence resonance energy transfer (FRET). Labels can provide signals detectable by fluorescence, radioactivity, colorimetry, gravimetry, X-ray diffraction or absorption, magnetism, enzymatic activity, characteristics of mass or behavior affected by mass (e.g., MALDI time-of-flight mass spectrometry), and the like. A label can be a charged moiety (positive or negative charge) or alternatively, can be charge neutral. In some cases, the label is a fluorescent dye. The fluorescent dye can be squaric acid-based dyes. The squaric acid-based dyes can be selected from cyclobutenedione derivatives, symmetrical and unsymmetrical squaraines, substituted cephalosporin compounds, fluorinated squaraine compositions, alkylalkoxy squaraines, or squarylium compounds. The squaric acid-based dyes can be selected from a red fluorescent dye and an orange fluorescent dye, such as the red fluorescent dye comprising 1,3-bis(1,3-dihydro-1,3,3-trimethyl-2H-indol-2-ylidene)methyl]-2,4-dihydr-oxycyclobutenediylium, bis(inner salt) and the orange fluorescent dye comprising 2-(3,5-dimethylpyrrol-2-yl)-4-(3,5-dimethyl-2H-pyrrol-2-ylidene)-3-hydrox-y-2-cyclobuten-1-one. Labels can include or consist of nucleic acid or protein sequence, so long as the sequence comprising the label is detectable and/or quantifiable.

In some cases, the reagent comprises a cytotoxic agent, toxin, or chemotherapeutic agent. For example, the cytotoxic agent or toxin can be, but is not limited to, enzymatically active toxins and fragments thereof including diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin. *Sapaonaria officinalis* inhibitor, gelonin, mitogellin, restrictocin, phenomycin, enomycin, or the tricothecenes, or combinations or mixtures thereof. Examples of small molecule toxins can include, but are not limited to, a calicheamicin, maytansinoids, dolastatins, aurostatins, a trichothecene, or CC1065, or the derivatives of these toxins that have toxin activity. Examples of chemotherapeutic agents include, but are not limited to alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethyloinelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfanide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e. g., calicheamicin, especially calicheamicin gamma II and calicheamicin omegall (see, e.g., Nicolaou et al., *Angew. Chem Intl. Ed. Engl.*, 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholinodoxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2'-trichlorotriethylamine; trichoth-ecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engi-neered nanoparticle formulation of paclitaxel (ABRAX-ANE™), and docetaxel (TAXOTERE®); chloranbucil; 6-thioguanine; mercaptopurine; methotrexate; platinum agents such as cisplatin, oxaliplatin (e.g., ELOXATIN®), and carboplatin; vincas, which prevent tubulin polymeriza-tion from forming microtubules, including vinblastine (VELBAN®), vincristine (ONCOVIN®), vindesine (EL-DISINE®, FILDESIN®), and vinorelbine (NAVEL-BINE®); etoposide (VP-16): ifosfamide; mitoxantrone; leu-covorin; novantrone; edatrexate; daunomycin; aminopterin; ibandronate; topoisonmerase inhibitor RFS 2000; difluo-romethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zole-dronic acid/zoledronate (ZOMETA®), alendronate (FOSA-MAX®), pamidronate (AREDIA®), tiludronate (SKELID®), or risedronate (ACTONEL®); troxacitabine (a 1,3-dioxolane nucleoside cytosine analog); antisense oligo-nucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SUT-11248 (sunitinib, SIUTENT®, Pfizer): perifosine, COX-2 inhibitor (e.g. cele-coxib or etoricoxib), proteosome inhibitor (e.g. PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); tyrosine kinase inhibitors (see defi-nition below); serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin. Additional chemotherapeutic agents can include "anti-hormonal agents" or "endocrine therapeu-tics" which act to regulate, reduce, block, or inhibit the effects of hormones that can promote the growth of cancer. They can be hormones themselves, including, but not lim-ited to: anti-estrogens with mixed agonist/antagonist profile, including, tamoxifen (NOLVADEX®), 4-hydroxytamox-ifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as ful-vestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibi-tors such as formestane and exemestane (AROMASIN®), and nonsteroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releasing hormone agonists, including leuprolide (LUPRON® and ELI-GARD®), goserelin, buserelin, and tripterelin; sex steroids, including progestines such as megestrol acetate and medroxyprogesterone acetate, estrogens such as diethylstil-bestrol and premarin, and androgens/retinoids such as flu-oxymesterone, all transretionic acid and fenretinide; ona-pristone; anti-progesterones; estrogen receptor down-regulators (ERDs); anti-androgens such as flutamide, nilutamide and bicalutamide; and pharmaceutically accept-able salts, acids or derivatives of any of the above; as well as combinations of two or more of the above.

In some cases, particles processed using a multi-stream device as provided herein can be processed by chemical and/or enzymatic reactions within the bump array to impart fluorescent, magnetic, or radioactive properties to these molecules.

G. Flow-Through Incubator

In some cases, the contact time of particles in a flow stream can be prolonged by passing them through a flow-through incubator provided herein. In some cases, when the particles flow from a first DLD array to a second DLD array in a flow stream, the flow-through incubator can be fluidi-cally connected with the two DLD arrays, thus extending the travel distance of the particles in the flow stream. In some cases, the flow stream can comprise a reaction solution (e.g., with a reagent, e.g., an antibody). Thus, the flow-through incubator can prolong the incubation time of the particles in the reaction solution. In some cases, the incubation time can be prolonged by the flow-through incubator without increas-ing the flow rate of the particles. The flow rate in the flow-through incubator can be less than, equal to, or more than the flow rate in DLD array upstream or downstream of the flow-through incubator. In some cases, particles of at least a predetermined size are directed to a flow-through incubator. In some cases, particles of less than a predeter-mined size are directed to a flow-through incubator.

Figure 54A:
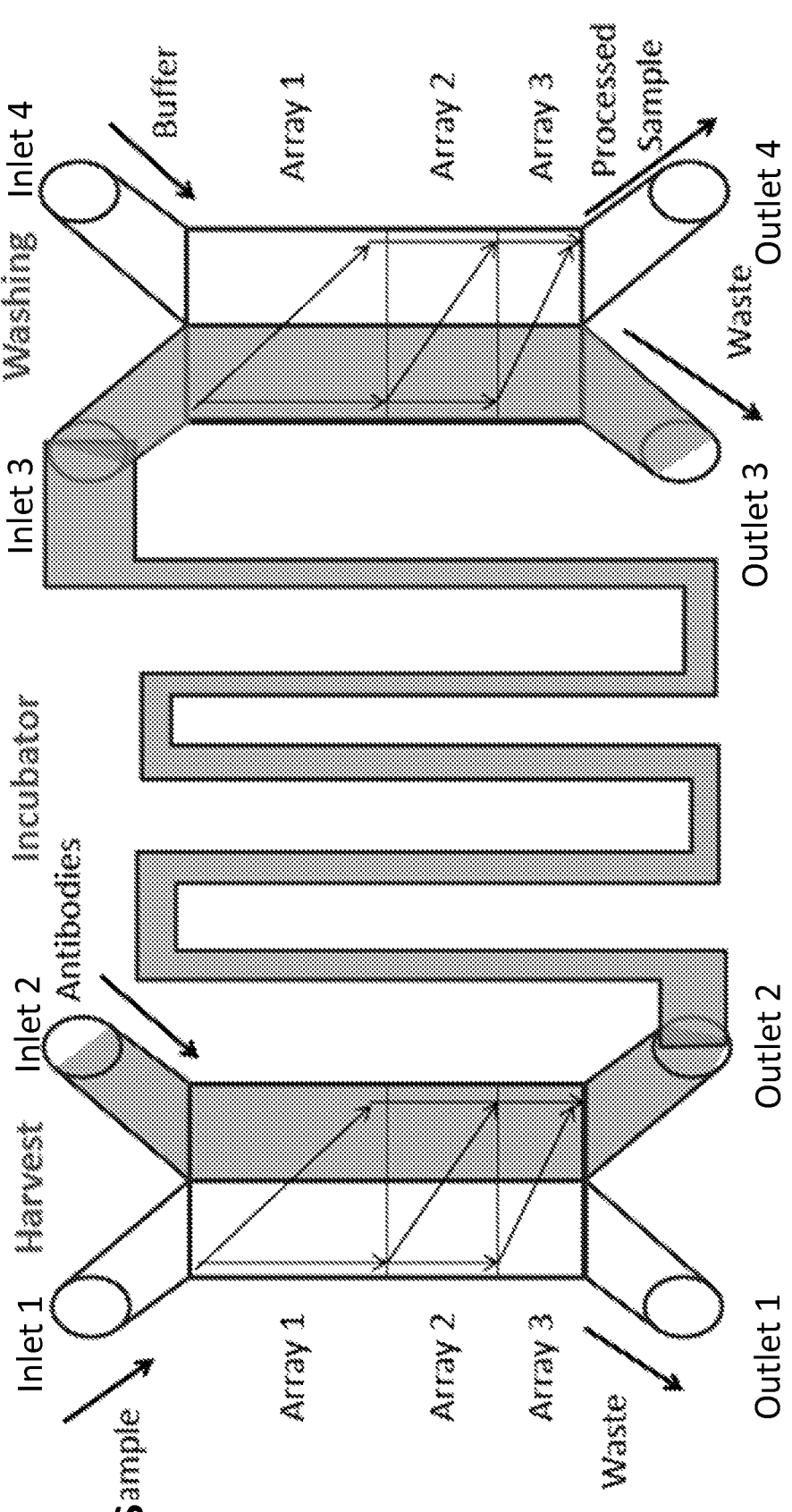
FIGS. 54A-B show an exemplary flow-through incubators.

In some cases, the flow-through incubator can be con-nected with one or more microfluidic chips provided herein. For example, the flow-through incubator can be connected with a component of a microfluidic chip for processing particles provided herein. For example, the flow-through incubator can be a channel on the chip. The channel can be fluidically connected with two DLD) arrays (e.g., two arrays of obstacles) on the chip. In some cases, the flow-through incubator can comprise a linear channel. In some cases, the flow-through incubator can comprise a channel with a curve region. In some cases, the flow-through incubator can com-prise a serpentine channel. The flow-through incubator can comprise one or more DLD arrays disclosed herein. FIG. 54A shows an exemplary serpentine flow-through incubator connecting two microfluidic channels, each of which com-prises 3 DLD arrays. Input particles can be deflected into a flow stream with antibodies for labeling the particles. The particles deflected to outlet 2 can flow to the flow-through incubator, and the time of incubation of the particles with the antibodies can be prolonged by passage the flow-through incubator. The labeled particles can be flowed from the flow-through incubator to inlet 3 of the second microfluidic channel with an array of obstacles for washing, concentra-tion, and/or other processing.

The flow-through incubator can comprise a channel with at least one turn. In some cases, the channel can have more than one turn. For example, the channel can be a serpentine channel. In some cases, the flow-through incubator can comprise a channel with at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 turns. In some cases, the flow-through incubator can comprise a channel with 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 turns.

Figure 54B:
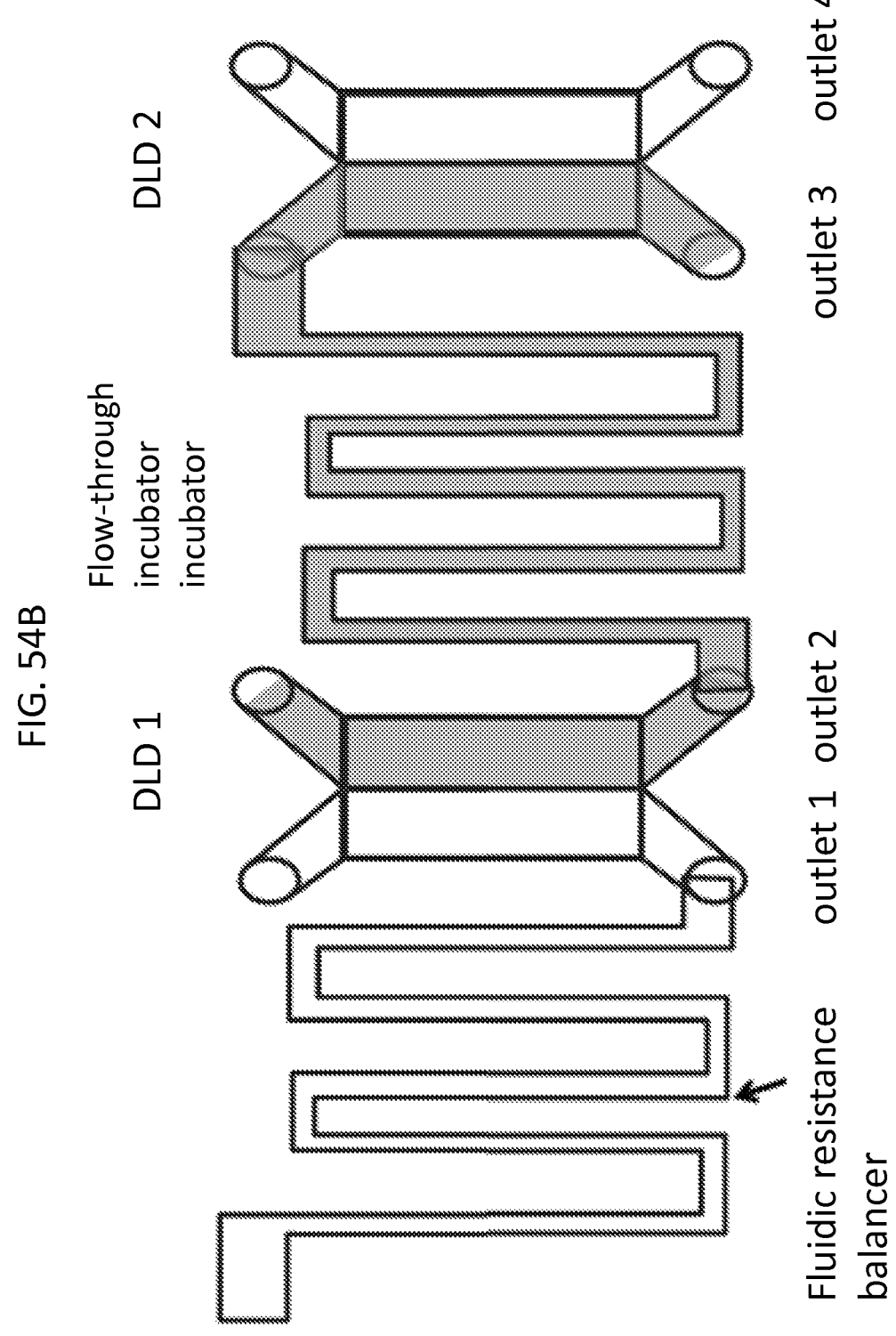
Figure 55:
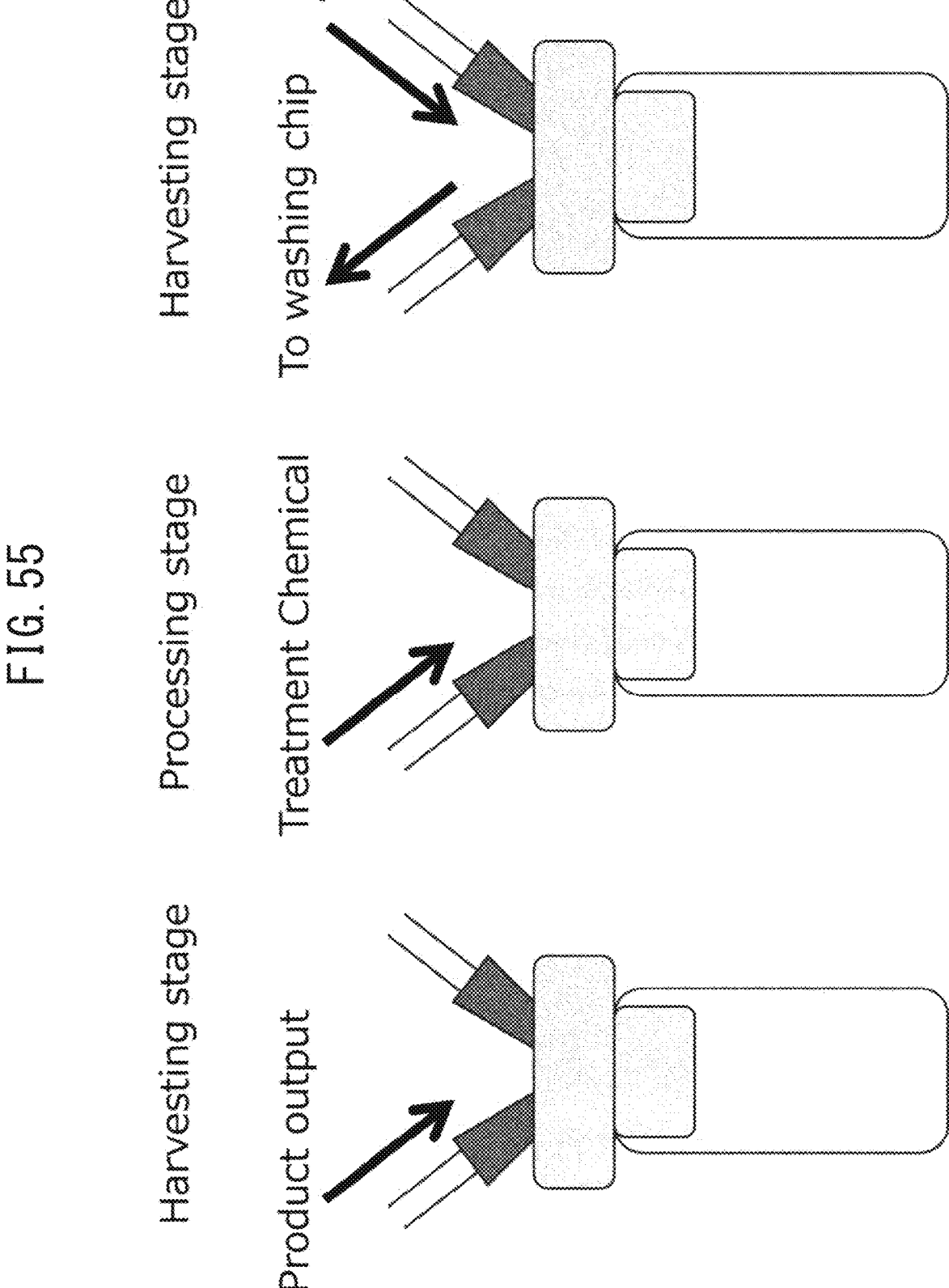
FIG. 55 shows an exemplary off-chip incubator. The incubator can be a glass vial with ports to connect with one or more microfluidic chips.

In some cases, a chip comprising the flow-through incubator can comprise a balancer for balancing fluidic resistances of different flow paths. The balancer can be used to balance the back pressure generated by the flow-through incubator. In some cases, the balancer can be substantially the same as the flow-through incubator, and connected to another outlet in the microfluidic device. In some cases, the balancer can be in a configuration different from the flow-through incubator, but can create the same fluidic resistance as the flow-through incubator. In some cases, the balancer can be a fluidic pressure control. For example, the fluidic pressure control can generate a negative pressure that can balance the back pressure generated by the flow-through incubator. For example, the component for balancing fluidic resistances can be a channel on the chip. In one case, the component for balancing fluidic resistance can be fluidically connected with the flow-through incubator. FIG. 54B shows an exemplary balancer. A flow-through incubator is connected with outlet 2 on the microfluidic channel comprising an array (DLD 1). A balancer for balancing the flow resistance in the flow-through incubator is connected to outlet 1 on the microfluidic channel comprising an array (DLD 1). The balancer can be configured to be the same as the flow-through incubator and connected to DLD 1 in a manner mirroring the flow-through incubator.

In some cases, the flow-through incubator on a chip can be a channel with a length of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, or 400 mm. A flow-through incubator, e.g., a serpentine channel, can comprise one or more connected segments, wherein each of these segments have one or more of these lengths.

In some cases, the flow-through incubator on a chip can be a channel with a length of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, or 400 mm. In one case, the flow-through incubator can be a channel with a length of about 30 mm. A flow-through incubator can comprise one or more connected segments with one or more of these lengths.

In some cases, the flow-through incubator on a chip can be a channel with a depth of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, 450, 500, 550, 600, 650, 700, 750, 800, 850, 900, 950 or 1000 μm.

In some cases, the flow-through incubator on a chip can be a channel with a depth of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, 450, 500, 550, 600, 650, 700, 750, 800, 850, 900, 950 or 1000 μm. For example, the flow-through incubator on a chip can be a channel with a depth of about 100 μm.

In some cases, the flow-through incubator on a chip can be a channel with a width of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 μM.

In some cases, the flow-through incubator on a chip can be a channel with a width of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 μm. For example, the flow-through incubator on a chip can be a channel with a width of about 100 μm. The width and/or depth of the flow-through incubator can vary along the length of the flow-through incubator.

In some cases, a microfluidic chip can comprise one or more flow-through incubators. The flow-through incubators can be used prolong the contact time of particles in different flow streams. In some cases, a microfluidic chip can comprise at least 1, 2, 3, 4, 5, 6, 7, 8, 9, 10, 11, 12, 13, 14, 15, 16, 17, 18, 19, or 20 flow-through incubators. In some cases, a microfluidic chip can comprise 1, 2, 3, 4, 5, 6, 7, 8, 9, 10, 11, 12, 13, 14, 15, 16, 17, 18, 19, or 20 flow-through incubators.

In some cases, the flow-through incubator can comprise a component that promotes the particles to move relative to the flow stream in the incubator. Moving of the cells relative the flow stream can allow the particles to move the different parts of the flow stream which have different concentrations of reagent. In some cases, such components can include an array of obstacles, e.g., obstacles deflecting the particles to a direction that is not parallel to the flow stream. In some cases, the component can include an inlet introducing a second flow stream in the channel. In some cases, the component can be a curved region in the flow-through incubator. Fluid in a flow-through incubator can be subjected to agitation via force internal or external to the flow-through incubator. For example, a magnetic stirrer (e.g., stir bar) can be located within the flow-through incubator, and a chip comprising a flow-through incubator can be placed on a magnetic stir plate, and the fluid in the flow-through incubator can be agitated with a stir bar. A chip with a flow-through incubuator can be placed on a rotating or oscillating platform, or can be subjected to vortexing, in order to agitate the fluid in the flow-through incubator.

The time a particle can spend in a flow-through incubator can 10 sec to about 30 sec, about 30 sec to about 1 min, about 1 min to about 5 min, about 5 min to about 10 min, about 10 min to about 15 min, about 15 min to about 30 min, about 30 min to 1 hr, about 1 hr to about 2 hr, about 1 hour to about 12 hr, about 12 hr to 24 hr, about 24 hr to about 48 hr, or about 2 days to about 7 days. The time a particle can spend in a flow-through incubator can be about, or at least 30 sec, 1 min, 5 min, 10 min, 15 min, 30 min, 1 hr, 2 hr, 12 hr, 24 hr, 48 hr, or 7 days. In some cases, flow in the flow-through incubator can be stopped and incubation can occur under conditions of no flow.

The temperature of the flow-through incubator can be regulated. The temperature of the flow-through incubator can be regulated separately than the temperature of fluidly connected DLD arrays, or the temperature of the flow-through incubator and one or more DLD arrays can be regulated at the same time. The temperature of the flow-through incubator can be held constant. The temperature of the flow-through incubator can be about, or at least 4° C., 16° C., 25° C., 30° C., 37° C., 50° C., 60° C., 65° C., 72° C., or 95° C. Temperature in the off-chip incubator can be cycled.

The flow in the flow-through incubator can be reversed. For example, pressure can be applied to move a liquid back and forth in a flow-through incubator.

In one example, a flow-through incubator with a maximum incubation time of about 10 min comprises 20 parallel channels of 3 cm in length, width of 100 μm, and depth of 100 μm, at fluid velocity of about 1 mm/s. The chip area can be 2 serpentine channels×3 cm length of each segment×20 segments×(100 μm width channel+100 μm spacing between channels)+2 DLD×7 cm length of DLD×600 μm width of DLD=3.68 cm².

H. Off-Chip Incubator

In some cases, an incubator provided herein can be an off-chip component fluidically connected to a chip. An off-chip incubator can be connected to a chip that is not a "car wash" chip. In some cases, an off-chip incubator can be a flow-through off-chip incubator. In some cases, the off-chip incubator can be a container. The off-chip incubator can be fluidically connected with a first microfluidic channel (e.g., a channel comprising a DLD array) and a second microfluidic channel (e.g., a channel comprising a DLD array), and the off-chip incubator and the first microfluidic channel can comprise the same solution. In this example, cells can stay in contact with the solution when flowing from the first microfluidic channel (e.g., a channel comprising a DLD array) to the second microfluidic channel (e.g., a channel comprising a DLD array) through the flow-through incubator. The first and/or the second microfluidic channels can be a component in a microfluidic chip for processing cells. The container can be fluidically connected with one or more microfluidic chips for processing particles herein. In some cases, the off-chip incubator can be connected with a first microfluidic chip, but not connected with a second microfluidic chip. The incubator can collect the processed particles from the first microfluidic chip. The collected particles can be introduced to a second microfluidic chip for further processing. In some cases, an off-chip incubator can comprise one or more flow controllers. The flow controllers can control the flow rate of particles flowing into and/or out of the flow-through incubator. In some cases, the off-chip incubator can be a reservoir on a plate, a test tube, a vial, tubing, or a capillary.

In some cases, particles of at least a predetermined size are directed to an off-chip incubator. In some cases, particles of less than a predetermined size are directed to an off-chip incubator.

An off-chip flow-through incubator can comprise one or more ports for fluidic connection to other devices, e.g., a microfluidic chip. An off-chip incubator can have about 1, 2, 3, 4, 5, 6, 7, 8, 9, or 10 ports for fluidic connection to one or more devices. In some cases, fluid that enters an off-chip incubator from a first port of the off-chip incubator also exits from the first port of the off-chip incubator. In some cases, fluid that enters an off-chip incubator from a first port exits from a second port of the off-chip incubator. In some cases, first particles of at least a predetermined size are passed through a channel comprising a DLD array, and the first particles of at least a predetermined size exit the channel comprising the DLD array from an outlet and enter the off-chip incubator. The first particles of at least a predetermined size are incubated in the off-chip incubator for a period of time. A chemical treatment can be introduced into the off-chip incubator, e.g., an antibody.

The time a particle can spend in an off-chip incubator can about 10 sec to 30 sec, 30 sec to about 1 min, about 1 min to about 5 min, about 5 min to about 10 min, about 10 min to about 15 min, about 15 min to about 30 min, about 30 min to 1 hr, about 1 hr to about 2 hr, about 1 hour to about 12 hr, about 12 hr to 24 hr, about 24 hr to about 48 hr, or about 2 days to about 7 days. The time a particle can spend in an off-chip incubator can be at least 10 sec, 30 sec, 1 min, 5 min, 10 min, 15 min, 30 min, 1 hr, 2 hr, 12 hr, 24 hr, 48 hr, or 7 days. Flow in the off-chip incubator can be stopped and incubation can occur under conditions of no flow. Flow in an off-chip incubator can be continuous.

The temperature of the off-chip incubator can be regulated. The temperature of the off-chip incubator can be regulated separately than the temperature of fluidly connected channels with DLD arrays, or the temperature of the off-chip incubator and one or more channels with DLD arrays can be regulated at the same time. The temperature of the off-chip incubator can be held constant. The temperature of the off-chip incubator can be about, or at least, 4° C., 16° C., 25° C., 30° C., 37° C., 50° C., 60° C., 65° C., 72° C., or 95° C. Temperature in the off-chip incubator can be cycled.

The flow in the off-chip incubator can be reversed. For example, pressure can be applied to move a liquid back and forth in an off-chip incubator.

Fluid in an off-chip incubator can be subjected to agitation via force internal or external to the off-chip incubator. For example, a magnetic stirrer (e.g., stir bar) can be located within the off-chip incubator, and the off-chip incubator can be placed on a magnetic stir plate, and the fluid in the off-chip incubator can be agitated with a stir bar. An off-chip incubator can be placed on a rotating or oscillating platform, or can be subjected to vortexing, in order to agitate the fluid in the off-chip incubator.

The volume of an off-chip incubator can be about 100 µl to about 500 µl, about 500 µl to about 1 mL, about 1 mL to about 5 mL, or about 5 mL to about 10 mL, about 10 mL to 50 mL, about 50 mL to about 100 mL, about 100 mL to about 500 mL, about 500 mL to about 1000 mL, about 1 L to about 5 L, or about 5 L to about 10 L. The volume of an off-chip incubator can be about 100 µl, 500 µl, 1 mL, 5 mL, 10 mL, 50 mL, 100 mL, 500 mL, 1000 mL, 5 L, or 10 L. The volume of an off-chip incubator can be at least 100 µl, 500 µl, 1 mL, 5 mL, 10 mL, 50 mL, 100 mL, 500 mL, 1000 mL, 5 L, or 10 L.

A reagent can be located in an off-chip incubator when a particle reaches the off-chip incubator. In some cases, a particle enters the off-chip incubator before the reagent enters the off-chip incubator. Reactions can occur in the off-chip incubator, e.g., antibody/cell surface marker binding, cell lysis, intracellular labeling, fixation, permeabilization, or a nucleic acid manipulation (e.g., PCR). An off-chip incubator can be monitored to follow a reaction, e.g., by spectrophotometric equipment, imaging equipment, etc. An off-chip incubator can comprise a surface compatible for cell adhesion. In some cases, an off-chip incubator is treated to prevent cell adhesion. Flow to or from an off-chip incubator can be modulated manually (e.g., with a syringe pump) or automatically.

I. Device Features

As described herein, a multi-stream (e.g., 'car wash') device as provided herein can comprise a channel with a plurality of inlets, a plurality of outlets, and an array of obstacles disposed there between. Exemplary devices can be the devices illustrated in FIGS. 18A-B, 19, 20A-B, 24A-B, 27A-B, and 32. In some cases, a device as provided herein can comprises a channel with at least one input, at least one output, and an array of obstacles disposed there between. Exemplary devices can be the devices illustrated in FIGS. 39 and 40. Examples of parameters of devices are illustrated in Table 2.

TABLE 2

| Channel widths | | | |
|---|---|---|---|
| | A/A2 | B | C |
| Blood inlet channel width (µm) | 50 | 100 | 150 |
| Buffer inlet channel width (µm) | 55 | 110 | 110 |
| Product outlet channel width (µm) | 49 | 98 | 98 |

TABLE 3

| Gap size (edge-to-edge distance between posts)/post diameter (µm) | | |
|---|---|---|
| | A | B | C |
| Section 1 | 18/27 | 44/66 | 90/135 |
| Section 2 | 12/18 | 30/45 | 60/90 |
| Section 3 | 8/12 | 20/30 | 40/60 |

Figure 39:
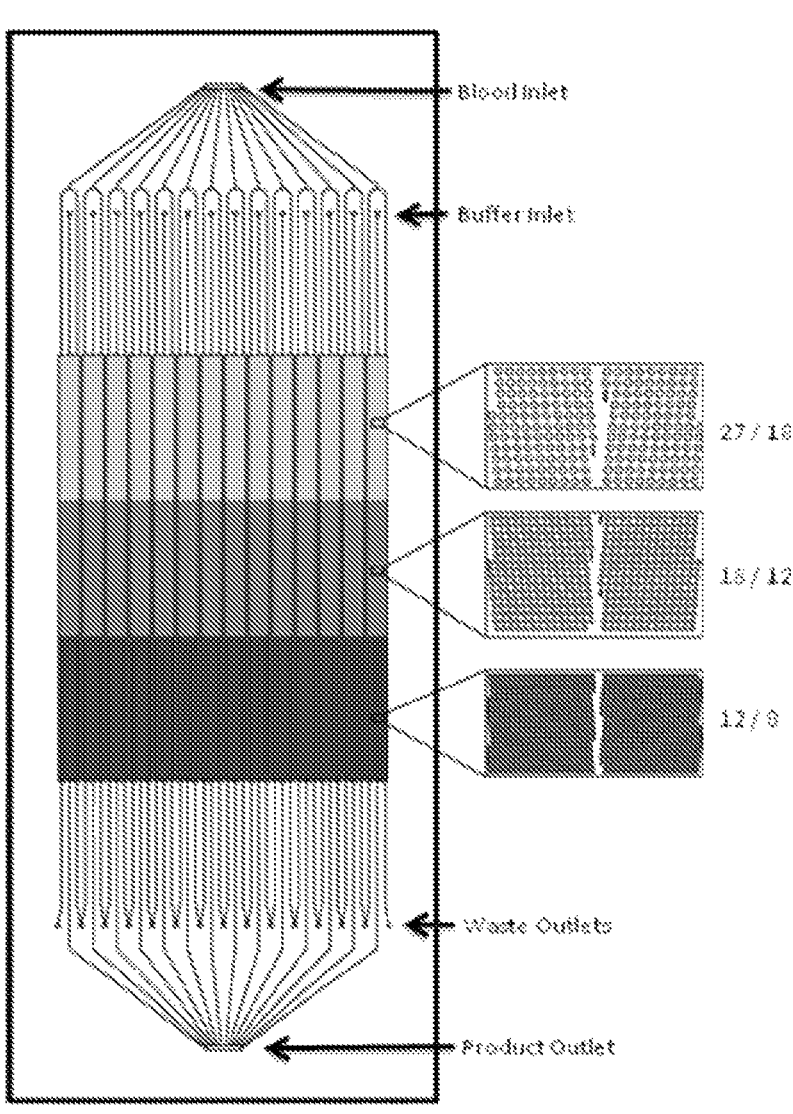
FIG. 39 illustrates an embodiment of a device comprising an array of obstacles comprising 14 channels.

FIG. 39 shows a design of an A chip. The A chip comprises a three zone (section) design with progressively smaller pillars and gaps. Gap size and post diameter are described in Table 2. The device can comprise an inlet, e.g., for blood, an inlet for buffer, waste outlets, and a product outlet. The A chip can comprise 14 parallel channels. The total channel volume (including 0.5 mm vias) (a via can be a hole that can connect the backside of a chip, (e.g., where the manifold connection can occur) to the top side of the chip (i.e., where the array is located) can be 118 µL. The throughput of the device is about 4-8 mL/hr. The processing time for an 8 mL sample can be about 1 to about 2 hours. The A chip can be made with silicon. The A chip can be made with polypropylene, poly(methyl methacrylate) (PMMA), or cyclo-olefin polymer (COP). In some cases, between about 5 mL and about 20 mL of sample can be applied to the device. In some cases, between about 1 µL and about 5 mL of sample can be applied to the device.

Figure 40:
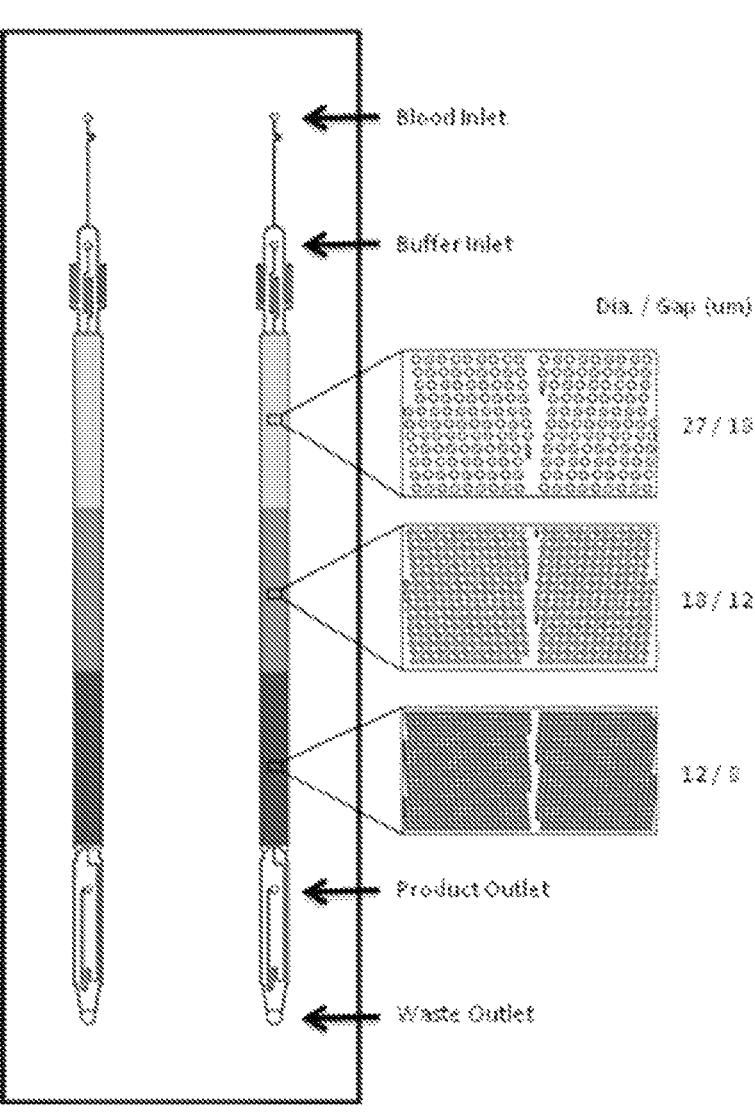
FIG. 40 illustrates an embodiment of a device comprising an array of obstacles comprising 2 channels.
Figure 41:
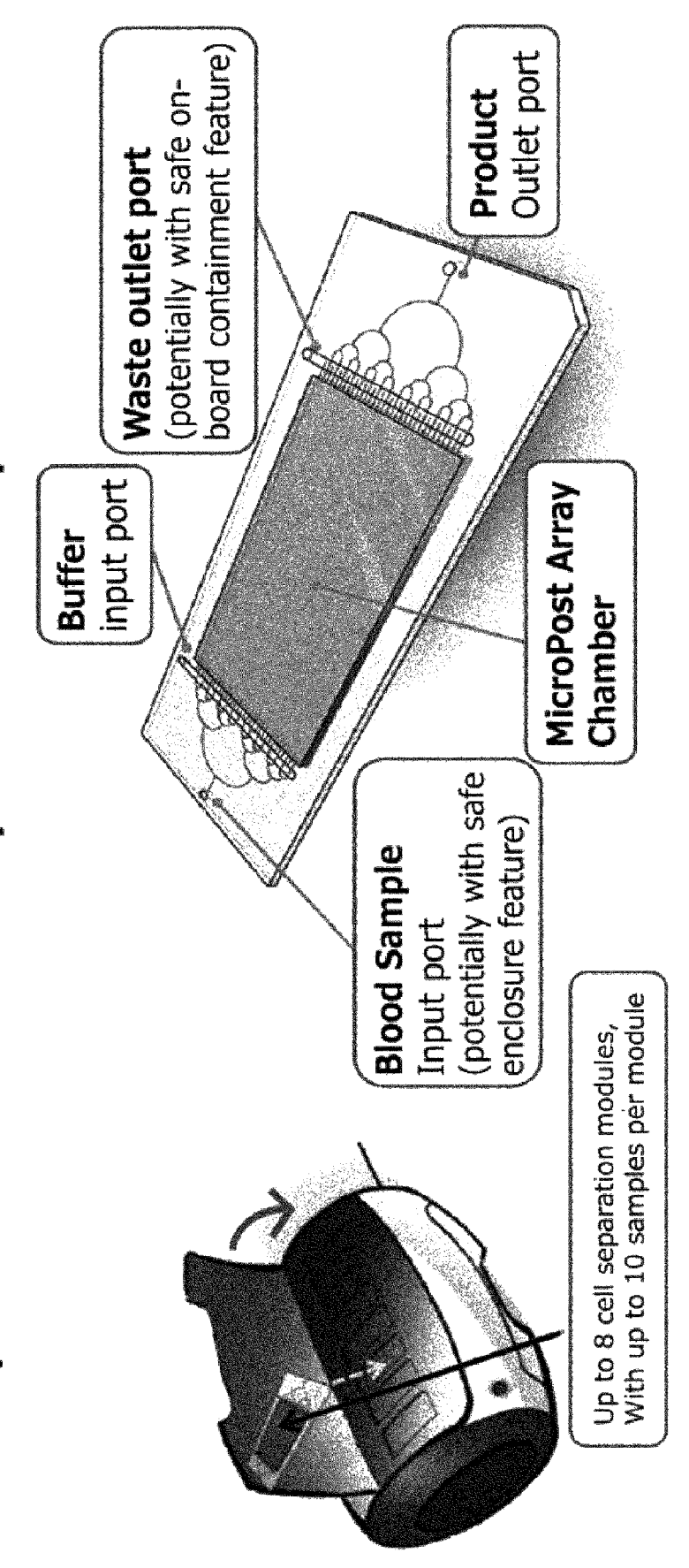
FIG. 41 illustrates a desktop instrument and a disposable cell separation module. Up to 8 cell separation modules can be used in the desktop instrument, with up to 10 samples per module. The instrument can be stand alone or can be integrated in-line with other equipment. A disposable cell separation module can comprise a blood sample input port (in some cases with a safe enclosure feature), a micropost array chamber, a product outlet port, a waste outlet port (in some cases with safe on-board containment feature, and a buffer input port.

FIG. 40 shows another example of a device (A2). The A2 chip comprises a three zone design with progressively smaller pillars and gaps. Gap sizes and post diameters are described in Table 3. The depth of the channel is 60 µm. Each A2 chip comprises 2 independent channels. The total channel volume (including 0.5 mm via) is about 3.85 µL. The throughput for the device can be about 0.12 to about 0.24 mL/hr, or about 0.4 to about 0.8 mL/hr. The processing time for a 100 µL sample can be about 25 to about 50 min. The A2 chip can be made with silicon. The A2 chip can be made with polypropylene, poly(methyl methacrylate) (PMMA), or cyclo-olefin polymer (COP). The device can be used to process about 50 to about 500 uL of sample. The device can be used to process about 1 to about 50 uL of sample.

i. Channels

In some cases, a device as provided herein comprises a channel, wherein the channel is bounded by a first wall and a second wall, wherein the second wall opposes the first wall, and wherein the first and second wall are parallel to each other. The channel can comprise an input portion or area comprising a plurality of inlets and an output portion or area comprising a plurality of outlets. Each of the plurality of inlets can be configured to flow or allow passage of a flow stream or stream tube comprising a fluid, wherein each of the flow streams or stream tubes flows parallel to each other flow stream or stream tube from the input portion of the device to the outlet portion of the device. In some cases, each of a plurality of flow streams moves from an inlet to an outlet directly across from or opposing the inlet. In some cases, a device comprises a channel with at least one inlet and at least one outlet. In some cases, a device comprises a channel with two inlets and two outlets. In some cases, a device comprises a channel with more than two inlets and more than two outlets. In some cases, a first inlet to a channel is a sample inlet and a second inlet to a channel is a buffer inlet. In some cases, a first inlet to a channel is a sample inlet, a second inlet to a channel is a reagent inlet, and a third inlet is a buffer inlet. A single flow stream can originate from a single inlet. A single flow stream can originate from two or more adjacent inlets (e.g., FIG. 19). In some cases, a first outlet to a channel is a product outlet and a second outlet to a channel is a waste outlet. In some cases, a first outlet of a plurality of outlets to a channel is a product outlet and each of the remaining plurality of outlets comprises a waste outlet. Each of the remaining plurality of outlets can comprise a distinct outlet for a flow stream originating from an inlet present in an input portion of a device as provided herein comprising the inlet and the waste outlet, wherein the inlet is directly opposed to or across from the waste outlet. In some cases, a channel comprises an array of obstacles between a plurality of inlets and a plurality of outlets. In some cases, the array of obstacles comprises zones or sections of obstacles, wherein each section comprises obstacles of substantially the same diameter and size and gaps between obstacles of substantially the same size.

(a) Channel Width

In some cases, channel width is about 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mm.

In some cases channel width is at least 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mm.

In some cases, channel width is less than 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mm.

In some cases, channel width is about 1 to about 10 mm, about 2 to about 9 mm, about 3 to about 8 mm, about 10 to about 20 mm, about 20 to about 30 mm, about 30 to about 40 mm, about 40 to about 60 mm, about 60 to about 70 mm, or about 70 to about 100 mm.

(b) Channel Length

In some cases, channel length is about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, or 200 mm.

In some cases, channel length is less than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, or 200 mm.

In some cases, channel length is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, or 200 mm.

In some cases, channel length is about 1 to about 10 mm, about 2 to about 9 mm, about 3 to about 8 mm, about 10 to about 20 mm, about 20 to about 30 mm, about 30 to about 40 mm, about 40 to about 60 mm, about 60 to about 70 mm, about 70 to about 100 mm, or about 100 to about 200 mm.

(c) Channel Depth

In some cases, a channel has a depth of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, 450, 500, 550, 600, 650, 700, 750, 800, 850, 900, 950 or 1000 µm.

In some cases, a channel has a depth of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, 450, 500, 550, 600, 650, 700, 750, 800, 850, 900, 950 or 1000 µm.

In some cases, a channel has a depth less than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, 450, 500, 550, 600, 650, 700, 750, 800, 850, 900, 950 or 1000 µm.

In some cases, a channel has a depth of about 10 to about 30 µm, about 20 to about 40 µm, about 30 to about 50 µm, about 50 to about 100 µm, about 100 to about 200 µm, about 200 to about 400 µm, about 400 to about 600 µm, or about 600 to about 1000 µm.

(d) Number of Channels Per Device (Chip)

In some cases, a device comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 channels.

In some cases, a device comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 channels.

In some cases, a device comprises about 2 to about 10 channels, about 10 to about 20 channels, about 20 to about 30 channels, about 30 to about 40 channels, about 40 to about 50 channels, about 50 to about 60 channels, about 60 to about 70 channels, or about 70 to about 100 channels.

(e) Channel Volume

In some cases, a total volume of a channel is about 0.001, 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, or 200 mL.

In some cases, a total volume of a channel is at least 0.001, 0.005, 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, or 200 mL.

In some cases, a total volume of a channel is about 0.001 to about 0.01 mL, about 0.01 to about 0.1 mL, about 0.1 to about 0.5 mL, about 1 to about 2 mL, about 2 to about 3 mL, about 3 to about 5 mL, about 5 to about 10 mL, about 10 to about 20 mL, or about 20 to about 50 mL.

In some cases a device comprises multiple channels. In some cases, a total volume of the channels in a device is any of the volumes listed above multiplied by the number of channels in the device.

In some cases, device as provide herein is adapted to process as low as ~10 µl and as high as 500 µl. In some cases, a device as provided herein is adapted to process between 500 µl and 20 or 40 ml. In some cases, a device as provided herein is adapted to process between more than 40 ml.

(f) Zones (Stages) within a Channel

A device described herein can have a plurality of zones (stages, or sections). A zone can be an area on a device with the same or similar sized post (obstacles) and gaps. In some cases, a channel in a device comprises 1, 2, 3, 4, 5, 6, 7, 8, 9, or 10 zones. In some cases, a channel in a device comprises at least 1, 2, 3, 4, 5, 6, 7, 8, 9, or 10 zones.

In some cases, a sample, e.g., a biological sample, can comprise particles with a broad range of sizes. If a particle in a sample is larger than a gap, the particle can clog the channel. In some cases, multiple separation stages with different gap and post sizes can be used. In some cases, post diameter and gap size is smaller in a second zone relative to a first zone. In some cases, a device comprises a plurality of zones, wherein when a fluid is applied to an inlet of the device, it flows through a plurality of zones in a channel, e.g., at least 1, 2, 3, 4, 5, 6, 7, 8, 9, or 10 zones. In some cases, post diameter and/or gap sizes get progressively smaller as a fluid flows from and inlet to an outlet across zones in a channel. A zone can about 0.5, 0.7, 0.8, 0.9, 1, 1.1, 1.2, 1.3, 1.4, 1.5, 1.6, or 1.7 cm in length.

(g) Gap Size (Edge-to-Edge Distance Between Posts or Obstacles)

In some cases, gap size in an array of obstacles (edge-to-edge distance between posts or obstacles) is about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87. 88, 89, 90, 91, 92, 93, 94, 95, 96, 97, 98, 99, 100, 125, 150, 175, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or 3000 µm.

In some cases, gap size in an array of obstacles is at least 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87. 88, 89, 90, 91, 92, 93, 94, 95, 96, 97, 98, 99, 100, 125, 150, 175, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or 3000 µm.

In some cases, gap size in an array of obstacles is less than 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87. 88, 89, 90, 91, 92, 93, 94, 95, 96, 97, 98, 99, 100, 125, 150, 175, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or 3000 µm.

In some cases, gap size is about 1 µm to about 10 µm, about 10 µm to about 20 µm, about 20 µm to about 30 µm, about 30 µm to about 40 µm, about 40 µm to about 50 µm, about 50 µm to about 60 µm, about 60 µm to about 70 µm, about 70 µm to about 80 µm, about 80 µm to about 90 µm, about 90 µm to about 100 µm, about 100 µm to about 110 µm, about 110 µm to about 120 µm, about 120 µm to about 130 µm, about 130 µm to about 140 µm, about 140 µm to about 150 µm, about 150 µm to about 160 µm, about 160 µm to about 170 µm, about 170 µm to about 180 µm, about 180 µm to about 190 µm, about 190 µm to about 200 µm, about 200 µm to about 250 µm, about 250 µm to about 300 µm, about 300 µm to about 400 µm, about 400 µm to about 500 µm, about 500 µm to about 600 µm, about 600 µm to about 700 µm, about 700 µm to about 800 µm, about 800 µm to about 900 µm, about 900 µm to about 1000 µm, about 1000 µm to about 1500 µm, about 1500 µm to about 2000 µm, about 2000 µm to about 2500 µm, or about 2500 µm to about 3000 µm.

(h) Post (Obstacle) Diameter

In some cases, post (obstacle) diameter is about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87. 88, 89, 90, 91, 92, 93, 94, 95, 96, 97, 98, 99, 100, 105, 110, 115, 120, 125, 130, 135, 140, 145, 150, 155, 160, 170, 175, 180, 185, 190, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or 3000 µm.

In some cases, post (obstacle) diameter is at least 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87. 88, 89, 90, 91, 92, 93, 94, 95, 96, 97, 98, 99, 100, 105, 110, 115, 120, 125, 130, 135, 140, 145, 150, 155, 160, 170, 175, 180, 185, 190, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or 3000 μm.

In some cases, post (obstacle) diameter is less than 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87. 88, 89, 90, 91, 92, 93, 94, 95, 96, 97, 98, 99, 100, 105, 110, 115, 120, 125, 130, 135, 140, 145, 150, 155, 160, 170, 175, 180, 185, 190, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or 3000 μm.

(i) Obstacle Cross-Sectional Shape

In some cases, the cross-sectional shape of a post or obstacle is a circle, triangle, square, rectangle, pentagon, hexagon, heptagon, octagon, nonagon, decagon, hendeca-gon, dodecagon, hexadecagon, icosagon, or star. In some cases, a triangle is an acute triangle, equiliateral triangle, isosceles triangle, obtuse triangle, rational triangle, right triangle (30-60-90 triangle, isosceles right triangle, Kepler triangle), or scalene triangle. In some cases, the cross-sectional shape of a post or obstacle is a quadrilateral, e.g., a cyclic quadrilateral, square, kite, parallelogram, rhombus, Lozeng, rhomboid, rectangle, tangential quadrilateral, trap-ezoid, trapezium, or isososceles trapezoid. In some cases, the cross-sectional shape of a post or obstacle is a crescent, ellipse, lune, oval, Reuleauz polygon, Reuleaux triangle, lens, vesica piscis, salinon, semicircle, tomoe, magatama, triquetra, asteroid, deltoid super ellipse, or tomahawk. In some cases, a cross-sectional shape with a point has a sharpened point. In some cases, a cross-sectional shape with a point has a rounded point. In some cases, a cross-sectional shape with more than one point has at least one rounded point and at least one sharpened point.

In some cases, a post (obstacle) has a cylindrical shape.

(j) Distance of Posts (Obstacles) from an Inlet

A first row of posts can be spaced less than about 1000, 950, 900, 850, 800, 750, 700, 650, 600, 550, or 500 450, 400, 350, 300, 250, 200, 150, 100, 50, 40, 30, 20, 10, or 5 μm from an input.

(k) Tilt Angle

In some cases an array of obstacles has a tilt angle $\epsilon$ (with respect to the direction of fluid flow) of 1/3, 1/4, 1/5, 1/6, 1/7, 1/8, 1/9, 1/10, 1/11, 1/12, 1/13, 1/14, 1/15, 1/16, 1/17, 1/18, 1/19, 1/20, 1/21, 1/22, 1/23, 1/24, 1/25, 1/26, 1/27, 1/28, 1/29, 1/30, 1/31, 1/32, 1/33, 1/34, 1/35, 1/36, 1/37, 1/38, 1/39, 1/40, 1/41, 1/42, 1/43, 1/44, 1/45, 1/46, 1/47, 1/48, 1/49, 1/50, 1/51, 1/52, 1/53, 1/54, 1/55, 1/56, 1/57, 1/58, 1/59, 1/60, 1/61, 1/62, 1/63, 1/64, 1/65, 1/66, 1/67, 1/68, 1/69, 1/70, 1/71, 1/72, 1/73, 1/74, 1/75, 1/76, 1/77, 1/78, 1/79, 1/80, 1/81, 1/82, 1/83, 1/84, 1/85, 1/86, 1/87, 1/88, 1/89, 1/90, 1/91, 1/92, 1/93, 1/94, 1/95, 1/96, 1/97, 1/98, 1/99, 1/100, 1/110, 1/120, 1/130, 1/140, 1/150, 1/160, 1/170, 1/180, 1/190, 1/200, 1/300, 1/400, 1/500, 1/600, 1/700, 1/800, 1/900, 1/1000, 1/2000, 1/3000, 1/4000, 1/5000, 1/6000, 1/7000, 1/8000, 1/9000, or 1/10,000 radian.

In some cases, $\epsilon$ is less than 1/3, 1/4, 1/5, 1/6, 1/7, 1/8, 1/9, 1/10, 1/11, 1/12, 1/13, 1/14, 1/15, 1/16, 1/17, 1/18, 1/19, 1/20, 1/21, 1/22, 1/23, 1/24, 1/25, 1/26, 1/27, 1/28, 1/29, 1/30, 1/31, 1/32, 1/33, 1/34, 1/35, 1/36, 1/37, 1/38, 1/39, 1/40, 1/41, 1/42, 1/43, 1/44, 1/45, 1/46, 1/47, 1/48, 1/49, 1/50, 1/51, 1/52, 1/53, 1/54, 1/55, 1/56, 1/57, 1/58, 1/59, 1/60, 1/61, 1/62, 1/63, 1/64, 1/65, 1/66, 1/67, 1/68, 1/69, 1/70, 1/71, 1/72, 1/73, 1/74, 1/75, 1/76, 1/77, 1/78, 1/79, 1/80, 1/81, 1/82, 1/83, 1/84, 1/85, 1/86, 1/87, 1/88, 1/89, 1/90, 1/91, 1/92, 1/93, 1/94, 1/95, 1/96, 1/97, 1/98, 1/99, 1/100, 1/110, 1/120, 1/130, 1/140, 1/150, 1/160, 1/170, 1/180, 1/190, 1/200, 1/300, 1/400, 1/500, 1/600, 1/700, 1/800, 1/900, 1/1000, 1/2000, 1/3000, 1/4000, 1/5000, 1/6000, 1/7000, 1/8000, 1/9000, or 1/10,000 radian.

In some cases, the tilt angle is between about 1/1000 to about 1/3, or about 1/100 to about 1/5, or about 1/1000 to about 1/100, or about 1/500 to about 1/100, or about 1/50 to about 1/3.

(l) Inlet or Inlet Channel Width

In some cases, each of a plurality of inlets in a device as provided herein comprising the plurality of inlets has the same or substantially the same width. In some cases, each of a plurality of inlets in a device as provided herein compris-ing the plurality of inlets has a different or substantially different width. In some cases, one or more of a plurality of inlets in a device as provided herein comprising a plurality of inlets comprises a sample input, wherein the sample input has a different or substantially different width than each of the other plurality of inlets. In some cases, each inlet of a plurality of inlets is an inlet channel, wherein the inlet channel is bounded by two opposing walls. Each inlet or inlet channel can correspond to a flow stream. In some cases, an inlet (e.g., sample, buffer, and/or reagent) channel width is about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87. 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 230, 235, 240, 245, 250, 300, 350, 400, 450, 500, 550, 600, 650, 700, 750, 800, 850, 900, 950, 1000, 1100, 1200, 1300, 1400, or 1500 μm.

In some cases, an inlet (e.g., sample, buffer, and/or reagent) channel width is at least 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87. 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 230, 235, 240, 245, 250, 300, 350, 400, 450, 500, 550, 600, 650, 700, 750, 800, 850, 900, 950, 1000, 1100, 1200, 1300, 1400, or 1500 μm.

In some cases, an inlet (e.g., sample, buffer, and/or reagent) channel width is less than 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87. 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 230, 235, 240, 245, 250, 300, 350, 400, 450, 500, 550, 600, 650, 700, 750, 800, 850, 900, 950, 1000, 1100, 1200, 1300, 1400, or 1500 μm.

In some cases, an inlet (e.g., sample, buffer, and/or reagent) channel width is about 1 to about 10 μm, about 10 to about 20 μm, about 20 to about 30 μm, about 30 to about 60 μm, about 60 to about 90 μm, about 90 to about 120 μm, about 120 to about 180 μm, about 180 to about 250 μm, about 250 to about 500 μm, about 500 to about 1000 μm, about 1000 to about 1500 μm.

(m) Product Outlet or Product Outlet Channel Width

In some cases, each of a plurality of outlets in a device as provided herein comprising the plurality of outlets has the same or substantially the same width. In some cases, each of a plurality of outlets in a device as provided herein comprising the plurality of outlets has a different or substantially different width. In some cases, one or more of a plurality of outlets in a device as provided herein comprising a plurality of outlets comprises a sample input, wherein the sample input has a different or substantially different width than each of the other plurality of outlets. In some cases, each outlet of a plurality of outlets is an outlet channel, wherein the outlet channel is bounded by two opposing walls. Each outlet or outlet channel can correspond to a flow stream. In some cases, an outlet (e.g., product, waste (e.g., reagent, and/or buffer)) channel width is about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 170, 175, 180, 185, 190, 200, 250, 300, 350, 400, 450, 500, 550, 600, 650, 700, 750, 800, 850, 900, 950, 1000, 1100, 1200, 1300, 1400, or 1500 μm.

In some cases, an outlet (e.g., product, waste (e.g., reagent, and/or buffer)) channel width is at least 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87. 88, 89, 90, 91, 92, 93, 94, 95, 96, 97, 98, 99, 100, 105, 110, 115, 120, 125, 130, 135, 140, 145, 150, 155, 160, 170, 175, 180, 185, 190, 200, 250, 300, 350, 400, 450, 500, 550, 600, 650, 700, 750, 800, 850, 900, 950, 1000, 1100, 1200, 1300, 1400, or 1500 μm.

In some cases, an outlet (e.g., product, waste (e.g., reagent, and/or buffer)) channel width is less than 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87. 88, 89, 90, 91, 92, 93, 94, 95, 96, 97, 98, 99, 100, 105, 110, 115, 120, 125, 130, 135, 140, 145, 150, 155, 160, 170, 175, 180, 185, 190, 200, 250, 300, 350, 400, 450, 500, 550, 600, 650, 700, 750, 800, 850, 900, 950, 1000, 1100, 1200, 1300, 1400, or 1500 μm.

In some cases, an outlet (e.g., product, waste (e.g., reagent, and/or buffer)) channel width is about 1 to about 10 μm, about 10 to about 20 μm, about 20 to about 30 μm, about 30 to about 60 μm, about 60 to about 90 μm, about 90 to about 120 μm, about 120 to about 180 μm, about 180 to about 250 μm, about 250 to about 500 μm, about 500 to about 1000 μm, about 1000 to about 1500 μm. In some cases, the ratio of a width of a product outlet at a base of a DLD array to the width of a waste outlet at a base of a DLD array is about 10:1, 9:1, 8:1, 7:1, 6:1, 5:1, 4:1, 3:1, 2;1, 1:1, 1:2, 1:3, 1:4, 1:5, 1:6, 1:7, 1:8, 1:9, or 1:10. The ratio of a width of a product outlet at a base of a DLD array to the width of a waste outlet at a base of a DLD array can be at least 10:1, 9:1, 8:1, 7:1, 6:1, 5:1, 4:1, 3:1, 2;1, 1:1, 1:2, 1:3, 1:4, 1:5, 1:6, 1:7, 1:8, 1:9, or 1:10.

(n) Separator Wall Length

In some cases, a separator wall extends into an array of obstacles in a device as provided herein. The separator wall can extend for at least, at most, more than, less than or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% of the length of a channel that comprises the array of obstacles and the separator wall.

In some cases, separator wall length is about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, or 200 mm.

In some cases, separator wall length is less than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, or 200 mm.

In some cases, separator wall is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, or 200 mm.

In some cases, separator wall is about 1 to about 10 mm, about 2 to about 9 mm, about 3 to about 8 mm, about 10 to about 20 mm, about 20 to about 30 mm, about 30 to about 40 mm, about 40 to about 60 mm, about 60 to about 70 mm, about 70 to about 100 mm, or about 100 to about 200 mm.

(o) Separator Wall Width

In some cases, a separator wall in a device as provided herein has the same width along the entire length of the separator wall. The separator wall can taper, wherein a first end of the separator wall has a larger width than a second end of the separator wall.

In some cases, separator wall width is about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300, 350, 400, 450, 500, 750, or 1000 μm.

In some cases, separator wall width is at least 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300, 350, 400, 450, 500, 750, or 1000 μm.

In some cases, separator wall width is less than 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300, 350, 400, 450, 500, 750, or 1000 μm.

In some cases, separator wall width is about 1 to about 10 μm, about 2 to about 9 μm, about 3 to about 8 μm, about 10 to about 20 μm, about 20 to about 30 μm, about 30 to about 40 μm, about 40 to about 60 μm, about 60 to about 70 μm, about 70 to about 100 μm, about 100 to about 250, about 250 to about 500, or about 500 to about 1000 μm.

In some cases, a predetermined size is at least 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1000 μm.

In some cases, a predetermined size is about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1000 μm.

In some cases, a predetermined size is less than 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 μm.

(p) Gap Width Between Separator Walls

In some cases, a gap exists between adjacent separator walls in a multi-stream (e.g., 'car wash') device as provided herein. The gap can be configured for particles (e.g., cells) being deflected through an array of obstacle in a device as provided herein can pass there between. In some cases, a gap width between separator walls (e.g., opposing separator walls) is about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87. 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 230, 235, 240, 245, 250, 300, 350, 400, 450, 500, 550, 600, 650, 700, 750, 800, 850, 900, 950, 1000, 1100, 1200, 1300, 1400, or 1500 μm.

In some cases, a gap width between separator walls (e.g., opposing separator walls) is at least 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87. 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 230, 235, 240, 245, 250, 300, 350, 400, 450, 500, 550, 600, 650, 700, 750, 800, 850, 900, 950, 1000, 1100, 1200, 1300, 1400, or 1500 μm.

In some cases, a gap width between separator walls (e.g., opposing separator walls) is less than 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87. 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 230, 235, 240, 245, 250, 300, 350, 400, 450, 500, 550, 600, 650, 700, 750, 800, 850, 900, 950, 1000, 1100, 1200, 1300, 1400, or 1500 µm.

In some cases, a gap width between separator walls (e.g., opposing separator walls) is about 1 to about 10 µm, about 10 to about 20 µm, about 20 to about 30 µm, about 30 to about 60 µm, about 60 to about 90 µm, about 90 to about 120 µm, about 120 to about 180 µm, about 180 to about 250 µm, about 250 to about 500 µm, about 500 to about 1000 µm, about 1000 to about 1500 µm.

(q) Channel Configurations

In some cases, a device can have a configuration of a device as described in U.S. Pat. No. 8,021,614. In some cases, a channel in a device comprises mirrored arrays of obstacles, in which one array of obstacles is configured to deflect a particle of at least a predetermined size to a center bypass channel, and a second array of obstacles adjacent to the first array of obstacles also directs particles of at least a first predetermined size to the center bypass channel. In some cases, the bypass channel comprises a wall that separates the first array of obstacles and the second array of obstacles. In some cases, the bypass channel does not comprise a wall that separates the first array of obstacles and the second array of obstacles. In some cases, a channel with a mirrored array comprises at least two inlets. In some cases, a sample outlet is in fluid communication with the bypass channel. In some cases, a channel with a mirrored array comprises at least one waste outlet. In some cases, a channel with a mirrored array comprises a plurality of inlets and a plurality or outlets with an array of obstacles disposed between therein, wherein each of the arrays in the mirrored array, and wherein the channel is configured to flow a plurality of fluids from the plurality of inlets to the plurality of outlets. Each of the plurality of fluids can be flowed parallel to adjacent fluid flows. In some cases, a multi-stream (e.g., 'car wash') device comprising a mirrored array as described herein further comprises one or more separator walls between adjacent flow streams. In some cases, channel with a mirrored array comprises at least one waste outlet.

In some cases, a channel does not comprise a mirrored array. In some cases, a channel comprises a first array of obstacles that direct particles of at least a predetermined size to a bypass channel adjacent to a wall of the channel. In some cases, a channel comprises a plurality of bypass channels. In some cases, a channel comprises two mirrored arrays of obstacles, two inlets, and a central buffer stream for concentrating particles from each of the mirrored array of obstacles. In some cases, a channel comprises one inlet. In some cases, a channel comprises two inlets.

(r) Flow Properties

In some cases, flow through a device comprising an array of obstacles is laminar.

The methods, compositions, devices, systems, and/or kits described herein can facilitate rapid flow rate through a device. In some cases, a flow rate through a device is at least 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87. 88, 89, 90, 91, 92, 93, 94, 95, 96, 97, 98, 99, 100, 105, 110, 115, 120, 125, 130, 135, 140, 145, 150, 155, 160, 170, 175, 180, 185, 190, 200, 250, 300, 350, 400, 450, or 500 mL/min.

In some cases, a flow rate through a device is about 0.01, 0.02, 0.03, 0.04, 0.05, 0.06, 0.07, 0.08, 0.09, 0.1, 0.2, 0.3, 0.4. 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87. 88, 89, 90, 91, 92, 93, 94, 95, 96, 97, 98, 99, 100, 105, 110, 115, 120, 125, 130, 135, 140, 145, 150, 155, 160, 170, 175, 180, 185, 190, 200, 250, 300, 350, 400, 450, or 500 mL/min.

In some cases, a flow rate through a device is less than 0.01, 0.02, 0.03, 0.04, 0.05, 0.06, 0.07, 0.08, 0.09, 0.1, 0.2, 0.3, 0.4. 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87. 88, 89, 90, 91, 92, 93, 94, 95, 96, 97, 98, 99, 100, 105, 110, 115, 120, 125, 130, 135, 140, 145, 150, 155, 160, 170, 175, 180, 185, 190, 200, 250, 300, 350, 400, 450, or 500 mL/min.

In some cases, a flow rate through a device is about 0.05 to about 0.1 mL/min, about 0.1 to about 0.5 mL/min, about 0.5 to about 1 mL/min, about 1 to about 5 mL/min, about 5 to about 10 mL/min, about 10 to about 20 mL/min, about 20 to about 50 mL/min, about 50 to about 100 mL/min, about 100 to about 200 mL/min, or about 200 to about 500 mL/min.

In some cases, a fluid velocity is at least 1, 5, 10, 20, 30, 40, 50, 60, 70, 80, 90, 100, 150, 200, 300, 400, 500, 600, 700, 800, 900, 1000, 2000, 3000, 4000, 5000, 6000, 7000, 8000, 9000, or 10,000 mm/sec.

In some cases, a fluid velocity is about 1, 5, 10, 20, 30, 40, 50, 60, 70, 80, 90, 100, 150, 200, 300, 400, 500, 600, 700, 800, 900, 1000, 2000, 3000, 4000, 5000, 6000, 7000, 8000, 9000, or 10,000 mm/sec.

In some cases, a fluid velocity is less than 1, 5, 10, 20, 30, 40, 50, 60, 70, 80, 90, 100, 150, 200, 300, 400, 500, 600, 700, 800, 900, 1000, 2000, 3000, 4000, 5000, 6000, 7000, 8000, 9000, or 10,000 mm/sec.

In some cases, shear stress is about 10, 50, 100, 500, 1000, 5000, 10,000, 25,000, 50,000, 75,000, 100,000, 200,000, 300,000, 400,000, 500,000, 600,000, 700,000, 800,000, 900, 000 or 1,000,000 s$^{-1}$.

In some cases, shear stress is less than 10, 50, 100, 500, 1000, 5000, 10,000, 25,000, 50,000, 75,000, 100,000, 200, 000, 300,000, 400,000, 500,000, 600,000, 700,000, 800,000, 900,000 or 1,000,000 s$^{-1}$.

In some cases, shear stress is more than 10, 50, 100, 500, 1000, 5000, 10,000, 25,000, 50,000, 75,000, 100,000, 200, 000, 300,000, 400,000, 500,000, 600,000, 700,000, 800,000, 900,000 or 1,000,000 s$^{-1}$.

(s) Pressure

In some cases, a sample is flowed through a device at a pressure of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 6, 7, 8, 9, 10, 11, 12, 13, 14, 15, 16, 17, 18, 19, 20, 21, 22, 23, 24, 25, 26, 27, 28, 29, or 30 atm.

In some cases, a sample is flowed through a device at a pressure of at least 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 6, 7, 8, 9, 10, 11, 12, 13, 14, 15, 16, 17, 18, 19, 20, 21, 22, 23, 24, 25, 26, 27, 28, 29, or 30 atm.

In some cases, a sample is flowed through a device at a pressure of less than 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 6, 7, 8, 9, 10, 11, 12, 13, 14, 15, 16, 17, 18, 19, 20, 21, 22, 23, 24, 25, 26, 27, 28, 29, or 30 atm.

(t) Predetermined Size (Critical Size)

In some cases, a device as described herein can be used to deflect particles of at least a predetermined size to a first outlet (e.g., product) and particles less than a predetermined size to a second (e.g., waste) outlet. In some cases, a predetermined size is about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1000 μm.

In some cases, a predetermined size is less than 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1000 μm.

In some cases, a predetermined size is more than 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1000 μm.

In some cases, a device comprises an array of obstacles, wherein the obstacles comprise obstacles with a diameter of 18 μm, and the array of obstacles comprise rows or obstacles with a gap of 18 μm, wherein a subsequent row has a 1/42 row shift. In some case, the obstacles are semi-mirrored. Semi-mirrored can mean that the layout can reflect the array across the center line (i.e., the collection channel) and then shift that reflected array down towards the outlet by a certain number of rows. In some cases, the number of rows is 5. The width of the collection channel can be kept uniform or substantially more uniform than if the obstacles were to be truly mirrored. The arrays on either side of the collection channel can be identical, but just shifted from each other in the direction of the flow.

(u) Obstacle Coating

In some cases, obstacles comprise an affinity capture agent, e.g., an antibody, other protein-binding partner, or nucleic acid. Obstacles can comprise specific affinity-capture agent to capture specific particles in a sample. Affinity capture is described, e.g., in PCT Publication No. WO2012094642, which is herein incorporated by reference in its entirety.

(v) On-Chip Cleaning System

Figure 33A:
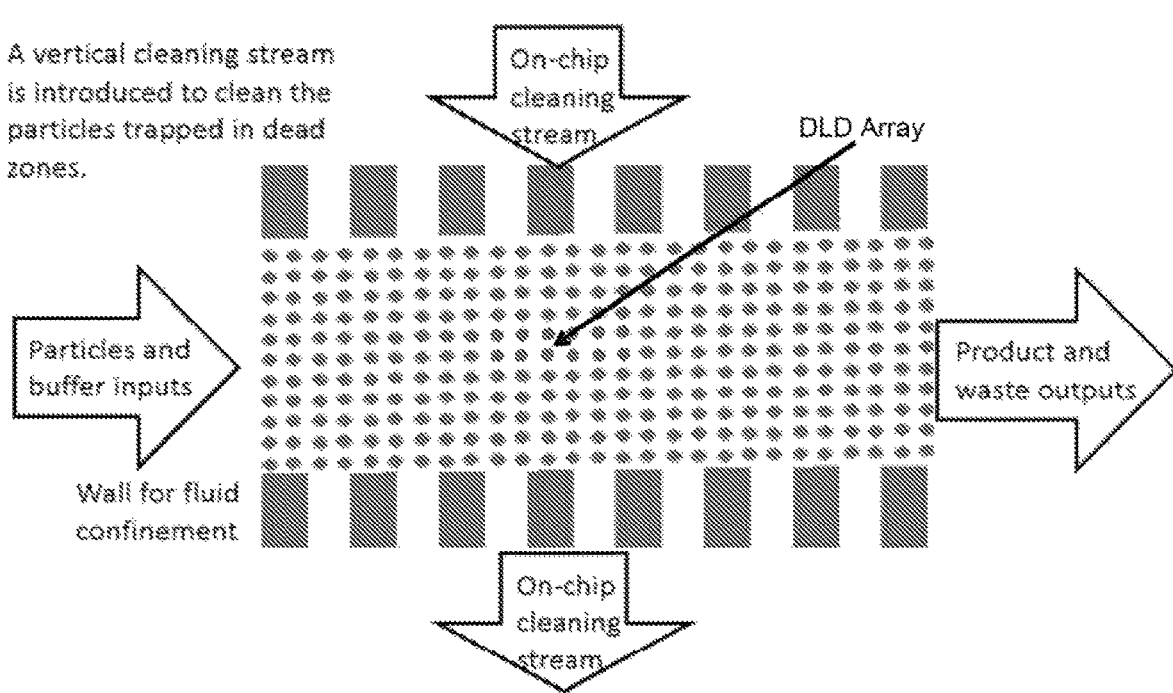
FIG. 33A shows a DLD array with an on-chip cleaning system, which comprises inlets and outlets in the pair of opposing walls for fluid confinement.
Figure 33B:
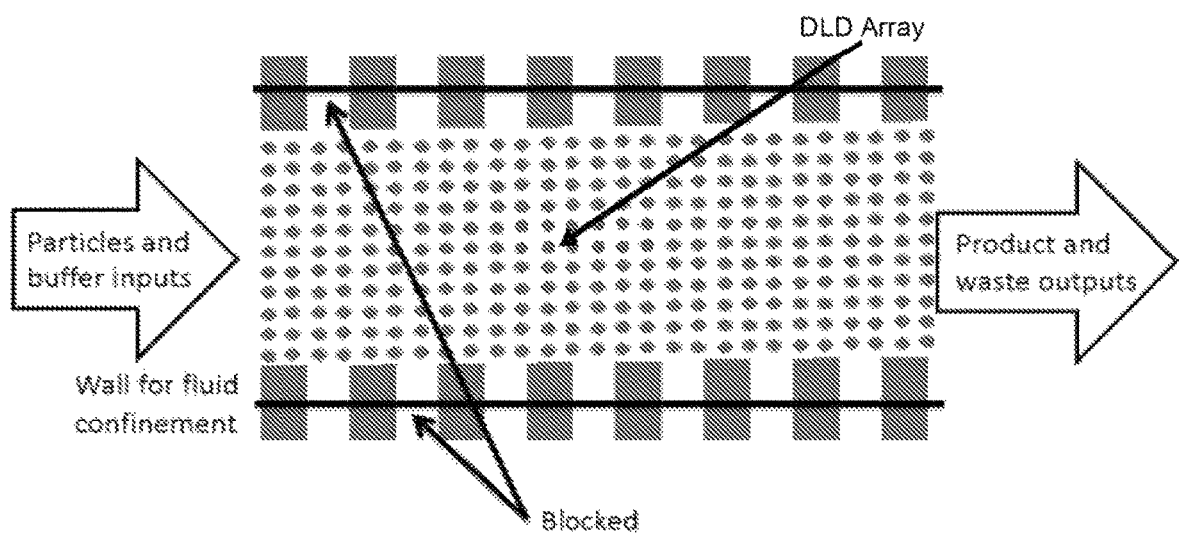
FIG. 33B shows blocking of the on-chip cleaning system while the DLD array is in the bump mode (e.g. sample or fluid comprising particles (e.g., cells) are flowing from left to right through DLD array).
Figure 33C:
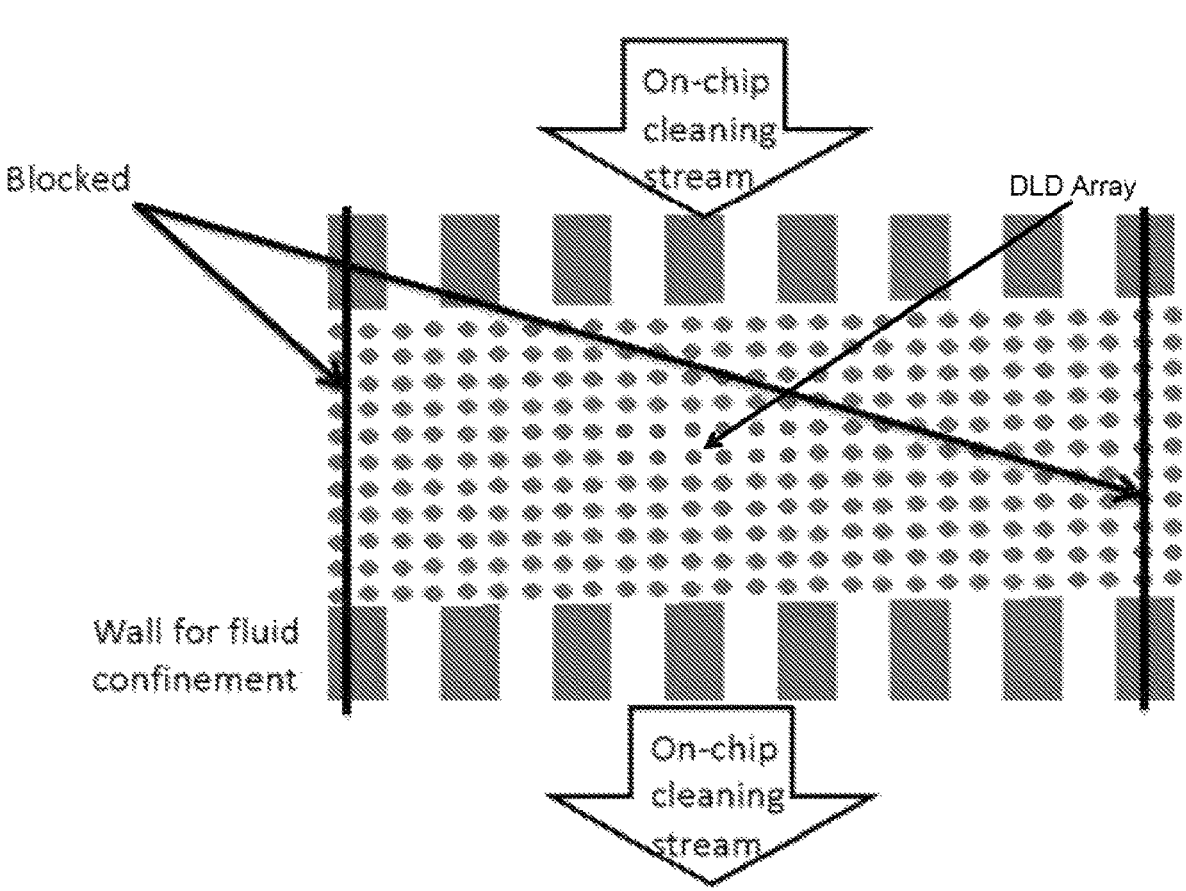
FIG. 33C shows blocking of the channel comprising the DLD array during cleaning of the DLD array using an on-chip cleaning system as described herein.

In some cases, devices described herein can comprise an integrated system for on-chip cleaning. Examples of the self cleaning system are illustrated in FIG. 33A-C. In some cases, the on-chip cleaning system comprises openings in walls of a channel such that fluid can be flowed through the openings, where the fluid flow is substantially perpendicular to the usual flow path of the channel. The cleaning system can be used to remove particles, e.g., cells trapped in an array of obstacles. In some cases, openings are present in only one wall that bounds a channel. In some cases, openings are present in both walls that bound a channel.

FIG. 33A illustrates a device comprising a deterministic lateral displacement (DLD) array also comprises an on-chip cleaning system. Sample and buffer inputs are illustrated at the left of the channel, and product and waste outputs are illustrated at the right. Walls for fluid containment are illustrated. The on-chip cleaning system is illustrated in an "open" configuration with openings in the walls that bound the DLD array. A fluid is illustrated flowing from the top of the schematic to the bottom of the schematic at a right angle to the particle and buffer flow direction.

FIG. 33B illustrates an on-chip cleaning system in a closed configuration. In this configuration, openings in the walls that bound the channel are blocked.

FIG. 33C illustrates an on-chip cleaning system in an open configuration. In this configuration, openings in the walls that bound the channel are unblocked. In some cases, as illustrated in FIG. 33C, the inlet and outlet ends of the channel can be blocked while the openings in the wall are in the open position. In some cases, inlet and/or outlet ends of the channel are not blocked when the openings in the wall are in an unblocked configuration.

In some case blocking and unblocking of the openings in the walls is controlled manually or automatically. In some cases, blocking and unblocking of the openings in the walls is controlled electronically.

In some cases, an on-chip cleaning system is activated when a sensor is triggered. In some cases, the sensor is a pressure sensor (e.g., if backpressure in the device rises above a threshold (e.g., due to clogging), an alert can be sent that the on-chip cleaning system can be ultilized, or the on-chip cleaning system can be activated automatically). In some case, the sensor is an optical sensor, e.g., an optical system, e.g., a microscope. In some cases, the optical system can monitor the device to detect clogging, e.g., by detection of trapped fluorescent particles. In some cases, the sensor is a spectrophotometer that detects obstruction of a light path through the bottom and top of the device (e.g., reduction in transmission of light through the device indicates clogging).

Any device comprising a channel comprising an array of obstacles can comprise an on-chip cleaning system. The array of obstacles can be a symmetric array of obstacles, asymmetric array of obstacles, mirrored array of obstacles, a mirrored array of obstacles with a central bypass channel with or without a wall, or a semi-mirrored array of obstacles.

The on-chip cleaning system can be organized in a variety of configurations. The number of openings in the walls that bound a channel can be dependent on the length of the channel. In some cases, each wall comprises a plurality of openings, e.g., at least 2, 5, 10, 20, 50, 75, 100, 200, 500, 750, 1000, 5000, or 10,000. In some cases, each wall comprises at most 2, 5, 10, 20, 50, 75, 100, 200, 500, 750, 1000, 5000, or 10,000 openings. In some cases, each of the openings in a wall is in an unblocked or blocked configuration. In some cases, not all of the openings in a wall are in an unblocked or blocked configuration. In some cases, at least 2, 5, 10, 20, 50, 70, 90, or 100% of openings in a side of a wall are configured to be a blocked or unblocked configuration. In some cases, less than 2, 5, 10, 20, 50, 70, 90, or 100% of openings in a side of a wall are configured to be in a blocked or unblocked configuration.

Each of the openings in the walls of a channel can have a diameter of at least 0.1, 0.2, 0.3, 0.4, 0.5, 0.6, 0.7, 0.8, 0.9, 1, 2, 3, 4, 5, 6, 7, 8, 9, 10, 20, 30, 40, or 50 μm. In some cases, each of the openings in a wall of channel has a diameter of less than 0.1, 0.2, 0.3, 0.4, 0.5, 0.6, 0.7, 0.8, 0.9, 1, 2, 3, 4, 5, 6, 7, 8, 9, 10, 20, 30, 40, or 50 μm. In some cases, each of the openings in a wall of channel has a diameter of about 0.1, 0.2, 0.3, 0.4, 0.5, 0.6, 0.7, 0.8, 0.9, 1, 2, 3, 4, 5, 6, 7, 8, 9, 10, 20, 30, 40, or 50 μm. In some cases, openings in a wall of a channel are connected to flow paths. In some cases, each of the flow paths is under control of the same fluid flow system. In some cases, each of the flow paths is not under control of the same fluid flow system.

A flow rate of a cleaning solution using the on-chip cleaning system can be at least 0.1, 0.2, 0.3, 0.4, 0.5, 0.6, 0.7, 0.8, 0.9, 1, 2, 3, 4, 5, 6, 7, 8, 9, 10, 20, 30, 40, or 50 mL/min.

A Flow rate of a cleaning solution using the on-chip cleaning system can less than 0.1, 0.2, 0.3, 0.4, 0.5, 0.6, 0.7, 0.8, 0.9, 1, 2, 3, 4, 5, 6, 7, 8, 9, 10, 20, 30, 40, or 50 mL/min.

A flow rate of a cleaning solution using the on-chip cleaning system can be about 0.1, 0.2, 0.3, 0.4, 0.5, 0.6, 0.7, 0.8, 0.9, 1, 2, 3, 4, 5, 6, 7, 8, 9, 10, 20, 30, 40, or 50 mL/min.

Flow through the openings in a wall of a channel can be powered by a pump, e.g., syringe pump or high pressure pump. In some cases, operation of an on-chip cleaning system is automated. In some case, operation of an on-chip cleaning system is conducted through an electronic device, e.g., a computer.

A cleaning solution used in an on-chip cleaning system can comprise one or more agents, e.g., a detergent (e.g., 2-aminoethyl methan thiosulfonate hydrobromide, CHAPS, CHAPSO, digitonin, lithium dodecyl sulfate, n-dodecyl-beta-D-maltopyranoside, n-octyl-beta-d-glucopyranoside, NDSB-195, NDSB-201, NDSB-211, NDSB-221, NDSB-256, NONIDET-P40, Pluronic F68, Pluronic F-127, MTSES, Tween-20, Tween-80, Tween-40, sodium dodecyl sulfate (SDS), Triton X-100, Triton X-114, MTSET, sulfo-betaine-10, sulfobetaine-12, or sulfobetaine-14), alcohol (e.g., ethanol, methanol), buffer (e.g., Tris-HCl, Trizma, HEPES, MES, phosphate buffer, potassium buffer), enzyme (DNase, RNase, protease, restriction enzyme), reducing agent (DTT, beta-mercaptoethanol), chelating agent (e.g., EDTA (e.g., 1 mM, 5 mM), EGTA (e.g., 1 mM, 5 mM)), anti-bacterial agent, antibiotic (e.g., chloramphenicol, ampicillin, kanamycin, erythromycin, gentamicin, neomycin, nelimicin, streptomycin, tobramycin, penicillin, bacitracin, polymyxin B, ciproflaxin, or tetracycline), anti-fungal agent, anti-viral agent, protease inhibitor, acid (e.g., hydrochloric acid, sulfuric acid, tartaric acid, nitric acid, phosphoric acid, boric acid, methanesulfonic acid, acetic acid, citric acid, formic acid, or fluoroacetic acid), base (e.g., NaOH). In some cases, the cleaning solution comprises about 1 to about 20% ethanol, or about 10 to about 20% ethanol, or less than 20% ethanol.

A cleaning solution can comprise F108, which can be a bifunctional block copolymer surfactant.

In some cases, multiple solutions are flowed through the cleaning system in succession.

In some cases, a cleaning solution is applied to a device and is allowed to remain in the device for at least 1, 5, 10, 30, or 60 min, or about least 4, 8, 12, 16, 20, or 24 hrs, or at least 3, 5, 7, 14, 21, or 28 days. In some cases, a cleaning solution is applied to a device and is allowed to remain in the device for less than about 1, 5, 10, 30, or 60 min, or less than 4, 8, 12, 16, 20, or 24 hrs, or less than 3, 5, 7, 14, 21, or 28 days.

In some cases, a cleaning solution is washed out with water.

Example 8 describes use of an on-chip cleaning system.

In some cases, the size-based separation methods described herein do not make use of a centrifuge and/or sedimentation. In some cases, the size-based separation methods described herein do make use of a centrifuge or sedimentation.

(w) Taper Angle

An obstacle, or pillar can be cylindrical. In some cases, obstacles on a device are not perfectly cylindrical. An obstacle, or at least 50% of obstacles in an array, can have a taper angle of less than 10, 9, 8, 7, 6, 5, 4.5, 4, 3.5, 3, 2.5, 2, 1.5, 1, 0.5, 0.4, 0.3, 0.2, or 0.1°. An obstacle can have a taper angle of 0°. An obstacle, or at least 50% of obstacles in an array, can have a taper angle of about 0.1 to about 1, about 1 to about 2, about 2 to about 3, about 3 to about 4, or about 1 to about 4°.

(x) Sets of Arrays

In some cases, a channel can comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 sets of arrays. In some cases, a channel can comprise less than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 sets of arrays. In some cases, a channel can comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 sets of arrays.

J. Materials of Construction and Surface Chemistry

In some embodiments, a device is made by hot embossing PMMA and polycarbonate. Due to their low cost and compatibility with replication-based fabrication methods, thermoplastics can represent an attractive family of materials for the fabrication of lab-on-a-chip platforms. A diverse range of thermoplastic materials suitable for microfluidic fabrication is available, offering a wide selection of mechanical and chemical properties that can be leveraged and further tailored for specific applications. High-throughput embossing methods such as reel-to-reel processing of thermoplastics is an attractive method for industrial microfluidic chip production. The use of single chip hot embossing can be a cost-effective technique for realizing high-quality microfluidic devices during the prototyping stage. Methods for the replication of microscale features in two thermoplastics, polymethylmethacrylate (PMMA) and/or polycarbonate (PC) are described herein using hot embossing from a silicon template fabricated by deep reactive-ion etching. Further details can be found in "Microfluidic device fabrication by thermoplastic hot-embossing" by Yang and Devoe, Methods A device can be sealed and bonded in any suitable manner. The main challenge can be bonding planar microfluidic parts together hermetically without affecting the shape and size of micro-sized channels. A number of bonding techniques such as induction heating are suitable. The channels can be fabricated by using Excimer laser equipment. Further details can be found in "Sealing and bonding techniques for polymer-based microfluidic devices" by Abdirahman Yussuf, Igor Sbarski, Jason Hayes and Matthew Solomon, which is hereby incorporated by reference herein in its entirety.

Further bonding techniques include Adhesive Bonding, Pressure sensitive tape/Lamination, Thermal Fusion Bonding, Solvent Bonding, Localized welding, Surface treatment and combinations thereof. Further details can be found in "Bonding of thermoplastic polymer microfluidics" by Chia-Wen Tsao and Don L. DeVoe, Microfluid Nanofluid (2009) 6:1-16, which is herby incorporated by reference herein in its entirety.

In some embodiments, the device is made from a polymer and/or plastic. The polymer and/or plastic can be hydrophilic and/or wettable. Table 4 summarizes properties of some plastics.

TABLE 4

| Summary of physical properties for common microfluidic thermoplastics | | | | | | | | | |
|---|---|---|---|---|---|---|---|---|---|
| Polymer | Acronym | $T_g$ (° C.) | $T_m$ (° C.) | CTE $(10^{-6°} C.^{-1})$ | Water absorption (% ) | Solvent resistance | Acid/base resistance | Optical transmissivity Visible | $UV^a$ |
| Cyclic olelin (co)polymer | COC/COP | 70-155 | 190-320 | 60-80 | 0.01 | Excellent | Good | Excellent | Excellent |
| Polymethylmethacrylate | PMMA | 100-122 | 250-260 | 70-150 | 0.3-0.6 | Good | Good | Excellent | Good |
| Polycarbonate | PC | 145-148 | 260-270 | 60-70 | 0.12-0.34 | Good | Good | Excellent | Poor |
| Polystyrene | PS | 92-100 | 240-260 | 10-150 | 0.02-0.15 | Poor | Good | Excellent | Poor |
| Polypropylene | PP | −20 | 160 | 18-185 | 0.10 | Good | Good | Good | Fair |
| Polyetheretherketone | PEEK | 147-158 | 340-350 | 47-54 | 0.1-0.5 | Excellent | Good | Poor | Poor |
| Polyethylene terephthalate | PET | 69-78 | 248-260 | 48-78 | 0.1-0.3 | Excellent | Excellent | Good | Good |
| Polyethylene | PE | −30 | 120-130 | 180-230 | 0.01 | Excellent | Excellent | Fair | Fair |
| Polyvinylidene chloride | PVDC | 0 | 76 | 190 | 0.10 | Good | Good | Good | Poor |
| Polyvinyl chloride | PVC | 80 | 180-210 | 50 | 0.04-0.4 | Good | Excellent | Good | Poor |
| Polysulfone | PSU | 170-187 | 180-190 | 55-60 | 0.3-0.4 | Fair | Good | Fair | Poor |

$T_m$ melting temperature.
CTE coefficient of thermal expansion
[a] high UV transmissivity often requires the selection of special polymer grades, e.g. without stabilizers or other additives Mol. Biol. 2013; 949: 115-23, which is herby incorporated by reference herein in its entirety. In some cases, a device is made of polypropylene.

In some cases, the materials and designs can be optimized for making effective and inexpensive systems and devices herein. In some cases, provided herein also include prototypes of automated system platform with operator interface that can control fluid flow through the microfluidic chips. For example, the system platform can be designed to be easy and cost-effective to operate and to occupy a small bench-top footprint. In some cases, the methods, systems, and devices provided herein can be expected to achieve greater than >90% white blood cells (WBCs) yield in no more than 10 minutes of total processing time.

In some cases, a device comprises a polymer. In some cases, a device is made by injection molding. In some cases, a device is manufactured by a photolithographic technique. In some cases, a device is manufactured by soft embossing. In some cases, the embossing occurs on a polymer chip. In some cases, a device comprises plastic.

A device can be fabricated in any suitable manner. Some techniques include Replica molding, Softlithography with PDMS, Thermoset polyester, Embossing, Injection Molding, Laser Ablation and combinations thereof. Further details can be found in "Disposable microfluidic devices: fabrication, function and application" by Gina S. Fiorini and Daniel T. Chiu, BioTechniques 38:429-446 (March 2005), which is herby incorporated by reference herein in its entirety. The book "Lab on a Chip Technology" edited by Keith E. Herold and Avraham Rasooly, Caister Academic Press Norfolk UK (2009) is a resource for methods of fabrication, and such which is hereby incorporated by reference herein in its entirety. A device can be manufactured by cast molding or reactive injection molding.

Exemplary materials for fabricating the devices of the invention include glass, silicon, steel, nickel, polymers, e.g., poly(methylmethacrylate) (PMMA), polycarbonate, polystyrene, polyethylene, polyolefins, silicones (e.g., poly(dimethylsiloxane)), polypropylene, cis-polyisoprene (rubber), poly(vinyl chloride) (PVC), poly(vinyl acetate) (PVAc), polychloroprene (neoprene), polytetrafluoroethylene (Teflon), poly(vinylidene chloride) (SaranA), and cyclic olefin polymer (COP) and cyclic olefin copolymer (COC) and combinations thereof. Other materials are known in the art. For example, deep Reactive Ion Etch (DRIE) can be used to fabricate silicon-based devices with small gaps, small obstacles and large aspect ratios (ratio of obstacle height to lateral dimension). Thermoforming (embossing, injection molding) of plastic devices may also be used. Additional methods include photolithography (e.g., stereolithography or x-ray photolithography), molding, embossing, silicon micromachining, wet or dry chemical etching, milling, diamond cutting, Lithographie Galvanoformung and Abformung (LIGA), and electroplating. For example, for glass, traditional silicon fabrication techniques of photolithography followed by wet (KOH) or dry etching (reactive ion etching with fluorine or other reactive gas) may be employed. Techniques such as laser micromachining can be adopted for plastic materials with high photon absorption efficiency. This technique is suitable for lower throughput fabrication because of the serial nature of the process. For mass-produced plastic devices, thermoplastic injection molding, and compression molding can be suitable. Conventional thermoplastic injection molding used for mass-fabrication of compact discs (which preserves fidelity of features in sub-microns) may also be employed to fabricate the devices. For example, the device features are replicated on a glass master by conventional photolithography. The glass master is electroformed to yield a tough, thermal shock resistant, thermally conductive, hard mold. This mold serves as the master template for injection molding or compression molding the features into a plastic device. Depending on the plastic material used to fabricate the devices and the requirements on optical quality and throughput of the finished product, compression molding or injection molding may be chosen as the method of manufacture. Compression molding (also called hot embossing or relief imprinting) can have the advantage of being compatible with high molecular weight polymers, which can be excellent for small structures and may replicate high aspect ratio structures but has longer cycle times. Injection molding can work well for low aspect ratio structures and can be suitable for low molecular weight polymers. A device can be made using any of the materials described herein. In some cases, the surface of the (plastic) device is treated to make it hydrophilic and/or wettable. Surfaces in devices, e.g., microfluidic devices, can play a critical role because they can define properties such as wetting, adsorption and repellency of biomolecules, biomolecular recognition using surface-immobilized receptors, sealing and bonding of different materials. In some cases, two types of treatments can be used to modify the surface properties of a device, e.g., a microfluidics device: wet chemical treatments and gas phase treatments. Wet treatments can be simple in terms of infrastructure requirements; they can be flexible and fast to develop from a research standpoint. Surface treatment of a device, e.g., microfluidics device, for production can be however best achieved using dry processes based on plasma and chemical vapor deposition. These treatments can eliminate the need for rinsing and drying steps, have high throughput capability and are highly reproducible.

In some cases, the treatment is a wet chemical treatment. Among the wet chemical treatments available, the formation of self-assembled monolayers (SAMs) is one of the most versatile and easy to use surface treatments. SAMs have been developed on metals, silicon oxides and polymers.

Molecules in SAMs can pack closely and can be composed of a headgroup that can bind covalently to the substrate, an alkyl chain and a terminal functional group. The thickness of the SAM can depend on the length of the alkyl chain and density of the molecules on the surface and is typically a few nanometers. SAMs can be easy to prepare and can be patterned with sub-micrometer lateral resolution. Different terminal groups can be used for defining the wetting properties of the surface as well as the affinity for or repellency of proteins. For glass surfaces, oxides and polymers that can be oxidized, grafting alkylsiloxanes to surfaces might be the simplest and most economical method. A wettability gradient from superhydrophobic to hydrophilic can be achieved by superposing a SAM-based wetting gradient onto microstructures in silicon that have varying lateral spacing.

Polymeric SAMs can comprise block copolymers and can have various three-dimensional structures, which can give the opportunity to vary their mode of grafting to a surface and the types of functionalities that they carry. Such layers can reach a significant thickness of several hundreds of nanometers and protect/functionalize surfaces more reliably than thinner monolayers. For example, a poly(oligo(ethyleneglycol)methacrylate) polymer brush can coat glass devices, e.g., chips, e.g., microfluidic chips to make them hydrophilic and antifouling.

Coating polymers onto surfaces to modify their properties is possible. For example, poly(ethyleneglycol) can be used to "biologically" passivate device, e.g., microfluidic device materials and can be grafted onto PMMA surfaces of capillary electrophoresis microchips to make them hydrophilic. Poly(tetrafluoroethylene) can be used to make chemically resistant devices, e.g., microfluidic devices. Polymeric materials employed to fabricate devices, e.g., microfluidic devices, can be modified in many ways. In some cases, functional groups such as amines or carboxylic acids that are either in the native polymer or added by means of wet chemistry or plasma treatment are used to crosslink proteins and nucleic acids. DNA can be attached to COC and PMMA substrates using surface amine groups. Surfactants such as Pluronic® can be used to make surfaces hydrophilic and protein repellant by adding Pluronic® to PDMS formulations. In some cases, a layer of PMMA is spin coated on a device, e.g., microfluidic chip and PMMA is "doped" with hydroxypropyl cellulose to vary its contact angle.

Proteins can be used on surfaces to change surface wettability, to passivate a surface from non-specific protein binding and for functionalization. Proteins readily adsorb to hydrophobic substrates such as PDMS and polystyrene. By exploiting this property, PDMS substrates can be coated with neutravidin to immobilize biotinylated proteins or biotinylated dextran. Antibody coatings can be optimized depending on the hydrophobicity of the polymeric substrate. Bovine serum albumin can be used protein to passivate surfaces from non-specific adsorption and is easy to deposit spontaneously from solution to hydrophobic surfaces. On a hydrophilic substrate, a layer of hydrophobic poly(tetrafluoroethylene) can first be coated to enable the subsequent deposition of bovine serum albumin. Heparin, a biological molecule widely used as an anticoagulant, can be deposited from solution onto PDMS to make channels, e.g., microchannels hydrophilic while preventing adhesion of blood cells and proteins.

In some embodiments, a device undergoes a gas phase treatment. Plasma processing not only can modify the chemistry of a polymeric surface but it also can affect its roughness significantly thereby exacerbating wetting properties to make surfaces superhydrophilic and fluorocarbons can be plasma deposited to make surfaces superhydrophobic. Polymeric surfaces can be patterned using ultraviolet light to initiate radical polymerization followed by covalent grafting of polymers. Plasma-induced grafting can be used to attach poly(ethyleneglycol) onto polyamide and polyester surfaces to render them antifouling. Dextran can be a polysaccharide comprising many glucose molecules that can be coated to make hydrophilic antifouling surfaces. In some cases, a starting point to modifying polymers is to introduce surface hydroxyl groups using a plasma treatment followed by grafting a silane and dextran layer. Similarly, PDMS can be superficially oxidized using ultraviolet light for grafting a dextran hydrogel.

The large surface to volume ratio of devices, e.g., microfluidic structures can make any potential surface-analyte/ reagent interaction a potential issue. Therefore, irrespective of the method used to treat the surfaces of a microfluidic device for POC testing, in some cases the surfaces of the device can not attract and deplete analytes or biochemicals that are needed for the test. In some cases, surface treatments do not interfere with signal generation and acquisition principles of the device. Further details can be found in "Capillary microfluidic chips for point of care testing: from research tools to decentralized medical diagnostics" a thesis by Luc Gervais, Ecole polytechnique federale de Lausanne, 23 June, 2011, which is hereby incorporated by reference herein in its entirety.

To reduce non-specific adsorption of cells or compounds, e.g., released by lysed cells or found in biological samples, onto the channel walls, one or more channel walls may be chemically modified to be non-adherent or repulsive. The walls may be coated with a thin film coating (e.g., a monolayer) of commercial non-stick reagents, such as those used to form hydrogels. Additional examples chemical species that may be used to modify the channel walls include oligoethylene glycols, fluorinated polymers, organosilanes, thiols, poly-ethylene glycol, hyaluronic acid, bovine serum albumin, poly-vinyl alcohol, mucin, poly-HEMA, methacrylated PEG, and agarose. Charged polymers may also be employed to repel oppositely charged species. The type of chemical species used for repulsion and the method of attachment to the channel walls can depend on the nature of the species being repelled and the nature of the walls and the species being attached. Such surface modification techniques are well known in the art. The walls may be functionalized before or after the device is assembled. The channel walls may also be coated in order to capture materials in the sample, e.g., membrane fragments or proteins.

V. Properties of Particles Flowed Through Devices

The methods, compositions, devices, systems, and/or kits described herein can be used for high-throughput processing (e.g., chemical and/or enzymatic treatment), purification, isolation, and/or concentration of particles. The methods, compositions, devices, systems, and/or kits described herein can be used to isolate particles with relatively high purity, yield, and/or viability if the particles are living, e.g., cells or organisms). One or more samples can be applied to one or more inlets on a device. One or more buffers can be applied to one or more inlets on a device. Particles of at least a critical (predetermined) size can be passed through an array of obstacles and be deflected to one outlet, and particles less than the critical size can pass to another outlet.

An array of obstacles can comprise any cross-sectional shape, obstacle diameter, gap size, tilt angle, and/or array pattern geometry described herein.

Temperature of a flowing liquid, or ambient temperature, or temperature of a device, can be about −20, −10, 0, 4, 10, 15, 20, 22, 23, 24, 25, 26, 30, 35, 37, 40, 45, 50, 55, 60, 65, 70, 75, 80, 85, 90, 95, or 100° C. Temperature of a flowing liquid, or ambient temperature, or temperature of a device, can be less than −20, −10, 0, 4, 10, 15, 20, 22, 23, 24, 25, 26, 30, 35, 37, 40, 45, 50, 55, 60, 65, 70, 75, 80, 85, 90, 95, or 100° C. Temperature of a flowing liquid, or ambient temperature, or temperature of a device, can be more than −20, −10, 0, 4, 10, 15, 20, 22, 23, 24, 25, 26, 30, 35, 37, 40, 45, 50, 55, 60, 65, 70, 75, 80, 85, 90, 95, or 100° C. Temperature of a flowing liquid, or ambient temperature, or temperature of a device can be about −20 to about −10° C., about −10 to about 0° C., about 0 to about 4° C., about 4 to about 25° C., about 25 to about 30° C., about 30 to about 37° C., about 37 to about 50° C., about 50 to about 65° C., or about 65 to about 100° C.

A. Purity

In some cases, methods, compositions, devices, systems, and/or kits described herein can be used to isolate first particles, e.g., cells that are about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% pure.

In some cases, methods, compositions, devices, systems, and/or kits described herein can be used to isolate first particles, e.g., cells that are at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% pure.

In some cases, methods, compositions, devices, systems, and/or kits described herein can be used to isolate first particles, e.g., cells, that are about 1 to about 10% pure, about 10% to about 20% pure, about 20% to about 30% pure, about 30% to about 40% pure, about 40% to about 50% pure, about 50% to about 60% pure, about 60% to about 70% pure, about 70% to about 80% pure, about 80% to about 90% pure, or about 90% to about 100% pure.

In some cases, devices and methods described herein are used to isolate leukocytes from whole blood. In some cases, devices and methods described herein remove over 99% of erythrocytes, platelets, plasma proteins, and unbound staining from leukocytes. In some cases, leukocytes are removed from serum B. Yield In some cases, methods, compositions, devices, systems, and/or kits described herein can be used to give a yield of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% of first particles, e.g., cells from a sample.

In some cases, methods, compositions, devices, systems, and/or kits described herein can be used to give a yield of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% of first particles e.g., cells from a sample.

In some cases, methods, compositions, devices, systems, and/or kits described herein can be used to give a yield of about 1% to about 10%, about 10% to about 20%, about 20% to about 30%, about 30% to about 40%, about 40% to about 50%, about 50% to about 60%, about 60% to about 70%, about 70% to about 80%, about 80% to about 90%, or about 90% to about 100% of first particles, e.g., cells from a sample.

In some cases, devices and methods described herein are used to isolate leukocytes from whole blood. In some cases, at least 80%, 85%, or 90% of leukocytes are recovered from a whole blood sample without introducing bias among the leukocyte population.

C. Viability

In some cases, particles in a sample are alive (e.g., cell or organism). In some cases, methods, compositions, devices, systems, and/or kits described herein can be used to isolate particles (e.g., cells, organisms) that are about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% viable.

In some cases, methods, compositions, devices, systems, and/or kits described herein can be used to isolate particles (e.g., cells, organisms) that are at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% viable.

In some cases, methods, compositions, devices, systems, and/or kits described herein can be used to isolate particles (e.g., cells, organisms) that are at about 1% to about 10% viable, about 10% to about 20% viable, about 20% to about 30% viable, about 30% to about 40% viable, about 40% to about 50% viable, about 50% to about 60% viable, about 60% to about 70% viable, about 70% to about 80% viable, about 80% to about 90% viable, or about 90% to about 100% viable.

In some cases, a sample comprises leukocytes and erythrocytes. In some cases, the method, compositions, devices, systems, and/or kits described herein can be used to process (e.g., chemical and/or enzymatic treatment), wash, and then isolate leukocytes from a sample such that the leukocytes are greater than 90% pure (i.e. less than 10% erythrocytes), greater than 90% of the leukocytes in the sample are isolated (greater than 90% yield), and greater than 90% of the leukocytes in the sample are viable.

VI. Applications

These devices and methods described herein can be a general replacement for centrifugation in cell processing. Leading suppliers of clinical and research instruments can be searching for alternatives to the current cell processing methods (3). In some cases, the methods using a DLD microfluidic technology are as described in U.S. Patent Publication No. US2010/0059414.

In some cases, a device as provided herein is used for Bead-based immune- and nucleic-acid assays (e.g., Luminex assays, BD CBA)

In some cases, a device as provided herein is used for cell-surface immunofluorescence.

In some cases, a device as provided herein is used for cell surface labeling (e.g., immunofluorescence) combined with intra-cellular labeling.

In some cases, a device as provided herein is used for Leukemia phenotyping and genotyping including washing away interfering soluble blood components In some cases, a device as provided herein is used for in-situ nucleic acid analysis (e.g., fluorescence in-situ hybridization).

In some cases, a device as provided herein is used for cell cycle synchronization by size selection of cell cycle phases.

In some cases, a device as provided herein is used to purify by size, label, and concentrate cells from small cell samples like cerebrospinal fluid.

In some cases, a device as provided herein is used for industrial functionalized particle manufacturing (e.g. anti-body labelled micro-particles for bioassays).

In some cases, a device as provided herein is used to remove large particles/cells for sensitive detection of bac-teria, virus, or exosomes in biological samples (e.g., blood).

Figure 16:
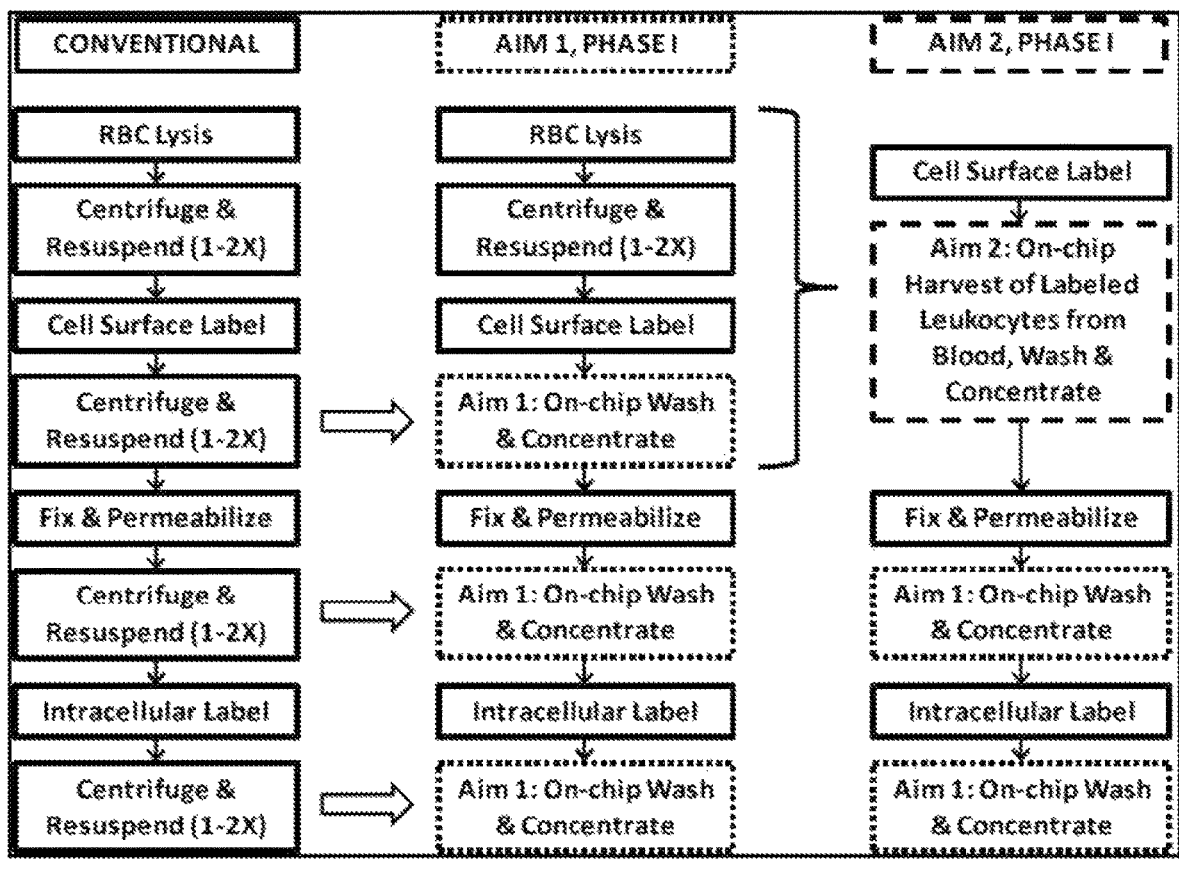
FIG. 16 shows conventional methods (left) for processing cells (e.g., leukocytes) and two embodiments of the methods described herein (vertically down the center and vertically down the right)

In some cases, up to at least 8 centrifugal wash/concen-trate steps can be reduced to 3 on-chip processes of <5-10 min each for 0.1-1 ml samples (e.g., blood) (FIG. 16). Downstream applications can go far beyond flow cytometry, and can range from laboratory research to existing and new clinical diagnostics.

A. DLD Microfluidic Technology to Wash and Concentrate Leukocytes from Blood.

As shown in FIG. 16, conventional processes for labeling of leukocytes (left) and the reduction of the up to 8 cen-trifugal wash/concentrate steps to 3 on-chip microfluidic steps (middle and right) using a device as provided herein. The embodiment going vertically down the center replaces each centrifugal wash/concentrate step with an on-chip wash/concentrate process. The embodiment going vertically down the right avoids erythrocyte lysis entirely, isolating/harvesting/washing/concentrating leukocytes (and leukemia cells) from blood samples in a single step after the Surface Labeling step.

DLD separation can outperform standard centrifugal pro-cedures. For example, processing (e.g., on-chip microfluidic Washing/Concentrating) a sample comprising leukocytes and labeling reagent (e.g., antibodies) in a device as pro-vided herein, can harvest >90% of leukocytes at >90% viability while removing >99% unbound fluorescent or Fixation/permeabilization reagents with no skewing of sub-populations.

FIG. 17A shows a DLD array designed to "bump" *E. coli* (>1 um size). The bacterial suspension is input on the left, and flows left to right, confined by the walls of the micro-fluidic device. The micropost array causes the fluorescent (GFP-containing) bacteria (seen as the white blurred band) to flow along the tilted array axis, so that they move down to accumulate against the lower array wall, while the fluid stream continues straight ahead. The bacteria concentrate along the lower edge of the device, seen as the growing bold white streak. By separately collecting this concentrated output from its own output channel, distant from the waste fluid output channel, bacteria can be concentrated by 50-fold during the ~100 sees they took to flow across the DLD device.

The device shown in FIG. 17A can be extended to include 2 input streams: stream 1 can be a suspension of leukocytes after labeling with Mabs (or treatment with Fixation/per-meabilization reagents); stream 2 can be buffer fluid (as shown in FIG. 17B). The redesigned bump array can cause large cells, such as leukocytes (>8 um diameter, and leukemia cells, ~8-20 um) to move at an angle to the input fluid flow, whereas dissolved molecules or small suspended particles or molecules in solution (e.g. immunomagnetic beads, fluorescent Mabs, Fixation/permeabilization reagents) tend to move left to right, in or following the fluid flow. The microchip can operate at low Reynolds number, so the flow is laminar and not turbulent; thus, the 2 streams move in parallel. As in FIG. 17A, the desired cells (leukocytes and leukemia cells) concentrate at the lower edge of the array. By routing most of the output fluid to a waste channel and the concentrated cells to a product channel, washing and concentration can be achieved at the same time.

In addition to leukocyte harvesting, DLD technology can achieve concurrent washing of the cells. Whole blood can be incubated with CD45 FITC for 30 minutes at room temperature, then leukocytes can be removed from the blood using a device as provided herein. A reduction in fluorescence in the cell-free product of ≥99% can be achieved after leukocyte harvesting on the device, indicating efficient removal of fluorescent Mab.

As shown in FIG. 17: (a) Top view: Example of DLD mechanism showing uniform input of fluorescent (white) *E. coli* bacteria in a tilted post array being bumped downwards at an angle to the fluid flow, to become highly concentrated against the lower array wall and then collected, while fluid moves horizontally (7). (b) Schematic "washing" of leukocytes and/or leukemia cells by extension of FIG. 17A by adding an input buffer stream. Only large leukocytes can move down to the buffer stream and lower wall. (c) Time-lapse image of leukocytes (blue from nuclear stain) being harvested out of a stream of blood (reddish/white) moving left to right using a chip with design as in FIG. 17B. Note that the tilted array of microposts can be seen.

In some cases, 0.1-1 ml of blood are processed in <5-10 minutes, with a leukocyte yield >90%, no skewing of cell types compared to input cells or conventional methods, and >99% removal of unbound fluorescent Mab and Fixation/permeabilization reagents. In some cases, the cells are moved away from the input stream faster than the input stream widens due to diffusion toward the clean buffer stream. While diffusion coefficients of the large particles, e.g., leukocytes and leukemia cellscan be negligible to first order approximation, the diffusion coefficients of the Mabs or Fixation/permeabilization reagents are generally not negligible. In some cases, these dissolved or suspended molecules are much smaller than cells and thus have a high diffusion coefficient. Unwanted spreading of these reagents can cause contamination of the leukocyte output. Increasing the tilt angle can help prevent spreading, but can reduce the gap between the posts for a fixed cell size, which can be undesirable due to occasional very large cells. Another option is to lengthen the chip, since the cell displacement can be linear with length of the array and the spreading (diffusion) increases only as the square root. However, this can have the drawback of requiring a more expensive chip. In some embodiments, DLD is microscopically a deterministic process, not a random one, such as gel electrophoresis. Thus, running a DLD microfluidic process faster cannot change the path of the desired cells, and high speed can reduce the time for unwanted reagent diffusion. In some cases, the fluid speed is ~0.1 mm/sec. Thus, running through a chip of typical length (~3 cm) can take 5 minutes, which can be too slow not only for the goal of leukocyte throughput, but also to prevent the unwanted diffusion. In some cases, the bumping process operates well with little or minimal cell damage even at speeds of >100 mm/sec (i.e. flow rates>1 ml/min). Flow speed can be varied as required to reduce reagent contamination of the output. Qualitative images of results with *E. coli* (5) indicate that this diffusion problem for washing away reagents can be overcome at modest flow speeds.

A second potential challenge is the wide range of cell size of different types of leukocytes and leukemia cells. This can be addressed by using triangular instead of round posts, which allows for a larger gap between posts than with round posts, due to flow anisotropies in the gap. Finally, after Fixation/permeabilization, the cells can be "stiffer" than before, and thus act as if they have a different diameter in the DLD chip. If this is observed, a DLD chip with a slightly larger critical size can be needed for cells after Fixation/permeabilization.

B. Microfluidic Leukocyte Harvesting and DLD Wash/Concentrate in a Single Step

The conventional erythrocyte Lysis Step and the subsequent centrifugal Wash/Concentrate Step can be replaced by a single DLD microfluidic step. In addition to >90% yield and viability with thorough removal of labeling and Fixation/permeabilization reagents, some embodiments also achieve this microfluidic Wash/Concentrate system to deplete >99% of erythrocytes from a whole blood sample incubated with fluorescent Mabs.

Because they are larger size than red blood cells, leukocytes can be bumped out from an input stream of whole or diluted blood in a DLD chip. In some cases, a device as provided herein is configured to directly surface label leukocytes present in blood (without any lysis or removal of erythrocytes), followed by harvesting, washing, and concentrating the immunostained leukocytes directly from the blood (FIG. 17C). This can allow the complete leukocyte preparation process to be accomplished with only 3 on-chip Wash/Concentrate steps. Note that the microchip can be designed so that the smaller red blood cells (from unlysed blood), platelets, and non-cellular plasma constituents are not bumped; thus, the output can contain only the harvested, washed, and concentrated leukocytes.

In some cases, an input stream comprises leukocytes in whole blood with Mabs added thereto. The blood can be diluted with running buffer. In some cases, a larger volume of input is required due to the input comprising concentrated leukocytes, larger amounts of Mabs (to compensate for the dilution factor) are thereby required for optimal immunostaining.

In some instances, cells are immunostained exactly as described herein, except the starting cell preparation can comprise unlysed blood, rather than lysed blood. Immunostained cells can undergo the developed on-chip Leukocyte Harvest/Wash/Concentrate Step, then enumerated by flow cytometry. Results can be compared vs. cells immunostained after a conventional erythrocyte Lysis Step. Statistical comparisons of viability, yield, purity, and leukocyte subsets can be performed.

White blood cells (WBCs) of interest can be stained with one or more fluorescence-labeled tags (e.g., monoclonal antibodies (Mabs). WBC subtypes can be distinguished by leukocyte differentiation Mabs that bind specifically to (gly-co)proteins found on the surface (e.g., cell membrane) of a key WBC subtype, selectively (e.g., Cytokeratin+ epithelial cancer stem cells). To label molecules found within the cell, the cell can be permeabilized through a fixation/permeabilization (Fix/Perm) process which can stabilize the cell's structures and allow the labels to enter the cell. Washing steps can be performed to remove unbound fluorescent Mabs, dyes, and debris. A "Wash" can entail spinning the cells into a pellet using a centrifuge, aspirating or decanting the supernatant, and resuspending the cells in a buffer of other medium.

In some embodiments, 99% of erythrocytes are removed (i.e. obtain leukocytes<10% contaminated by erythrocytes). In some cases, the viscosity of blood (due to the 1000-fold higher numbers of erythrocytes) is higher compared to a suspension of leukocytes in buffer. This can change the internal dynamics of the flow patterns near the boundary between the buffer and the blood. At least three approaches can be used to solve this problem: (a) driving the blood input and the buffer input at different pressures, (b) replacing the pressure-driven approach with a fixed flow rate (syringe pump) approach, and (c) diluting the blood (e.g. 3-5-fold) to reduce its viscosity. The latter approach can be the most straightforward, although it can require higher flow rates to achieve throughput targets. In some cases, an output is achieved that concentrates leukocytes by 30-fold from the (diluted) input. In practice, this can require a fairly wide (and thus long) chip, which can be limited by the ~100 mm starting wafer size. Options include using a fabrication facility capable of larger wafer sizes (e.g. 200 mm), or cascading chips—one chip does the harvesting and initial concentration (FIG. 17C), and then the fluid flows through a second chip designed for concentration (like that of FIG. 17A). Finally, if the triangular post approach for wide gaps does not eliminate clogging due to anomalously large cells (e.g. >30 um), pre-filtering may be performed, or a third chip in series can be used to remove >30 um-sized cells.

In some embodiments, a device as provided herein replaces conventional lysis and centrifugal steps for harvesting leukocytes (and leukemia cells) from blood, and centrifugal Wash/Concentrate steps after cell surface labeling, Fixation/permeabilization, and intracellular labeling with rapid and repeatable on-chip processes, as described herein.

In some cases, the method resembles a "Car Wash" approach, in which (analogously) a car is subjected to multiple sequential treatments (e.g. wash, rinse, wax, dry) as it moves through the car wash process (FIG. 18A). Building on the concept of FIG. 18B, blood enters a chip, and the desired cells are moved through sequential parallel streams of chemicals (labels, fixation/permeabilization reagents, etc.) to accomplish one step after another. In some cases, blood which has already been labeled with a cell surface marker (but not washed) enters a device as provided herein in the top stream (flowing left to right), and relatively large leukocytes and leukemia cells are induced to flow downwards at an angle to the fluid flow by the DLD bumping process to be harvested out of the blood. The cells then flow through a stream for fixing and permeabilizing the cells' membranes, then through a stream for intracellular labeling. Finally, the cell surface/intracellular labeled cells are washed and concentrated and collected at the bottom edge of the array.

Figure 18B:
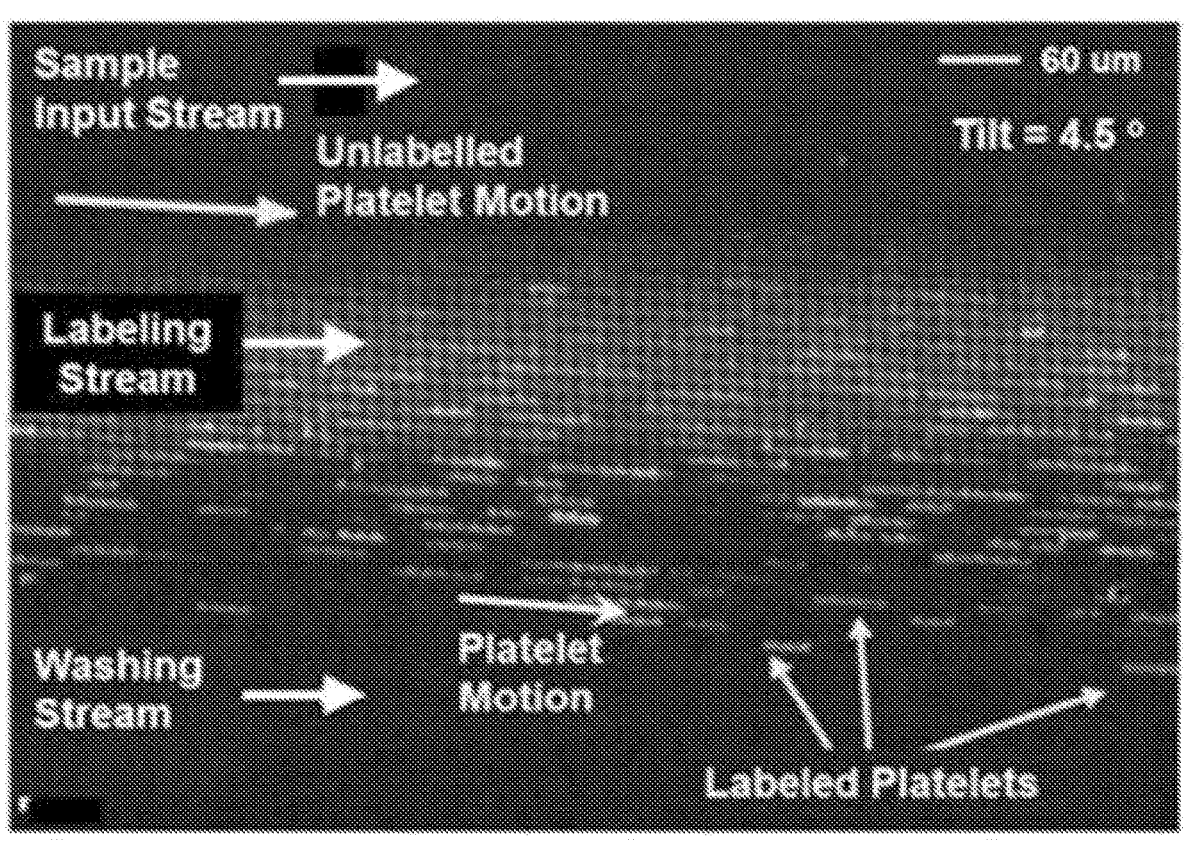
FIG. 18B shows false color fluorescent time lapse image of platelets moving downward in a DLD array. Demonstration of moving cells (in this case, platelets) by DLD across a "processing stream" and into a wash buffer stream as in FIG. 18A. False-color fluorescent time-lapse image of platelets moving down-wards in a DLD array across 3 parallel on-chip streams for on-chip label and wash. Upper Stream: input of unlabeled (invisible) platelets; Middle stream: phycoerythrin-conjugated CD41 label; Lower Stream: labeled platelets in stream of wash buffer.

On-chip labeling of cells by moving them into a labeling stream and subsequent removal of the labeled cells from the labeling stream can be done using previously isolated but unlabeled blood platelets as the input and a CD41 fluorescent label for the labeling stream (FIG. 18B). On-chip lysis of cells by moving them across a stream of lysis agents can be performed. On-chip lysis is not required for the "Car Wash" of FIG. 18A, but it provides the possibility of on-chip sequential chemical processing for steps such as Fixation/permeabilization prior to intracellular staining. Required incubation times and concentrations, yields, and broadening of the incubation or Fixation/permeabilization streams due to diffusion can be determined.

FIG. 18A shows a schematic view of a "Car Wash" concept for multiple sequential chemical treatment processing on chip for a cell preparation. A single continuous-flow process combines all steps in FIG. 16 into a single chip. FIG. 18B shows false-color fluorescent time-lapse image of platelets moving downwards in a DLD array across 3 parallel on-chip streams for on-chip label and wash. Upper Stream: input of unlabeled (invisible) platelets; Middle stream: phycoerythrin-conjugated CD41 label; Lower Stream: labeled platelets in wash buffer.

C. NGS Library Generation Using DLD Array

In some cases, the devices, methods, compositions, systems and/or kits provided herein are used for processing (e.g., chemical and/or enzymatic processing or treating) a sample from a cell to a nucleic acid. The processing can be serial. In some cases, the devices, methods, compositions, systems and/or kits provided herein are used for serially processing a sample from a plurality of cells to a plurality of nucleic acids, wherein the plurality of nucleic acids comprise nucleic acids in a nucleic acid library. Devices, methods, and/or systems are described, e.g., in PCT Publication No. WO2013020089, which is herein incorporated by reference in its entirety. The cell can be processed (e.g., chemical and/or enzymatic processing or treating) using a device herein to high molecular weight ("HMW") nucleic acid using at least one chemical and/or enzymatic reagent stream flowing through at least one DLD bump array. The nucleic acid library can be configured for use in a sequencing platform. The sequencing platform can be any next generation sequencing platform known in the art. In some cases, a device as provided herein to process (e.g., chemical and/or enzymatic processing or treating) cells to nucleic acid is used to process a high volume of a sample comprising the cells. The sample can be at least 10 ml. In some cases, a device as provided herein to process (e.g., chemical and/or enzymatic processing or treating) cells to nucleic acid is used to process (e.g., chemical and/or enzymatic processing or treating) at a high flow rate. In some cases, the devices as provided herein to process (e.g., chemical and/or enzymatic processing or treating) cells in a sample comprising cells from cells to nucleic acids comprises at least one separator wall as provided herein. The at least one separator wall is configured to separate a flow stream comprising a reagent (e.g., chemical and/or enzymatic reagent as provided herein) from an adjacent flow stream. In some cases, the devices as provided herein to process (e.g., chemical and/or enzymatic processing or treating) cells in a sample comprising cells from cells to nucleic acids comprises an 'on-chip' self cleaning system as provided herein. In some cases, the devices as provided herein to process (e.g., chemical and/or enzymatic processing or treating) cells in a sample comprising cells from cells to nucleic acids comprises at least one separator wall, and an 'on-chip' self cleaning system as provided herein.

In some cases, a HMW nucleic acid as isolated by devices and methods provided herein has an effective hydrodynamic radius that is greater than a critical size of the DLD array in a device provided herein. The method can include receiving the HMW nucleic acid at least one bump array, and contacting the HMW nucleic acid with at least one chemical and/or enzymatic reagent stream, wherein the at least one chemical and/or enzymatic reagent stream flows in the direction of bulk fluid flow through the bump array, whereas the HMW nucleic acid flows at an angle to the direction of bulk fluid flow. The HMW nucleic acid can react with the at least one chemical and/or enzymatic reagent stream.

In some cases, a device and/or system as provided herein includes at least one bump array (e.g., DLD array) device that has one or more bump arrays. The bump array device can serially treat and purify nucleic acid fluid samples. Multiple cycles of treatment and purification can be carried out using a single flow device in a single continuous flow operation. The treatments can be chemical and/or enzymatic. The nucleic acids can be purified from cells and/or complex liquid biological sample, such as whole blood. The bump array device can also be used for performing various processing of the purified nucleic acids. Non-limiting examples of such processing can include at least one of the following: phosphorylation, dephosphorylation, restriction digestion, ligation, denaturation, hybridization, processing by polymerases, fluorescent or radioactive labeling, chemical modification of DNA bases or backbone groups, enzymatic or chemical excision of modified bases, staining of nucleic acids with chromophores or fluorophores, etc. and/or others and/or any combination thereof. The nucleic acids can be particle bound nucleic acids, where nucleic acids can be attached to microparticles. This can allow for processing of small nucleic acids. The particles can render the attached nucleic acids bumpable in arrays with easily manufactured array dimensions.

In some cases, a device and/or system as provided herein is used in a method for processing of fluids. The processing can include purification of fluids which can be accomplished by flowing a complex fluid sample into a bump array, using a bump array to isolate nucleic acid containing cells or particles of interest on the basis of particle size, using a bump array to contact isolated particles with one or one reagent streams that can release nucleic acid from the particles in substantially pure form, and using a bump array to move purified nucleic acids out of the reagent stream. Once the purified nucleic acids are moved out of the reagent stream, the purified nucleic acids can be substantially free from other cellular and sample components and can be substantially free from reagent stream components of the bump array.

In some cases, a device and/or system as provided herein comprises a series of bump (e.g., DLD) arrays connected in series so that the product output of one bump array is connected to a sample input of a subsequent individual bump array. In some cases, a single bump array is used for all steps. Cell fractionation and reagent treatments can be accomplished in physically distinct regions of a single bump array. The input sample can be avian or mammalian blood and the nucleic-acid-containing particles can be white blood cells. The input sample can be avian or mammalian blood and the nucleic-acid-containing particles can be circulating tumor cells. The input sample can be avian or mammalian whole blood and the nucleic-acid-containing particles can be white blood cells, bacteria, viruses, fungi, parasitic protozoans and/or any others as provided herein and/or any combination thereof.

In some cases, a device and/or system as provided herein provide a serial processing of high molecular weight nucleic acids by chemical and/or enzymatic means on devices as provided herein comprising bump (e.g., DLD) arrays. The HMW nucleic acid can have an effective hydrodynamic diameter that can be greater than the critical diameter of the bump array and the HMW nucleic acid can be contacted with at least a first reagent stream, where the first reagent stream can flow in the direction of bulk fluid flow and where the HMW nucleic acid is bumped through the first reagent stream and can react with the first reagents.

In some cases, a device and/or system as provided herein provide a serial processing of HMW nucleic acids by one or more chemical or enzymatic means that can be accomplished by flowing a sample of HMW nucleic acids into a bump array, using a bump array to contact HMW nucleic acids with at least one reagent streams that can modify the nucleic acids (e.g., chemically, enzymatically, etc.), and, optionally, using a bump array to remove purified nucleic acids from the reagent stream.

In some cases, a device and/or system as provided herein comprises individual bump arrays connected in a series of bump arrays so that the product output of one bump array is connected to the sample input of a subsequent individual bump array in the series. The bump arrays can be the same bump arrays (and the cell fractionation and reagent treatments can be accomplished in physically distinct regions of one continuous bump array). In some cases, a DNA sample is capable of being bound (covalently or noncovalently) to microparticles, wherein the microparticles are bumpable, whereby the microparticles act as carriers to take the DNA through modification reactions in subsequent reagent streams.

In some cases, a device and/or system as provided herein provides for processing of whole blood to produce a pure nucleic acid. A device and/or system as provided herein can be used to produce a modified pure nucleic acid. The modified pure nucleic acid can be a DNA sequencing library and/or a recombinant DNA library.

In some cases, a device as provided herein is used in a system that can accept a whole blood sample as input and produce a genomic DNA library suitable for next-generation sequencing ("NGS"). Library construction can take place in a single automated process without any user intervention. The system can lower the cost and labor of NGS sequencing and accelerate movement of NGS technology into diagnostic settings. The system can be scalable to accommodate samples containing very few cells (e.g., a single cell level), which can be important in treatment of cancer and/or other important medical problems or large sample (e.g., at least 10 ml), which can be important for high-throughput techniques.

In some cases, a device and/or system as provided herein includes a microfluidic, continuous-flow design. Liquid samples containing particles (e.g., cells, nuclei, and large macromolecules such as randomly-coiled HMW DNA) can be pumped through flow cells that can be populated by a regular array of micron-sized posts. The spacing and alignment of the posts can be arranged so that particles above a certain critical size can be "bumped" by the posts into a flow path that runs diagonally across the direction of bulk liquid flow. In contrast, sample components smaller than the critical size can travel straight along with the bulk flow. Using this mechanism, larger sample components can be separated and purified from smaller components laterally across the chip.

Samples can flow through these bump arrays under conditions of laminar flow (Reynolds number, $R_e$, <<1), so that discrete reagent streams can be introduced into arrays without significant lateral mixing. Large particles can be bumped diagonally into, and out of, such reagent streams to perform chemical or enzymatic reactions on the particles. The devices as provided herein can be used to purify leukocyte nuclei, purify DNA, and enzymatically modify DNA for generation of NGS libraries.

In some cases, a device and/or system as provided herein is used in a method for sequentially processing blood samples using bump arrays. A few microliters ("µl") of blood can be obtained. Blood cells can be separated from plasma. Cells can be washed with a buffer stream as they are separated from the plasma. In some cases, the cells are lysed. Washed cells can be lysed by bumping them through a reagent stream containing non-ionic detergent. The non-ionic detergent can be any non-ionic detergent known in the art. After removing the lysis reagent, intact leukocyte nuclei can be bumped diagonally through a wash buffer stream. Cytoplasmic contents too small to bump (e.g., below a critical size of a DLD bump array) can be carried out of the array in the detergent lysis stream. Chromosomal DNA can be isolated and/or purified. Washed leukocyte nuclei can be bumped through a nuclear lysis reagent stream to remove all lipid and nuclear proteins from HMW chromosomal DNA. The nuclear lysis reagent stream can comprise a protein denaturant (e.g., guanidine isothiocyanate) for extracting nucleic acid (e.g. HW chromosomal DNA) from proteins (e.g., histone proteins). In some cases, guanidine isothiocyanate is present in a separate stream from the nuclear lysis stream. Array dimensions in a device as provided herein can be chosen so that HMW DNA, in its double-stranded random-coil configuration, can be bumped diagonally out of the lysis reagent stream. All or substantially all nuclear lipids, RNA, and proteins too small to bump (e.g., below a critical size of a DLD bump array) can be carried out of the array in the lysis stream. In some cases purified DNA is reacted with a transposase-adapted reagent to generate library cointegrates. Purified HMW DNA can be bumped through a reagent stream containing a transposase complex that can be preloaded with sequencing-adapter-modified transposon ends. A method using a device as provided herein can provide a transposase complex in which the transposon-adapted ends of the transposasome can be on the same linear piece of DNA. As a result, a reaction of the transposasome with the HMW DNA can generate a colinear insertion product that can increase the size of the HMW DNA target. The target DNA can remain bumpable, wherein the target DNA can be separated from the transposasome reagent stream and unreacted adapter DNA. HMW cointegrates can be purified from the transposase reagent stream. Cointegrates can be reacted with restriction enzyme to generate a sequencing library. The library can be separated from uncut HMW DNA and recovered from the bump array. In some cases, a final sequencing library produced by a method using a device and/or system as provided herein can be cleaved from the HMW co-integrate DNA by bumping the DNA through a restriction enzyme reagent stream. The enzyme can cleave engineered sites in the modified transposon that lie just outside of the sequencing adapters. The cleaved library can be low in molecular weight (about 200-2000 bp), and can be no longer bumpable. The library can be removed from the array in the restriction enzyme stream. Uncleaved, unreacted HMW DNA can be bumped out of the reagent stream diagonally (and can be recovered).

In some cases, the devices, methods, compositions, systems and/or kits provided herein include micron-sized post arrays with high structural rigidity and high aspect ratios for the purposes of processing fluid samples. The bump arrays can be manufactured from silicon, cyclic olefin resin, molded plastic disposable flow cells, as well as any other materials.

In some cases, the devices, methods, compositions, systems and/or kits provided herein separate or fractionate, analyze, and/or collect purified or processed polynucleic acid analytes or fractions derived from a raw biological sample as provided herein.

In some cases, the devices, methods, compositions, systems and/or kits provided herein process smaller nucleic acid molecules by attaching the nucleic acids to microparticles that are adapted to be bumped in a bump (e.g., DLD array). The microparticles can act as carriers for transporting the attached nucleic acids through reagent streams for modification of the nucleic acids. For example, emulsion PCR with primer-modified microparticles can be used for generation of DNA sequencing template beads (Ion Torrent and 454 sequencing methods; Rothberg et al. 2011. Nature v475, pp 348-352; Margulies et al., Nature. V437, pp 376-380). In some cases, emulsion PCR methods can be used for evaluation of the frequency of rare mutant genes in tissue from cancer patients (Vogelstein's "BEAMing" method, Diehl et al. Nature Methods. 2006 v3 pp 551-559). In some cases, the devices, methods, compositions, systems and/or kits provided herein are used to process particle-based emulsion PCR by combining washing, denaturation, and primer hybridization into a single bump array process. For example, a bump array can be designed with post spacing chosen so that the critical diameter of the array can be less than that of the microparticles used for the emulsion PCR. This can ensure that the microparticles can be bumped consistently at all positions within the array. After emulsion PCR, the emulsion can be broken and the aqueous particles fraction can be fed into a device comprising a bump array as provided herein near the upper left hand corner. As particles enter the array, the particles can be deflected toward an opposing boundary wall, while the PCR reagents can flow downward in the direction of bulk flow. A suitable wash buffer can be fed into the top of the array immediately to the right of the particle input port. As the particles are bumped out of the input stream, the particles can pass through the wash buffer stream, which can clean away additional PCR reagent. As the particles move further down the array, the particles can enter a denaturing reagent stream (e.g., which can contain about 20-200 mM KOH or NaOH with about 1-10 mM EDTA), which can convert the double-stranded amplicons on the particles to single-stranded form. The non-covalently bound amplicon strand can be washed down the array with the denaturant stream, and the particles can be bumped rightward into a neutralizing buffer that can be suitable for hybridization reactions in the next step. Generally, such neutralizing buffer can contain a buffer (for example, 20-200 mM Tris-HCl, pH 7.5-8.0) and monovalent ions to support hybridization (for example, 20-500 mM NaCl). The particles can then be bumped through a hybridization reagent stream containing sequencing primer (in the case of the 454/Ion Torrent applications), or labeled oligonucleotide probe (in the case of the BEAMing application). The reagent stream can have oligo probes in the low micromolar concentration range (about 0.1 micromolar to about 50 micromolar), and can have about the same ionic strength as the neutralizing buffer stream described above. The ionic strength can be adjusted higher or lower as needed to achieve the correct stringency of hybridization. In the final processing step of the array, the hybridized particles can be bumped out of the hybridization stream into a final wash buffer stream. This final wash buffer is chosen according to the downstream application to be used (sequencing in the case of 454/Ion applications, fluorescent particle sorting in the case of the BEAMing assay). The hybridized, washed particles are collected from the output port of the final wash buffer located near the lower right corner of the array.

VII. Downstream Applications

Particles processed (e.g., chemically or enzymatically processed or treated), purified, isolated, and/or concentrated using methods, compositions, devices, systems, and/or kits described herein can be stored and/or used in downstream applications. Described herein are various applications for particles that have been processed (e.g., chemically processed or treated), purified, isolated, and/or concentrated using methods, compositions, devices, systems, and/or kits described herein Although this disclosure discusses leukocyte and stem cell processing for flow cytometry the same technology can be used for multiple existing and new cellular and other (e.g. DNA, RNA) tests for cancer and other diseases.

In some cases, the devices, compositions, systems, kits and/or methods described herein are used to prepare samples for nucleic acid (e.g., DNA or RNA) sequencing. Nucleic acids can be isolated from any type of cell including prokaryotic, eukaryotic, archaea, single celled organisms, multi-cellular organisms or tissues (e.g., plants or animals), and the like. The nucleic acid can be sequenced in any manner, including single molecule or shotgun sequencing, in a nanopore, by detecting a change in pH upon nucleotide incorporation events, by fluorescence detection of incorporated or released dyes, etc. . . . . The cells are lysed and nucleic acid is sorted from cellular debris using the post arrays as described herein. The nucleic acid can be concentrated to any suitable concentration and/or purified to any suitable purity (e.g., at least 70%, at least 80%, at least 90%, at least 95%, at least 99%, at least 99.9%, and the like).

A. Blood Banking (e.g., Cryopreservation)

In some cases, blood is separated into components using devices and methods described herein, and the components are stored. In some cases, erythrocytes are isolated or purified. In some cases, erythrocytes are stored at from about 1 to about 6° C. In some cases, erythrocytes are stored for about 20 to about 60 days, or about 30 to about 50 days, or up to 42 days. In some cases, erythrocytes are frozen (e.g., with a cryoprotectant, e.g., glycerol) and stored at, e.g., less than −60° C., e.g., for at least 10 years. In some cases, stored erythrocytes are used for transfusion. In some cases, isolated erythrocytes are administered to a patient after trauma, surgery, blood loss, or a patient with a blood disorder, e.g., sickle cell anemia.

In some cases, plasma is isolated and frozen for later use. In some cases, plasma is stored for up to a year. Plasma can be administered to a subject, e.g., a burn patient, subject in shock, or subject with a bleeding disorder.

In some cases, platelets are isolated. In some cases, platelets are isolated, e.g., for transfusion. In some cases, isolated platelets are stored at room temperature, e.g., for about 5 to 7 days. In some cases, platelets are administered to a subject with cancer, an organ transplant, or a subject who is undergoing, or has undergone, surgery.

In some cases, an isolated blood component is cryoprecipitated anti-haemophilic factor (cryoprecipitated AHF). Cryoprecipitated AHF can be stored frozen for about a year. In some cases, Cryoprecipitated AHF is administered to a subject with hemophila or Von Willebrand disease.

Other blood components that can be isolated and stored are granulocytes. In some cases, granulocytes are used transfusion within 24 hrs after collection. In some cases, granulocytes are administered to subject to treat infections that are unresponsive to antibiotic therapy.

In some cases, lymphocytes are isolated and may be stored, with or without gene modification, prior to administration to patients with cancer or infectious or other diseases.

In some cases, purified particles, e.g., cells, e.g., stem cells, e.g., HSCs are preserved, e.g., cryopreserved. Methods of cryopreservation are described, e.g., in Berz et al (2007) Cryopreservation of Hematopoietic Stem Cells. Am J Hematol. 82: 463-472, which is herein incorporated by reference. In some cases, a heparinized plasmalyte solution and/or dimethylsulfoxide (DMSO) (e.g., 10% DMSO) are added to purified particles, e.g., cells, e.g., HSCs. In some cases, the purified particles, e.g., HSCs are in a solution with a final concentration of DMSO of less than 20, 19, 18, 17, 16, 15, 14, 13, 12, 11, 10, 9, 8, 7, 6, 5, 4, 3, 2, 1, or 0.5% DMSO. In some cases, particles, e.g., cells, e.g., HSCs, are in a solution with a final DMSO concentration of about 2 to about 10%, or about 5% to about 15%. In some cases, leukocytes are cryopreserved.

In some cases, purified particles, e.g., cells, e.g., stem cells, e.g., HSCs are combined with saline and or serum albumin. In some cases, a cryoprotectant is hydroxyethyl starch (HES), propylene glycol, alpha tocopherol, catalase, ascorbic acid, trehalose, or capase inhibitor (e.g., zVAD-fmk). In some cases, a cryoprotectant is a glycol (e.g., ethylene glycol, propylene glycol, or glycerol). In some cases, a cryoprotectant is 2-Methyl-2, 4-pentanediol (MPD). In some cases, a cryoprotectant is sucrose. In some cases, purified particles, e.g., cells, e.g., stem cells, e.g., HSCs are mixed with more than one cryoprotectant.

In some cases, purified particles, e.g., cells, e.g., stem cells, HSCs are frozen to a temperature of less 5° C., than −79° C., less than −155° C. or less than −195° C. In some cases, particles, e.g., cells, e.g., stem cells, e.g., HSCs are frozen to a temperature of about 4° C. of about −80° C., −156° C. or −196° C. In some cases, purified particles, e.g., cells, e.g., stem cells, e.g., HSCs are frozen to from about −196° C. to about −80° C. In some cases, purified particles, e.g., cells, e.g., stem cells, e.g., HSCs are stored in a liquid phase of a nitrogen tank. In some cases, purified particles, e.g., cells, e.g., stem cells, e.g., HSCs are store in a vapor nitrogen phase.

In some cases, purified particles, e.g., cells, e.g., stem cells, e.g., HSCs are frozen at a controlled rate freezing, e.g., at a rate of 1-2° C./min up to a temperature point of about −40° C. Then, the freezing process down to a target of −120° C. is performed can be performed a faster pace, about 3-5° C./min. In some cases, purified particles, e.g., cells, e.g., HSCs are cooled to a temperature of −4° C., then placed in a freezer at −80° C.

In some cases, purified particles, e.g., cells, e.g., stem cells, e.g., HSCs are cryopreserved for at least 1, 10, 30, 180, or 365 days. In some cases, HSCs are cryopreserved for at least 1, 5, 10, 20, 30, 50, 75, or 100 years.

In some cases, purified particles, e.g., cells, e.g., stem cells, e.g., HSCs are cryopreserved at a density of less than $10^{-11}$, $10^{-10}$, $10^{-9}$, $10^{-8}$, $10^{-7}$, $10^{-6}$, $10^{-5}$ cells/mL. In some cases, purified particles, e.g., cells, e.g., stem cells, e.g., HSCs are cryopreserved at a density of at least $10^{-11}$, $10^{-10}$, $10^{-9}$, $10^{-8}$, $10^{-7}$, $10^{-6}$, $10^{-5}$ cells/mL.

In some cases, cryopreserved purified particles, e.g., cells, e.g., stem cells, e.g., HSCs are thawed at 37° C. (e.g., in a water bath, gel pads). In some cases, cyropreserved purified particles, e.g., cells, e.g., HSCs are thawed at a temperature of about 0° C. to about 37° C.

In some cases, a cryopresevative (e.g., DMSO) is washed out of purified particles, e.g., cells, e.g., HSC sample after thawing. In some cases, a thawed purified particle, e.g., cell, e.g., stem cell, e.g., HSC sample is diluted in human serum albumin (HSA) (e.g., 2.5%) and dextran 40 (e.g., 5%). The sample can then be centrifuged or passed through a microfluidic device described herein, e.g., at a temperature of 10° C. In some cases, an HSA/dextran solution is added to the purified particles, e.g., cells, e.g., stem cells, e.g., HSCs again. In some cases, the DMSO concentration is less than 1.7%, e.g., washing and/or dilution. In some cases, stem cells, e.g., HSCs with a DMSO concentration of less than 1.7% is infused in a subject.

In some case, cyropreserved purified particles, e.g., cells, e.g., stem cells, e.g., HSCs are stored in a container. In some cases, a container is an ethinyl vinyl acetate (EVA) container. In some cases, a container is gamma irradiated. In some cases, a container is a stainless steel container. In some cases, a container comprises, PVC, polyolefin, or polyethelene. In some cases, a container comprises Teflon, Kaplon, FEP, and/or polyimide.

In some cases, purified cells, e.g., stem cells, e.g., HSCs are evaluated by cell counting for total nucleated cells and CD34+ cells (e.g., by flow cytometry); trypan blue exclusion for viability, 7-acinoactinomycin for viability, or propidium iodide for viability; engraftment in NOD/SCID (immunodeficient mice), or a clonogenic assay (e.g., CFU-Sd12 assay in mice; CFU-GM; CFU-GEMM; BFU-E, or LTC-IC).

B. Cancer Treatment

In some cases, purified, isolated, and/or concentrated stems cells, e.g., HSCs can be used to treat cancer, e.g. cancer of the blood, e.g., leukemia or lymphoma. In some cases, purified, isolated, and/or concentrated stem cells, e.g., HSCs are obtained from a subject and subsequently administered to the same subject. The stem cells can travel to the bone marrow and begin to produce new blood cells.

In some cases, stem cells, e.g., HSCs are obtained from a first subject and administered to second subject (e.g., relative, e.g., sister or brother of the first subject). In some cases, the first subject and second subject are not relatives. In some cases, the second subject is a matched donor. In some cases, the first subject and the second subject have similar human leukocyte antigens. In some cases, the first subject and the second subject do not have similar human leukocyte antigens. In some cases, a subject diagnosed with or suspected of having, acute lymphoblastic leukemia, acute myeloblastic leukemia, chronic myelogoneous leukemia (CML), Hodgkin's disease, multiple myeloma, or non-Hodgkin' lymphoma is administered HSCs.

In some cases, administration of stem cells to a subject comprises use of an intravenous (IV) line. In some cases, the transplant takes about 1 to about 5 hours. After entering the blood stream, the cells can travel to the bone marrow. Engraftment (normal blood production) can occur within about 2 to about 4 weeks after transplantation. In some cases, the methods, compositions, devices, systems, and kits described herein are used to monitor engraftment.

In some cases, a subject receives a bone marrow transplant (BMT). In some cases, a subject receives a peripheral blood stem cell transplant (PBSCT). In some cases, a transplant is an autologous transplant (the subject receive his/her own stem cells).

In some cases, a transplant is a syngeneic transplant (a subject receives stem cells from his/her identical twin). In some cases, a transplant is an allogeneic transplant (a subject receives stem cells from his/her brother, sister, parent, or person unrelated to the subject.

In some cases, stem cells are purified from bone marrow in the pelvic bone or sternum. In some cases, PBSCs are processed and/or purified by apheresis or leukapheresis. In some cases, stem cells are processed and/or purified from umbilical cord or placenta In some cases, processed, purified, isolated, or concentrated stem cells, e.g., HSCs are administered to a subject with CML, and the subject is also administered imatinib mesylate (Gleevec™). In some cases, the subject is administered stem cells, e.g., HSCs without receiving imatinib mesylate.

In some cases, a subject who receives stem cells e.g., HSCs is resistant to chemotherapy.

In some cases, a subject who receives stem cells, e.g., HSCs is a newborn, infant, child, teenager, young adult, middle aged person, or elderly person.

In some cases, subject who receives stem cells, e.g., HSCs has neuroblastoma, Ewing's sarcoma, desmoplatic small-round cell tumor, or chronic granulomatous disease.

In some cases, a mini-transplant is used. In some cases, a tandem transplant is used, involving two sequential courses of high-dose chemotherapy and stem cell transplant.

In some cases, a subject, e.g., a cancer patient, is administered radiation or chemotherapy, and the radiation or chemotherapy targets hematopoietic cells, which can be destroyed by radiation or chemotherapy. In some cases, processed, purified, isolated, and/or concentrated HSCs from the subject can be transplanted into the subject to replace cells destroyed by chemotherapy. Introducing the subject's own HSCs can reduce the chance of immune mismatch or graft-versus-host disease. In some cases, only CD34+, Thy-1+ cells are transplanted into the subject.

In some cases, stem cells are administered to a subject who is in remission (signs and symptoms of cancer have disappeared).

In some cases, the transplantation of stem cells processed and/or purified using methods and devices described herein can result in a reduction of the risk of graft versus host disease by a least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% relative to transplantation of stem cells purified by conventional methods.

In some cases, a subject who is administered stem cells has one or more of the following cancers: acute myeloid leukemia; bladder cancer, including upper tract tumors and urothelial carcinoma of the prostate; bone cancer, including chondrosarcoma, Ewing's sarcoma, and osteosarcoma; breast cancer, including noninvasive, invasive, phyllodes tumor, Paget's disease, and breast cancer during pregnancy; central nervous system cancers, adult low-grade infiltrative supratentorial astrocytoma/oligodendroglioma, adult intracranial ependymoma, anaplastic astrocytoma/anaplastic oligodendroglioma/glioblastoma multiforme, limited (1-3) metastatic lesions, multiple (>3) metastatic lesions, carcinomatous lymphomatous meningitis, nonimmunosuppressed primary CNS lymphoma, and metastatic spine tumors; cervical cancer, chronic myelogenous leukemia (CML); colon cancer, rectal cancer, anal carcinoma; esophageal cancer; gastric (stomach) cancer; head and neck cancers, including ethmoid sinus tumors, maxillary sinus tumors, salivary gland tumors, cancer of the lip, cancer of the oral cavity, cancer of the oropharynx, cancer of the hypopharynx, occult primary, cancer of the glottic larynx, cancer of the supraglottic larynx, cancer of the nasopharynx, and advanced head and neck cancer; hepatobiliary cancers, including hepatocellular carcinoma, gallbladder cancer, intrahepatic cholangiocarcinoma, and extrahepatic cholangiocarcinoma; Hodgkin disease/lymphoma; kidney cancer; melanoma; multiple myeloma, systemic light chain amyloidosis, Waldenstrom's macroglobulinemia; myelodysplastic syndromes; neuroendocrine tumors, including multiple endocrine neoplasia, type 1, multiple endocrine neoplasia, type 2, carcinoid tumors, islet cell tumors, pheochromocytoma, poorly differentiated/small cell/atypical lung carcinoids; Non-Hodgkin's Lymphomas, including chronic lymphocytic leukemia/small lymphocytic lymphoma, follicular lymphoma, marginal zone lymphoma, mantle cell lymphoma, diffuse large B-Cell lymphoma, Burkitt's lymphoma, lymphoblastic lymphoma, AIDS-Related B-Cell lymphoma, peripheral T-Cell lymphoma, and mycosis fungoides/Sezary Syndrome; non-melanoma skin cancers, including basal and squamous cell skin cancers, dermatofibrosarcoma protuberans, Merkel cell carcinoma; non-small cell lung cancer (NSCLC), including thymic malignancies; occult primary; ovarian cancer, including epithelial ovarian cancer, borderline epithelial ovarian cancer (Low Malignant Potential), and less common ovarian histologies; pancreatic adenocarcinoma; prostate cancer; small cell lung cancer and lung neuroendocrine tumors; soft tissue sarcoma, including soft-tissue extremity, retroperitoneal, intra-abdominal sarcoma, and desmoid; testicular cancer, thymic malignancies, including thyroid carcinoma, nodule evaluation, papillary carcinoma, follicular carcinoma, Hiirthle cell neoplasm, medullary carcinoma, and anaplastic carcinoma; uterine neoplasms, including endometrial cancer or uterine sarcoma.

In some cases, stem cells, e.g., HSCs are processed, purified, isolated, and/or concentrated, e.g., from an HLA-matched subject, and the HSCs are transplanted into another person, e.g., a sibling of the subject, wherein the sibling has cancer. In some cases, the transplanted HSCs show antitumor activity (graft-verus-tumor treatment of cancer).

In some cases, Natural Killer (NK) cells are used in immunotherapy, e.g., for cancer, e.g., leukemia. Uses of NK cells are described, e.g., in Grywacz et al. (2008) Use of natural killer cells as immunotherapy for leukaemia. Best Pract Res Clin Haematol. 3: 467-483 and Miller (2013) Therapeutic applications: natural killer cells in the clinic. Hematology 2013:247-253, which are herein incorporated by reference in their entireties.

C. Cancer Diagnosis

In some cases, cells isolated using the methods, compositions, devices, systems, and kits described herein are used to diagnose a cancer described herein, e.g., a blood cancer, e.g., leukemia, lymphoma, or myeloma. In some cases, the leukemia is adult acute lymphoblastic leukemia, childhood acute lymphoblastic leukemia, adult acute myeloid leukemia, childhood acute myeloid leukemia, chronic lymphocytic leukemia, chronic myelogenous leukemia, or hairy cell leukemia. In some cases, the lymphoma is AIDS-related lymphoma, cutaneous T-cell lymphoma, adult Hodgkin Lymphoma, childhood Hodgkin Lymphoma, mycosis fungoides, adult Non-Hodgkin Lymphoma, childhood Non-Hodgkin Lymphoma, primary Central Nervous System Lymphoma, Sézary Syndrome, cutaneous T-Cell Lymphoma, or Waldenström Macroglobulinemia. In some cases, the blood cancer is a chronic myeloproliferative disorder, Langerhans cell histiocytosis, multiple myeloma, plasma cell neoplasm, a myelodysplastic syndrome, a myelodysplastic/myeloproliferative neoplasm.

In some cases, leukocytes are evaluated with a leukemia and lymphoma research panel. In some cases, a research panel is used to look for sets of proteins, e.g., cell surface and/or intracellular proteins that serve as markers for subtypes of normal leukocytes and hematologic malignancies. In some cases, the panel is evaluated with flow cytometry. The panel can be, e.g., a BD Euroflow multicolor antibody panel (see http://www.bdbiosciences.com/eu/documents/ EuroFlow_datasheet_new.pdf). The marker in the BD Euroflow multicolor antibody panel can be, e.g., CD-11c CD22, CD24, CD45, CD49d, CD 123, Igk, CD10, CD27, CD38, CD43, CD81, TCRγδ, β-2 microglobulin, CD9, CD71, CD79b, Igλ, IREM-2 (CD300e), CD2, CD3, CD4, CD7, CD8, CD16, CD16, CD20, CD23, CD36, CD38, CD41a, CD42a, CD45, CD56, CD64, CD105, CD138, CD200, Igλ, Igκ and, HLA-DR. The label (e.g., fluorochrome) associated with the marker in the BD Euroflow multicolor antibody panel can be FITC, PE, V450, PE-Cy™7, PerCP-Cy5.5, APC-H7, V500-C, APC, PacB, or PacO.

In some cases, leukocytes recovered using devices and/or methods described herein are evaluated in B-cell analysis (kappa and lambda ratio). Comparing the ratio of kappa-to-lambda can be used to determine whether a subject might have a plasma cell tumor, e.g., multiple myeloma, monoclonal gammopathy of undetermined significance (MGUS), Smoldering myeloma, solitary plasmacytoma of the bone, or AL amyloidosis.

In some cases, free light chain production is assessed, which can be prognostic of a worse outcome in multiple myeloma or chronic lymphocytic leukemia.

D. Blood Disorders

In some cases, processed (e.g., chemically and/or enzymatically processed or treated), purified, isolated, or concentrated HSCs are administered to a subject with a hereditary blood disorder. The hereditary blood disorder can be, e.g., aplastic anemia, beta-thalassemia, Blackfan-Diamond syndrome, globoid cell leukodystrophy, sickle-cell anemia, severe combined immunodeficiency, X-linked lymphoproliferative syndrome, or Wiskott-Aldrich syndrome. Inborn errors of metabolism that can be treated with bone marrow transplants include: Hunter's syndrome, Hurler's syndrome, Lesch Nyhan syndrome, and osteopetrosis. In some cases, the hereditary blood disorder is Fanconi anemia.

In some cases, processed (e.g., chemically processed or treated), purified, isolated, or concentrated HSCs are administered to a subject to treat a blood disorder, e.g., amyloidois, anemia, essential thrombocythemia, Fanconi anemia, Gaucher disease, hemochromatosis, hemolytic anemia, hemophilia, hypereosinophilia, idiopathic thrombocytopenic purpura, an inherited bone marrow failure syndrome, iron-deficiency anemia, Langerhan Cell histiocytosis, leucopenia, mastocytosis, myelofibrosis, a myeloprofilerative disorder, pernicious anemia, polycythermia vera, porphyria, sickle cell anemia, a thalassemia, thrombocytopenia, thrombocytosis, thrombotic thrombocytopenic purpura, or von Willebrand disease.

In some cases, particles (e.g., cells) processed (e.g., chemically and/or enzymatically processed or treated), purified, isolated, and/or concentrated using methods described herein are used to diagnose a blood disorder, e.g., an blood disorder described herein.

E. Autoimmune Disease

Stem cells, e.g., HSCs processed (e.g., chemically and/or enzymatically processed or treated), purified, isolated, and/or concentrated using the methods, compositions, devices, systems, and/or kits described herein can be administered to a subject to treat an autoimmune disease. In some cases, stem cells, e.g., HSCs purified, isolated, and/or concentrated using the methods, compositions, devices, systems, and/or kits can be administered to a subject with an autoimmune disorder that affects heart, brain, nerves, muscle, skin, eye, joint, lung, kidney, gland, the digestive tract, or blood vessels. In some cases, an autoimmune disorder can be rheumatoid arthritis, Graves' disease, thryrioditis, scleroderma, systemic sclerosis, vitiligo, systemic lupus erythematosus (SLE), alopecia areata, autoimmune hemolytic anemia, autoimmune hepatitis, dermatomyositis, diabetes (type 1), juvenile idiopathic arthritis, glomerulonephritis, Guillain-Barré syndrome, idiopathic thrombocytopenic purpura, myasthenia gravis, myocarditis, multiple sclerosis, pemphigus/pemphigoid, pernicious anemia, polyarteritis nodosa, polymyositis, primary biliary cirrhosis, psoriasis, scleroderma/systemic sclerosis, Sjögren's syndrome, uveitis, or granulomatosis with polyangiitis (Wegener's).

F. Other Uses of Stem Cells

In some cases, stem cells processed (e.g., chemically and/or enzymatically processed or treated), purified, isolated, and/or concentrated using the methods, compositions, devices, systems, and/or kits described herein can be used to treat Alzheimer's diseases, spinal cord injury, stroke, burns, heart disease, or osteoarthritis. In some cases, stem cells can be used to treat cardiovascular disease.

In some cases, stem cells are used to treat a subject with a neurological or neurocognitive condition. The neurological or neurocognitive condition can be a neurological disorder listed on the National Institute of Neurological Disorders and Stroke webpage (www.ninds.nih.gov/disorders/disorder_index.htm). In some embodiments, the subject can have a sign or symptom. The neurological or neurocognitive condition, or symptom, can be, e.g., abarognosis (e.g., loss of the ability to detect the weight of an object held in the hand or to discern the difference in weight between two objects), acid lipase disease, acid maltase deficiency, acquired epileptiform aphasia, absence of the septum pellucidum, acute disseminated encephalomyelitis, adie's pupil, Adie's syndrome, adrenoleukodystrophy, agenesis of the corpus callosum, agnosia, Aicardi syndrome, Aicardi-Goutieres syndrome disorder, AIDS—neurological complications, akathisia, alcohol related disorders, Alexander disease, Alien hand syndrome (anarchic hand), allochiria, Alpers' disease, altitude sickness, alternating hemiplegia, Alzheimer's disease, amyotrophic lateral sclerosis, anencephaly, aneurysm, Angelman syndrome, angiomatosis, anoxia, Antiphospholipid syndrome, aphasia, apraxia, arachnoid cysts, arachnoiditis, arnold-chiari malformation, Asperger syndrome, arteriovenous malformation, ataxia, ataxias and cerebellar or spinocerebellar degeneration, ataxia telangiectasia, atrial fibrillation, stroke, attention deficit hyperactivity disorder, auditory processing disorder, autism, autonomic dysfunction, back pain, Barth syndrome, Batten disease, becker's myotonia, Behcet's disease, bell's palsy, benign essential blepharospasm, benign focal amyotrophy, benign intracranial hypertension, Bernhardt-Roth syndrome, bilateral frontoparietal polymicrogyria, Binswanger's disease, blepharospasm, Bloch-Sulzberger syndrome, brachial plexus birth injuries, brachial plexus injury, Bradbury-Eggleston syndrome, brain or spinal tumor, brain abscess, brain aneurysm, brain damage, brain injury, brain tumor, Brown-Sequard syndrome, bulbospinal muscular atrophy, CADASIL (cerebral autosomal dominant arteriopathy subcortical infarcts and leukoencephalopathy), Canavan disease, Carpal tunnel syndrome, causalgia, cavernomas, cavernous angioma, cavernous malformation, Central cervical cord Syndrome, Central cord syndrome, Central pain syndrome, central pontine myelinolysis, centronuclear myopathy, cephalic disorder, ceramidase deficiency, cerebellar degeneration, cerebellar hypoplasia, cerebral aneurysm, cerebral arteriosclerosis, cerebral atrophy, cerebral beriberi, cerebral cavernous malformation, cerebral gigantism, cerebral hypoxia, cerebral palsy, cerebral vasculitis, Cerebro-Oculo-Facio-Skeletal syndrome (COFS), cervical spinal stenosis, Charcot-Marie-Tooth disease, chiari malformation, Cholesterol ester storage disease, chorea, choreoacanthocytosis, Chronic fatigue syndrome, chronic inflammatory demyelinating polyneuropathy (CIDP), chronic orthostatic intolerance, chronic pain, Cockayne syndrome type II, Coffin-Lowry syndrome, colpocephaly, coma, Complex regional pain syndrome, compression neuropathy, concussion, congenital facial diplegia, congenital myasthenia, congenital myopathy, congenital vascular cavernous malformations, corticobasal degeneration, cranial arteritis, craniosynostosis, cree encephalitis, Creutzfeldt-Jakob disease, cumulative trauma disorders, Cushing's syndrome, Cytomegalic inclusion body disease (CIBD), cytomegalovirus infection, Dancing eyes-dancing feet syndrome (opsoclonus myoclonus syndrome), Dandy-Walker syndrome (DWS), Dawson disease, decompression sickness, De morsier's syndrome, dejerine-klumpke palsy, Dejerine-Sottas disease, Delayed sleep phase syndrome, dementia, dementia—multi-infarct, dementia—semantic, dementia—subcortical, dementia with lewy bodies, dentate cerebellar ataxia, dentatorubral atrophy, depression, dermatomyositis, developmental dyspraxia, Devic's syndrome, diabetes, diabetic neuropathy, diffuse sclerosis, Dravet syndrome, dysautonomia, dyscalculia, dysgraphia, dyslexia, dysphagia, dyspraxia, dyssynergia cerebellaris myoclonica, dyssynergia cerebellaris progressiva, dystonia, dystonias, Early infantile epileptic, Empty sella syndrome, encephalitis, encephalitis lethargica, encephalocele, encephalopathy, encephalopathy (familial infantile), encephalotrigeminal angiomatosis, encopresis, epilepsy, epileptic hemiplegia, erb's palsy, erb-duchenne and dejerine-klumpke palsies, erythromelalgia, essential tremor, extrapontine myelinolysis, Fabry's disease, Fahr's syndrome, fainting, familial dysautonomia, familial hemangioma, familial idiopathic basal ganglia calcification, familial periodic paralyses, familial spastic paralysis, Farber's disease, febrile seizures, fibromuscular dysplasia, fibromyalgia, Fisher syndrome, floppy infant syndrome, foot drop, Foville's syndrome, friedreich's ataxia, frontotemporal dementia, Gaucher's disease, generalized gangliosidoses, Gerstmann's syndrome, Gerstmann-Straussler-Scheinker disease, giant axonal neuropathy, giant cell arteritis, Giant cell inclusion disease, globoid cell leukodystrophy, glossopharyngeal neuralgia, Glycogen storage disease, gray matter heterotopia, Guillain-Barre syndrome, Hallervorden-Spatz disease, head injury, headache, hemicrania continua, hemifacial spasm, hemiplegia alterans, hereditary neuropathies, hereditary spastic paraplegia, heredopathia atactica polyneuritiformis, herpes zoster, herpes zoster oticus, Hirayama syndrome, Holmes-Adie syndrome, holoprosencephaly, HTLV-1 associated myelopathy, HIV infection, Hughes syndrome, Huntington's disease, hydranencephaly, hydrocephalus, hydrocephalus—normal pressure, hydromyelia, hypercortisolism, hypersomnia, hypertension, hypertonia, hypotonia, hypoxia, immune-mediated encephalomyelitis, inclusion body myositis, incontinentia pigmenti, infantile hypotonia, infantile neuroaxonal dystrophy, Infantile phytanic acid storage disease, Infantile refsum disease, infantile spasms, inflammatory myopathy, inflammatory myopathies, iniencephaly, intestinal lipodystrophy, intracranial cyst, intracranial hypertension, Isaac's syndrome, Joubert syndrome, Karak syndrome, Kearns-Sayre syndrome, Kennedy disease, Kinsbourne syndrome, Kleine-Levin syndrome, Klippel feil syndrome, Klippel-Trenaunay syndrome (KTS), Kluver-Bucy syndrome, Korsakoff s amnesic syndrome, Krabbe disease, Kugelberg-Welander disease, kuru, Lafora disease, lambert-eaton myasthenic syndrome, Landau-Kleffner syndrome, lateral femoral cutaneous nerve entrapment, Lateral medullary (wallenberg) syndrome, learning disabilities, Leigh's disease, Lennox-Gastaut syndrome, Lesch-Nyhan syndrome, leukodystrophy, Levine-Critchley syndrome, lewy body dementia, Lipid storage diseases, lipoid proteinosis, lissencephaly, Locked-In syndrome, Lou Gehrig's, lumbar disc disease, lumbar spinal stenosis, lupus—neurological sequelae, lyme disease—neurological sequelae, Machado-Joseph disease (spinocerebellar ataxia type 3), macrencephaly, macropsia, megalencephaly, Melkersson-Rosenthal syndrome, Menieres disease, meningitis, meningitis and encephalitis, Menkes disease, meralgia paresthetica, metachromatic leukodystrophy, metabolic disorders, microcephaly, micropsia, migraine, Miller fisher syndrome, mini-stroke (transient ischemic attack), misophonia, mitochondrial myopathy, Mobius syndrome, Moebius syndrome, monomelic amyotrophy, mood disorder, Motor neurone disease, motor skills disorder, Moyamoya disease, mucolipidoses, mucopolysaccharidoses, multi-infarct dementia, multifocal motor neuropathy, multiple sclerosis, multiple system atrophy, multiple system atrophy with orthostatic hypotension, muscular dystrophy, myalgic encephalomyelitis, myasthenia—congenital, myasthenia gravis, myelinoclastic diffuse sclerosis, myoclonic encephalopathy of infants, myoclonus, myopathy, myopathy—congenital, myopathy—thyrotoxic, myotonia, myotonia congenita, myotubular myopathy, narcolepsy, neuroacanthocytosis, neurodegeneration with brain iron accumulation, neurofibromatosis, Neuroleptic malignant syndrome, neurological complications of AIDS, neurological complications of lyme disease, neurological consequences of cytomegalovirus infection, neurological manifestations of AIDS, neurological manifestations of pompe disease, neurological sequelae of lupus, neuromyelitis optica, neuromyotonia, neuronal ceroid lipofuscinosis, neuronal migration disorders, neuropathy—hereditary, neurosarcoidosis, neurosyphilis, neurotoxicity, neurotoxic insult, nevus cavernosus, Niemann-pick disease, Non 24-hour sleep-wake syndrome, nonverbal learning disorder, normal pressure hydrocephalus, O'Sullivan-McLeod syndrome, occipital neuralgia, occult spinal dysraphism sequence, Ohtahara syndrome, olivopontocerebellar atrophy, opsoclonus myoclonus, Opsoclonus myoclonus syndrome, optic neuritis, orthostatic hypotension, Overuse syndrome, chronic pain, palinopsia, panic disorder, pantothenate kinase-associated neurodegeneration, paramyotonia congenita, Paraneoplastic diseases, paresthesia, Parkinson's disease, paroxysmal attacks, paroxysmal choreoathetosis, paroxysmal hemicrania, Parry-Romberg syndrome, Pelizaeus-Merzbacher disease, Pena shokeir II syndrome, perineural cysts, periodic paralyses, peripheral neuropathy, periventricular leukomalacia, persistent vegetative state, pervasive developmental disorders, photic sneeze reflex, Phytanic acid storage disease, Pick's disease, pinched nerve, Piriformis syndrome, pituitary tumors, PMG, polio, polymicrogyria, polymyositis, Pompe disease, porencephaly, Post-polio syndrome, postherpetic neuralgia (PHN), postinfectious encephalomyelitis, postural hypotension, Postural orthostatic tachycardia syndrome, Postural tachycardia syndrome, Prader-Willi syndrome, primary dentatum atrophy, primary lateral sclerosis, primary progressive aphasia, Prion diseases, progressive hemifacial atrophy, progressive locomotor ataxia, progressive multifocal leukoencephalopathy, progressive sclerosing pohodystrophy, progressive supranuclear palsy, prosopagnosia, Pseudo-Torch syndrome, Pseudotoxoplasmosis syndrome, pseudotumor cerebri, Rabies, Ramsay hunt syndrome type I, Ramsay hunt syndrome type II, Ramsay hunt syndrome type III, Rasmussen's encephalitis, Reflex neurovascular dystrophy, Reflex sympathetic dystrophy syndrome, Refsum disease, Refsum disease—infantile, repetitive motion disorders, repetitive stress injury, Restless legs syndrome, retrovirus-associated myelopathy, Rett syndrome, Reye's syndrome, rheumatic encephalitis, rhythmic movement disorder, Riley-Day syndrome, Romberg syndrome, sacral nerve root cysts, saint vitus dance, Salivary gland disease, Sandhoff disease, Schilder's disease, schizencephaly, schizophrenia, Seitelberger disease, seizure disorder, semantic dementia, sensory integration dysfunction, septo-optic dysplasia, severe myoclonic epilepsy of infancy (SMEI), Shaken baby syndrome, shingles, Shy-Drager syndrome, Sjogren's syndrome, sleep apnea, sleeping sickness, sanitation, Sotos syndrome, spasticity, spina bifida, spinal cord infarction, spinal cord injury, spinal cord tumors, spinal muscular atrophy, spinocerebellar ataxia, spinocerebellar atrophy, spinocerebellar degeneration, Steele-Richardson-Olszewski syndrome, Stiff-Person syndrome, striatonigral degeneration, stroke, Sturge-Weber syndrome, subacute sclerosing panencephalitis, subcortical arteriosclerotic encephalopathy, SUNCT headache, superficial siderosis, swallowing disorders, Sydenham's chorea, syncope, synesthesia, syphilitic spinal sclerosis, syringohydromyelia, syringomyelia, systemic lupus erythematosus, tabes dorsalis, tardive dyskinesia, tardive dysphrenia, tarlov cyst, Tarsal tunnel syndrome, Tay-Sachs disease, temporal arteritis, tetanus, Tethered spinal cord syndrome, Thomsen disease, thomsen's myotonia, Thoracic outlet syndrome, thyrotoxic myopathy, tic douloureux, todd's paralysis, Tourette syndrome, toxic encephalopathy, transient ischemic attack, transmissible spongiform encephalopathies, transverse myelitis, traumatic brain injury, tremor, trigeminal neuralgia, tropical spastic paraparesis, Troyer syndrome, trypanosomiasis, tuberous sclerosis, ubisiosis, uremia, vascular erectile tumor, vasculitis syndromes of the central and peripheral nervous systems, viliuisk encephalomyelitis (VE), Von economo's disease, Von Hippel-Lindau disease (VHL), Von recklinghausen's disease, Wallenberg's syndrome, Werdnig-Hoffman disease, Wernicke-Korsakoff syndrome, West syndrome, Whiplash, Whipple's disease, Williams syndrome, Wilson's disease, Wolman's disease, X-linked spinal and bulbar muscular atrophy, or Zellweger syndrome.

G. Microscopy

In some cases, particles that are processed (e.g., chemically and/or enzymatically processed or treated), purified, isolated, and/or concentrated using the methods, compositions, devices, systems, and/or kits described herein (e.g., cells) can be analyzed by microscopy. In some cases, the microscopy can be optical, electron, or scanning probe microsopy. In some case, optical microscopy comprises use of bright field, oblique illumination, cross-polarized light, dispersion staining, dark field, phase contrast, differential interference contrast, interference reflection microscopy, fluorescence (e.g., when particles, e.g., cells, are immunostained), confocal, single plane illumination microscopy, light sheet fluorescence microscopy, deconvolution, or serial time-encoded amplified microscopy.

In some cases, electron microscopy comprises transmission electron microscopy (TEM) or scanning electron microscopy (SEM).

In some cases, a scanning probe microscope comprises an atomic force microscopy, a scanning tunneling microscopy, or a photonic force microscope.

In some cases, a microscope is an ultrasonic force microscope (UFM).

In some cases, microscopy comprises ultraviolet microscopy. In some cases, microscopy comprises infrared microscopy. In some cases, microscopy comprises digital holographic microscopy, digital pathology (virtual microscopy), or laser microscopy.

In some cases, a microscope is in fluid communication with a device for treatment and/or purification described herein. In some cases, a microscope is in fluid communication with a device for treatment and/or purification, wherein the microscope is downstream of a device for treatment and/or purification. In some cases, a microscope is in fluid communication with a device for treatment and/or purification upstream of the device for purification. In some cases, a microscope is in fluid communication with a device for treatment and/or purification upstream and downstream of the device for treatment and/or purification. In some cases, a microscope is configured to allow viewing a device for treatment and/or purification described herein.

H. Flow Cytometry

In some cases, particles (e.g., cells) that are processed (e.g., chemically and/or enzymatically processed or treated), purified, isolated, and/or concentrated using the methods, compositions, devices, systems, and/or kits described herein can be analyzed by flow cytometry. Manipulation of cells in devices in a flow cytometer can be accomplished using hydrodynamic forces. A suspension of particles (e.g., cells) can be injected into the center of a flowing sheath fluid. In some cases, forces of the surrounding sheath fluid confine the sample stream to a narrow core that can carry cells through a path of a laser that can excite associated fluorophores and create a scatter pattern.

Flow cytometry can comprise fluorescence-activated cell sorting (FACS). In some cases, a sample is subject to flow cytometry, e.g., FACS, before the sample is applied to device for treatment and/or purification described herein. In some cases, a flow cytometer is in fluid communication with a device for treatment and/or purification described herein; in some cases, a flow cytometer is fluidly connected upstream of a device for treatment and/or purification; in some cases, a flow cytometer is fluidly connected downstream of a device for treatment and/or purification described herein. In some cases, a flow cytometer is fluidly connected upstream and downstream of a device for treatment and/or purification described herein.

In some cases, particles (e.g., cells) that are analyzed by flow cytometry are labeled. In some cases, particles (e.g., cells) that are analyzed by flow cytometry are labeled using a "car wash" device as provided herein. The particles can be cells. The labeling of the cells can be surface labeling and/or intracellular labeling. In some cases, the particles are labeled with a fluorophore. In some cases, a fluorophore is attached to an antibody, and the antibody attaches to a particle (e.g., cell). In some cases, an antibody can attached to a cell membrane. In some cases, a particle is labeled with a quantum dot.

FACS can be used to sort a heterogenous mixture of particles, e.g., cells, into two or more containers. FACS can be based on the light scattering and fluorescent characteristics of each type of cell. A suspension of particles (e.g., cells) can be entrained in a flowing stream of liquid. There can be separation between particles in the liquid. The stream of particles (e.g., cells) can be broken into droplets (e.g., by a vibrating mechanism). In some cases, only one particle (e.g., cell) is in each droplet. In some cases, the before the stream breaks into droplets, the liquid passes through a fluroscence measuring station. The fluorescence characteristics can be measured. A charge can be given to each droplet based on the fluorescence measurement, and the charged droplets can pass through an electrostatic deflection system that can divert droplets to containers based on charge.

In some cases, leukocytes recovered using methods and/or devices described herein are stained with anti-Kappa-FITC (fluorescein isothiocyanate), anti-Lamda-PE (phycoerythrin), 7AAD-PerCP, and/or CD-19-APC (allophycocyanin), CD-45-APC-Cy7. A flow cytometer can be used to process and/or analyze particles, e.g., cells.

I. Acoustic Focusing

In some cases, particles processed (e.g., chemically and/or enzymatically processed or treated), purified, isolated, and/or concentrated using methods, compositions, devices, systems, and/or kits described herein are subjected to an acoustic focusing flow cytometer (e.g., Attune® Acoustic Focusing Flow Cytometer; Life Technologies™). In some cases, an acoustic focusing is used on a sample before the sample is applied to a device comprising an array of ordered obstacles. Multiple nodes of acoustically focused particles can be used. See e.g., U.S. Pat. No. 8,830,451, incorporated herein by reference. In some cases, one focal node is used.

Acoustic focusing cytometry can use ultrasonic waves (e.g., over 2 MHz) rather than hydrodynamic forces to position cells in a focused line along a central axis of a capillary. (see e.g., www.lifetechnologies.com/us/en/home/life-science/cell-analysis/flow-cytometry/flow-cytometers/attune-acoustic-focusing-flow-cytometer/acoustic-focusing-technology-overview.htm). Acoustic focusing can be independent of sample input rate. Acoustic focusing can enable cells to be tightly focused at a point of laser interrogation. Acoustic focusing can occur without high velocity or high volumetric sheath fluid. In some cases, volumetric syringe pumps can enable absolute cell counting without beads.

In some cases, acoustic resonance is driven by a piezoelectric device.

Acoustic focusing can make use of an optical cell for sample interrogation, one or more lasers, and electronics for collecting fluorescence and/or scatter information. In some cases, acoustic focusing makes use of a pump, e.g., a syringe pump. In some cases, a frequency used in acoustic focusing is about 0.1, 0.2, 0.3, 0.4, 0.5, 0.6, 0.7, 0.8, 0.09, 1, 1.5, 2, 2.5, 3, 3.5, 4, 4.5, 5, 5.5, or 6 MHz.

In some cases, a flow rate in an acoustic focusing cytometer is at least 10, 25, 50, 100, 200, 500, 1000, 2000, or 5000 $\mu$L/min.

J. Analysis of Nucleic Acids or Proteins

In some cases, a particle (e.g., nucleic acid and/or protein) processed (e.g., chemically and/or enzymatically processed or treated), purified, isolated, and/or concentrated using methods, compositions, devices, systems, and/or kits described herein can be analyzed using one or more of the following techniques: genetic testing using G-banded karotyping, fragile X testing, chromosomal microarray (CMA, also known as comparative genomic hybridization (CGH)) (e.g., to test for submicroscopic genomic deletions and/or duplications), array-based comparative genomic hybridization, detecting single nucleotide polymorphisms (SNPs) with arrays, subtelomeric fluorescence in situ hybridization (ST-FISH) (e.g., to detect submicroscopic copy-number variants (CNVs)), expression profiling, DNA microarray, high-density oligonucleotide microarray, whole-genome RNA expression array, peptide microarray, enzyme-linked immunosorbent assay (ELISA), genome sequencing, de novo sequencing, 454 sequencing (Roche), pyrosequencing, Helicos True Single Molecule Sequencing, SOLiD™ sequencing (Applied Biosystems, Life Technologies), SOL-EXA sequencing (Illumina sequencing), nanosequencing, chemical-sensitive field effect transistor (chemFET) array sequencing (Ion Torrent), ion semiconductor sequencing (Ion Torrent), DNA nanoball sequencing, nanopore sequencing, Pacific Biosciences SMRT sequencing, Genia Technologies nanopore single-molecule DNA sequencing, Oxford Nanopore single-molecule DNA sequencing, polony sequencing, copy number variation (CNV) analysis sequencing, small nucleotide polymorphism (SNP) analysis, immunohistochemistry (IHC), immunoctyochemistry (ICC), mass spectrometry, tandem mass spectrometry, matrix-assisted laser desorption ionization time of flight mass spectrometry (MALDI-TOF MS), in-situ hybridization, fluorescent in-situ hybridization (FISH), chromogenic in-situ hybridization (CISH), silver in situ hybridization (SISH), polymerase chain reaction (PCR), digital PCR (dPCR), reverse transcription PCR, quantitative PCR (Q-PCR), single marker qPCR, real-time PCR, nCounter Analysis (Nanostring technology), Western blotting, Southern blotting, SDS-PAGE, gel electrophoresis, or Northern blotting. In some cases, analysis comprise exome sequencing.

In some cases, nucleic acid is analyzed using technology from Sage Sciences, Inc. In some cases, analysis comprises DNA sizing. In some cases, DNA sizing is performed with disposable gel cassettes with precast agarose (Pippin, Sage Sciences).

In some cases, nucleic acid is analyzed using reduced-representation genome sequencing. In some case, nucleic acid is analyzed using RADseq (restriction site associate DNA sequencing). DNA is separated along a gel column until a programmed fragment rage reaches a branch point. An active electrode is then switched to divert DNA to a membrane-bound buffer chamber. When a size range has been collected, an active electrode is switched back to a separation channel. A desired sample can be removed with a pipette. DNA sizing can be 90 bp to 1.5 KB (Pippen Prep) and 50 bp to 50 Kb (BluePippen). Pippen Pulse can be a pulsed-field electrophoresis power supply that can be used with analytical gels that can allow users to resolve DNA out to 100 kb and beyond.

In some cases, a SageELF (electrophoretic lateral fractionators) can be used for whole sample fractionation for DNA and/or protein. A whole protein or DNA sample can simultaneously be fractionated into at least 12 continguous size fractions. DNA and/or proteins are separated by size in an agarose separation column. Following separation, a second set of laterally positioned electrodes can be activated to electroelute samples into chambers.

K. Next Generation Sequencing

In some cases, a nucleic acid (polynucleotide) processed (e.g., chemically and/or enzymatically processed or treated), purified, isolated, and/or concentrated using methods, compositions, devices, systems, and/or kits described herein is analyzed using next generation sequencing. In some cases, the next generation sequencing comprises Helicos True Single Molecule Sequencing (tSMS) (see e.g., Harris T. D. et al. (2008) Science 320:106-109); 454 sequencing (Roche) (see e.g., Margulies, M. et al. 2005, Nature, 437, 376-380); SOLiD technology (Applied Biosystems); SOLEXA sequencing (Illumina); single molecule, real-time (SMRT™) technology of Pacific Biosciences; or nanopore sequencing (Soni G V and Meller A. (2007) Clin Chem 53: 1996-2001; Oxford Nanopore, Genia Technologies, and Nabsys); semiconductor sequencing (Ion Torrent (Life Technologies); Personal Genome Machine); DNA nanoball sequencing (e.g., Complete Genomics); sequencing using technology from Dover Systems (Polonator). Methods next generation sequencing are described, e.g., in PCT Publication No. WO2012149472, which is herein incorporated by reference in its entirety.

L. Nucleic Acid Library Construction

In some cases, nucleic acids processed (e.g., chemically and/or enzymatically processed or treated), purified, isolated, and/or concentrated using methods, compositions, devices, systems, and/or kits described herein are used to construct a library, e.g., a next generation sequencing library. A liquid containing nucleic acid (e.g., cells, nuclei) can be flowed through a channel in a device comprising an array of obstacles. The array of obstacles can be configured to deflect particles of a predetermined size (critical size) into a flow path that is diagonal to the direction of bulk fluid flow. Smaller particles can be directed with the bulk fluid flow. Adapters can be added to nucleic acids before the nucleic acids are flowed through a device, while the nucleic acids are being flowed through a device, or after nucleic acids have flowed through a device. In some cases, adapters are compatible with sequencing using Iluminia sequencing or 454 sequencing. The adaptors can comprise sequences that are complementary to one or more sequencing primers. Nucleic acids larger and/or smaller than a critical size can be used for library formation, e.g., next generation sequencing library formation.

In some cases, nucleic acids are amplified before being flowed through a device comprising an array of obstacles. In some cases, nucleic acids are amplified after being flowed through a device comprising an array of obstacles. In some cases, particles of at least a critical size are amplified after being flowed through a device comprising an array of obstacles. In some cases, particles of less than a critical size are amplified after being flowed through a device comprising an array of obstacles.

In some cases, adaptors comprise barcodes. Barcodes can be used to identify a sample, organism, or cell from which a nucleic acid is derived.

Methods of next generation sequencing library formation are described in U.S. Patent Application Publication No. 20130079251, which is herein incorporated by reference in its entirety.

M. Cell Culture

In some cases, cells processed (chemically and/or enyzmatically processed or treated), purified, isolated, and/or concentrated using methods, compositions, devices, systems, and/or kits described herein are used for cell culture. In some cases, isolated cells, e.g., stem cells, can be differentiated in culture. In some cases, purified, isolated, and/or concentrated stem cells are used for ex vivo expansion. In some cases, stem cell subjected to ex vivo expansion purified.

In some cases, an HSC is used to give rise to blood cells, e.g., red blood cells, B lymphocytes, T lymphocytes, natural killer cells, neutrophils, basophils, eosinophils, monocytes, and macrophages. A mesenchymal stem cell can give rise to, e.g., bone cells (osteocytes), cartilage cells (chondrocytes), fat cells (adipocytes), and other kinds of connective tissue cells such as those in tendons. A neural stem cell can give rise to, e.g., nerve cells (neurons) and two categories of non-neuronal cells, e.g., astrocytes and oligodendrocytes. In some cases, a stem cell is an epithelial stem cell. An epithelial stem cell can line the digestive tract and can occur in deep crypts. An epithelial stem cell can give rise to absorptive cells, goblet cells, paneth cells, and/or enteroendocrine cells. In some cases, a stem cell is skin stem cell. A skin stem cell can occur in the basal layer of epidermis and at the base of hair follicles. An epidermal stem cell can give rise to keratinocytes, which can migrate to the surface of the skin and form a protective layer. Follicular stem cells can give rise to both the hair follicle and to the epidermis.

In some cases, cells are grown in serum-free medium. In some cases, cell culture comprises one or more growth factors. In some cases, culture medium comprises Dulbecco's modified eagle medium (DMEM), sodium azide, ascorbic acid, alpha-MEM basal medium, Iscov'es modified Dulbecco's medium (IMDM), L-glutamine, MEM non-essential amino acid, 2-mercaptoethanol, sodium bicarbonate, poly (2-hydroxyehtyl methacrylate (p-HEMA), NaOH, Percoll, PBS, PBS (without calcium and magnesium), gelatin from porcine skin, Type A, EDTA, EDTA 0.5 M, pH 8.0, MTG, monothioglycerol, fetal bovine serum defined, tyrpsin 0.05%/EDTA 0.5 mM, collagenase Type IV, neupogen, leukine, human M-CSF, Human FGF-basi, human Flt3-ligand, human Il-1beta, Human IL-3, human IL-4, human IL-5, human sRANKL, human TGF-beta1, human TNF-alpha, 1alpha, 25-dihydorxyvitamin D3, trypan blue solution, 0.4%, immersion oil, 7-aad, 7-aminoactinomycin D, bovine serum albumin Fraction V, and/or ethanol.

In some cases, antibodies are used to analyze differentiation of hematopoietic progentiors and myeloid lineages form human pluripotent stem cells. Antibodies can include anti-human CD1a, anti-human CD2, anti-human CD3, anti-human CD3, anti-human CD7, anti-human CD10, anti-human CD11b, anti-human CD13, anti-human CD14, anti-human CD15, anti-human CD16, anti-human CD16, anti-human CD19, anti-human CD34, anti-human CD41a, anti-human CD45, anti-human CD64, anti-human CD66b, anti-human CD90 (Thy-1), anti-human CD115, anti-human CD117, anti-human CD123, anti-human CD163, or anti-human CD235a. Hematopoietic differentiation of stem cells is described, e.g., at crm.nih.gov/stemcell_types/HSC/UWisc_HSC.asp.

In some cases, total leukocytes and three main populations (lymphocyte, monocyte, and granulocyte) are compared to ABX hematology analyzer count.

VIII. Systems

In some cases, devices comprising an array of obstacles as described herein are part of a system. In some cases, a system comprises at least 1, 2, 3, 4, 5, 6, 7, 8, 9, 10, 11, 12, 13, 14, 15, 16, 17, 18, 19, or 20 devices that are coupled, e.g., fluidly coupled. In some cases, a chamber or reservoir is upstream of a device comprising an array of obstacles. A chamber or reservoir can comprise a sample. A first chamber or reservoir can be fluidly coupled to a second chamber. The second chamber or reservoir can be used to manipulate particles, e.g., label particles.

In some cases, a system comprises a reaction chamber. In a reaction chamber, particles can be reacted, e.g., cells can be labeled, e.g., with a fluorescent antibody. In some cases, cells are lysed in a reaction chamber. In some cases, a cell lysis reagent comprises a detergent. In some cases, a detergent comprises Triton X-100, SDS, CHAPs, or Tween-20.

In some cases, a system comprises a pump. In some cases, a pump is fluidly connected to an inlet or outlet on a device comprising an array of obstacles. A pump can be connected to a device comprising an array of obstacles directly or indirectly. In some cases, a pump is connected to a chamber, e.g., a reaction chamber.

In some cases, a system comprises a means of propelling particles through a device or chamber. In some cases, electrical, electrophoretic, electro-osmotic, centrifugal gravitational, hydrodynamic, pressure gradient, or capillary forces are used to propel particles or fluids.

In some cases, a device comprising and array of obstacles is fluidly connected to a downstream apparatus. In some cases, the downstream apparatus permits analysis of particles from an outlet of the device. In some cases, the downstream apparatus is a microscope, flow cytometer, sequencing machine, next-generation sequencing machine, mass spectrometer, HPLC, gas chromatograph, atomic absorption spectrometer, fluorescence detector, radioactivity counter, scintillation counter, or spectrophotometer, cell counter, or coagulometer.

In some cases, a system comprises a computer. A computer can be in electrical communication with a device comprising an array of obstacles.

In some cases, a sample is filtered before being applied to a device comprising an array of obstacles. In some cases, a sample is passed through a filter after the sample has passed through a device comprising an array of obstacles. In some cases, a filtration system is in fluid communication with a device comprising an array of obstacles. In some cases, a filtration system is not in fluid communication with a device comprising an array of obstacles. In some cases, a filter is a syringe filter. In some cases, a filter comprises a pore size of 0.2 microns or 0.45 microns. In some cases, a filter comprises a 20 micron filter. In some cases, a filter comprises a pore size of at least 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87. 88, 89, 90, 91, 92, 93, 94, 95, 96, 97, 98, 99, 100, or 200 microns.

In some cases, a filter comprises a pore size of less than 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or 200 microns.

In some cases, a filter comprises a pore size of about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or 200 microns.

Systems are described, e.g., in PCT Publication No. WO2012024194, which is herein incorporated by reference in its entirety.

In some cases, a plurality of devices, e.g., microfluidic chips, can be operated simultaneously with a module. In some cases, a plurality of devices (e.g., at least 2, 3, 4, 5, 6, 7, 8, 9, 10, 11, 12, 13, 14, 15, 20, 50, 100, or 200) can be operated simultaneously with a module. In some cases, a plurality of devices can be placed inside a module, wherein each device comprises at least one channel comprising an array of obstacles. In some cases, sample application, buffer application, sample flow, buffer flow, and/or outlet collection in each of the devices can be controlled by the module.

In some cases, a module is a desktop instrument as shown in FIG. 30. In some cases, a module is electronically coupled to a computer. In some cases, a module is coupled with one or more other components, e.g., microscope, flow cytometer, next-generation sequencing machine, etc.

In some cases, a device as provided herein can be part of a system. In some cases, a device as provided herein is part of a system for processing and analyzing particle. The system can comprise: a plurality of reservoirs, a device as provided herein, and an analytical device. The reservoir can comprise a sample comprising particles, a wash buffer, or a reagent. The device can be any device as provided herein. The device can be in fluid communication with each of the plurality of reservoirs. The device can be adapted to process particles from the sample comprising particles. In some cases, the processing comprises flowing the sample comprising particles from a reservoir comprising the sample into an input of a device, and passing the particles through the device. The passing can comprises flowing the particles from the input through a plurality of parallel flow streams within the device, wherein at least one of the parallel flow streams comprises a reagent which flows from at least one of the plurality of reservoirs, and wherein the device comprises an array of obstacles, whereby the passing the particles through the device serves to process the particles as well as separate the particles by size. The analytical device can be in fluid communication with at least one of a plurality of outlet ports of the device. The analytical device can be configured to perform an analysis of particles processed by the device. In some cases, the analytical device can be any downstream apparatus disclosed herein. In some cases, the analytical device can be a device that performs any of the analyses disclosed herein. In one case, the analytical device can be a cell sorter, e.g., a flow cytometry.

Some manual process can be error-prone. For example, a manual process can introduce cytotoxic reagents, can deliver low cell yields, can selectively lose cells, can be time-consuming and can require considerable human skill and expertise to generate a uniform sample that has high yield, purity, and viability. In unfractionated human blood, red blood cells (RBCs) can greatly outnumber platelets, and white blood cells (WBCs) at about 650:40:1, respectively. In some cases, a white blood cell fraction is enriched by (1) destruction of RBC fraction (hypotonic RBC lysis), 2) separation of cells using a density gradient (e.g., Ficoll-Hypaque), or 3) using immunomagnetic particles.

IX. Devices and Systems

A suite of products for processing blood samples can be developed using microchips of various designs resulting described herein. These microchips can be designed to have handle different sample types and applications and be different shapes.

A "Sample Preparation System" (SPS) can be used. The SPS can be integrated and optimized, and comprised of an instrument that drives fluidics streams from a series of microfluidic-DLD-chip-consumables along with instrument operating protocols that can provide differing functionalities, depending on the requirements of the application.

The instrument can be the "controller" of the microchips and can provide input/output fluidics, buffer/reagent reservoirs and automation software to operate the chips. The number of fluid inputs and outputs can be determined by the requirements of each assay. The software can automate system setup, operation, and shutdown.

A series of microfluidic chips with specified levels of capability can be offered to maximize flexibility in meeting customer requirements. The chip design and associated protocols can yield as a discrete product. The chip can be integrated into a cartridge that fits into the instrument. The chip geometry can be determined by the functional throughput requirements, i.e. numbers of samples per chip, sample volume, and time to process. The chip designs can accommodate multiple independent samples depending on user requirements and cost per sample.

Examples of Sample Preparation System 1.0 (SPS 1.0) are described in Examples 13, 14, and 15. Examples of Sample Preparation System (SPS 2.0/Car Wash) are described in Examples 16, 17, 18, and 19. They can comprise an instrument, a suite of chips, and processing protocols. SPS 2.0 can accomplish multiple cell processing steps, analogous to a multistep "car wash". Conceptually similar to a car moving through a car wash that may be subjected to multiple sequential treatments (e.g. wash, rinse, wax, dry), cells flowing through the chip can be gently guided by the geometry of the posts through a programmable sequence of buffers and reagents to label, fix, permeabilize, and wash them while RBCs, platelets, and smaller particles are removed. This process can yield a "clean" preparation of target cells that can provide high quality flow cytometric results. FIGS. 46 and 47 and Example 24 provide an overview of products.

There is a need for new methods to improve the efficiency of sample preparation for the extensively used analytic method of flow cytometry. Multi-parameter flow cytometry can be a powerful and widely used technology in research and clinical diagnostic testing for cancer and many other diseases (12-14). For example, flow cytometry can be a vital analytic support tool for cell subset analysis and microsphere-based cytokine quantitation in the emerging field of immunotherapy for cancer (15). Additional important research and emerging clinical applications can include cell sorting for single cell genomics, proteomics, and metabolomics (17), subpopulation analysis for cancer and immunological diseases (18), and assessment for cardiovascular risk (19).

The microfluidic cell processing technology described herein can provide alternatives to current cell processing methods (20). Microfluidic DLD chip processes can harvest cells from a flow of fluid on the basis of size (21). Particles above a certain critical size (e,g,m, WBCs) can "bump" off the posts to flow in a direction along the tilted array axis (hence the device can be referred to as a "bump array;" FIG. 17) Smaller particles and dissolved molecules, such as red blood cells (RBCs), platelets, soluble and particulate serum constituents, Mabs, and chemical reagents can flow straight ahead, on average, with the fluid stream. Thus, after traveling across the microfluidic chip, the larger cells can have flowed out of and away from the fluid stream of the original input mixture and can be collected separately. The process can be used to remove a range of objects from an input fluid, ranging from large DNA oligomers (~100 kpb) to *E. coli* and other bacteria, platelets, RBCs and WBCs (21-23). The critical size determining which path the cells or other objects follow can be controlled by the design of the micropost array (e.g., post size and shape, gaps between posts, axis tilt angle) (24).

Methods, devices and systems provided herein can perform on-chip labeling and washing of WBCs, after harvesting them from an input stream of whole blood on the same chip, by passing them through a stream of Rhodamine 6G, although the results were not quantified (28). A "separator wall" concept is also described herein can both confined cells to the central process stream for a longer time and slowed the diffusion of reagents (28).

EXAMPLES

Example 1: Fabrication

Chips are fabricated using highly anisotropic deep reactive ion etching (DRIE) in crystalline silicon polished substrates using a "Bosch" process which cycles between etching and sidewall passivation steps, so the post sidewall differs from vertical by only ~1°. Optical lithography defines the patterns. Through-holes are micro-machined through the substrate enable fluid loading/unloading from the backside, which are mated to a plastic jig with connectors to input sources and output collection. The chip is pre-treated with Triblock copolymer F108 (2 g/l) to reduce cell adhesion. The chip design parameters (e.g. critical size for bumping behavior) are adjusted to obtain a high yield.

Example 2: Operation

Leukocytes from 0.1-1 ml of erythrocyte-lysed whole blood (optionally diluted with buffer (PBS without calcium and magnesium, containing 1% BSA and 4 mM EDTA), and optionally spiked with leukemia cells) are incubated ("immunostained") with fluorescent Mabs against multiple leukocyte differentiation cell surface antigens (i.e. CD45/CD14/15 (to enumerate monogranulocytic cell types), CD3/4/8 (to enumerate the common T lymphocyte subsets), CD19/56/14 (to identify B lymphocytes and NK cells), CD45/CD235a/CD71 (to identify any contaminating erythroid cells) and with a viability dye. This is done conventionally, i.e. off chip. Cells are then washed and concentrated to ~1-10 million cells/ml using DLD chips designed to move leukocytes and leukemia cells from the initial stream of the input cell suspension containing fluorescent Mabs to the output stream of fresh buffer against the chip wall (FIG. 17B).

The method can recover >90% of the input leukocytes, concentrated back to their original concentration in whole blood (~1-10 million cells/ml), at a flow rate of ~200 ul/min. Leukocyte viability is assessed by viability dye (goal: >90% viability), and immunolabeling is assessed by flow cytometry (FACS) to determine content of each major leukocyte cell type (i.e. yield of each of the above leukocyte types and optionally labeled spiked leukemia cells; In some cases, >90% yield of each cell type) vs the identical cells processed by standard centrifugal Wash/Concentrate methods. Quality of immunostaining of each cell type is compared after microfluidic vs standard Wash/Concentration. The amount of residual fluorescent Mabs contaminating the leukocytes obtained by both techniques by measuring fluorescence of cell-free aliquots of the starting sample and of the leukocyte products (goal: <1% of starting Mab remaining) is quantified. These fluorescence measurements are performed in triplicate wells of a 96-well plate using a fluorescence plate reader.

Analogous experiments are performed after an off-chip Fixation/permeabilization reaction on leukocytes from 0.1-1 ml of erythrocyte-lysed whole blood (optionally diluted with buffer, and optionally spiked with leukemia cells). The presence of significant amounts of residual Fixation/permeabilization reagents are determined indirectly by the level of subsequent non-selective binding of irrelevant fluorescent Mabs (fluorescent isotype control Mabs). Finally, similar experiments are performed after intracellular labeling and residual free fluorescent antibody in the leukocyte product are measured.

When the device and protocols are optimized to routinely produce output leukocytes meeting the desired criteria, a series of several successive experiments (number of experiments subject to statistical significance and power calculations) are conducted where leukocytes from a given blood sample are Wash/Concentrated simultaneously in the microfluidic device vs by an experienced individual using conventional centrifugal procedures. Statistical comparisons of cell viability, yield, purity, and leukocyte subsets are performed.

Example 3: Leukocytes from UCB

Leukocytes can be harvested from a variety of tissues. Table 5 shows leukocyte enrichment experiments from umbilical cord blood (UCB). The starting sample is 3 ml UCB, diluted 1:1 with running buffer. The leukocyte-enriched output product contained erythrocyte levels below detection (Hemavet cell counter), so product purity is determined by multicolor FACS analysis using labels against CD45, CD14, CD235a, and a viable nucleic acid dye. For the combined fractions, erythrocyte depletion is 99%, leukocyte recovery is 87%, and leukocyte purity (i.e. 100%-% erythrocytes) is 81-88%. There is some dead volume the instrument configuration, so a small portion of sample remains in the system and is not processed. With some minor engineering changes, the full sample can be sorted, and the leukocyte recovery may rise to ≥90%. Viability by trypan blue dye exclusion is >90% in all fractions. Granulocytes, lymphocytes, and monocytes are close to the initial "differential leukocyte" ratios.

TABLE 5

| | Starting | Product 1 | Product 2 | Product 3 | Product 4 | Product 5 |
|---|---|---|---|---|---|---|
| WBC count (K/ul) | 5.36 | 2.16 | 2.60 | 1.62 | 2.54 | 1.64 |
| RBC count (M/ul) | 2.41 | <0.01* | <0.01* | <0.01* | <0.01* | <0.01* |
| Volume (ml) | 3.00 | 0.45 | 0.42 | 0.47 | 3.5 | 1 |
| Yield | | 87% (for the combined Products) | | | | |
| % Viability | >90 | >90 | >90 | >90 | >90 | >90 |
| % Purity | 0.54 | 81 | 88 | Not done | 86 | Not done |
| % Granulocytes | 63.9 | 61.6 | 56.8 | Not done | 51.9 | Not done |
| % Lymphocytes | 18.6 | 17.8 | 21.1 | Not done | 25.7 | Not done |
| % Monocytes | 7.21 | 6.61 | 7.19 | Not done | 9.83 | Not done |

In some cases, separate and wash leukocytes from lysed whole blood has confirmed removal of >99% of erythrocytes, platelets, plasma proteins, and unbound Mabs, and close to 90% leucocyte recovery without introducing bias among the leucocyte subpopulations (3).

Example 4: Bead Test in Multi-Stream Microfluidic Device

Figure 20A:
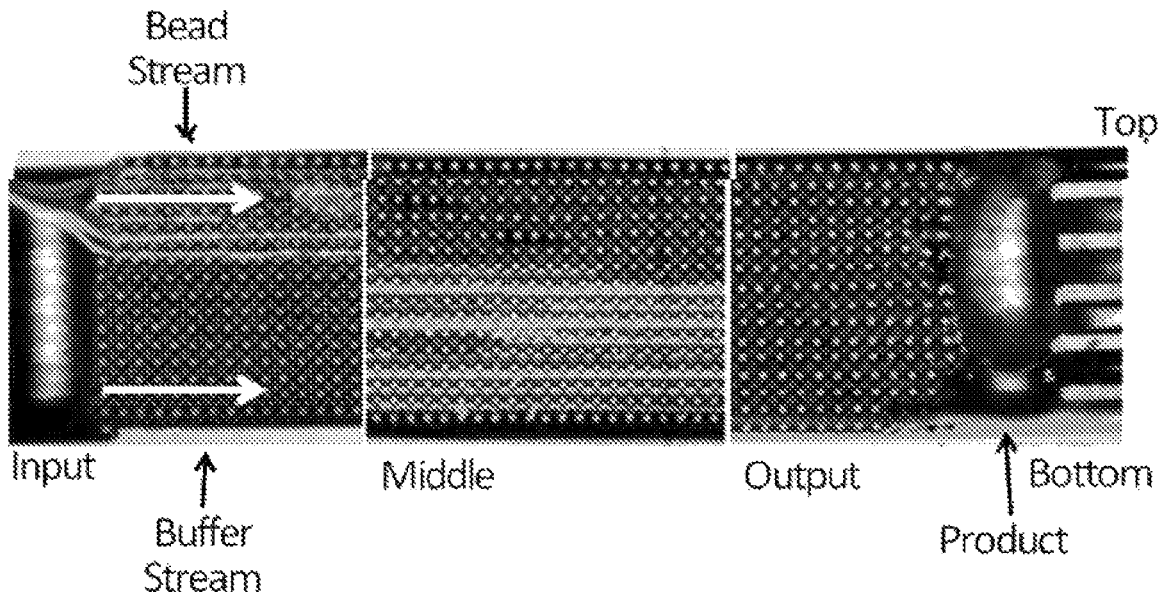
FIG. 20A shows 10 μm beads flowing from an input, middle, and output portion of a multi-stream "car wash" DLD array as shown in FIG. 19.
Figure 20B:
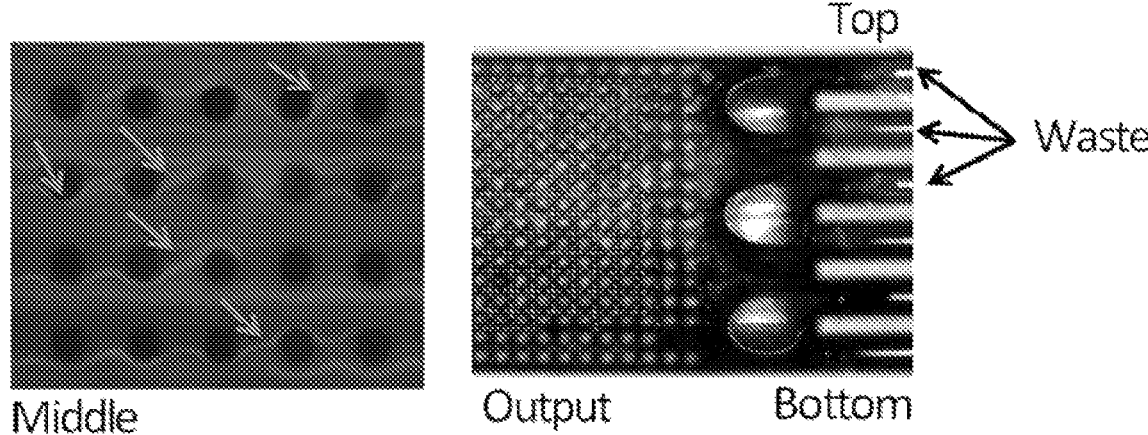
FIG. 20B shows 2 μm beads flowing from a middle, and output portion of a multi-stream "car wash" DLD array as shown in FIG. 19.
Figure 21:
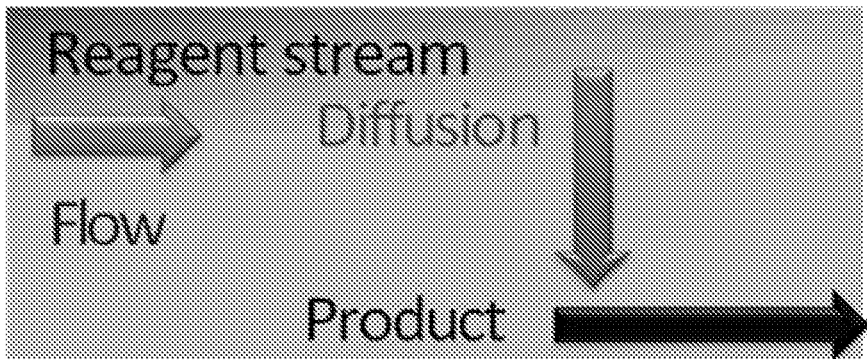
FIG. 21 shows a schematic of the diffusion between a reagent stream and an adjacent parallel flow stream as the parallel flow streams flow within a microfluidic channel.

In this example, a sample comprising fluorescently labeled 10 μm and 2 μm test beads are flowed through a microfluidic device comprising a DLD array as depicted in FIG. 19. As shown in FIG. 19, the device was configured to flow 3 flow streams in parallel from the inlet portion of the device through a DLD bump array to the outlet portion of the device. As shown in FIG. 19, the inlet portion of the device comprises 2 input wells each for the sample flow stream, the reagent flow stream and wash buffer flow stream, and 2 output wells on the outlet portion of the device, wherein each of the input and output wells is bounded by opposing walls. Each of the sample, reagent, and buffer inputs had a width of 126 microns, with an overall chip length of ~3 cm. In this example, a bead stream comprising the labeled 10 μm and 2 μm test beads and two buffer streams are flowed through the multi-stream DLD array comprising device. The DLD bump array comprised circular obstacles or microposts with a diameter of 18 μm, a gap between microposts of 18 μm, a row shift of 1/42, and a critical size of about 5 μm. The 10 μm beads were designed to mimic cell types in a solution like blood with a diameter greater than the critical size (e.g., leukocytes, diameter of about 7 μm), while the 2 μm labeled beads were designed to mimic smaller cells types in a solution like blood (e.g., red blood cells, diameter of about 2 μm). FIG. 20A shows that the 10 μm labeled beads were primarily bumped from the top of the DLD array to the last output well of the device. FIG. 20B shows that the 2 μm labeled beads were generally flowed from the sample input wells to the top four output wells of the device.

Figure 24B:
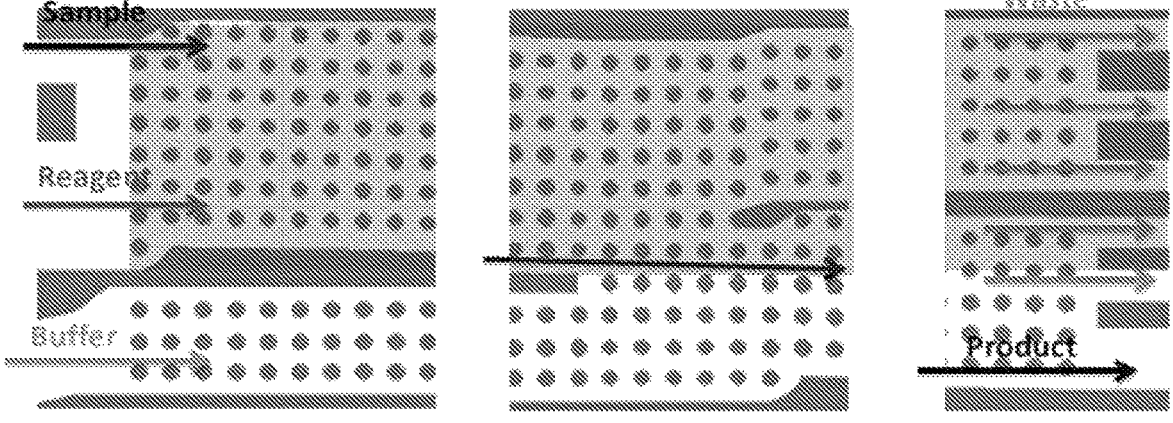
FIG. 24B shows input, middle, and output views of a multi-steam "car wash" DLD array as described in FIG. 24A comprising a pair of opposing separator walls that extend into the array of obstacles for multiple sequential chemical processing.
Figure 25:
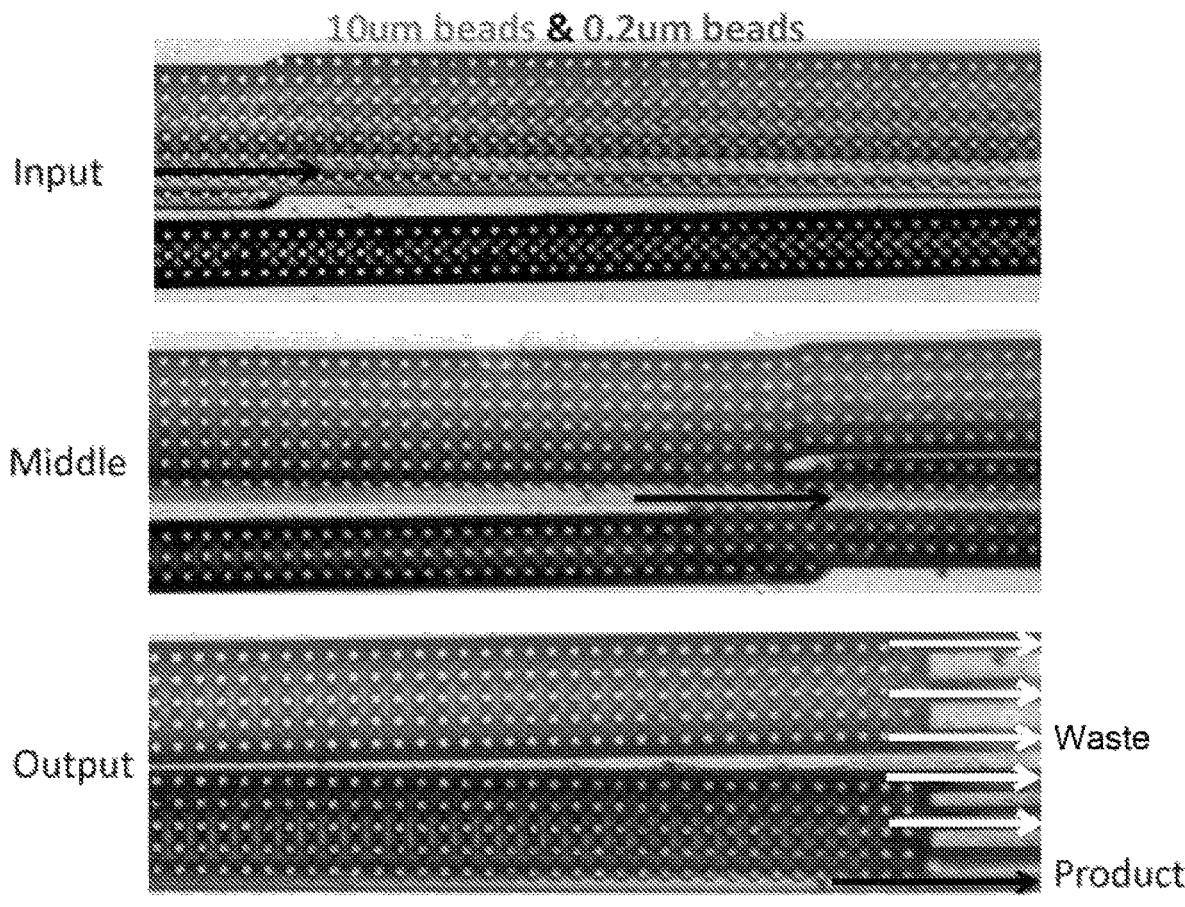
FIG. 25 shows the results of running a sample comprising 2 μm and 10 μm labeled beads through a "car wash" DLD array comprising a pair of opposing separator walls as depicted in FIGS. 24A and B.

Example 5: Bead Test in Multi-Stream Microfluidic Device Comprising Separator Walls In this example, diffusional mixing between parallel flow streams was tested by flowing 10 and 0.2 μm labeled test beads through a modified multi-stream (car wash) microfluidic device comprising a pair of opposing walls within the DLD array and oriented parallel to the flow direction as depicted in FIGS. 24A and B. The modified limited-source diffusion model depicted in FIG. 22 was developed to describe spreading of the central chemical stream in the device depicted in FIGS. 24A and B vs. in the device depicted in FIG. 19. In this example, the device used to test the 10 and 0.2 μm labeled test beads was designed to contain a critical size of 7 microns such that particles above this size were driven across the chemical stream and smaller particles flowed along the fluid flow direction. As can be seen in FIG. 25, 90% of the particles (10-micron test beads) in the source stream were successfully moved across the chemical stream and concentrated and harvested at the output. The contamination was measured by using the 0.2 micron fluorescent beads as a marker for the location of the central stream chemical. As seen in Table 1, the diffusion constant ($1 \times 10^{-8}$ $cm^2\ s^{-1}$) of the 0.2 micron beads was comparable to that of most monoclonal antibody labels, as would be used in conventional and modified designs. The fluorescence in the central and output streams for both the conventional (FIG. 19) and modified (FIGS. 24A and B) device was shown in FIG. 26. Overall, a 20× reduction in contamination was observed in the output at a low flow rate (>0.1 mm/s) and a 10× reduction at a high flow rate (>1 mm/s) using the device depicted in FIGS. 24A and B, which was in good agreement with simulation. Further, the time spent in the central processing stream was increased by a factor of 3. In summary, the device design in FIGS. 24A and 24B enabled a practical limitation for continuous-stream on-chip chemical processing and washing of cells to be improved by over an order of magnitude.

Figure 23:
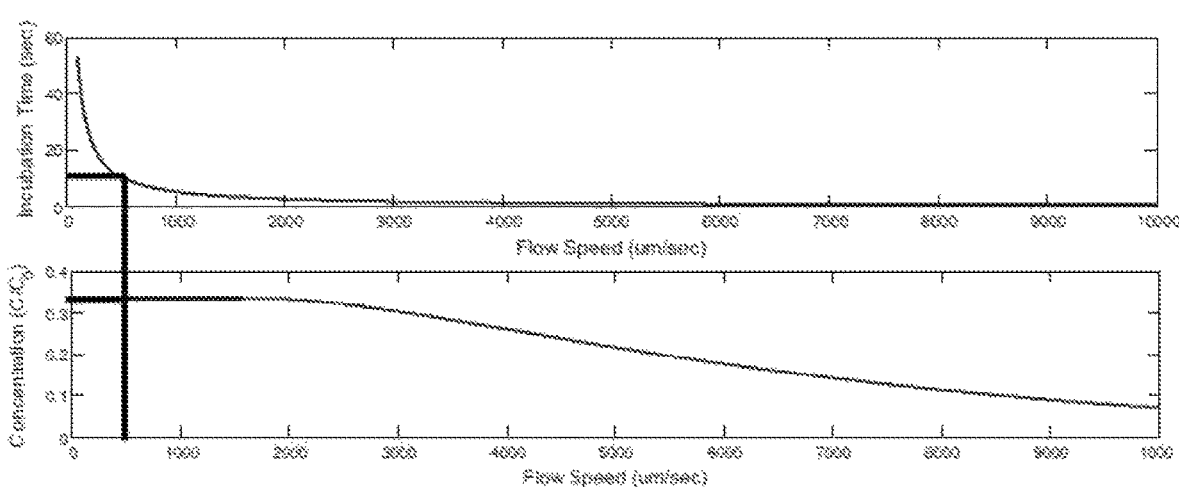
FIG. 23 shows the relationship between incubation time and flow speed (top) as well as the relationship between concentration and flow speed (bottom) in a "car wash" chip as depicted in FIGS. 18A and 19.
Figure 31:
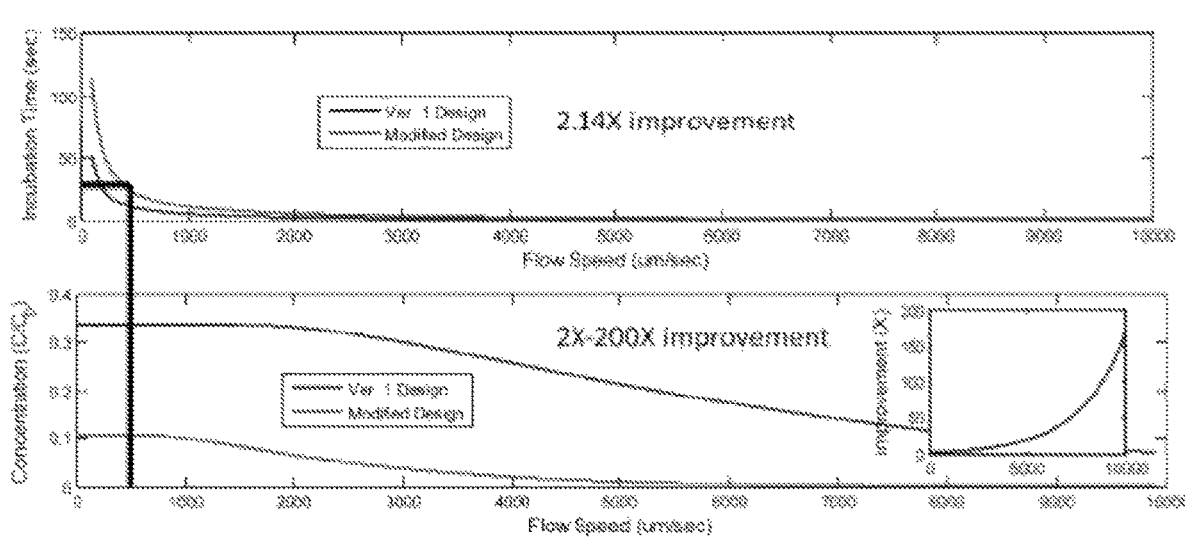
FIG. 31 shows the relationship between incubation time and flow speed (top) as well as the relationship between concentration and flow speed (bottom) in a "car wash" chip with (Modified design.

Example 6: Testing Diffusional Mixing Between Adjacent Flow Streams in Two "Car Wash" Devices In this example, diffusion mixing of a methanol reagent stream with an adjacent parallel flowing buffer stream was tested in device as depicted in FIG. 19 or FIG. 24B. FIG. 23 showed the relationship between concentration of a reagent (i.e., methanol; diffusion coefficient in water of $10^{-5}$ $cm^2$/sec) and incubation time with flow speed for a device as depicted in FIG. 19, wherein the device had an overall length of 3 cm, sample, reagent and buffer input widths of 126 μm, circular microposts with 18 μm diameter, a gap of 18 μm, a row shift of 1/42, and a critical size of ~5 μm. As can be seen, a 10 second incubation time led to output with methanol at 33% of that in the reagent stream. In comparison, FIG. 31 showed the relationship between concentration of a reagent (i.e., methanol; diffusion coefficient in water of $10^{-5}$ $cm^2$/sec) and incubation time with flow speed for a device as depicted in FIG. 24B, wherein the device had an overall length of 3 cm, an input separator wall with a length of 6 mm, an output separator wall with a length of 12 mm, sample, reagent and buffer input widths of 126 μm, circular microposts with 18 μm diameter, a gap of 18 μm, a row shift of 1/42, and a critical size of ~5 μm. In summary, the modified device design in FIG. 24B showed a 2-200× reduction in the concentration of methanol and a 2.14× improvement in incubation time at low flow speeds. Thus with the modified design, the same incubation time can be run at higher flow speeds, while at the same flow speed, the modified design can achieve higher wash efficiency.

Figure 27A:
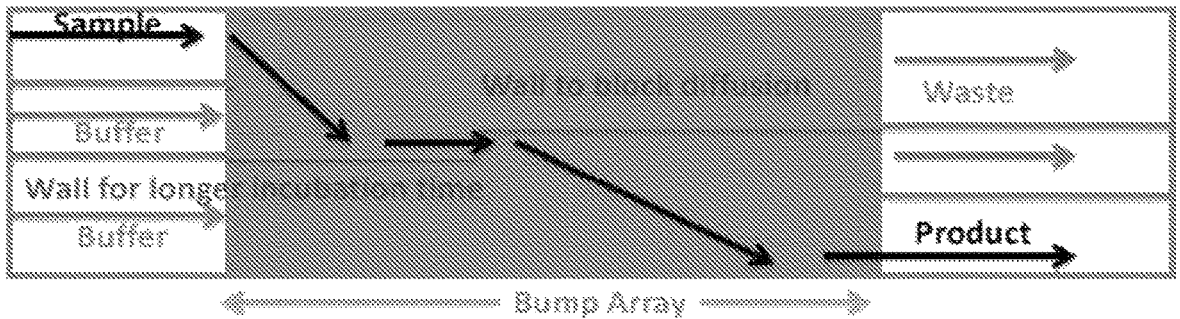
FIG. 27A shows a model of "car wash" chip comprising a sample stream, and 2 adjacent buffer streams further comprising a pair of opposing separator walls that extend into the interior of the bump array and separate the two buffer streams.
Figure 27B:
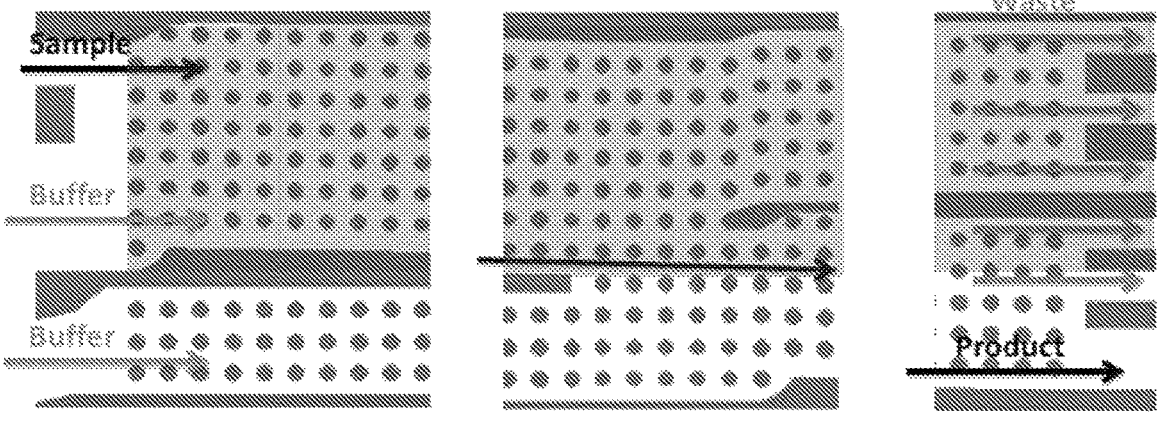
FIG. 27B shows input, middle, and output views of a multi-steam "car wash" DLD array as described in FIG. 27A comprising a pair of opposing separator walls that extend into the array of obstacles for multiple sequential chemical processing.
Figure 28:
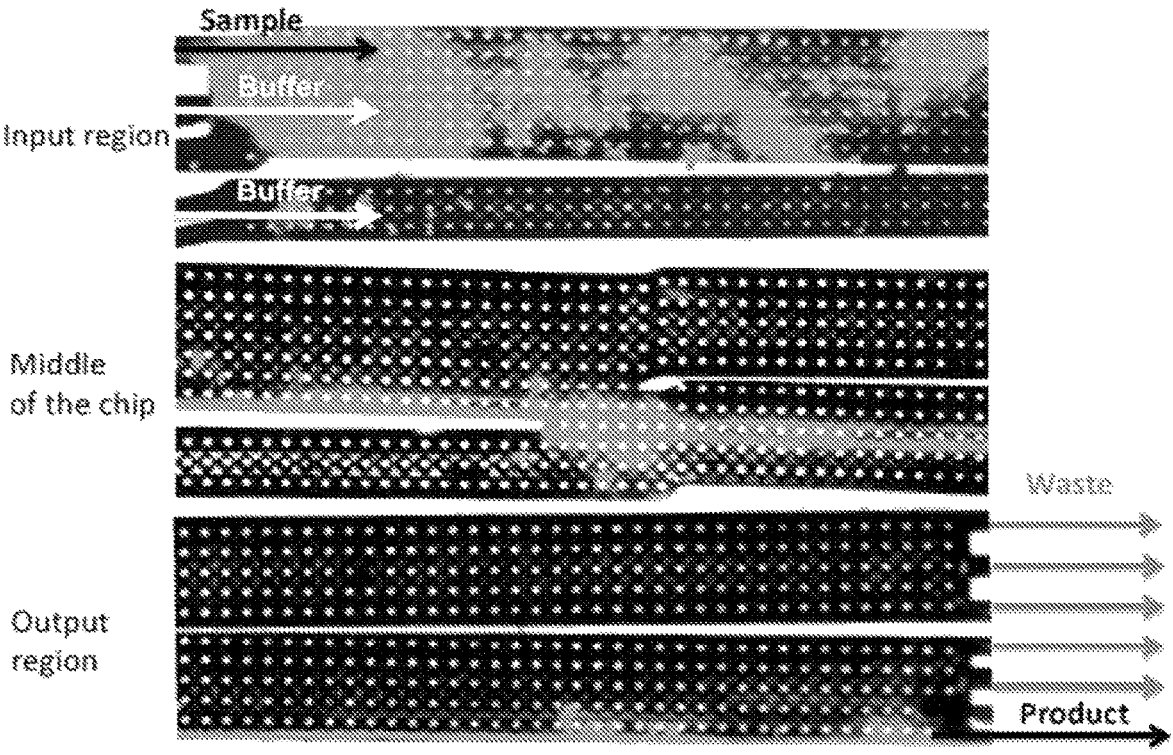
FIG. 28 shows the results of running a blood sample through a "car wash" DLD array comprising a pair of opposing separator walls as depicted in FIGS. 27A and B.
Figure 29B:
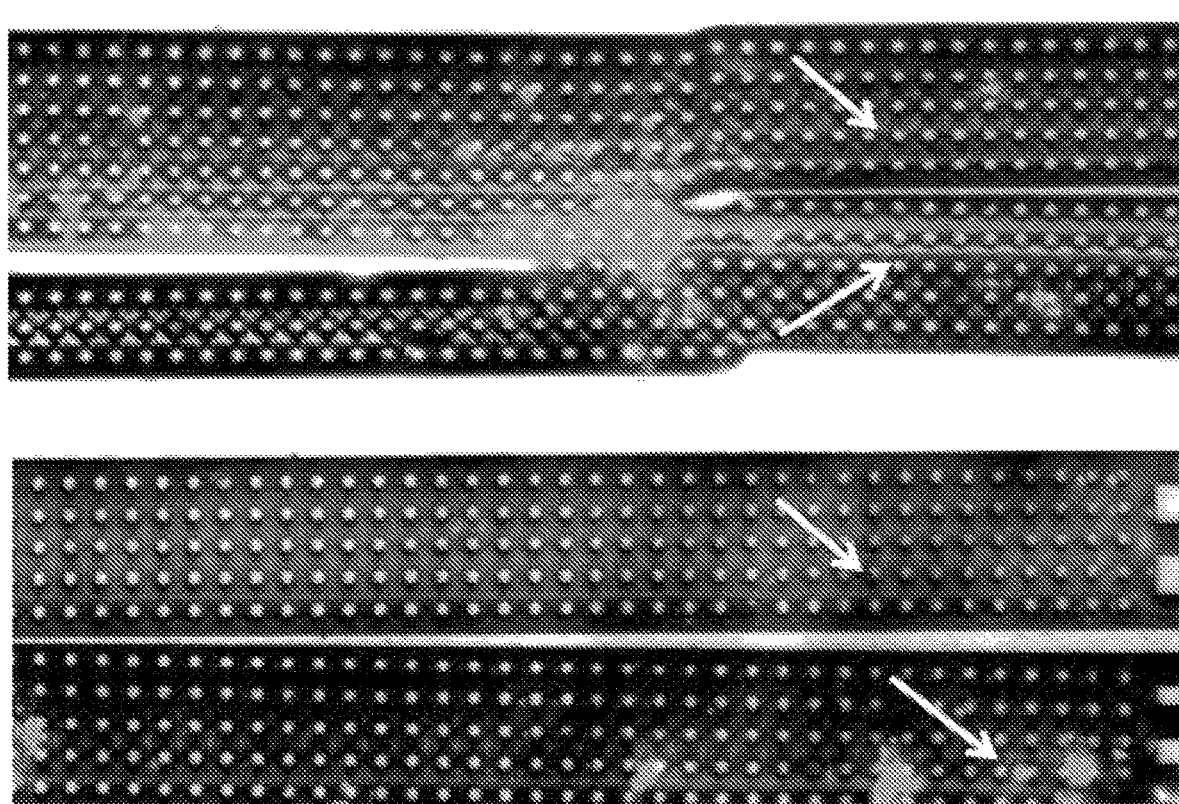
FIG. 29B shows magnified views of areas of potential clogging in the middle and output portions of the array of obstacles shown in FIG. 29A.

Example 7: Blood Test in Multi-Stream Microfluidic Device Comprising Separator Walls In this example, diffusional mixing between parallel flow streams was tested with blood being flowed through a modified multi-stream (car wash) microfluidic device comprising a pair of opposing walls within the DLD array and oriented parallel to the flow direction as depicted in FIGS. 27A and 27B. In this example, blood was diluted 4-fold, the red blood cells were lysed, and the resulting blood sample was centrifuged to remove the platelets. Subsequently, 5 mls of the processed fluorescently labeled blood sample is then run through a device as depicted in FIGS. 27A and 27B at a flow speed of 0.1 ml/min for 50 minutes. As can be seen in FIG. 28, a significant portion of the labeled blood cells in the source stream were successfully moved across the chemical stream, through the gap between the input separator and out separator walls, and concentrated and harvested at the output. FIG. 30 showed the difference between the blood input and the outputs of the device, which showed successful removal of the RBCs. Some clogging was observed in the various regions of the device as observed in FIGS. 29A and 29B.

Example 8: Bead Test in Microfluidic Device with On-Chip Cleaning System

Figure 34A:
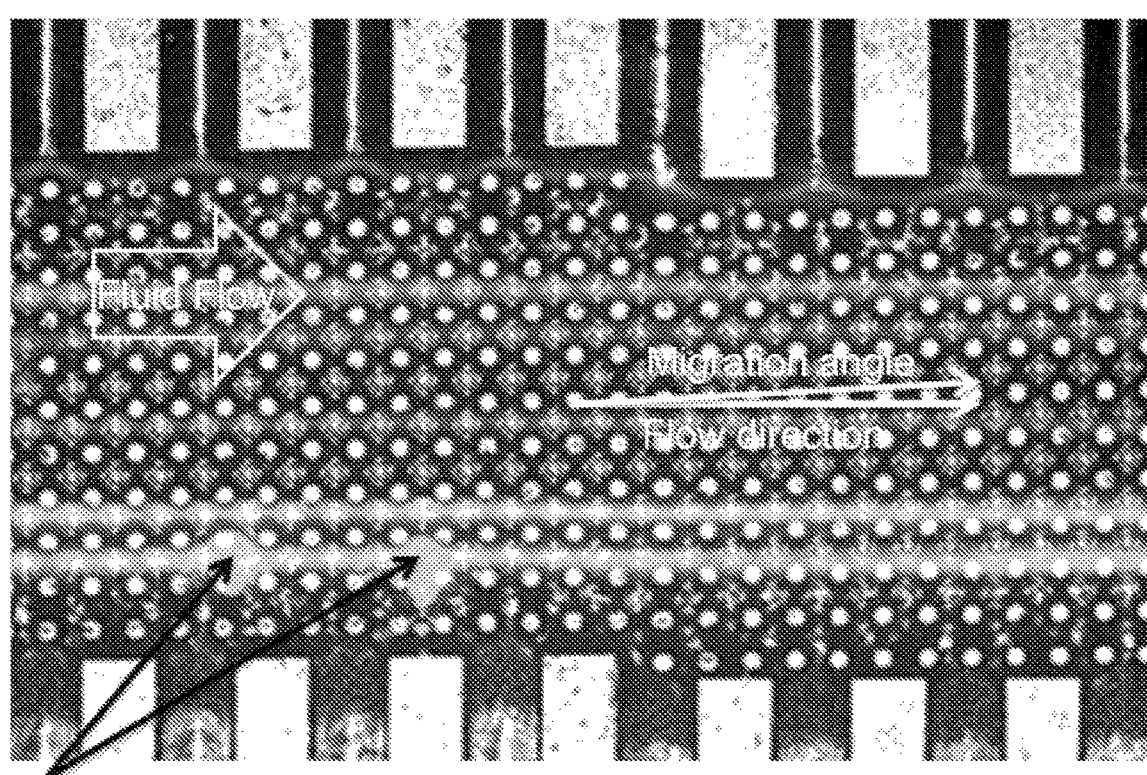
FIG. 34A shows clogged beads in a DLD array comprising an on-chip cleaning system as depicted in FIGS. 33A-C following flowing of labeled beads through the DLD array during the bump mode.

In this example, a sample comprising fluorescently labeled 10 μm test beads were flowed through a microfluidic device comprising a DLD array and an on-chip cleaning system as depicted in FIGS. 34A and C. The device used in this example comprises microposts with a diameter of 18 μm, a gap between microposts of 18 μm, a row shift of 1/42, and a critical size of about 7 μm. 6 mls of a sample comprising 10 μm green fluorescently labeled beads ($1 \times 10^5$ beads/ml) was flowed through the device at 0.1 mL/min for 60 minutes in the bump mode, followed by 5 ml of F108 buffer flow at 0.5 ml/min to remove any remaining unclogged beads. Finally, 5 ml of a cleaning stream (also F108 buffer) was flowed at 0.5 mL/min in the cleaning mode to clean the device. As shown in FIG. 34A and the top of 34B, clogged beads were observed in the device following the bump mode, which were substantially removed following the cleaning mode (bottom of FIG. 34B).

Example 9: Reducing Clogging

FIG. 36 illustrates results of experiments identifying calcium-dependent integrins and thrombin-induced platelet activation as the dominant contributors to platelet-induced clogging of DID arrays. The bottom line is that FIG. 36 shows how an approximately 3× increase in the flow rate can be used to achieve a further reduction in clogging on top of that achieved by 5 mM EDTA and 40 uM PPACK. [NOTE: these plots show on the x (horizontal) axis the volume of blood that has been processed through an array, and on the y (vertical) axis the fluorescence of leukocytes stuck in the array. Diluted blood was actually processed, but this x-axis represents the amount of undiluted blood that was used before dilution and which flowed through the chip. The leukocytes were tagged with a fluorescent dye before putting the blood in the array, so the fluorescence measures the number of stuck cells. This array was an array with 40 micron triangular posts and the gap width is 27 micron.

The array had parameters commonly used for isolation of leukocytes, or circulating tumor cells. The human blood was supplied by a vendor and treated with a level of 1 ml/ACD per 8 ml blood. (before the 3:1 dilution). Typical ACD is composed of 22.0 g/L C3434 (Citric Acid, trisodium salt, dihydrate); 7.3 g/L C0759 (Citric Acid, anhydrous); and 24.5 g/L G7528 (D-(+)-Glucose).

Standard test conditions involve diluting the sample blood 3:1 with a buffer before processing. The average flow rate is ~4 cm/s. The depth of the etched array in silicon was ~0.15 mm. The standard run time was 30 minutes. ~3 ml of the diluted blood mixture was processed in this time, corresponding to 0.75 ml of whole blood. Additives were added to the diluted mixture before processing. The leukocytes were tagged with a fluorescent dye before putting the blood in the array, whereby the fluorescence measures the number of stuck cells.

Note in FIG. 36 that the following experimental observations for different additives to input are noted: 1 mM EDTA (1 mM in the diluted blood input) gives a rapid increase in the fluorescence signal (from stuck leukocytes) indicating rapid clogging; 5 mM EDTA (in the diluted blood input) reduces clogging to about 1/8 of the level of 1 mM EDTA; ACD (1 ml per 9 ml of the diluted blood input) reduces clogging similar to 5 mM EDTA. Heparin (40 units per ml of the diluted blood input (with no EDTA) shows some reduction in clogging. Adding 40 uM PPACK to the 5 mM EDTA reduces the clogging to a nearly undetectable level. Increasing the flow rate by a factor of ~3× (with 5 mM EDTA and 40 uM PPACK) gives ~2.3 mL of whole blood throughput in the chip in one array in 30 minutes for one array, and still negligible clogging.

Figure 37:
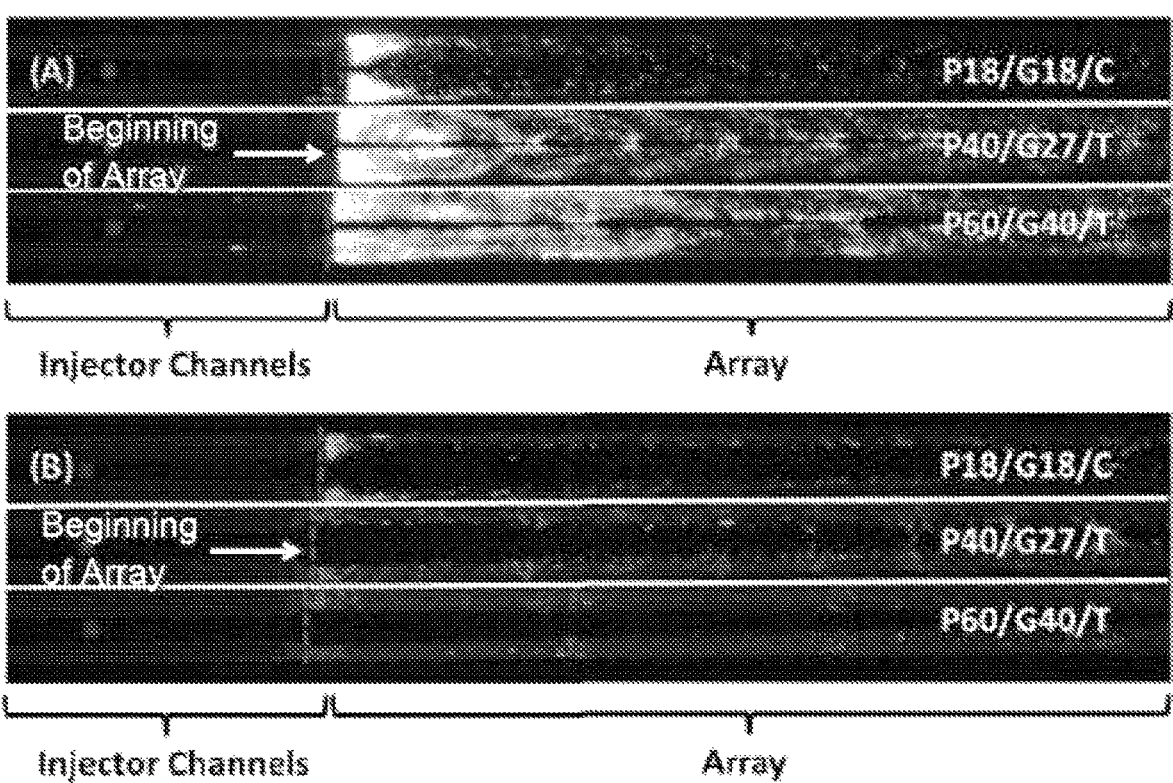
FIG. 37 shows images of clogging in arrays with three different parameters for (a) 1 mM EDTA and (b) 5 mM EDTA and 40 μM PPACK. The volume of blood through each channel and the flow rate was the same in both (a) and (b). The flow direction was left to right. Green indicated stuck or clogged leukocytes.

These results have been demonstrated for both circular and triangular posts with array parameters that are commonly used for isolation of leukocytes and circulating tumor cells from blood. FIG. 37 shows images of the clogging with 1 mM EDTA and with 5 mM EDTA+40 uM PPACK for each of three different array parameters. The top two arrays (P18/G18/C [[post diameter 18 um; gap 18 um; circular posts]] and P40/G27/T [[posts 40 um; gap 27 um; triangular posts]]) have parameters commonly used for isolation of leukocytes, while the bottom array (P60/G40/T [[posts 60 um; gap 40 um; triangular posts]]) can commonly be used for isolation of circulating tumor cells. The conclusion is that the combination of an agent to reduce calcium dependent pathways (such as calcium chelating agent (5 mM EDTA) and a thrombin inhibitor (40 uM PPACK) works best in all chip designs.

Figure 38:
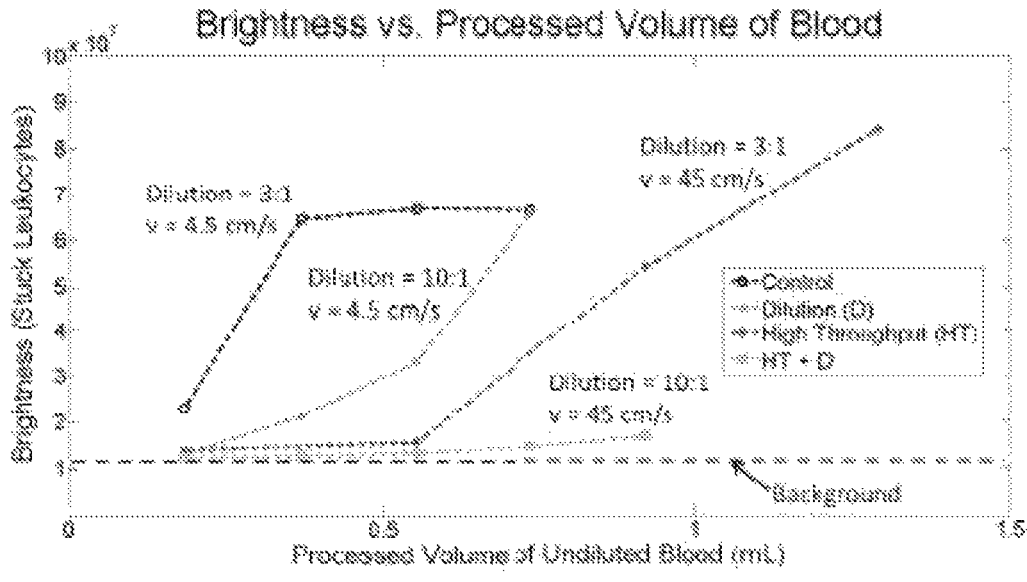
FIG. 38 shows the effect of flow rate and blood dilution on clogging of a DLD array as provided herein.

Example 10: Experiments Identifying Effects of Higher Flow Rates and Greater Blood Dilutions on Clogging in DLD Arrays In a supporting experiment (FIG. 38) to Example 9, it is shown that higher flow rates and greater blood dilutions can be used to further reduce clogging in the micro post array. The data is all for the same condition of a 1 mM EDTA in the diluted blood input to the chip. The times of each experiment are different, but the key is the amount of fluorescence (representing stuck leukocytes) for a given equivalent whole blood of input. This should be as small as possible for the same amount of blood input. The hypothesis that the higher flow rate allows less time for platelet aggregates to form in the array and provides a greater force to prevent platelet-post adhesion, and that the higher dilution prevents the formation of platelet aggregates by minimizing platelet-platelet interaction. FIG. 38 shows that a combination of a 3× increase in blood dilution and a 10× increase in flow rate each reduce clogging, with the combination reduce clogging by a factor of 10×.

In summary, Examples 9 and 10 demonstrated that >2.25 mL of blood can be processed per DLD array at a level of clogging well below that at which chip performance begins to degrade. This corresponds to >30 ml of blood per standard chip with 15 DLD arrays. Furthermore, given the fact that clogging does not seem to increase vs. time for the best case (high-throughput, PPACK, and EDTA in FIG. 36), from our results >250 mL of blood can be processed using a standard chip with 15 DLD arrays before clogging begins to significantly degrade device performance. This achievement can be attributed to four measures that reduced clogging: 1. Disabling the activity of calcium-dependent integrins on platelets and/or decreasing calcium dependent thrombin formation by increasing the concentration of EDTA from 1 mM to 5 mM. Other methods which reduce or block calcium can act similarly. 2. Preventing thrombin-induced platelet activation and fibrin production through the use of the direct thrombin inhibitor PPACK at a concentration of 40 uM. Other methods which inhibit or reduce thrombin can act similarly. The following 2 experimental conditions also reduce clogging: 3. Higher flow rate (which can be due to less time for reactions leading to clogging to occur). 4. Higher dilution (which can be due to minimized platelet-platelet interaction that leads to the formation of platelet aggregates.)

Example 11: DLD Microfluidic Technology to Wash and Concentrate Leukocytes from Blood White blood cells (WBCs), which are larger than other cell types and debris in normal blood, move at an angle compared to the fluid flow direction (FIG. 17B, 17C). WBCs moved out of the input stream and into a clean buffer stream, and were thus effectively washed free of other cells and unbound Mab without the need for conventional RBC lysis or centrifugation.

Figure 43:
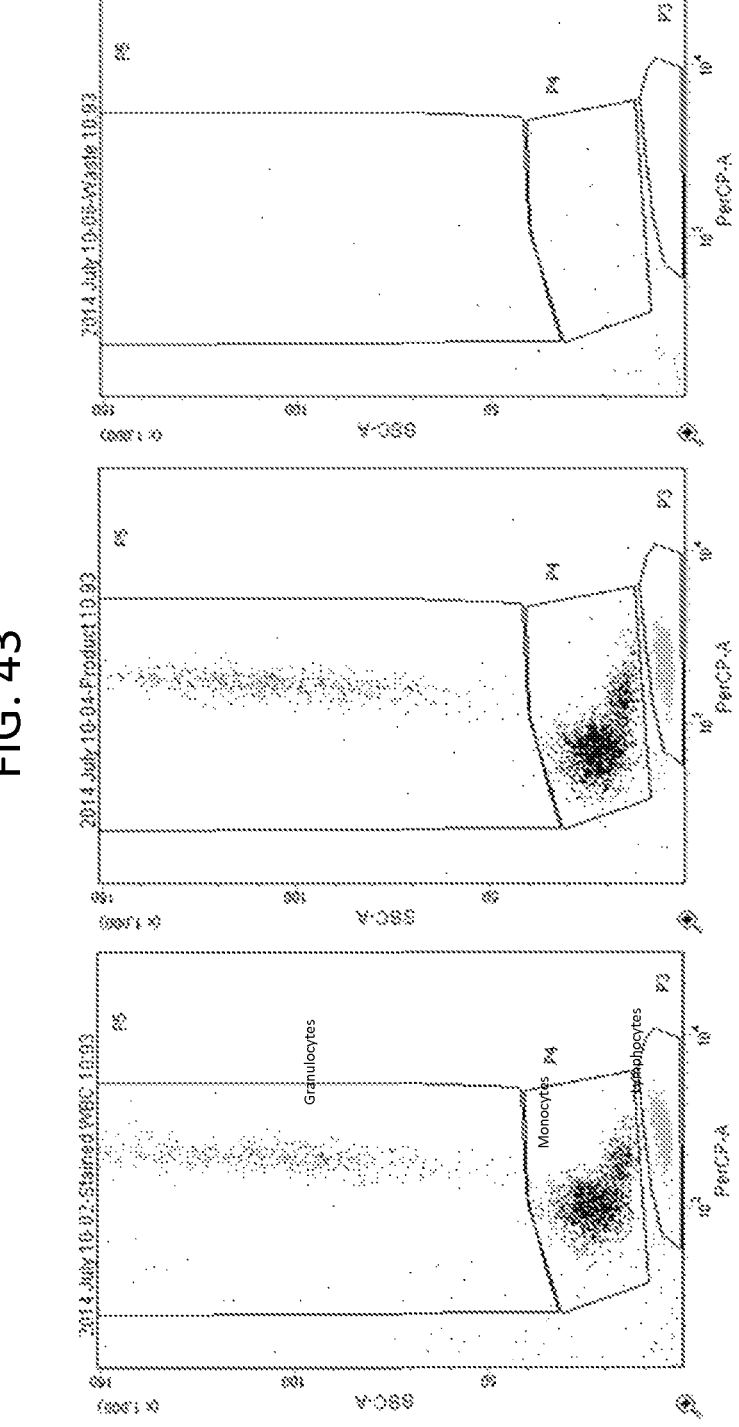
FIG. 43 illustrates flow cytometry cytograms showing WBCs collected by on-chip wash and concentration of the WBCs. Y-axis: side light scattering; X-axis: CD45 immuno-labeling.

WBC fractions collected by conventional RBC lysis and centrifugation were labeled with fluorescent Mabs against CD19 (pan-B lymphocyte marker) and CD3 (pan-T lymphocyte marker) off-chip, then small samples (about 100 μL diluted with 100 μL buffer) were washed on-chip. The product and waste fractions were analyzed by cell counting and flow cytometry. In a representative run (Table 6 and FIG. 43), 97% of WBCs were recovered in the product fraction, in a smaller, more concentrated volume than the input sample. Cell viability consistently was greater than 90%. Recoveries of greater than 90% were achieved for all 3 major WBC subsets (granulocytes, monocytes, lymphocytes), and each subpopulation was distinct and had excellent flow cytometric signal intensity, similar to the input sample. Lymphocytes are the smallest WBCs, so may be most suspected to be lost during the size-based DLD processing; nevertheless, it was found that the numbers of CD3+ T cells and CD19+ B cells were preserved in the product, as was their labeling quality. This result indicated that DLD chip harvesting preserved the quality of these subsequent flow cytometric analyses.

Removal of unbound label can be useful in flow cytometry to reduce background, increase signal precision, and prevent nonspecific reagent binding to cells during potential subsequent fixation/permeabilization steps. Therefore, fluorescence of centrifuged input and output samples was measured with a fluorimeter (microtiter plate reader set to detect fluorescence of unbound fluorochrome-conjugated Mabs). A series of experiments showed that chip washing removed initial fluorescence ranging from about 99% removal to at/below the limit of detection. The latter equated to greater than 91% removal of free Mab. Instrument sensitivity can be modified to detect ultra-low levels of fluorescence in order to measure a higher degree of Mab removal.

TABLE 6

Washing of a WBC fraction on the DLD chips yielded 97% recovery of WBCs with no skewing of WBC subset distribution. This is a representative run from several runs with similar results.

|  | Input | Output Product |
|---|---|---|
| WBC count (K/μL) | 1.5 | 1.6 |
| Volume (μL) | 200 | 181 |
| Total % WBC recovery |  | 97 |
| % Granulocytes | 13.0 | 11.2 |
| % Monocytes | 49.6 | 51.6 |
| % Lymphocytes | 37.4 | 37.2 |
| % CD3+ T cells | 59.7 | 61.0 |
| % CD19+ B cells | 20.7 | 20.4 |

Example 12: Combining Microfluidic Leukocyte Harvesting with the DLD Wash/Concentrate System into a Single Step RBCs can be present in blood at a 1,000-fold excess over WBCs. Thus, removing RBCs before analysis can be useful to avoid long flow cytometric analysis times. Using a fluorescence threshold during flow cytometry can overcome this issue to some extent, but this can cause loss of light scatter information that helps to distinguish cell types. Therefore, residual RBCs were measured by microscopy, Hemavet and Coulter counters, and flow cytometry. Whole blood was labeled off-chip with CD19 and CD3. DLD chip input was ~100 ul whole blood diluted in 100 ul buffer.
WBC Recovery and RBC Removal.

Table 7 shows the results of a representative experiment. WBC recovery was 97% and the percentages of the WBC subpopulations are essentially identical in product vs. input. In a series of 9 experiments repeated over several weeks, an average of 99±4% of the input WBCs were recovered in the product fraction, and 2.1±0.6% of WBCs in the waste fraction. On average, greater than 99.5% of starting RBCs were removed from the product fraction. Subset analysis in the product fraction indicated that the distribution of the 3 major WBC subpopulations was maintained in the product to within 1% of their distribution in the input. The average for 6 experiments with stained whole blood showed that the variation was only 0.8±0.4% for granulocytes, 0.4±0.2% for monocytes and 1.0±0.4% for lymphocytes—demonstrating consistent results across samples and over time.

TABLE 7

Washing and harvesting WBCs from whole blood on the DLD chips yielded ≥97% recovery of WBCs with >99.5% removal of RBCs and no skewing of the subpopulations. This is a representative run from several that gave similar results.

|  | Input | Output Product |
|---|---|---|
| WBC count (K/ul) | 2.9 | 3.1 |
| RBC count (M/ul) | 1.99 | 0.01 |
| Volume (ul) | 200 | 181 |
| Total % WBC recovery |  | 97 |
| % Granulocytes | 59.9 | 61 |
| % Monocytes | 5.4 | 5.5 |
| % Lymphocytes | 34.7 | 33.5 |
| % CD3+ T-cells | 74.4 | 76.3 |
| % CD19+ B-cells | 15.0 | 13.6 |

Clogging.

The issue that cells from whole blood might aggregate or clot and clog the channels in DLD chips was addressed. Clogging can be an issue when input sample sizes were much more than 100 μL of whole blood. Adding anticoagulants, such as a calcium chelator (5 mM EDTA) and a thrombin inhibitor (40 μM D-Phenylalanyl-L-prolyl-L-arginine chloromethyl ketone; PPACK) can allow greater than 2000 μL blood through a single channel on a DLD chip without clogging (data not shown).
Conclusion.

The results shown herein demonstrate that DLD chips as described herein can harvest Mab-labeled WBCs from an input incubation mixture of fluorescent Mabs in human whole blood with high WBC recovery and viability, while depleting RBCs and unbound Mabs, and without skewing the distribution of WBC subsets (Table 8). Free Mabs were removed to the limit of detection, greatly increasing S/N ratios of flow cytograms. These results were consistent among 3 collaborating laboratories and using devices fabricated from both silicon/glass and plastic. Finally, flow cytometric analysis results of cells processed on the chips were in high quality.

TABLE 8

Summary of results of WBC harvesting and washing using DLD chips
Result obtained 99 ± 4% recovery of WBCs in product fraction, N = 9
Populations of granulocytes, monocytes, lymphocytes in Product were within 1.0 ± 0.4% of those in input sample
>99.9% RBCs removed from Product fraction, N = 27
96-99% of WBCs in product were viable
≥90% of unbound Mabs removed from Product fraction, N = 3

Example 13: Microfluidic DLD Chip-Based System for Washing Human WBCs after Conventional Surface Labeling of Whole Blood Results FIG. 43 and Tables 6-8 describe the basic approach and results for washing WBCs that have been immunostained conventionally (e.g., off-chip) in whole blood. Because WBCs are larger than RBCs, platelets, plasma components, and Mabs, the DLD chip can harvest the WBCs out of an input stream of blood. Because the RBCs are efficiently depleted, it may not be necessary to lyse RBCs as in conventional processing. The DLD chip approach can effectively wash WBCs and reduce both the RBC count by greater than 99%. Yield can be greater than 90% of WBCs harvested in the output, with greater than 90% viability.

Methods.

Samples for multiple healthy blood donor can be used. WBC processing on-chip can be accomplished in less than 10 min for 100 µl samples. Flow cytometric evaluation of the input and output cells can expanded to enumerate several critical WBC subsets, using commercial multicolor Mab cocktails that are widely used in cancer research and diagnosis.

Outcome Measures.

Aliquots of the DLD chip input and output are characterized as in the Results above. Flow cytometric evaluation can be expanded using the following Mab cocktails for surface labeling (25-26) (these kits contain specified numbers of beads to allow flow cytometric total cell counts): CD4/CD8/CD3 Trucount (BD Tritest Cat#340401); CD3/ CD19/CD45 Trucount (BD Tritest Cat#340405); CD3/ CD16+56/CD45 Trucount (BD Tritest Cat#340403); CD45/ 14 (BD Simultest Cat#340040); CD34/CD45/Nucleic Acid Dye Procount Progenitor Cell Enumeration Kit (BD Cat#340498; determines total stem-progenitor cell count, total nucleated cell count and total WBC count); CD34/ CD45/7-AAD ISHAGE Stem Cell Enumeration Kit (BD Cat#344563; determines total stem-progenitor cell count by ISHAGE algorithm); IgG1/IgG1/CD45 Isotype Control (BD Tritest Cat#340385).

Samples from healthy adult volunteers with a panel of commonly used surface and intracellular labels can be used. Samples from patients with a variety of diagnoses such as cancer, infectious disease, etc., and representing adult, children and racial/ethnic minorities can be used.

Example 14: Microfluidic DLD Chip-Based System for Washing Human WBCs after Conventional Fixation and Permeabilization Before intracellular labeling, it can be necessary to stabilize ("fix") the cells using a chemical crosslinking reagent and then to permeabilize the cell and intracellular (e.g. nuclear) membranes to allow intracellular labels to enter the cell. For example, current protocols can use formaldehyde for fixation and methanol for permeabilization (29). After these steps, the cells can be washed to remove these denaturing chemicals, prior to incubation with the intracellular labeling reagents (e.g. Mabs). The fixation/permeabilization step can be performed on isolated WBCs off-chip, using a standard protocol, e.g., the one described in Chow et al., (Chow S, Hedley D, Grom P, Magari R, Jacobberger J W, Shankey T V. Whole blood fixation and permeabilization protocol with red blood cell lysis for flow cytometry of intracellular phosphorylated epitopes in leukocyte subpopulations. Cytometry A. 2005; 67(1):4-17), which is incorporated herein in its entirety. Then, the conventional centrifugation wash step is replaced with a DLD chip-based wash. The DLD chip-based wash is performed as in FIG. 17B, except that the input is the mixture of the isolated WBCs and the fixation/permeabilization reagents. The large fixed/permeabilized WBCs are bumped to the output, and the formaldehyde, methanol, etc. move straight through to the waste. Yield of WBCs is evaluated as in Preliminary Results. Rather than measure the residual levels of formaldehyde, methanol, etc., the DLD chip-washed fixed/permeabilized WBCs are immunostained and then evaluate the quality of the intracellular immunostaining, as compared to a separate aliquot of the same starting WBC sample labelled by a conventional manual protocol (e.g., all label and wash steps completed off-chip) (27), such as the one described in Chow et al., (Chow S, Hedley D, Grom P, Magari R, Jacobberger J W, Shankey T V. Whole blood fixation and permeabilization protocol with red blood cell lysis for flow cytometry of intracellular phosphorylated epitopes in leukocyte subpopulations. Cytometry A. 2005; 67(1):4-17), which is incorporated herein in its entirety.

Outcome Measures.

The following commercial Mabs and cocktails are used for intracellular labeling: Anti-pStat1-PE (BD Biosciences Cat#612564; detects phosphorylated Stat1 transcription factor); Anti-IFN-gamma (BD Biosciences Cat#554552); FITC BRDU Flow Kit (BD Pharmingen Cat#557891)+7-AAD Staining Solution (BD Pharmingen Cat#559925); Phosflow Kit (BD Cat#560750; detects p38 MAPK, ERK, Stat1, Stat3, Stat6, Human T cell cocktail; contains reagents to simultaneously analyze multiple T cell markers with one of several intracellular phosphoproteins to study T cell subset-specific signaling; FoxP3 staining kit: FoxP3/CD4/CD25 (BD Pharmingen Cat#560133; FoxP3 transcription factor is a marker for regulatory T cells (Treg), and is selectively expressed intracellularly by the majority of CD4+CD25++ T cells in blood while less than half of CD4+CD25+ cells are FoxP3+; Kit also contains CD4 and CD25 Mabs); FastImmune IFN-gamma/CD69/CD8/CD3 (BD Cat#346048; IFN-g is expressed intracellularly in most CD8+ T cells, by the TH1 and TH0 subsets of CD4+ T cells and by NK cells upon activation; CD69 is present on activated T, B and NK lymphocytes).

Example 15: Microfluidic DLD Chip-Based System for Washing Human WBCs after Conventional Intracellular Labeling After intracellular labeling, washing may be performed to remove the unbound intracellular labels. There are cell processing protocols for flow cytometric analysis that do not require washing. These methods can suffer from high background fluorescence. The DLD chips described herein can be used to replace the centrifugation and resuspension steps, and flow cytometry can be used to evaluate recovery and immunostaining of DLD chip-processed vs. conventionally (off-chip) processed cells, using the Mab cocktails.

Another potential advantage of DLD chip processing can be that the waste output from this step (FIG. 17C) should contain only the buffer and the unbound labels, with the amount of buffer roughly equal to that of the input. Thus this "waste" can contain the unused labels which may then be "recycled" to use again in future steps. This may be significant because of the high cost of some Mab labels, especially multi-Mab cocktails. This potential recycling of reagents is further evaluated herein.

Data Analysis and Outcome Measures:

To ensure that the results are representative of a future product, each of the DLD chip processes is examined (sequentially, as they are perfected) for robust reproducibility across multiple (e.g., greater than 10) donor blood samples using the DLD chips and automated microfluidic Platform System. Experimental results are compared to results from manual sample preparation by an expert cytometrist. Results from the chips may show better cell yield and comparable or better reproducibility as measured by the coefficient of variation of the subset numbers, and equivalent or higher S/N ratios. These results can be representative of the performance of products to be offered for licensing and sale.

For washing after the fixation/permeabilization and intracellular labeling steps, respectively, fixed/permeabilized WBCs can be slightly smaller and more rigid than viable WBCs. This feature can be important because bumping and the resulting DLD chip-based cell separation can depend on cell size and to a lesser degree on cell stiffness. Therefore, to optimize the bumping of the fixed/permeabilized WBCs, the post array parameters can be adjusted slightly compared to those used to date for viable WBCs. Further, the diffusion coefficient of methanol in buffer ($\sim 10^{-5}$ cm$^2$/s) is larger than that of Mabs ($\sim 10^{-6}$ cm$^2$/s). Thus the washed product is more likely to be contaminated by the fixation/permeabilization reagents (e.g. methanol) than by the unbound Mab labels. This feature can be addressed by slightly increasing the flow speed or making minor changes in the DLD chip design, such as an increased width of the buffer input, so that the reagents can diffuse farther (perpendicular to the fluid flow) to reach the output channel.

Example 16: Microfluidic DLD Chip-Based System to Harvest WBCs from Whole Blood, and then Surface Label and Wash them, all on the Same Chip (FIG. 42)

WBCs are first harvested on-chip from whole blood, followed by on-chip surface label and wash steps. The methods can increase process automation and allow potential recovery of unused label.
Methods.

A chip like that of FIG. 18A can be used, and a surface label such as CD45 Mab. The WBC labeling efficiency is adjusted by the label concentration and the dwell time in the central labeling stream. Dwell time, which is the incubation time, can be controlled by the flow speed of the fluid (typically about 1 mm/s), the width of the labelling stream (typically about 0.5 mm), and the tilt angle of the array (2° to 6°), to give about 10 s-20 s dwell time. The total flow time through the chip can be on the order of a few minutes. The yield of labeled WBCs (and the fluorescence intensity of each Mab-defined WBC subset, as determined by flow cytometry) is compared to that obtained using conventional off-chip labeling and washing methods. The recovery of unused label (by creating a separate chip output for it) is tested and measured by fluorescence compared to the input stream of the label. The fluid flow rates and chip design parameters can be adjusted in response.
Data Analysis.

The experiments can achieve: labelling (or fixation/permeabilization) yields as high as conventional methods, greater than 90% WBC recovery, greater than 99% RBCs removed, greater than 90% viability, greater than 90% removal of unbound Mabs and flow cytometric analysis quality comparable to that of conventionally processed cells.

Example 17: Microfluidic DLD Chip-Based System to Fix, Permeabilize, and Wash Surface-Labeled WBCs Fixation/permeabilization on-chip followed by on-chip washing is performed (FIG. 42).

Methods.

For on-chip labeling of permeabilized cells, the fixation/permeabilized cells are introduced into the cell input port of the chip and reacted with the fluorochrome-conjugated reagents listed in Examples 13 and 14. Flow cytometry is performed in parallel with manually processed cells. Data Analysis is as described for Example 16.

Example 18: Microfluidic DLD Chip-Based System to Intracellularly Label and Wash Surface-Labeled WBCs Intracellular labeling and washing are performed on the same chip (FIG. 42). A design like that of FIG. 18A is used, with fixation/permeabilizationed cells as the input and a surface label as the central process stream.
Methods.

Prior surface labeling and fixation/permeabilization steps are performed by conventional off-chip methods. The intracellular labels to be used include pStat1, the phosphorylated form of the Stat1 transcription factor and the cytokine IFN-gamma. Phycoerythrin-conjugated antibodies (e.g., BD Biosciences Cat#s 612564 and 554552) are used for the tests. Permeabilized cells are introduced into the cell input port of the chip and reacted with the fluorochrome-conjugated reagents. Flow cytometry is performed in parallel with manually processed cells. Examples 16, 17, and 18 are performed across multiple samples using a system platform provided in the disclosure (e.g., Examples 20 and 21). A chip with one or more separator walls is used.

Example 19: Microfluidic DLD Chi-Based System to Fix, Permeabilize, Intracellularly Label, Wash, and Concentrate WBCs on a Single Chip All the steps involved in WBC preparation for flow cytometry are combined onto a single DLD chip (FIG. 42).
Methods.

A chip design similar to that of FIG. 18A is used, with the detailed design of each region based on the outcome of Examples 16, 17, and 18. The chip has a single input (whole blood, which may already be labeled). The chip has at least 2 process streams (to enable fixation/permeabilization and intracellular labeling). The chip can have separate streams for fix and for perm. The chip has another stream for surface labeling after the cells have been harvested from whole blood. The chip has at least 3 buffer inputs, one final output channel for the prepared cells, and at least one waste output. Additional output channels can be used for collecting unused labels.
Outcome Measures:

See Example 15.
Data Analysis.

The automated approach is compared to conventional methods for yield, subset ratios, and flow cytometric measurements with at least 5 preparations from the same blood sample and for at least 10 donors. A sample can be run through two or three chips, one after the other.

Example 20: Chip Materials and Manufacture Prototype Application-Specific Microfluidic DLD Chins for WBC Processing As shown in FIG. 42 and described above, a separate chip and protocol can be designed depending on the desired protocol. Each of these systems can become a separate product. Chip geometry can be determined based on the product requirements of throughput, numbers of samples per chip and cost considerations. For example, to increase throughput, channel depth can be increased, more lanes can be added in parallel or the pressure drop across the chip can be increased. Further, the flow rate and design can be chosen, e.g. using the separator wall concept to increase the interaction time of the stain and cells, if required, without increasing output contamination.

Methods.

For each chip design, a computer-aided design (CAD) drawing is made with multiple replicates of the chip design fitted on the size of a 4" or 6" wafer. Using photomasks generated from the CAD drawings, a pattern with smooth near −90° sidewalls is etched in a Si wafer using the deep reactive-ion etching (DRIE) process. The Si chips can be used as masters to create plastic chips by soft embossing. First, a silicone rubber material is cast onto the Si chips to form a negative replica of the Si chip master. The hardened silicone is then used as an embossing tool to hot-emboss the microstructures into a thermoplastic material. Chips are made with different polymers such as COP (cyclic olefin polymer), PMMA (poly methyl methacrylate) and PP (polypropylene), with depths as great as 120 μm and gaps between pillars as small as 9 μm. The final plastic parts of ~1.5 μm which are accounted for by adjusting the CAD designs for this bias. After soft embossing, the chips are cleaned sealed with adhesive tape. Both PSA and heat activated adhesive tapes are used. The materials of choice include PMMA for the embossed chip and a hydrophilic heat activated adhesive tape for the lid. All designs and materials are chosen so that the system can be sterilized easily for future use in culturing cells after cell sorting, e.g. by either e-beam or ethanol.

Figure 44:
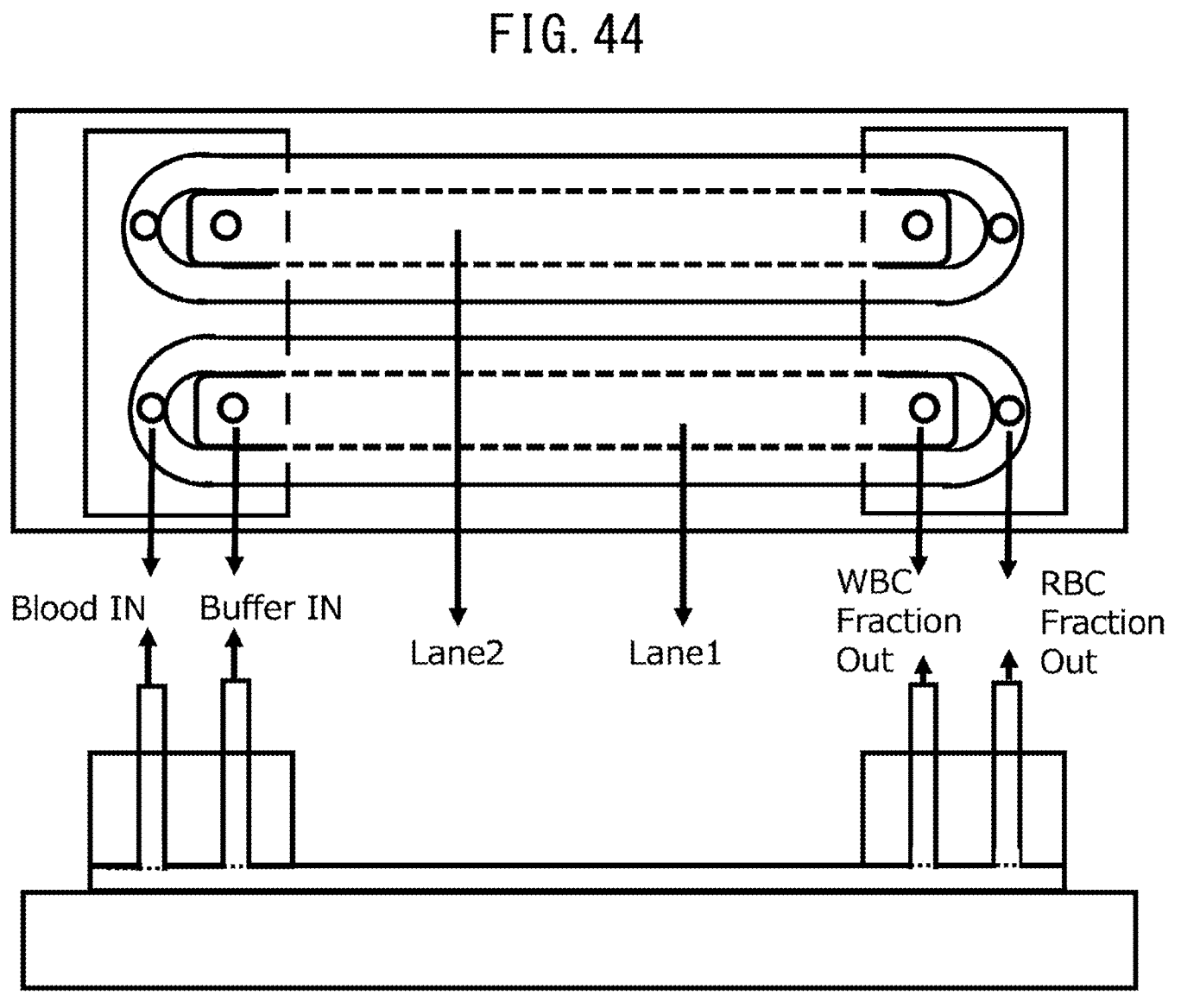

For each chip design, a manifold is designed with the necessary fluid inputs and outputs, with low dead volume. Multiple samples can be run in parallel on the same chip, to reduce the cost per sample using the chip technology. This can be done by fabricating multiple independent lanes on the same chip, where each lane can be independently load and have product extracted. For example, FIG. 44 shows a chip in a manifold having 2 independent channels per chip and each channel has 2 inputs and 2 outputs. A chip and system can be developed for 8 independent samples (each with input and outputs) on the same chip. The manifolds are made of acrylic polymer and utilize stainless steel tubing as inlet and outlet ports and hence the manifold can be sterilized easily.

For each chip design, the critical dimensions of the Si masters and the plastic chips are characterized. SEMs of cross-sections are calculated to measure etch depth of the Si master and the embossed depth of the plastic chips. Pillar diameters and gaps are measured using optical microscopy. All chips are inspected for defects such as missing pillars, bent pillars and debris. QC criteria for inspection of the chips are established. Since there is a lot of redundancy in the number of pillars, small defects such as a few missing pillars are acceptable and the chips are fully functional even with these small defects. For each chip design, a corresponding manifold and a set of run conditions (pressure timing scripts) are obtained to perform the various operations of labeling, wash, fixation/permeabilization, etc. on the chip. Chip performance is gauged first by doing dummy runs with buffer solutions before processing cell samples. Data analysis are performed.

Optionally, separate chips can be designed and the output of one chip can collected and manually introduced into the input of the next chip.

Example 21: Fabricating an Automated Platform Product to Control WBC Procession Via a User Interface An automated platform can perform 3 functions: 1) It can provide the proper flows to each of the input streams to the chip. This can be done by connecting the appropriate reservoir to each chip input, and applying the appropriate pressures to each one (typically a few psi). 2) It can collect the appropriate cells in the outputs for subsequent flow cytometry (or other characterization), or for further processing (off-chip or on another chip). This can be done by connecting each chip output to an empty collection reservoir, or potentially directly to another chip. 3) It can provide a simple user interface, with automation to specify the fluidics process to achieve desired output.

An instrument that contains hardware and software to control the flow of various fluidic streams through the microfluidic chip is designed. As described in Example 20, a manifold can be designed and fabricated to fit each DLD chip optimized. Multiple chip designs are tested, and hence multiple manifolds designed and fabricated can be used to fit the different chips. The instrument can have the capability to run all the various chip designs, and hence no major changes to the instrument maybe needed as new DLD chip/manifold designs are generated.

Methods.

An exemplary instrument controls a chip in a manifold, with 2 input streams and 2 output streams. The instrument has 2 independent pressure control sources so that the pressure of the 2 input streams can be independently controlled. A function of this platform is to keep the pressure stable without fluctuation during runs. Pressure sources that can be incorporated into this platform are readily available commercially (e.g. Fluigent). Up to 7 independent pressures, a maximum pressure of 20 psi and up to 6 output collection streams can be used. For running multiple independent samples on a chip, each independent pressure source can be distributed by the manifold to drive each sample individually. These capabilities can be designed into the instrument. Pressures on specific fluid streams may be changed during the course of a run. The pressures can be controlled through software, and a script can be written to change pressures at the desired times.

Each generation of chips are tested with multiple replicates and data are analyzed as described. Instrument functionality is tested by running buffer solutions through the microfluidic DLD device using pressure profile scripts. Multiple runs are done on each blood sample, and the desired output fractions are collected and characterized. The results are compared to anticipated performance for each chip design, and compared to cells processed conventionally (off-chip) in parallel. The reliability of the system is assessed by evaluating the variation over multiple runs with the same set up.

The instrument can connect to all the various manifold designs generated for each chip configuration. The instrument can be capable of storing the running conditions (pressure timing scripts) for each chip design, and a user can select and run the appropriate script for each design. Once the output fluid fractions are collected they are analyzed. Clogging can be prevented by using volumes on the order of 100 μL, or adding anti-clotting additives described in this disclosure.

Example 22: Microfluidic Chemical Processing
with On-Chin Washing by Deterministic Lateral
Displacement Arrays with Separator Walls This example describes a microfluidic device for on-chip chemical processing, such as staining, and subsequent washing of cells. "Separator walls" are introduced to increase the on-chip incubation time and to improve the quality of washing. Cells of interest are concentrated into a treatment stream of chemical reagents at the first separator wall for extended on-chip incubation without causing excess contamination at the output due to diffusion of the unreacted treatment chemicals, and then are directed to the washing stream before final collections. The second separator wall further reduces the output contamination from diffusion to the washing stream. With this approach, on-chip leukocyte staining with Rhodamine 6G and washing are demonstrated. Other conventional biological and analytical process can be replaced by the device.

Introduction

Preparation steps for the analysis of biological cells can involve the chemical treatment of the cells (such as staining by monoclonal antibodies, a fixation/permeabilization step, etc.). These steps can be followed by a "washing" step to remove the unbound labels or excess treatment chemicals from the treated cells, to yield treated and washed cells. Both the treatment and the washing can include multiple manual steps, such as pipetting, centrifugation, and re-suspension of a pellet after centrifugation. These steps can be labor-intensive and can cause variations to the quality of prepared cells and the results of subsequential analysis or diagnosis. (30)

Automated and integrated processing and preparation of cells can be performed to obtain more uniformly prepared samples. Some microfluidic devices can perform one of the cell preparation steps. M. A. McClain, et al. have shown a microchannel for on-chip cell lysis using electric field.(31) Conventional centrifugation (and washing) can be performed before (and after) the on-chip cell lysis. Moreover, the distinctive structures of these devices can lead to difficulties in higher level integration. J. Nguyen, et al. have presented a PDMS microfluidic system for on-chip blood cell preparation and analysis,(32) which has a design of multiple functional sections and can need accurate fluid controls to function correctly.

Other cell preparation and processing devices include a "centrifuge on-chip" device for cell preparation using simple rectangular shaped channels.(33) The underlying separation mechanism of on-chip vortices can limit the cell capture efficiency to 20% and purity to 40%. Integrated microfluidic devices for chemical treatment with high cell capture efficiency can be limited by the diffusion of the treatment chemical. The diffusion of the treatment chemical can cause a contamination at the output by the treatment chemical and a decrease of the effective concentration of the treatment chemical. A high fluid velocity can be used to avoid this diffusion. In one device, inertial lift force is utilized as the separation mechanism to give very high cell capture efficiency.(34) The cells are directed into a sodium carbonate stream from a hematoxylin suspension buffer with an acetic acid stream as diffusion barrier to avoid the mixture of sodium carbonate and hematoxylin suspension buffer. The fluid velocity can be ~0.6 m/s for a treatment chemical's diffusion constant of $10^{-9}$ m$^2$/s, which can achieved by a separate on-chip or off-chip incubation.

K. Morton et al. have presented a method for on-chip cell processing in a continuous-flow microfluidic chip, in which deterministic lateral displacement (DLD) arrays are used to move target cells into and then out of a treatment chemical processing stream.(35) High fluid velocities can be used to avoid the diffusion of the treatment chemical. The device design and high cell capture efficiency and purity (36, 37) make the device attractive. In this example, an on-chip cell processing and preparation approach are demonstrated to achieve both long incubation time and low contamination of the excess treatment chemical using "wall-separated" DLD arrays. The device is a three-input (sample stream, treatment stream, and washing stream) microfluidic device for on-chip leukocyte staining and washing using Rhodamine 6G (R6G) with little output contamination. R6G molecules can be used as a staining dye in biological analysis (38) and can have diffusion constant of $4\times10^{-10}$ m$^2$/s in water, close to that of ethanol, methanol, and 1-2 orders of magnitude higher than that of monoclonal antibodies, (39) all of which can be used in chemical and biological treatment.

Materials and Methods

Microfluidic Device Design

Figures 48A, 48B, 48C, 48D:
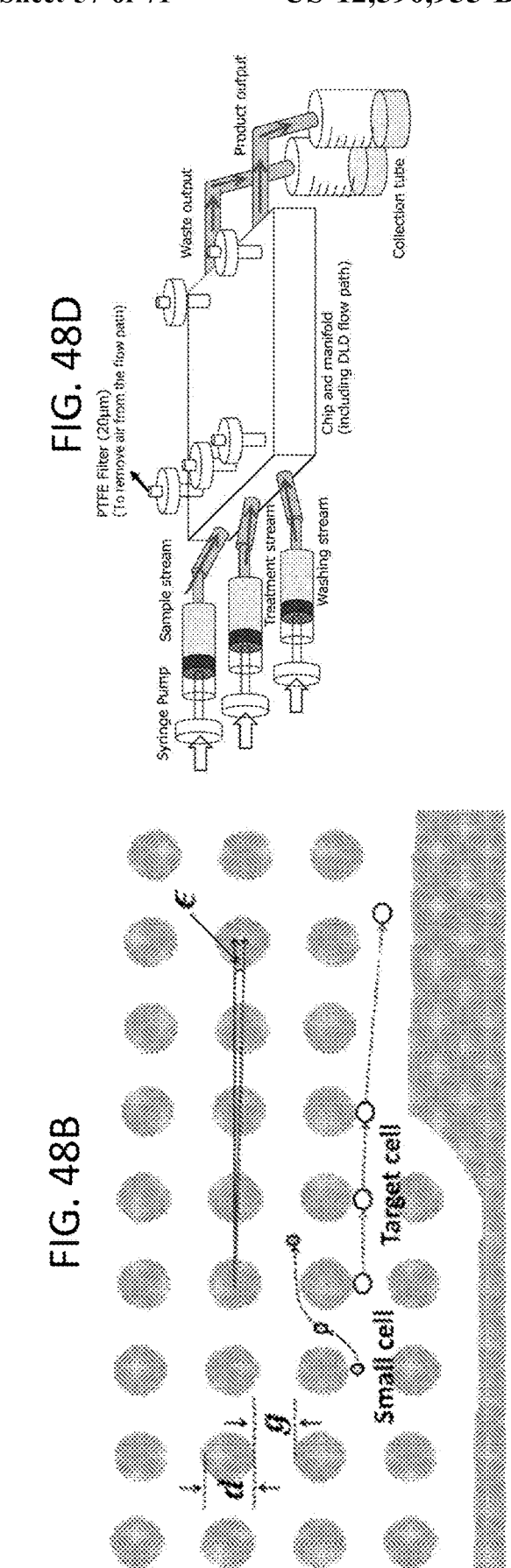
FIGS. 48A-D illustrate an example of separator walls of a DLD device.

FIG. 48A demonstrates the "wall-separated" deterministic lateral displacement (DLD) array design. The input includes three streams: a sample stream (diluted blood in our experiments), a treatment stream (such as staining chemicals), and a washing stream (such as bovine serum albumin (BSA) buffer). The output includes two streams: the product of treated and washed cells, and waste. In the central region there is a DLD array consisting of an array of posts slightly tilted by a small angle $\epsilon$ from the average flow direction imposed by the walls. Cells smaller than a critical size $D_c$ (small cell in FIG. 48B) can follow the stream waving around the posts in an average horizontal direction as pointed out by the black arrow. Cells larger than this critical size (target cell in FIG. 48B) can follow the axis of the post array, "bumping" off of the post in each column as pointed out by the red arrow.(40) The large cells move into the treatment stream to be treated and then out of the treatment stream to be washed and collected as product output (FIG. 48A).(34) The critical size can be determined by the geometry of the DLD array. (40) In this work, as shown in FIG. 48B, with d=18 μm diameter spherical posts and g=18 m gaps between the posts, and $\epsilon=1.36°$, the critical size ($D_c$) is about 6 μm. The wall edges of the DLD array are designed according to D. W. Inglis' guideline. (41)

A first wall can prevent any chemical diffusion (indicated by shading in FIG. 48A) towards the output while the cells are being incubated. The target cells or particles are concentrated at the first separator wall of length $l_1$=2 cm, and then they are directed into the washing stream. After the first separator wall, target cells can be bumped by the DLD array and driven into and across the washing stream to be collected. The treatment stream is now free to diffuse to the product output and the diffusion into the chip output is constrained only to this region, while the conventional DLD array has diffusion to the product output occurring all across the whole array. The treatment chemical can have shorter diffusion time in the "wall-separated" DLD array than that in conventional DLD array. The diffusion in this last region can again be suppressed by adding a second separator wall, of length $l_2$=1 cm in the current design. The second separator wall can reduce a portion of the chemical reagents from being able to diffuse towards the output channel. The gap ($w_{1\&2}$) between the first and second separator walls is 90 μm, which can be as small as possible to avoid treatment chemical reaching to the washing stream, but can be large enough to avoid the clogging of target cells.

Device Fabrication and Operation

Devices with and without separator walls were fabricated in silicon wafers using standard microfabrication techniques. Etching masks were formed on the silicon wafers using single-layer photolithography (Karl Suss, MA6) with AZ 4330 photoresist (AZ Electronic Materials, USA) and AZ 300 MIF developer. Samples were then anisotropically etched to 120 μm deep using a Samco RIE800iPB for Deep Reactive Ion Etching (DRIE). Inlets and outlets are through-wafer holes created by sandblasting using 50 μm diameter aluminum oxide particles (PrepStart, Danville Engineering, USA). The devices were sealed with 3M 9795R polyolefin sealing tape with a backplane glass coverslip in the bottom ("Lid" in FIG. 48C). The devices were mounted to a polycarbonate jig (FIG. 48C) connected to an external syringe pump (Fusion 400, Chemyx, USA). Then 0.2 μm Polytetrafluoroethylene (PTFE) filters were applied to the jig to allow air to be pushed out of the manifold. Finally, a stainless steel metal plate with a window for microscopic observation was used to hold the devices and the polycarbonate jig.

An inverted microscope (Nikon Eclipse Ti) was used to image the distribution of fluorescent R6G and labeled cells in the devices, with high pressure mercury lamp as an excitation source with a matching fluorescence filter set (TRITC, 532-556 nm excitation and 570-613 nm emission). Images and movies were recorded using a CoolSNAP ES2 CCD camera and NIS-Elements software.

FIG. 48D shows the entire syringe pump and microfluidic system. The system and tubing was first rinsed and wet with degassed 0.2% Pluronic F108 surfactant in deionized water and then the running buffer (see later). Next, the sample solution as the sample input stream, staining solution as the treatment input stream, and running buffer as the washing input stream were loaded into the syringe pump as device inputs, and driven through the microfluidic system to run experiments. The syringe pump was running in the range of 0.1 μL/min to 100 μL/min (total volume rate 0.3 μL/min to 300 μL/min for all three inputs) to form an average fluid velocity in the post gaps ranging from about 140 μm/s to 14 cm/s.

Preparation of Experiment Samples

The running buffer contained 150 mM NaCl at pH 7.2 containing 0.09% NaN3, 1% BSA, and 7 mM EDTA. 40 μM D-Phenylalanyl-prolyl-arginyl Chloromethyl Ketone (PPACK) could be added to the running buffer to further reduce on-chip clogging for long time device usage (>30 mins).(42) Venous EDTA-anticoagulated blood (purchased from Interstate Blood Bank, Inc., Memphis, TN, USA) was diluted 1:3 with the running buffer as the sample solution. The diluted blood was then used directly as the sample stream input, with no centrifugation or lysis steps. The staining solution (the treatment stream input) was 20 μg/L R6G in the running buffer.

Results and Discussion

Diffusion of Treatment Chemical

Figures 49A, 49B:
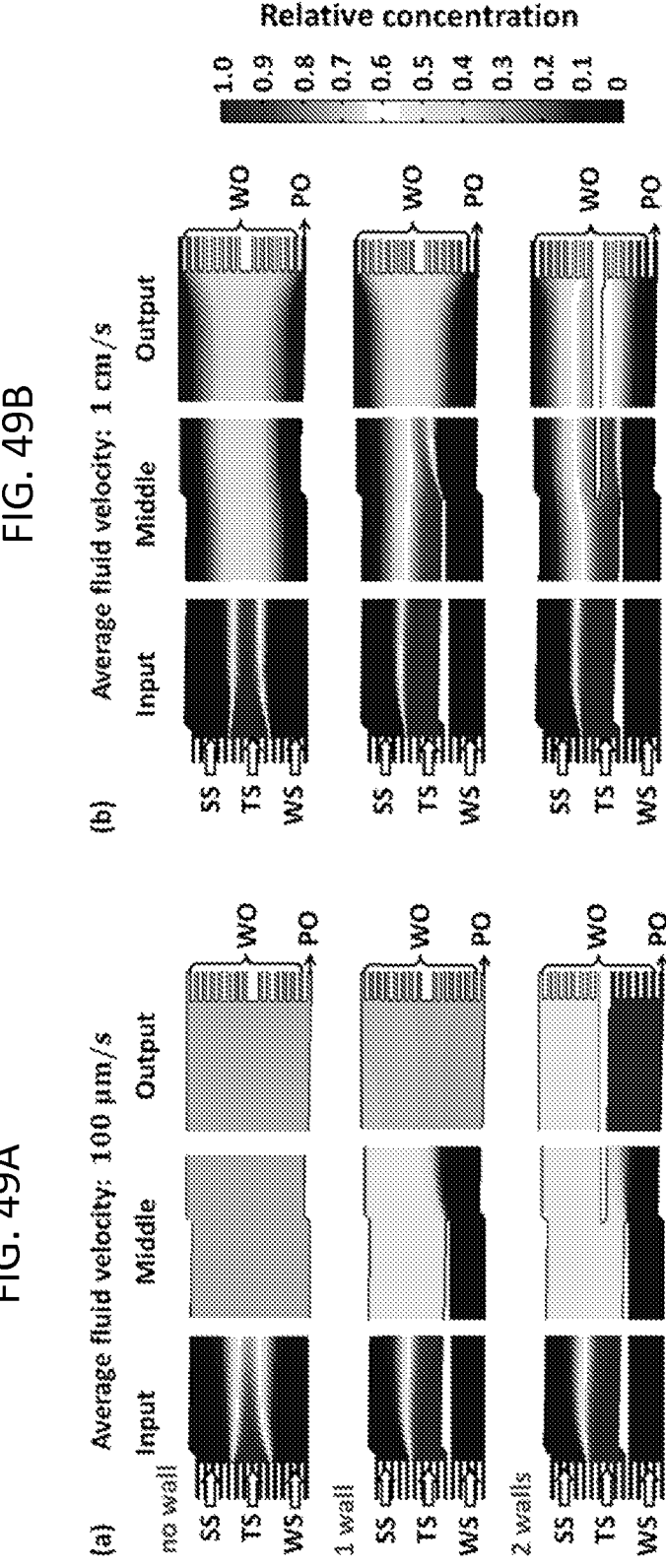
FIGS. 49A-B illustrate COMSOL simulations of relative concentration across devices. COMSOL simulations of relative concentration across devices with no separator wall, one separator wall, and two separator walls at average fluid velocity 100 μm/s and 1 cm/s. SS: sample input stream, TS: treatment input stream, WS: washing input stream, WO: waste output, and PO: product output. Each condition shows the input, middle, and output regions (0.8 mm long) of the devices. For 100 μm/s (1 cm/s), the relative output contamination is 0.33 (0.12), 0.32 (0.025), and 0.14 (0.017) with no, 1, and 2 separator walls respectively. The output contamination of the treatment chemical can be reduced effectively with the separator wall design.
Figures 50A, 50B:
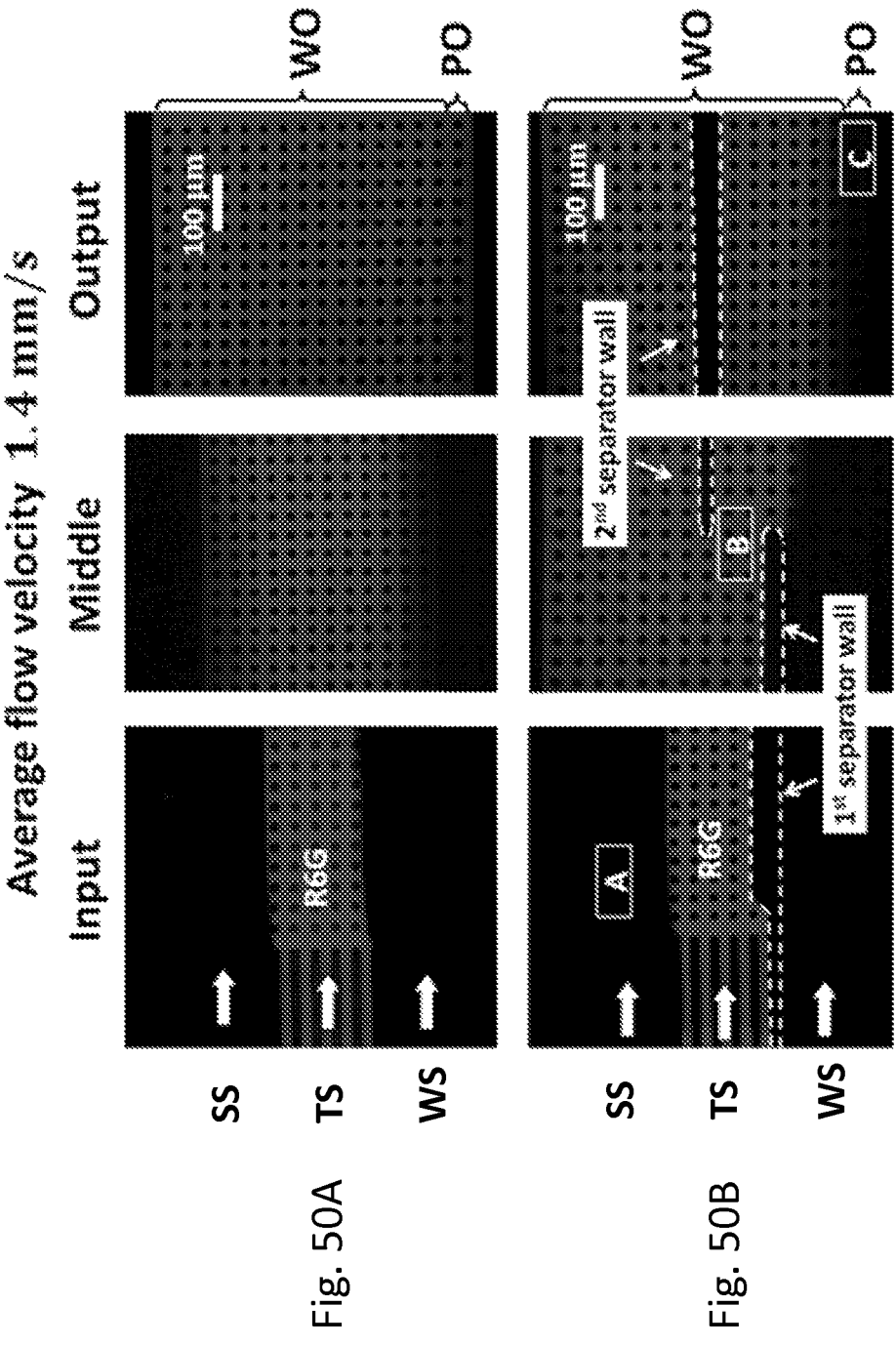
FIGS. 50A-B shows fluorescent images of R6G flowing in the treatment streams. Fluorescent images of R6G flowing in the treatment stream of FIG. 50A conventional DLD array and FIG. 50B DLD array with two separator walls, showing clear reduction of contamination at the product output. The average fluid velocity in post gaps is 1.4 mm/s.

Simulation results of the relative concentration of the treatment chemical (the ratio of the concentration of the treatment chemical to that in the input chemical stream) for devices with no separator wall, one separator wall, and two separator walls using COMSOL are shown in FIGS. 50A and B. The diffusion constant of the treatment chemical was set to be $4 \times 10^{-10}$ m²/s (the diffusion constant of R6G) and the posts were omitted from the simulation structure for computational simplicity. The relative concentration of the treatment chemical was shown at the chip input, middle of the chip, and the chip output. The reduction of treatment chemical contamination at the product output brought by the first and second separator walls can be seen from these simulation results. At average fluid velocity of 100 μm/s for the design with only the first separator wall (FIG. 49A), the treatment chemical was blocked by the first separator wall, but still had enough time in the last section of the chip to diffuse unboundedly across the entire flow path, so that the 1-wall design is little better than the conventional no wall design. The contamination in the product output was calculated as the average relative concentration of the treatment chemical over the 60 μm-wide product output channel. By implementing the second separator wall this relative contamination can be reduced down to 0.14. With the average fluid velocity of 1 cm/s (FIG. 49B), the diffusion time was reduced, but the conventional design still had an output contamination of relative concentration about 0.1. The output contamination was suppressed about 4.6 fold with the first separator wall design, and can be further reduced utilizing two separator walls down to 0.017.

The diffusion of R6G in the fabricated arrays without and with separator walls was experimentally measured by quantitative fluorescence microscopy. Similar to the simulation results, the output contamination due to the diffusion of R6G was evaluated by the average relative R6G concentration entering the product output. The relative R6G concentration was defined as the ratio of the fluorescence intensity of R6G to that of the treatment stream input, as the fluorescence intensity of R6G has a linear relation to its concentration at low concentration.(43) FIGS. 50A and B display the fluorescence images of the input, middle, output region of DLD arrays without and with separator walls of same length, but with otherwise identical dimensions. At average fluid velocity 1.4 mm/s in post gaps, the contamination at the product output almost reached saturated level about 0.3 in the conventional DLD array (FIG. 50A). In the wall-separated array, the presence of separator walls led to a 3 fold output contamination reduction down to about 0.1 (FIG. 50B).

Figure 50C:
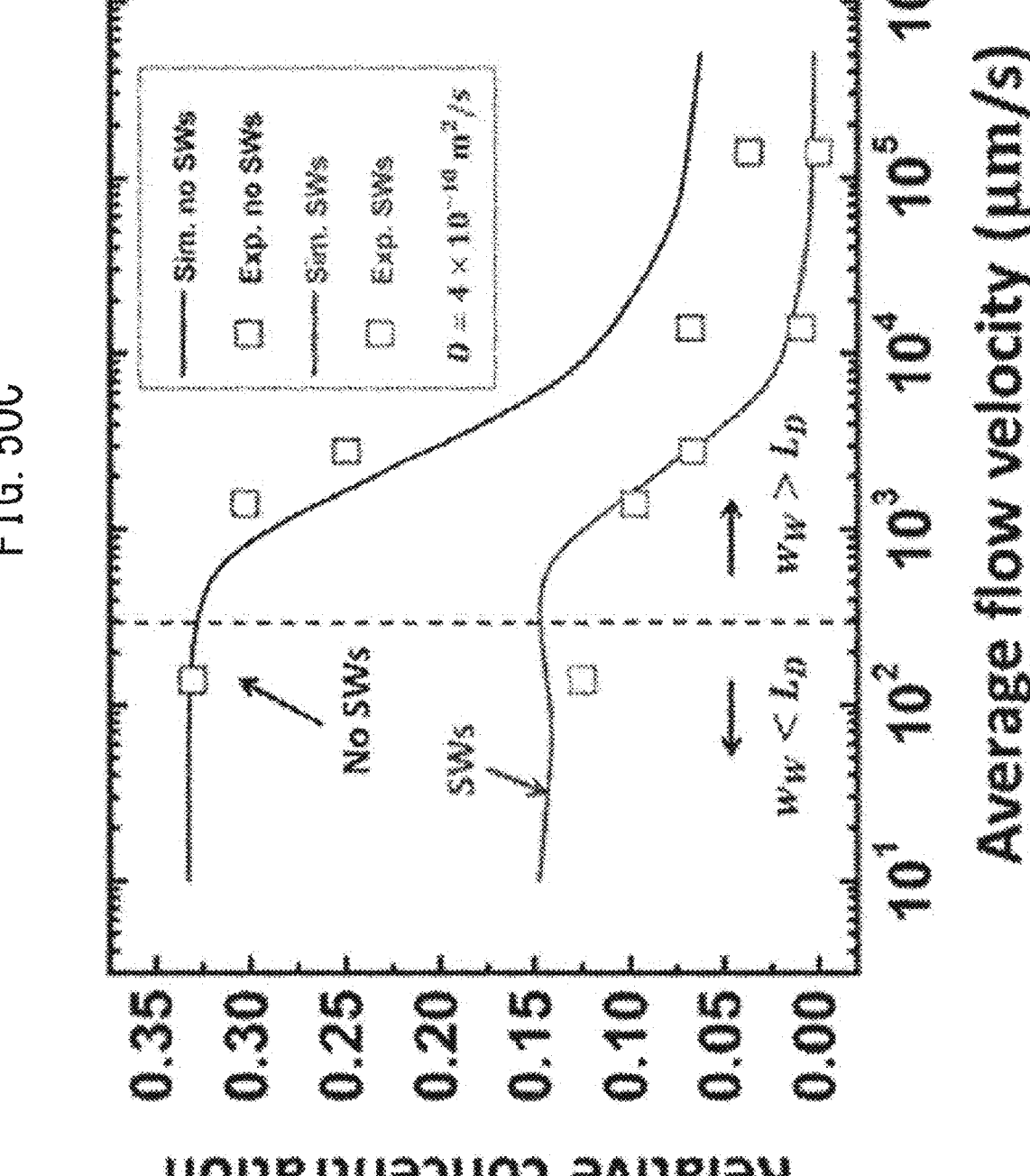
FIG. 50C Experimental and COMSOL simulation results of relative concentration versus average fluid velocity for both conventional (black) and wall-separated (red) DLD arrays. The open squares are experiment results measured as the ratio of the fluorescence intensity at the product output to that of the treatment stream input. The solid lines are the COMSOL simulation results. A dotted black line is drawn in FIG. 50C to point out the critical fluid velocity of 300 μm/s for the conventional design. R6G concentration is 20 μg/mL.

The experiment results at different fluid velocities agreed well with the numerical simulation, as shown in FIG. 50C. (The average fluid velocity was used for the COMSOL simulation, and the average fluid velocity in post gaps was used for experiments.) The output contamination depended on how fast the diffusion of the treatment chemical occurs compared to the rate at which the fluid moves through the device, classically characterized by Peclet number. For a device without separator walls, a critical velocity ($v_c$) can be the one which the diffusion length $L_D = \sqrt{D\tau}$ is equal to the distance from the treatment stream to the product output location, which is $w_w$, the width of the washing stream, where $\tau = L_{tot}/v_c$ is the time the fluid is in the device, and $L_{tot}$ is the total length of the device. Thus a critical fluid velocity can be written as:

$$v_c = \frac{DL_{tot}}{w_W^2} \qquad (1)$$

For a conventional DLD array, a vertical black dotted line in FIG. 50C can indicate this critical fluid velocity of 300 μm/s. At fluid velocity lower than $v_c$, $w_w < L_D$ and the contamination reaches a plateau. At fluid velocity higher than $v_c$, $w_w > L_D$ and the contamination drops.

For the "wall-separated" DLD array, the time for diffusion in the device can be reduced from $(l_1 + l_2)/v$ to $l_2/v$, where v is the average fluid velocity, and the $2^{nd}$ separator wall in the latter region of the device further can prevent some treatment chemical from being able to move to the output. The improvement in the output contamination reduction was 3 to 10 fold, depending on the fluid velocity (FIG. 50C). For example, from the experimental results, at average fluid velocity 14 mm/s in post gaps, the R6G concentration in the product output channel was reduced from 0.07 without separator walls to only 0.01 with the implementation of separator walls.

Incubation Time Vs. Output Contamination

The minimum incubation time can be a key factor of on-chip cell processing and preparation applications. The minimum incubation time was estimated in the "wall-separated" DLD array. The cells flowing into the device at the topmost boundary experienced the minimum incubation time (P1 in FIG. 48A). This minimum incubation time $t_{min}$ in the wall-separated DLD array was estimated as:

$$t_{min} \text{ in } \frac{w_T}{\epsilon v_{cell,DLD}} + \frac{\epsilon l_1 - w_T - w_S}{\epsilon v_{max}} \quad (2)$$

where $w_T$ and $w_S$ are the widths of treatment stream and sample stream respectively, $v_{cell,DLD}$ is the cell velocity in the DLD array, and $v_{max}$ is the maximum fluid velocity in the gaps. When the target cells flow in the DLD array, their velocity can change periodically from fast in the gaps to slow in the open regions. To estimate the minimum incubation time, the fluid velocity in post gaps was conservatively used. The target cells which were above the critical size and thus were "bumped" by the posts at every column of obstacles, moved alongside the posts as they follow the tilt angle (target cell in FIG. 48B). Assuming the large target cell moved at the fluid velocity of the streamline where the cell center was and a parabolic flow profile, the cell's velocity was $$v_{cell,DLD} \approx 4v_{max}\left(r_{cell}/g - r_{cell}^2/g^2\right),$$

where $r_{cell}$ was the radius of the target cells ($r_{cell}$ of 3.5μ. is assumed for leukocytes), and $v_{max}$ was the maximum fluid velocity in the post gaps and was 1.5 times the average fluid velocity.(30)

The first term of Eq. (2) is the incubation time approximation in the conventional DLD array. The second term of Eq. (2) is the additional incubation time gained by implementing the first separator wall. As the target cell further moves through the DLD array, it can be collected against the first separator wall, and it can be gradually driven to an equilibrium position where the wall effect lift force and the shear gradient lift force balance.(44) From experimental observations, the equilibrium position of leukocytes was close to the middle of the gap where the fluid velocity reaches a maximum ($v_{max}$) (FIG. 48B). The incubation time can be increased by increasing the total length of the first separator wall without any penalty of the contamination of treatment chemical in the product output.

Figure 51:
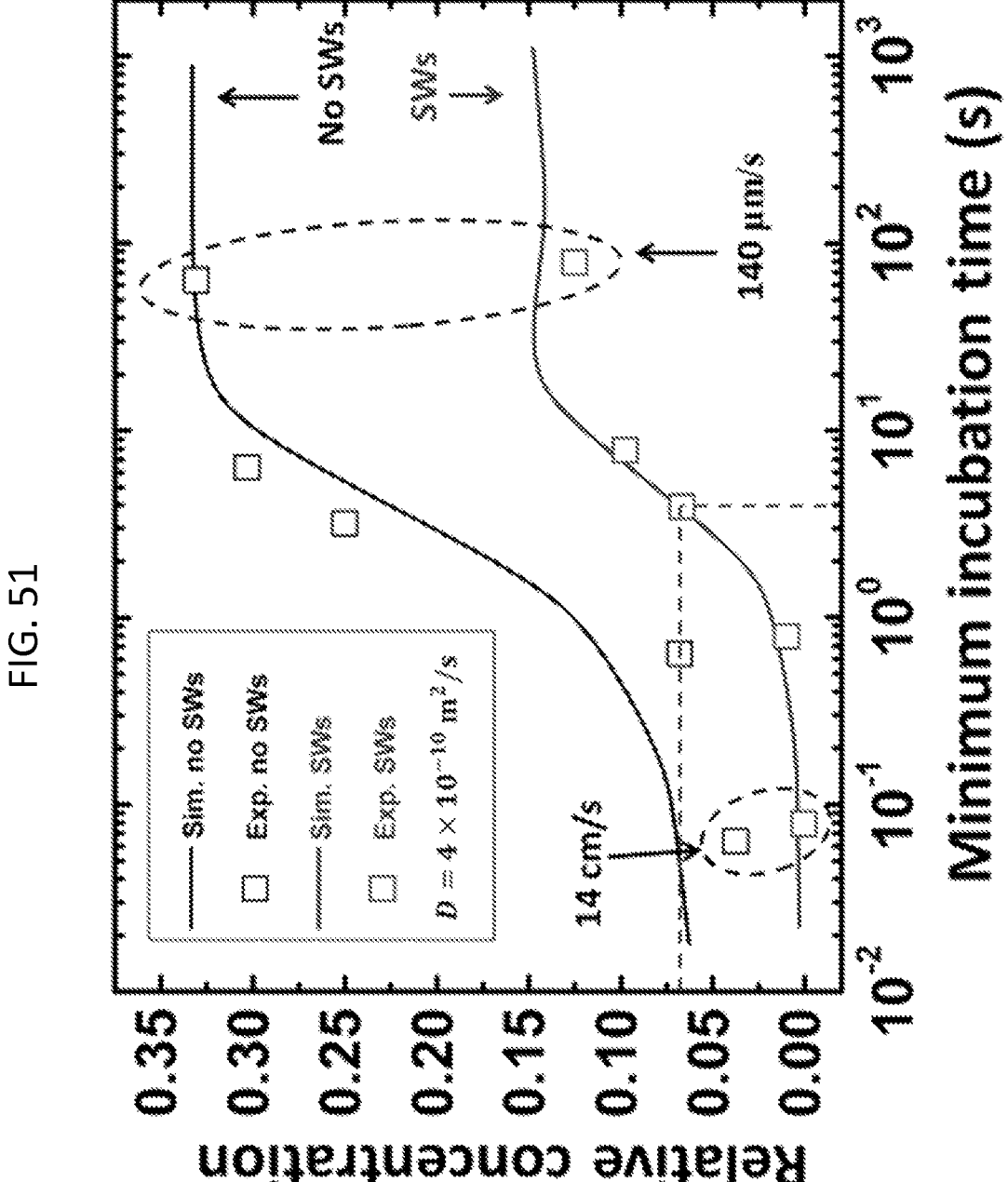
FIG. 51 shows experimental and COMSOL simulation results of relative concentration versus calculated minimum incubation time for both conventional (black) and wall-separated (red) DLD arrays, achieved by varying the average fluid velocity. The open squares are experimental results and the solid lines are the COMSOL simulation results. The condition for the two-separator wall design of an average fluid velocity in post gaps of 2.8 mm/s with ~4 s minimum incubation time and 0.067 product output contamination (indicated by red dotted lines) was selected for subsequential staining tests.

Experimental and COMSOL simulation results of the relative output contamination versus calculated minimum incubation time according to Eq. (2) for both conventional (black) and "wall-separated" (red) DLD arrays are shown in FIG. 51. For high fluid velocity, both incubation time and output contamination were low. They both raised as the fluid velocity was decreased. For a leukocyte staining test, average fluid velocity in post gaps of 2.8 mm/s was selected (pointed out by the red dash lines) as an experimental on-chip leukocyte staining condition, with ~4 s minimum incubation time and 0.067 product output contamination. As shown by the later experiments, leukocytes were stained with recognizable fluorescence intensity compared to very low background intensity of contamination at this condition.

Figure 52A:
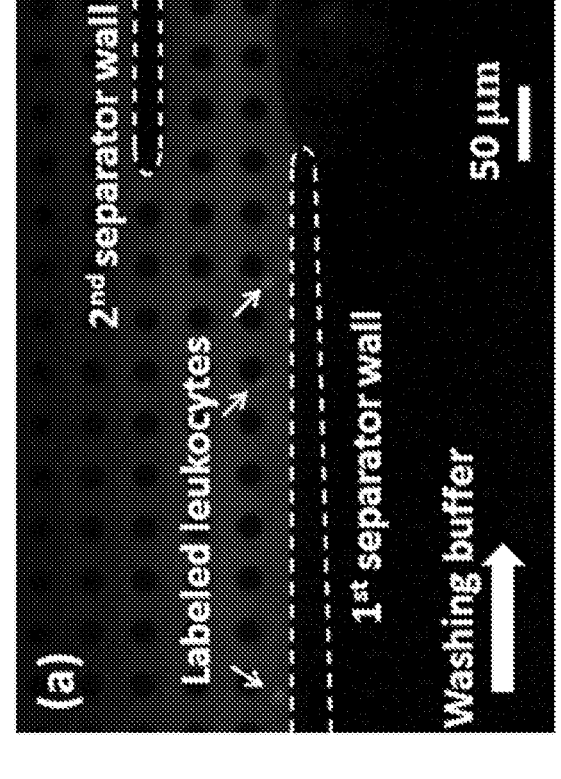
FIGS. 52A-B show fluorescent images of on-chip leukocyte staining with R6G with wall-separated DLD arrays using diluted human blood as the input, without any centrifugation or lysis. The average fluid velocity in post gaps is 2.8 mm/s.
Figure 52B:
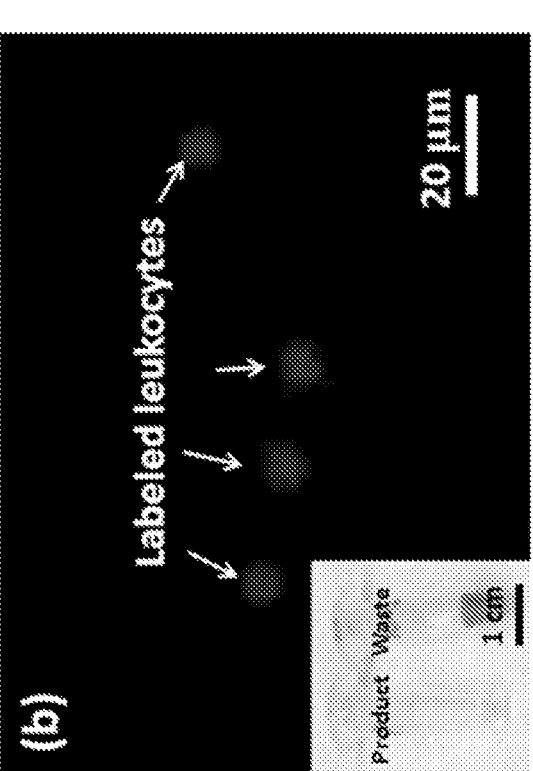

The wall-separated device was then used to demonstrate on-chip staining and washing of leukocytes with R6G, using diluted whole blood as the sample stream input. R6G can diffuse into the cells and attaches to their mitochondria.(39) The array separated the leukocytes out of the sample stream and then directed them into the treatment and the subsequential washing streams. The critical size ($D_c$) was about 6 μm in the DLD array measured by fluorescent beads of different sizes, which was below the size of most leukocytes. The diameter of erythrocytes was about 6-8 μm. However since their distinctive biconcave shape, they aligned to the fluid flow to behave as small particles and were not displaced in the array, thus following the average fluid direction.(45) Moreover, the size of the other content (platelets, proteins, etc.) of blood was mostly smaller than 6 μm, so that only leukocytes were harvested from the sample stream. Fluorescent microscopy was used to track the paths and staining of the cells (FIG. 52). In the input region, no fluorescent leukocytes or other cells could be seen as the cells were not yet labeled (FIG. 50B). The leukocytes were then concentrated and incubated along the first separator wall in the middle region of the wall-separated DLD array (FIG. 51A FIG. 50B). Finally, the labeled leukocytes were collected at the product output (FIG. 50B) and visible (FIG. 51B). The inset of FIG. 51B shows the product output and waste output vailed from one experiment of 200 μL diluted blood. A good separation of leukocytes from erythrocytes can be indicated by the notable color difference. In the fluorescence image of the product output stream, little fluorescence background were found, indicating a good staining by R6G and low contamination of unreacted R6G in the product output.

Conclusion

This example presents a wall-separated DLD array for integrated on-chip cell harvesting, chemical processing, and washing. The "wall-separated" design can improve the trade-off between long chemical treatment times and low output contamination at low fluid velocity, enabling both (i) increased incubation time, and (ii) less contamination of treatment chemical in the product output. Leukocytes can be separated from the whole blood, stained by R6G, and washed in a single DLD array device without any preprocessing of the blood or manual handling between steps. The device can also be applicable to other on-chip processing and washing steps such as labelling with monoclonal antibodies, fixation/permeabilization, and other novel applications.

Example 23: Purifying WBCs from Whole Blood Using DLDs with Different Obstacle Cross-Section Shapes Microfluidic chips with obstacles were used to purify white blood cells (WBCs) from whole blood. Design of the cross-section shapes of the obstacles can allow obtaining high yield of WBCs and low contamination from red blood cells (RBCs).

Microfluidic chips with obstacles having a diamond-shaped cross-section, (or a rotated square, where a vertex of the rotated square points in the direction of the flow of the sample), a triangle shaped cross-section, a round-shaped cross section, a square-shaped cross-section, and quarter-round shaped cross-section were used for purifying WBCs from whole blood samples. The flow rates of the samples were about 40 mL/hour.

Each of the microfluidic chips was silicon with a single DLD array etched to a depth of 150 μm. The average velocity in the gaps was about 10 cm/second. Each DLD array had a tilt of 1/42. The gaps in each array were 17 μm in width, and the obstacles were 19 μm in size. The blood sample used in the experiments was diluted 1:4 in a running buffer (PBS buffer) with a final concentration of 5 mM EDTA, 40 μM PPACK, and 1% BSA. Equal volumes of the blood sample and running buffer were run through the chip simultaneously so that WBCs were collected from the blood sample in the running buffer free of RBCs. The velocity was measured by the average flow rate divided by the cross-sectional area of the channel through which fluid flowed. The shear rate was calculated as the average velocity divided by half the gap width.

Figure 53A:
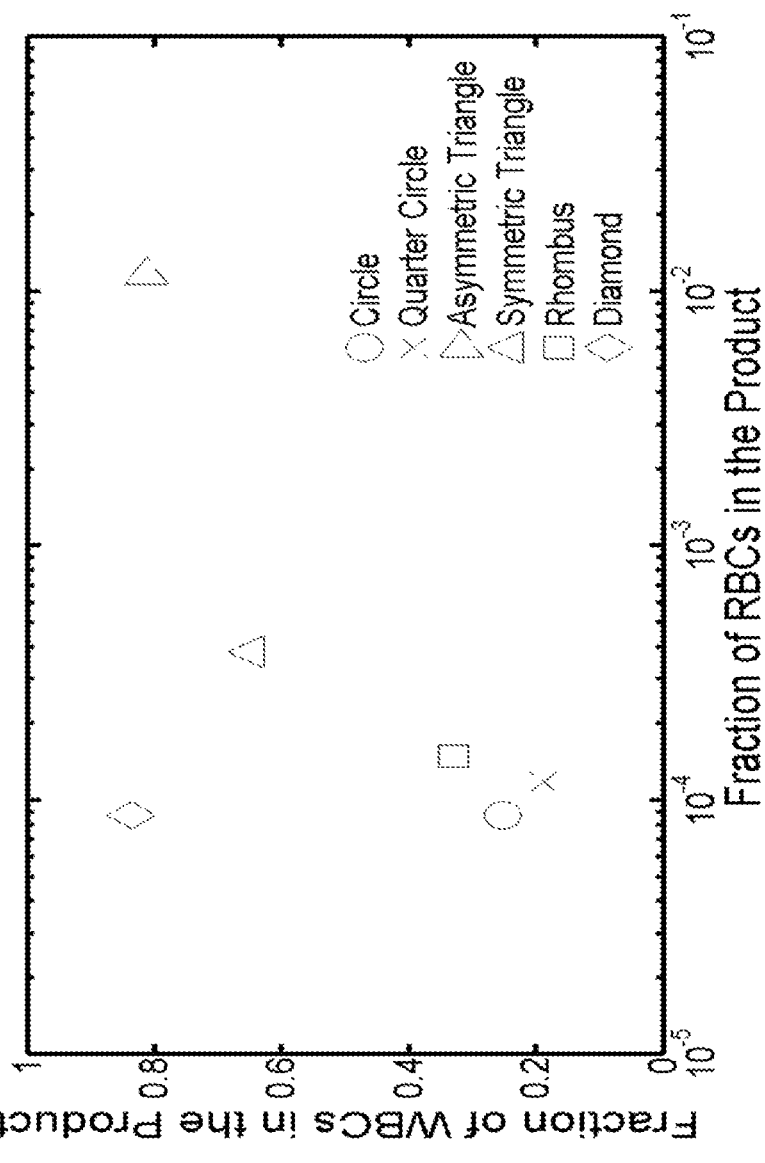

The WBCs yields and RBC contamination rates are shown in FIG. 53A for arrays with obstacles with different cross-sectional shapes. Among the obstacles with different cross-sectional shapes used in the experiments, an array with obstacles with a diamond cross-section purified WBCs with highest yield (over 80%) and with lowest RBCs contamination (less than 0.01%).

Figure 53B:
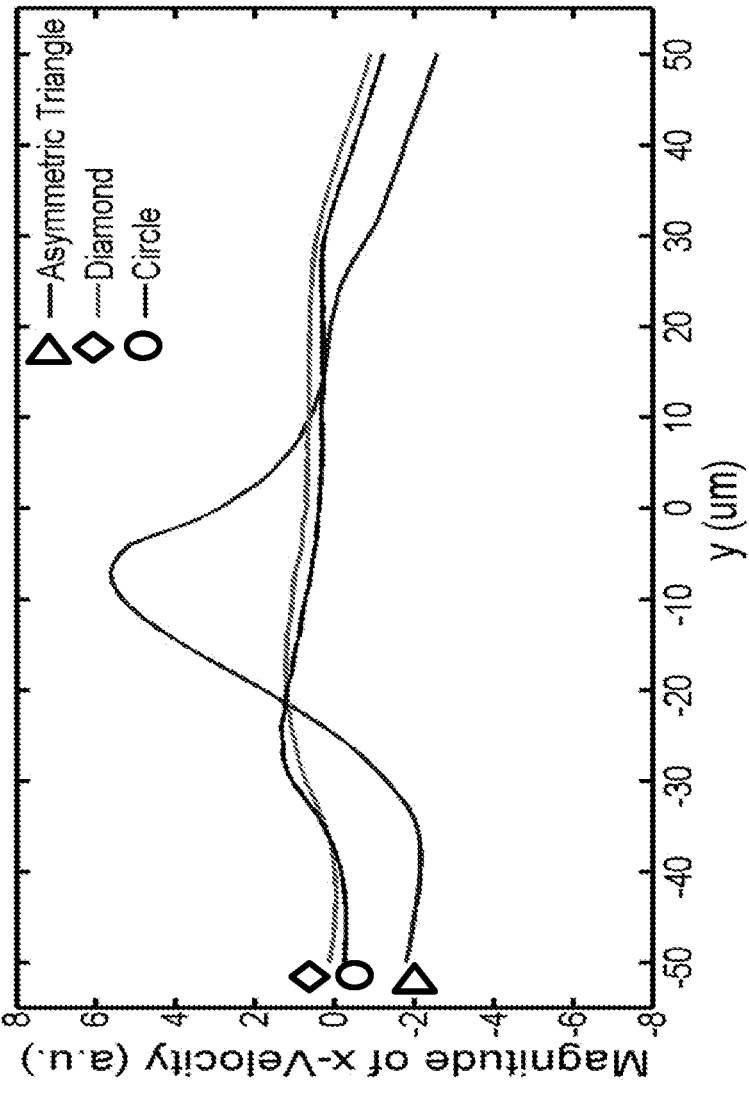
Figure 53C:
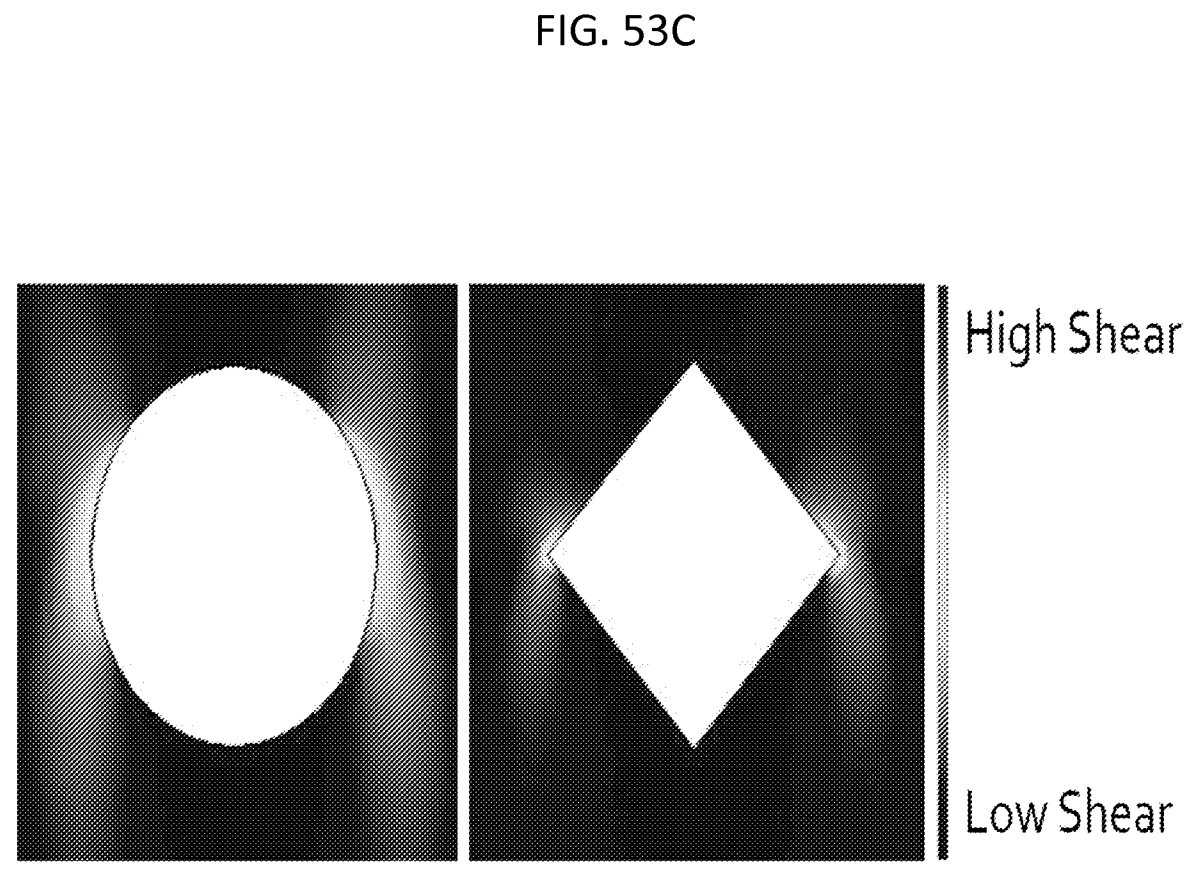

The separation of WBCs and RBCs and contamination of RBCs can be affected by the inertial effects created by obstacles with different cross-sectional shapes. FIG. 53B shows the inertial effects created by obstacles with diamond, triangular, and circular cross-sections. Inertial effects result in extra lateral (x-direction) displacement with asymmetric triangular posts but not with circular or diamond posts. Obstacles with different cross-sectional shapes can cause different level of deformation of WBCs. Obstacles with diamond cross-sections created less shear force compared to obstacles with circular cross-sections as shown in FIG. 53C. A high shear rate over a long arc length, which can be observed with posts with a circular cross-section, is not observed with posts with a diamond-shaped cross-section. A high shear rate over a long arc length can lead to WBC deformation that can result in low yields.

Example 24: DLD Microchips Summarized

Example 13 Microchip Product #1

Washes human WBC from human blood after conventional surface labeling.

Example 14 Microchip Product #2

Washes fixed/permed WBCs after conventional fixation/permeabilization.

Example 15 Microchip Product #3

Washes intracellular labeled WBCs after conventional intracellular labeling.

Example 16 Microchip Product #4

Harvests human WBC from human blood that is surface-labeled & washed on the chip.

Example 17 Microchip Product #5

Harvests surface-labeled human WBC that are fix/permed, washed on chip, stained with an intracellular stain off chip.

Example 18 Microchip Product #6

Human blood WBCs are surface stained and fix/permed off chip, then stained intracellularly and washed on chip.

Example 19 Microchip Product #7

A microfluidic DLD chip system for on-chip fix/perm, intracellular labeling of WBCs, with on-chip washing and concentrating.

Example 25: WBC Isolation Using Different Chip Configurations

Figure 56:
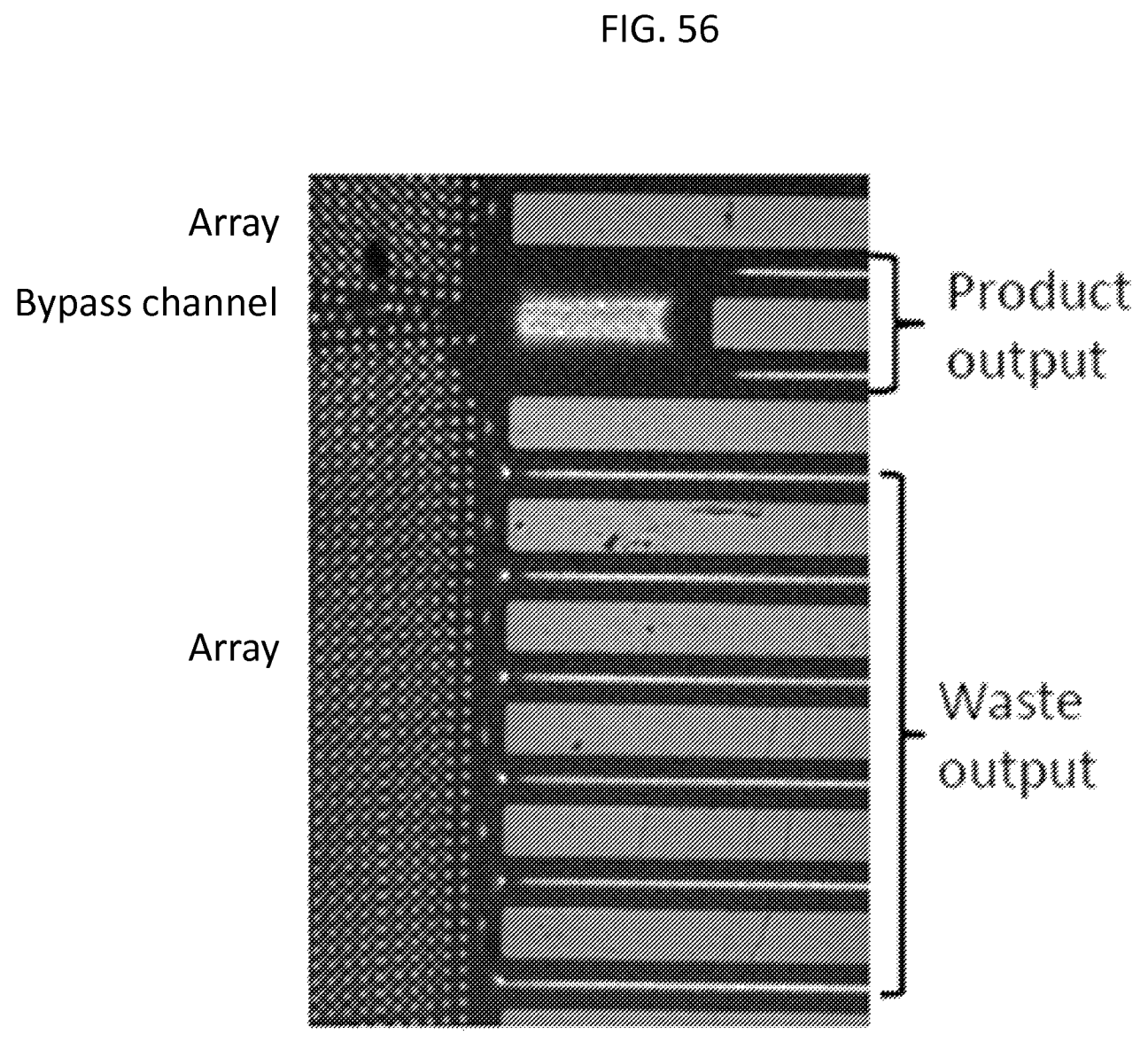

A: One-day old blood (Interstate Blood Bank) was dilute 1:5 (1 part blood, 4 parts buffer (1% BSA/PBS)), EDTA was added to 7 mM, and PPACK was added to 40 μM), sample was run on a silicon chip at a sample input running rate of 15 μL/min and a buffer input running rate of 45 μL/min. The silicon chip comprised a 3-zone DLD array. The 3-zone DLD array had 3 zones of circular posts of row shift 1/10, and depth of 100 μm. The 3 zones had posts of 27 μm, 18 μm, and 11 μm respectively. The 3 zones had gaps of 18 μm, 12 μm, or 11 μm, respectively. The length of each array was 1 cm, 1 cm, and 1.2 cm, respectively. The total length including the input and output regions was 7 cm. FIG. 56 shows the array 3 with 11 posts μm and 11 μm gaps. An input volume of 900 μL of sample was added over 60 min, and 2.7 mL of buffer was used. About 1.8 mL of product was collected through the outlet of FIG. 56. The WBC yield was 71%.

B: One-day old blood (Interstate Blood Bank) was dilute 1:5 (1 part blood, 4 parts buffer (1% BSA/PBS)), EDTA was added to 7 mM, and PPACK was added to 40 μM), sample was run on a silicon chip at a sample input running rate of 15 μL/min and a buffer input running rate of 45 μL/min. The silicon chip comprised a 3-zone DLD array. The 3-zone DLD array had 3 zones of circular posts of row shift 1/10, and depth of 100 μm. The 3 zones had posts of 27 μm, 18 μm, and 11 μm respectively. The 3 zones had gaps of 18 μm, 12 μm, or 11 μm, respectively. The length of each array was 1 cm, 1 cm, and 1.2 cm, respectively. The total length including the input and output regions was 7 cm. FIG. 57 shows the array 3 with 11 posts μm and 11 μm gaps. An input volume of 900 μL of sample was added over 60 min, and 2.7 mL of buffer was used. About 1.5 mL of product was collected through the outlet of FIG. 57. The WBC yield was 83%.

C: One-day old blood (Interstate Blood Bank) was dilute 1:5 (1 part blood, 4 parts buffer (1% BSA/PBS)), EDTA was added to 7 mM, and PPACK was added to 40 μM), sample was run on a silicon chip at a sample input running rate of 15 μL/min and a buffer input running rate of 45 μL/min. The silicon chip comprised a 3-zone DLD array. The 3-zone DLD array had 3 zones of circular posts of row shift 1/10, and depth of 100 μm. The 3 zones had posts of 27 μm, 18 μm, and 11 μm respectively. The 3 zones had gaps of 18 μm, 12 μm, or 11 μm, respectively. The length of each array was 1 cm, 1 cm, and 1.2 cm, respectively. The total length including the input and output regions was 7 cm. FIG. 58 shows the array 3 with 11 posts μm and 11 μm gaps. An input volume of 900 μL of sample was added over 60 min, and 2.7 mL of buffer was used. About 1.0 mL of product was collected through the outlet of FIG. 58. The WBC yield was 75%.

The results of the analysis are summarized in Table 9:

| | A | B | C |
|---|---|---|---|
| Array 3 gap | 11 μm | 11 μm | 11 μm |
| Product/Waste | 1:3 | 1:3 | 1:6 |
| Array 3 length | 1.2 cm | 1.2 cm | 1.2 cm |
| WBC yield | 71% | 83% | 75% |
| WBC:RBC | — | — | 1:2 |

REFERENCES, EACH OF WHICH ARE HEREIN
INCORPORATED BY REFERENCE IN THEIR
ENTIRETIES

1. Bendall S C, Simonds E F, Qiu P, Amir E D, Krutzik P O, Finck R, Bruggner R V, Melamed R, Trejo A, Ornatsky O I, Balderas R S, Plevritis S K, Sachs K, Pe'er D, Tanner S D, Nolan G P. Single-cell mass cytometry of differential immune and drug responses across a human hematopoietic continuum. Science 2011; 332: 687-696.
2. Huang L R, Cox E C, Austin R H, Sturm J C. Continuous particle separation through deterministic lateral displacement. Science 2004; 304(5673): 987-990.
3. Yu L, Donovan M, Warner B, Edmiston J S, Recktenwald D. A microfluidic approach for whole blood leucocyte isolation for leucocyte immunophenotyping by flow cytometry. Poster submitted to CYTO2012 in April 2012. Cited by permission.
4. Davis J A, Inglis D W, Morton K J, Lawrence D A, Huang L R, Chou S Y, et al. Deterministic hydrodynamics: taking blood apart. Proc Natl Acad Sci USA 2006; 103(40): 14779-14784.
5. Morton K J, Loutherback K, Inglis D W, Tsui O K, Sturm J C, Chou S Y, Austin R H. Crossing microfluidic streamlines to lyse, label and wash cells. Lab Chip 2008; 8: 1448-1453.
6. Inglis D W, Davis J A, Austin R H, Sturm J C. Critical particle size for fractionation by deterministic lateral displacement. Lab Chip 2006; 6(5): 655-658.
7. Loutherback K, Austin R H, Sturm J C. Critical size, dynamic range, and throughput improvements in sorting by deterministic lateral displacement enabled by triangular posts. Presented at the Symposium of the Materials Research Society, San Francisco, CA, April 2009.
8. Davis J. Microfluidic separation of blood components through deterministic lateral displacement. Ph.D. Thesis, Princeton University, 2008 (http://www.princeton.edu/-sturmlab/theses/Davis-Thesis.pdf).
9. Loutherback K, D'Silva J L, Liu L, Wu A, Sturm J C, Austin R H. Deterministic separation of cancer cells from blood at 10 mL/min. Submitted to Lab on a Chip in March 2012.
10. Loutherback K, Puchalla J, Austin R H, Sturm J C. Deterministic microfluidic ratchet. Phys Rev Lett 2009; 102(4): 045301.
11. Loutherback K, Chou K, Newman J, Puchalla J, Austin R, Sturm J. Improved performance of deterministic lateral displacement arrays with triangular posts. Microfluidics and Nanofluidics 2010; 9(6): 1143-1149.

12. Bendall S C, Nolan G P, Roederer M, Chattopadhyay P K. A deep profiler's guide to cytometry. Trends Immunol. 2012; 33(7):323-32. PMCID|3383392.
13. Bendall S C, Simonds E F, Qiu P, Amir el A D, Krutzik P O, Finck R, Bruggner R V, Melamed R, Trejo A, Ornatsky O I, Balderas R S, Plevritis S K, Sachs K, Pe'er D, Tanner S D, Nolan G P. Single-cell mass cytometry of differential immune and drug responses across a human hematopoietic continuum. Science. 2011; 332(6030):687-96. PMCID|3273988.
14. Mandy F, Varro R, Recktenwald D. Flow Cytometry Principles, Chapter 25. In: Vo-Dinh T, editor. Biomedical Photonics Handbook: CRC Press; 2003. p. 1-20
15. Maus M V, Fraietta J A, Levine B L, Kalos M, Zhao Y, June C H. Adoptive immunotherapy for cancer or viruses. Annu Rev Immunol. 2014; 32:189-225.
16. Morton K J, Loutherback K, Inglis D W, Tsui O K, Sturm J C, Chou S Y, Austin R H. Crossing microfluidic streamlines to lyse, label and wash cells. Lab Chip. 2008; 8(9): 1448-53.
17. Wang D, Bodovitz S. Single cell analysis: the new frontier in 'omics'. Trends Biotechnol. 2010; 28(6): 281-90. PMCID|2876223.
18. Martinez-Lopez J, Lahuerta J J, Pepin F, Gonzalez M, Barrio S, Ayala R, Puig N, Montalban M A, Paiva B, Weng L, Jimenez C, Sopena M, Moorhead M, Cedena T, Rapado I, Mateos M V, Rosinol L, Oriol A, Blanchard M J, Martinez R, Blade J, San Miguel J, Faham M, Garcia-Sanz R. Prognostic value of deep sequencing method for minimal residual disease detection in multiple myeloma. Blood. 2014; 123(20):3073-9. PMCID|4023416.
19. Moore J, Yvon P. High dimensional flow cytometry comes of age. European Pharmaceutical Review. 2012; 17(4):20-4.
20. Yu L, Donovan M, Warner B, Edmiston J, Recktenwald D. A microfluidic approach for whole blood leucocyte isolation for leucocyte immunophenotyping by flow cytometry. Poster. Cited by permission. CYTO2012; Jun. 23-27, 2012; Leipzig, Germany 2012.
21. Huang L R, Cox E C, Austin R H, Sturm J C. Continuous particle separation through deterministic lateral displacement. Science. 2004; 304(5673):987-90.
22. Davis J. Microfluidic separation of blood components through deterministic lateral displacement. Ph.D. Thesis: Princeton University; 2008.
23. Davis J A, Inglis D W, Morton K J, Lawrence D A, Huang L R, Chou S Y, Sturm J C, Austin R H. Deterministic hydrodynamics: taking blood apart. Proc Natl Acad Sci USA. 2006; 103(40):14779-84. PMCID|1595428.
24. Inglis D W, Davis J A, Austin R H, Sturm J C. Critical particle size for fractionation by deterministic lateral displacement. Lab Chip. 2006; 6(5):655-8.
25. Civin C I, Strauss L C, Brovall C, Fackler M J, Schwartz J F, Shaper J H. Antigenic analysis of hematopoiesis. III. A hematopoietic progenitor cell surface antigen defined by a monoclonal antibody raised against KG-1a cells. J Immunol. 1984; 133(1):157-65.
26. Lanier L L, Le A M, Civin C I, Loken M R, Phillips J H. The relationship of CD16 (Leu-11) and Leu-19 (NKH-1) antigen expression on human peripheral blood NK cells and cytotoxic T lymphocytes. J Immunol. 1986; 136(12):4480-6.
27. Chow S, Hedley D, Grom P, Magari R, Jacobberger J W, Shankey T V. Whole blood fixation and permeabilization protocol with red blood cell lysis for flow cytometry of intracellular phosphorylated epitopes in leukocyte subpopulations. Cytometry A. 2005; 67(1): 4-17.

28. Chen Y, D'Silva J, Austin R, Sturm J. Reduction of Output Contamination in On-chip Chemical Treatment and Washing using Separator Walls in Deterministic Lateral Displacement Arrays. Spring Symp Mat Res Soc; San Francisco, CA Apr. 21-25, 2014.

29. Flow Cytometry and Sorting Core Facility. One-step fixation/permeabilization Protocol. St. Michael's Hospital, Toronto, Ontario, Canada. http://www.stmichael-shospital.com/research/facilities/docs/Protocol1-On-estep-Fix-perm.doc.

30. O. Kolar and W. Zeman, Arch. Neurol., 18, 44-51 (1968).

31. M. A. McClain, C. T. Culbertson, S. C. Jacobson, N. L. Allbritton, C. E. Sims and J. M. Ramsey, Anal. Chem., 75, 5646-5655 (2003).

32. J. Nguyen, Y. Wei, Y. Zheng, C. Wang, and Y. Sun, Lab Chip, 15, 1533-1544 (2015).

33. A. Mach, J. H. Kim, A. Arshi, S. C. Hur, and D. Di Carlo, Lab Chip, 11, 2827-2834 (2011).

34. A. P. Tan, J. S. Dudani, A. Arshi, R. J. Lee, H. T. K. Tse, D. R. Gossett, and D. Di Carlo, Lab Chip, 14, 522-531 (2014).

35. K. J. Morton, K. Loutherback, D. W. Inglis, O. K. Tsui, J. C. Sturm, S. Y. Chou, and R. H. Austin, Lab Chip, 8, 1448-1453 (2008).

36. J. A. Davis, D. W. Inglis, K. J. Morton, D. A. Lawrence, L. R. Huang, S. Y. Chou, J. C. Sturm, and R. H. Austin, Proc. Natl. Acad. Sci. U.S.A., 103, 14779-14784 (2006)

37. D. W. Inglis, J. A. Davis, T. J. Zieziulewicz, D. A. Lawrence, R. H. Austin, and J. C. Sturm, J. Immuno. Methods, 329, 151-156 (2008).

38. A. R. L. Gear, J. Biol. Chem., 249, 3628-3637 (1974).

39. L. K. Tamm, Biochemistry, 27, 1450-1457 (1988).

40. D. W. Inglis, J. A. Davis, R. H. Austin, and J. C. Sturm, Lab Chip, 6, 655-658 (2006).

41. D. W. Inglis, Appl. Phys. Lett., 94, 013510 (2009).

42. J. D'Silva, R. H. Austin, and J. C. Sturm, Lab Chip, 15, 2240-2247 (2015).

43. F. M. Zehentbauer, C. Moretto, R. Stephen, T. Thevar, J. R. Gilchrist, D. Pokrajac, K. L. Richard, J. Kiefer, Spectrochim. Acta A, 121, 147-151 (2014).

44. L. Zeng, S. Balachandar, and P. Fischer, J. Fluid Mech., 536, 1-25 (2005).

45. K. K. Zeming, S. Ranjan, and Y. Zhang, Nat. Commun., 4, 1625 (2013).

While preferred embodiments have been shown and described herein, it will be obvious to those skilled in the art that such embodiments are provided by way of example only. Numerous variations, changes, and substitutions will now occur to those skilled in the art without departing from the descriptions provided herein. It should be understood that various alternatives to the embodiments described herein may be employed in practicing the methods and devices described herein. It is intended that the following claims define the scope of the invention and that methods and structures within the scope of these claims and their equivalents be covered thereby.

What is claimed is:

1. A system for processing first particles from a sample, the first particles comprising leukocytes or stem cells, the system comprising:

a) a microfluidic device, wherein the microfluidic device comprises:

i) a fluidic channel extending from a plurality of inlets to a plurality of outlets;

ii) a first array of obstacles arranged in rows in the channel, wherein each subsequent row of obstacles is shifted laterally with respect to a previous row, wherein the array of obstacles is configured to differentially deflect first particles of at least a predetermined size to a first outlet and second particles of less than the predetermined size to a second outlet, and wherein:

aa) surfaces of two adjacent obstacles in a row of the array of obstacles define a gap;

bb) the two adjacent obstacles defining the gap each have a polygonal cross-section, wherein the polygonal cross-section is disposed within the fluidic channel;

b) a flow through incubator comprising a first inlet configured to receive separated particles from the first outlet of the microfluidic device, a second inlet fluidically connected to a liquid source comprising a reagent, a serpentine channel, and at least one outlet, and c) a balancer that is fluidically connected to the second outlet of the microfluidic device such that a liquid exiting from the second outlet of the microfluidic device directly flows into the balancer, wherein the balancer is configured to have a fluidic resistance that is substantially the same as a fluidic resistance through the flow-through incubator, wherein the balancer comprises a fluidic pressure control comprising a second serpentine channel, and the fluidic pressure control is capable of generating negative pressure in the balancer.

2. The system of claim 1, wherein the serpentine channel of the flow through incubator comprises at least 20 turns.

3. The system of claim 2, wherein the reagent is a binding agent that binds to a cell surface marker selected from the group consisting of: CD3; CD4; CD8; CD19; CD20; CD28; CD34; CD38; CD45; and CD56 (wherein "CD" is an abbreviation for cluster of differentiation).

4. The system of claim 3, wherein an outlet of said incubator is fluidically connected to an inlet of a second microfluidic device.

5. The system of claim 1, wherein said incubator comprises one or more linear channels.

6. The system of claim 1 wherein the incubator is configured to mix a liquid in the incubator.

7. The system of claim 1, wherein the gap defined by the surfaces of said two adjacent obstacles comprises a shape that is substantially symmetrically oriented relative to a plane parallel to the direction of flow of a sample through the array of obstacles and equidistant from the center of the cross-section of each of the two obstacles in the row.

8. The system of claim 4, wherein the second microfluidic device comprises a deterministic lateral displacement (DLD) array.

9. A method for processing first particles of at least a predetermined size from a sample, wherein the first particles comprise leukocytes or stem cells, the method comprising:

a) providing a sample comprising the first particles of at least a predetermined size and second particles of less than the predetermined size; and b) passing the sample through the system of claim 1;

c) separating the first particles from the second particles using the microfluidic device; and d) incubating the first particles using the flow through incubator by applying the particles separated in b) to the first inlet of the flow through incubator.

10. The method of claim 9 wherein the reagent flows into said incubator through the second inlet.

11. The method of claim 10, wherein the reagent is selected from the group consisting of: a binding agent that binds to a cell surface marker; DNA; an enzyme; a drug; a permeabilization agent and a fixative.

12. The method of claim 9, wherein the separated first particles at the first outlet of the microfluidic device comprise at least 80% of the first particles in the sample.

13. The method of claim 9, wherein the serpentine channel comprises at least 20 turns.

\* \* \* \* \*